US009493782B2

(12) United States Patent
Cigan et al.

(10) Patent No.: US 9,493,782 B2
(45) Date of Patent: Nov. 15, 2016

(54) INDUCIBLE PROMOTER SEQUENCES FOR REGULATED EXPRESSION AND METHODS OF USE

(71) Applicant: PIONEER HI-BRED INTERNATIONAL INC, Johnston, IA (US)

(72) Inventors: Andrew Mark Cigan, Johnston, IA (US); Erica Unger-Wallace, Ames, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 514 days.

(21) Appl. No.: 13/896,437

(22) Filed: May 17, 2013

(65) Prior Publication Data

US 2013/0312137 A1 Nov. 21, 2013

Related U.S. Application Data

(60) Provisional application No. 61/648,758, filed on May 18, 2012.

(51) Int. Cl.
*C12N 15/82* (2006.01)

(52) U.S. Cl.
CPC ....... *C12N 15/8237* (2013.01); *C12N 15/8216* (2013.01); *C12N 15/8238* (2013.01); *C12N 15/8241* (2013.01)

(58) Field of Classification Search
None
See application file for complete search history.

(56) References Cited

U.S. PATENT DOCUMENTS

| | | | | |
|---|---|---|---|---|
| 5,364,780 | A | 11/1994 | Hershey et al. | |
| 5,792,932 | A * | 8/1998 | Marco et al. | 800/288 |
| 6,364,780 | B1 * | 4/2002 | Amborn et al. | 464/182 |
| 2007/0130645 | A1 | 6/2007 | Wu et al. | |
| 2011/0167517 | A1 | 7/2011 | Danilevskaya et al. | |

FOREIGN PATENT DOCUMENTS

| | | | |
|---|---|---|---|
| WO | 2007/077398 | A2 | 7/2007 |
| WO | 2013/066423 | A2 | 5/2013 |

OTHER PUBLICATIONS

Crane, Phil Trans: Biol Sci 359(1444):735-37 (2004).*
Fourgoux-Nicol et al., Plant Mol Biol 40:857-72 (1999).*
Potenza et al., In Vitro Cell Dev Biol Plant 40:1-22 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
A Mark Cigan et al., Phenotypic complementation of ms45 maize requires tapetal expression of MS45, Sex Plant Reprod. 2001, pp. 135-142, vol. 14.
Johan M.H. Stoop et al., Effect of Different Carbon Sources on Relative Growth Rate, Internal Carbohydrates, and Mannitol 1-Oxidoreductase Activity in Celery Suspension Cultures, Plant Physiol., 1993, pp. 1001-1008, vol. 103.
Johan M.H. Stoop et al., Mannitol metabolism in plants: a method for coping with stress, Trends in Plant Science, May 1996, pp. 139-144, vol. 1, No. 5.
Erica Unger et al., Selection and orientation of adjacent genes influences DAM-mediated male sterility in transformed maize, Transgenic Research, 2001, pp. 409-422, vol. 10.
Eli Zamski et al., Analysis of celery (*Apium graveolens*) mannitol dehydrogenase (Mtd) promoter regulation in Arabidopsis suggests roles for MTD in key environmental and metabolic responses, Plant Molecular Biology, 2001, pp. 621-631, vol. 47.
GenBank: AAP52597, May 5, 2011; GI No. 31430724.
GenBank: DP000086, May 5, 2011, GI No. 110288510.
NCBI Reference Sequence: NP_001147757.1, Dec. 27, 2015, GI No. 226528549.
Sorbidraft—08g016420—hypothetical protein, Gene ID: 8067199—XP002436634.
International Search Report and Written Opinion—PCT/US2013/041267, mailed Dec. 12, 2013.

* cited by examiner

*Primary Examiner* — Amjad Abraham
*Assistant Examiner* — Russell Boggs

(57) ABSTRACT

The plant promoter of a CBSU-Anther_Subtraction library (CAS1) gene encoding a mannitol dehydrogenase, and fragments thereof, and their use in promoting the expression of one or more heterologous nucleic acid fragments in an inducible manner in plants are described. These promoter fragments are also useful in creating recombinant DNA constructs comprising nucleic acid sequences encoding a desired gene product operably linked to such promoter fragments which can be utilized to transform plants and bring the expression of the gene product under external chemical and/or heat control in monocotyledonous and dicotyledonous plants.

19 Claims, 10 Drawing Sheets

C= Callus, L= leaf, A= anther RNA, -/+ CBSU

A. Maize callus, PHP16975 (1.7 kb promoter)
CBSU Dose treated

B. Maize Callus, PHP16974 (1.0 kb promoter)

Maize leaf, PHP16975, CBSU treated

Maize anther, PHP16973, CBSU induction

Lane 1, wildtype MS45 plant
Lane 2, Event 1, CBSU
Lane 3, Event 1, untreated
Lane 4, Event 2, CBSU
Lane 5, Event 2, untreated
Lane 6, Event 3, untreated
Lane 7, Event 3, CBSU Rice events, PHP16974, CBSU induction

INDUCIBLE PROMOTER SEQUENCES FOR REGULATED EXPRESSION AND METHODS OF USE

This application claims the benefit of U.S. Provisional Application No. 61/648,758, filed May 18, 2012; the entire content of which is herein incorporated by reference.

FIELD OF THE INVENTION

The present invention relates to a plant promoter, and fragments thereof, and their use in altering expression of at least one heterologous nucleic acid sequence in plants in an inducible manner. These promoter fragments are also useful in creating recombinant DNA constructs comprising nucleic acid sequences encoding a desired gene product operably linked to such promoter fragments which can be utilized to transform plants and bring the expression of the gene product under external chemical and/or stress control in monocotyledonous and dicotyledonous plants.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the enzyme and other related protein factors that attach to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. In some cases promoters are able to direct RNA synthesis when they are induced by external stimuli such as chemicals, stress, or biotic stimuli. These are called "inducible promoters".

The ability to externally control the expression of selected genes and thereby their gene products in plant cells and/or field grown plants can provide important agronomic and foodstuff benefits. This control is desirable for the regulation of genes that might be placed into transgenic plants and has many applications including, but not limited to, (1) prolonging or extending the accumulation of desirable nutritional food reserve in seeds, roots, (2) producing and accumulating products in plant tissues at a defined time in the developmental cycle such that these products are convenient for harvest and/or isolation, and (3) initiating the expression a pest-specific toxin at the site of pathogen attack. There is an ongoing interest in the isolation of novel inducible promoters which are capable of controlling the expression of a chimeric gene or (genes) at certain levels in a plant cell when exposed to external stimuli.

SUMMARY OF THE INVENTION

This invention relates to a plant promoter of a CBSU-Anther_Subtraction library (CAS1) gene encoding a mannitol dehydrogenase, and functional fragments thereof, and their use in promoting the expression of one or more heterologous nucleic acid fragments in an inducible manner in plants. These promoter fragments are also useful in creating recombinant DNA constructs comprising nucleic acid sequences encoding a desired gene product operably linked to such promoter fragments which can be utilized to transform plants and bring the expression of the gene product under external chemical and/or heat control in monocotyledonous and dicotyledonous plants. One embodiment of the invention concerns an isolated nucleic acid fragment comprising an inducible ZmCAS1 promoter wherein said promoter consists essentially of the nucleotide sequence set forth in SEQ ID NOs: 9 or 10, or said promoter consists essentially of a fragment that is substantially similar and functionally equivalent to the nucleotide sequence set forth in SEQ ID NOs: 9 or 10. The ZmCAS1 promoter can be induced by a chemical or stress treatment. The chemical can be a safener such as, but not limited to, N-(aminocarbonyl)-2-chlorobenzenesulfonamide (2-CBSU). The stress treatment can be a treatment such as, but not limited to, a heat shock treatment of a temperature greater than 26° C.

The invention also concerns a recombinant DNA construct comprising at least one heterologous nucleic acid fragment operably linked to the promoter of the invention.

In another embodiment, this invention concerns a cell, plant, or seed comprising a recombinant expression construct of the present disclosure.

In another embodiment, this invention concerns a plant stably transformed with a recombinant expression construct comprising a plant promoter and a heterologous nucleic acid fragment operably linked to said promoter, wherein said promoter is an inducible promoter and capable of controlling expression of said heterologous nucleic acid fragment in a plant cell, and further wherein said promoter comprises a fragment of SEQ ID NOs: 9 or 10.

In another embodiment, this invention concerns a method of expressing a coding sequence or a functional RNA in a plant cell comprising: a) introducing the recombinant DNA construct of the current disclosure into a plant cell, wherein at least one heterologous sequence comprises a coding sequence or a functional RNA, b) growing the plant cell of step a); c) induction of the inducible promoter by chemical or stress treatment on the plant cell of b); and, d) selecting a plant cell displaying expression of the coding sequence or the functional RNA of the recombinant DNA construct. In another embodiment, this invention concerns a method of expressing a coding sequence or a functional RNA driven by the promoter of the current invention in anther, callus, leaf or root cells.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1: Alignment the amino acid sequence encoded by the ZmCAS1 cDNA (SEQ ID NO:5) with a maize mannitol dehydrogenase (GI:226528549; SEQ ID NO:6) (A) and percent identity (B).

FIG. 2: Northern blot of maize anther RNA of wild-type fertile (F) and sterile (S) maize control plants (−) and maize CBSU treated plants (+). Maize anther RNA was analyzed with probes specific for ZmCAS1, IN2-2, 5126, MS45, ACTIN and UBI gene expression.

FIG. 3: Northern blot of maize callus (C), leaf (L) and anther (A) RNAs from wild-type maize tissues and CBSU-treated (+) tissues. Maize RNA was analyzed with probes specific for IN2-2 and ZmCAS1.

FIG. 4 shows A) maize callus transformed with PHP16975 comprising the 1.7 kb ZmCAS1 promoter for three different events (1, 2, 3) C=control maintenance media; 10=10 mg/l CBSU, 100=100 mg/l CBSU; B) maize callus transformed with PHP16974 comprising the truncated 1.0 kb ZmCAS1 promoter and induced with either CBSU or heat (37° C.); 26C=control callus at 26° C.; 26C+CBSU=CBSU treated callus at 26° C.; 37C=callus induced by heat treatment of 37° C. Results from seven events (1-7) are shown.

Figure 7:
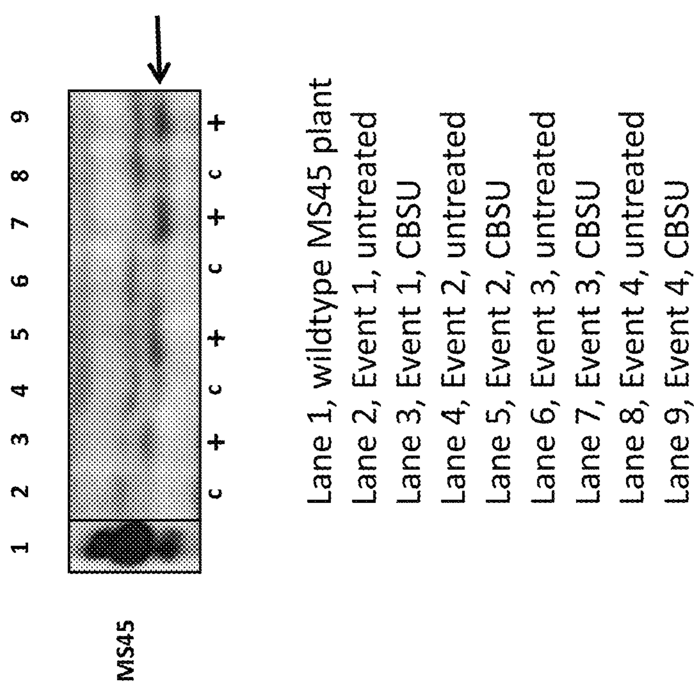

FIG. 7 shows a Western analysis of leaves from ms45/ms45 maize plants transformed with PHP16973 using antibodies directed against the maize MS45 protein. C=leaves from uninduced control plants, +=leaves from CBSU induced plants. Whole-cell anther extract from a wild-type MS45 plant is shown in Lane 1 and used to identify the mobility of the immunoreactive MS45 protein as indicated by the arrow.

Figure 8:
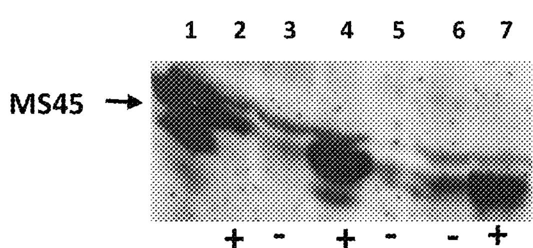

FIG. 8 shows a Western analysis of anthers from ms45/ms45 maize plants transformed with PHP16973 using antibodies directed against the maize MS45 protein. C=leaves from uninduced control plants, +=leaves from CBSU induced plants.

Figure 9:
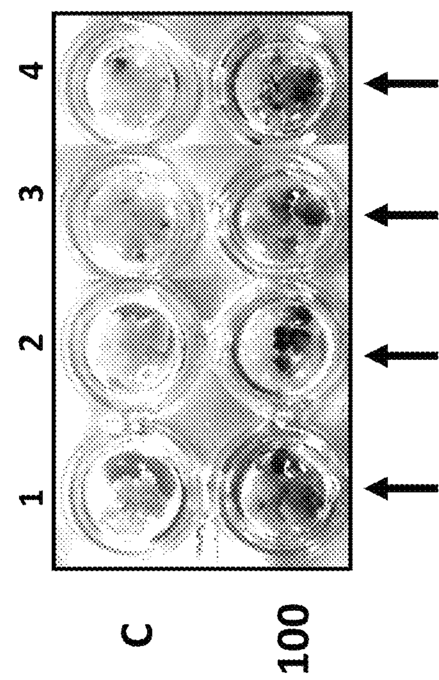

FIG. 9: Rice events transformed with PHP16974 show GUS expression when driven by the 1.0 kb ZmCAS1 promoter and induced by CBSU.

Figure 10:
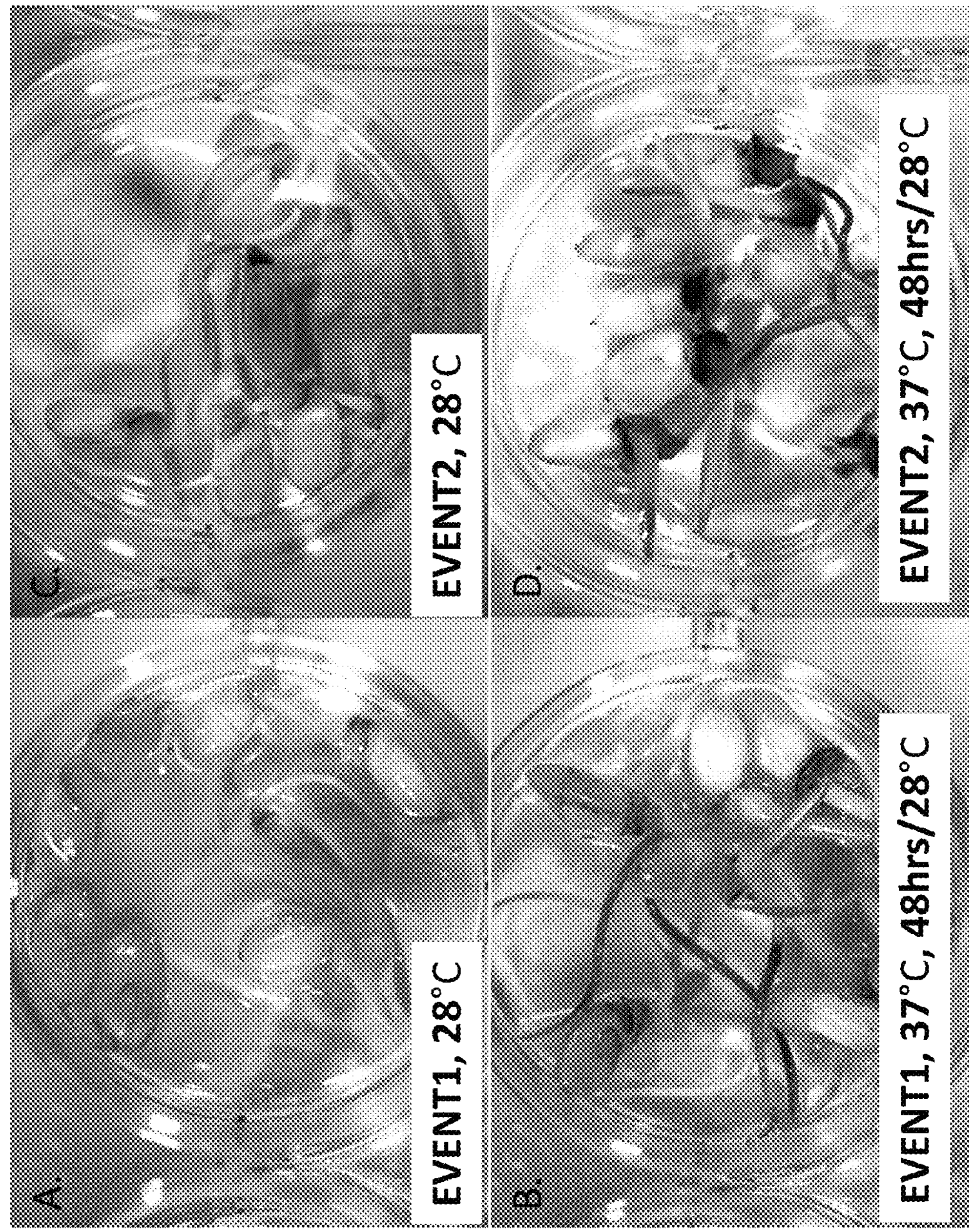

FIG. 10: Rice seedlings transformed with PHP16974 show GUS expression when driven by the 1.0 kb ZmCAS1 promoter and induced by CBSU.

The patent or application file contains at least one drawing executed in color. Copies of this patent or patent application publication with color drawing(s) will be provided by the Office upon request and payment of the necessary fee.

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984). The symbols and format used for nucleotide and amino acid sequence data comply with the rules set forth in 37 C.F.R. §1.822.

SEQ ID NO:1 DNA insert comprising the ZmCAS1c-1 cDNA.

SEQ ID NO:2 DNA insert comprising the ZmCAS1c-2 cDNA.

SEQ ID NO:3 A 1354 bp (base pair) SalI-NotI DNA insert comprising the maize ZmCAS1 full length cDNA.

SEQ ID NO:4 the 1338 bp maize ZmCAS1 full length cDNA.

SEQ ID NO:5 the amino acid sequence encoded by SEQ ID NO:4

SEQ ID NO:6 the amino acid sequence of a maize mannitol dehydrogenase (GI number 226528549, NP_001147757.1)

SEQ ID NO:7 a 4069 bp DNA fragment comprising the maize B73 ZmCAS1 promoter

SEQ ID NO:8 is the DNA sequence of the oligonucleotide used for mutagenesis to introduce RCAI DNA restriction site.

SEQ ID NO:9 is a 1049 bp truncated form of the maize ZmCAS1 promoter (bp 698-1746 of SEQ ID NO:10 also referred to as the 1.0 kb ZmCAS1 promoter.

SEQ ID NO:10 is 1746 bp maize ZmCAS1 promoter, also referred to as the 1.7 kb ZmCAS1 promoter.

SEQ ID NO: 11 is the nucleotide sequence of PHP16974 comprising the 1.0 kb ZmCAS1 promoter.

SEQ ID NO: 12 is the nucleotide sequence of PHP16975 comprising the 1.7 kb ZmCAS1 promoter.

SEQ ID NO: 13 is the nucleotide sequence of PHP16972 comprising the 1.0 kb ZmCAS1 promoter.

SEQ ID NO: 14 is the nucleotide sequence of PHP16973 comprising the 1.7 kb ZmCAS1 promoter.

SEQ ID NO: 15 is the HindIII-Rca1 fragment (ZMCAS1HINDIIIPRO) comprising the 1.0 kb ZmCAS1 promoter of SEQ ID NO:9.

SEQ ID NO: 16 is the BamH1-Rca1 fragment (ZMCAS1BAMPRO) comprising the 1.7 kb ZmCAS1 promoter of SEQ ID NO:10.

SEQ ID NO: 17 is the amino acid sequence of a mannitol dehydrogenase (AAP52597) from rice (*Oryza sativa*).

SEQ ID NO: 18 is a nucleotide sequence from a mannitol dehydrogenase gene region (DP000086) from rice (*Oryza sativa*).

SEQ ID NO: 19 is a nucleotide sequence of a putative 5'UTR-Promoter region from a mannitol dehydrogenase gene (DP000086) from rice (*Oryza sativa*).

SEQ ID NO: 20 is the amino acid sequence of a mannitol dehydrogenase (XP-002436634) from *Sorghum*.

SEQ ID NO: 21 is a nucleotide sequence from a mannitol dehydrogenase gene region (NC-012879) from *Sorghum*.

SEQ ID NO: 22 is a nucleotide sequence of a putative 5'UTR-Promoter region from a mannitol dehydrogenase gene (NC-012879) from *Sorghum*.

DETAILED DESCRIPTION OF THE INVENTION

The disclosure of all patents, patent applications, and publications cited herein are incorporated by reference in their entirety.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

As used herein and in the appended claims, the singular forms “a”, “an”, and “the” include plural reference unless the context clearly dictates otherwise. Thus, for example, reference to “a plant” includes a plurality of such plants, reference to “a cell” includes one or more cells and equivalents thereof known to those skilled in the art, and so forth.

In the context of this disclosure, a number of terms shall be utilized.

As used herein, a “ZmCAS1 promoter” refers to one type of inducible promoter. The native ZmCAS1 promoter is the promoter of a maize gene isolated from a CBSU-Anther_Subtraction library with significant homology to mannitol dehydrogenase genes identified in various plant species including maize that are deposited in National Center for Biotechnology Information (NCBI) database. The “ZmCAS1 promoter”, as used herein, also refers to fragments of the full-length native promoter that retain significant promoter activity. For example, a ZmCAS1 promoter can be 1.7 kb in length (SEQ ID NO:10) or a promoter-functioning fragment thereof, which includes, among others, the polynucleotide of SEQ ID NO: 9. A ZmCAS1 promoter also includes variants that are substantially similar and functionally equivalent to any portion of the nucleotide sequence, in increments of one base pair, between the 1.0 kb (SEQ ID NO:9) and 1.7 kb (SEQ ID NO:10) fragments and sequences.

The term “Promoter” refers to a nucleotide sequence capable of regulating the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. The promoter usually comprises a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the region upstream of the TATA box from the particular promoter region identified herein. Accordingly, an “enhancer” is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or abiotic conditions.

The promoter elements which enable the inducible expression in the desired tissue can be identified, isolated, and used with other core promoters to confirm inducible expression. By core promoter is meant the minimal sequence required to initiate transcription, such as the sequence called the TATA box which is common to promoters in genes encoding proteins. Thus, the ZmCAS1 promoter can optionally be used in conjunction with its own or core promoters from other sources. The promoter may be native or non-native to the cell in which it is found.

Promoters which cause a gene to be expressed in most cell types at most times are commonly referred to as “constitutive promoters”. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

High level, constitutive expression of the candidate gene under control of the 35S or UBI promoter may have pleiotropic effects, although candidate gene efficacy may be estimated when driven by a constitutive promoter. Use of inducible or stress-specific promoters may eliminate undesirable effects but retain the ability to enhance drought tolerance. This effect has been observed in *Arabidopsis* (Kasuga et al. (1999) Nature Biotechnol. 17:287-91).

The term “inducible promoter” refers to promoters that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

An example of a stress-inducible is RD29A promoter (Kasuga et al. (1999) Nature Biotechnol. 17:287-91). One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates. Also, one of ordinary skill in the art is familiar with protocols for simulating stress conditions such as osmotic stress, salt stress and temperature stress and for evaluating stress tolerance of plants that have been subjected to simulated or naturally-occurring stress conditions.

The sequences of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), *sorghum* (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), *citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, rice, cotton and *sorghum.*

This invention concerns an isolated nucleic acid fragment comprising an inducible ZmCAS1 promoter. This invention also concerns an isolated nucleic acid fragment comprising a promoter wherein said promoter consists essentially of the nucleotide sequence set forth in SEQ ID NO:9, or said promoter consists essentially of a fragment that is substantially similar and functionally equivalent to the nucleotide sequence set forth in SEQ ID NO:10. A nucleic acid fragment that is functionally equivalent to the instant ZmCAS1 promoter is any nucleic acid fragment that is capable of controlling the expression of a coding sequence or functional RNA in a similar manner to the ZmCAS1 promoter. The expression patterns of ZmCAS1 gene and its promoter are set forth in Examples 1-3.

The promoter activity of the maize genomic DNA fragment SEQ ID NO:9 or SEQ ID NO:10 upstream of the ZmCAS1 protein coding sequence was assessed by linking the fragment to a GUS gene or a MS45 gene, transforming the promoter:GUS (or MS45) expression cassette into maize, and analyzing GUS (or MS45) expression in various cell types of the transgenic plants (Examples 1-3). These results indicated that the nucleic acid fragment contained an inducible promoter.

In one embodiment, the invention is an isolated polynucleotide comprising, or consisting essentially of or consisting of:

a) a nucleotide sequence comprising the sequence set forth in SEQ ID NO:9 or a full-length complement thereof;

b) a nucleotide sequence comprising a fragment of SEQ ID NO:10, or a full-length complement thereof c) a nucleotide sequence comprising a sequence having at least 90% sequence identity, based on the BLASTN method of alignment, when compared to the nucleotide sequence of (a) or (b);

d) a nucleotide sequence comprising all or a fragment of a 1.7 kb 5' non-coding sequence of a mannitol dehydrogenase; or, e) a derivative of one of the nucleotide sequences indicated in (a), (b), or (c) obtained by substitution, addition and/or deletion of one or more nucleotides; and, wherein said nucleotide sequence is an inducible promoter.

In another embodiment of the invention the ZmCAS1 promoter is induced by a safener treatment of N-(aminocarbonyl)-2-chlorobenzenesulfonamide (2-CBSU). In another embodiment of the invention the ZmCAS1 promoter is induced by a heat treatment of a temperature greater than 26° C. and up to and including 37° C.

The terms “N-(aminocarbonyl)-2-chlorobenzenesulfonamide”, 2-CBSU” and “CBSU” are used interchangeably herein.

The promoter nucleotide sequences and methods disclosed herein are useful in regulating inducible expression of any heterologous nucleotide sequences in a host plant in order to alter the phenotype of a plant.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. Other gene of interest are genes allowing for site specific gene integration and gene stacking include, but not limited to, double-strand break inducing genes and recombinase genes. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

One embodiment of the invention relates to a recombinant DNA comprising the isolated polynucleotide of the invention operably linked to at least one heterologous nucleic acid sequence, wherein the heterologous nucleic acid sequence codes for a gene selected from the group consisting of: a double-strand break inducing gene, a recombinase gene, a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat and salt resistance in plants.

Another embodiment of the invention relates to a recombinant DNA comprising the isolated polynucleotide of the invention operably linked to at least one heterologous nucleic acid sequence, wherein the heterologous nucleic acid sequence encodes a protein selected from the group consisting of: a double-strand break inducing protein, a recombinase protein, a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

One embodiment of the invention, comprises a plant (for example, maize or a soybean plant) comprising in its genome a recombinant DNA construct comprising a polynucleotide operably linked to a promoter fragment of the invention, wherein said promoter fragment comprises at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 9 or 10, and wherein said plant exhibits an alteration of at least one agronomic characteristic when compared to a control plant not comprising said recombinant DNA construct.

Another embodiment of the invention, comprises a plant (for example, maize or a soybean plant) comprising in its genome a suppression DNA construct comprising a promoter fragment of the invention, wherein said promoter fragment comprises at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NOs: 9 or 10, and wherein said plant exhibits an alteration of at least one agronomic characteristic when compared to a control plant not comprising said recombinant DNA construct.

In any of the foregoing embodiments or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, early seedling vigor and seedling emergence under low temperature stress. For example, the alteration of at least one agronomic characteristic may be an increase in yield, greenness or biomass.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr Opin Cell Biol 5, 242-246 (1993); Roberts et al. Annu Rev Plant Mol Biol 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode) or drought resistance, oil quantity and quality, or those increasing yield or nutritional quality may be employed as desired.

The term "Anther" or "Anther tissue" refers to male plant tissue encompassing cells, cell-layers and cell types that give rise to pollen grains capable of effecting fertilization. These cells include but are not limited to archesporial cells, pollen mother cells, meiocytes, microspores, tapetum, supporting cell layers, pollen and cells derived from these cell types.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "fragment (or variant) that is functionally equivalent" and "functionally equivalent fragment (or variant)" are used interchangeably herein. These terms refer to a portion or subsequence or variant of the promoter sequence of the present invention in which the ability to initiate transcription or drive gene expression (such as to produce a certain phenotype) is retained. Fragments and variants can be obtained via methods such as site-directed mutagenesis and synthetic construction. As with the provided promoter sequences described herein, the contemplated fragments and variants operate to promote inducible expression of an operably linked heterologous nucleic acid sequence, forming a recombinant DNA construct (also, a chimeric gene). For example, the fragment or variant can be used in the design of recombinant DNA constructs to produce the desired phenotype in a transformed plant. Recombinant DNA constructs can be designed for use in co-suppression or antisense by linking a promoter fragment or variant thereof in the appropriate orientation relative to a heterologous nucleotide sequence.

A functional fragment of the regulatory sequence can be formed by one or more deletions from a larger sequence. For example, the 5' portion of a promoter up to the TATA box near the transcription start site can be deleted without abolishing promoter activity, as described by Opsahl-Sorteberg, H-G. et al., "Identification of a 49-bp fragment of the HvLTP2 promoter directing aleruone cell specific expression" Gene 341:49-58 (2004). Such variants should retain promoter activity. Activity can be measured by Northern blot analysis, reporter activity measurements when using transcriptional fusions, and the like. See, for example, Sambrook et al. (1989) Molecular Cloning: A Laboratory Manual (2nd ed. Cold Spring Harbor Laboratory, Cold Spring Harbor, N.Y.), herein incorporated by reference.

Sequences which hybridize to the regulatory sequences of the present invention are within the scope of the invention. Sequences that correspond to the promoter sequences of the present invention and hybridize to the promoter sequences disclosed herein will be at least 40% homologous, 50% homologous, 70% homologous, and even 85% 86%, 87%, 88%, 89%, 90%, 91%, 92%, 93%, 94%, 95%, 96%, 97%, 98%, 99% homologous or more with the disclosed sequence.

Smaller fragments may yet contain the regulatory properties of the promoter so identified and deletion analysis is one method of identifying essential regions. Deletion analysis can occur from both the 5' and 3' ends of the regulatory region. Fragments can be obtained by site-directed mutagenesis, mutagenesis using the polymerase chain reaction and the like. (See, Directed Mutagenesis: A Practical Approach IRL Press (1991)).

In some aspects of the present invention, the promoter fragments can comprise at least about 20 contiguous nucleotides, or at least about 50 contiguous nucleotides, or at least about 75 contiguous nucleotides, or at least about 100, 150, 200, 250, 300, 350, 400, 450, 500 contiguous nucleotides of SEQ ID NO:8 or up to the number of nucleotides present in a full-length nucleotide sequence disclosed herein (for example 1746, SEQ ID NO: 10).

In another aspect, a promoter fragment is the nucleotide sequence set forth in SEQ ID NO: 9 or SEQ ID NO: 10. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The isolated promoter sequences of the present invention can be modified to provide a range of inducible expression levels of the heterologous nucleotide sequence. Thus, less than the entire promoter regions may be utilized and the ability to drive expression of the coding sequence retained. As described in Examples 1-3, the 1.0 kb ZmCAS1 promoter fragment as well as the longer 1.7 kb ZmCAS1 promoter fragment were able to drive gene expression when induced by a chemical or stress treatment.

Modifications of the isolated promoter sequences of the present invention can provide for a range of inducible expression of the heterologous nucleotide sequence. Thus, they may be modified to be weak inducible promoters or strong inducible promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

In general, sequences that correspond to the nucleotide sequences of the present invention and hybridize to the nucleotide sequence disclosed herein will be at least 40% homologous, 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 40%, about 50%, about 70%, and even about 85% or more sequence similarity.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the inducible expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215: 403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The "5' non-coding sequences" refer to DNA sequences located upstream of a coding sequence which influence the transcription, RNA processing or stability, or translation of the associated coding sequence.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The term "constitutive promoter" refers to promoters active in all or most tissues of a plant at all or most developing stages. As with other promoters classified as "constitutive" (e.g. ubiquitin), some variation in absolute levels of expression can exist among different tissues or stages.

The term "constitutive promoter" or "tissue-independent" are used interchangeably herein.

The term "tissue specific promoter" refers to promoters that have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of soybean cell transformation is the use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "recombinant polynucleotide", "recombinant nucleotide", "recombinant DNA", "recombinant DNA construct" and "recombinant expression construct" are used interchangeably herein. A recombinant DNA construct comprises an artificial or heterologous combination of nucleic acid sequences, e.g., regulatory and coding sequences that are not found together in nature. For example, a recombinant DNA construct can comprise a plasmid vector or a fragment thereof comprising the instant inducible promoter and a heterologous polynucleotide of interest. In other embodiments, a recombinant construct may comprise regulatory sequences and coding sequences that are derived from maize, rice, *sorghum* or different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

It is demonstrated herein that the maize mannitol dehydrogenase gene promoter ZmCAS1 can, in fact, be used as an inducible promoter to drive efficient expression of transgenes, and that such promoter can be isolated and used by one skilled in the art. Induced GUS and MS45 expression has been observed in sink tissues such as anthers, callus, root and shoots of seedlings as well as developing leaves (Examples 1-3)

Mannitol metabolism plays an important role in plant responses to both biotic and abiotic stresses. (Stoop et al. 2001, Trends in Plant Science. Volume 1, Issue 5, May 1996, Pages 139-144). Celery plants exposed to high salinity showed an increased mannitol accumulation primarily caused by a decrease in mannitol dehydrogenase activity in sink tissues (Stoop and Pharr. 1993 Plant Physiol. 103:1001-1008). As shown in FIG. 1B, the ZmCAS1 cDNA (SEQ ID NO:5) showed a high % identity with a maize mannitol dehydrogenase (GI:226528549; SEQ ID NO:6), FIG. 1(B). Taken together with our observations that the ZmCAS1 promoter can be induced by a chemical such as a safener, or a stress such as a heat treatment, one can further test the ability of the ZmCAS1 promoter to be responsive to stresses such as, but not limited to, drought, osmotic or salt stress, or a combination thereof.

It is clear from the disclosure set forth herein that one of ordinary skill in the art could perform the following procedure:

1) operably linking the nucleic acid fragment containing the ZMCAS1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric ZmCAS1 promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the ZmCAS1 promoter in various cell types of transgenic plant tissues, e.g., leaves, roots, flowers, seeds, transformed with the chimeric ZmCAS1 promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention promoter or a fragment that is substantially similar and functionally equivalent to any portion of the nucleotide sequence set forth in SEQ ID NOs: 9 or 10 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to ZmCAS1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. Nos. 5,605,011, 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in Methods in Plant Molecular Biotechnology, supra; Klein et al, Bio/Technology 10:268 (1992); and Weising et al., Ann. Rev. Genet. 22: 421-477 (1988). For example, the DNA construct may be introduced into the genomic DNA of the plant cell using techniques such as microprojectile-mediated delivery, Klein et al., Nature 327: 70-73 (1987); electroporation, Fromm et al., Proc. Natl. Acad. Sci. 82: 5824 (1985); polyethylene glycol (PEG) precipitation, Paszkowski et al., EMBO J. 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, Mol. Gen. Genetics 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" Nature Biotechnology 14:745-750 (1996). The virulence functions of the *Agrobacterium tumefaciens* host will direct the insertion of the construct into the plant cell DNA when the cell is infected by the bacteria. See, for example Horsch et al., Science 233: 496-498 (1984), and Fraley et al., Proc. Natl. Acad. Sci. 80:4803 (1983).

Standard methods for transformation of canola are described at Moloney et al. "High Efficiency Transformation of *Brassica napus* using *Agrobacterium* Vectors" Plant Cell Reports 8:238-242 (1989). Corn transformation is described by Fromm et al, Bio/Technology 8:833 (1990). *Agrobacterium* is primarily used in dicots, but certain monocots such as maize can be transformed by *Agrobacterium* (U.S. Pat. No. 5,550,318). Rice transformation is described by Hiei et al., "Efficient Transformation of Rice (*Oryza sativa* L.) Mediated by *Agrobacterium* and Sequence Analysis of the Boundaries of the T-DNA" The Plant Journal 6(2): 271-282 (1994, Christou et al, Trends in Biotechnology 10:239 (1992) and Lee et al, Proc. Nat'l Acad. Sci. USA 88:6389 (1991). Wheat can be transformed by techniques similar to those used for transforming corn or rice. *Sorghum* transformation is described at Casas et al, supra and *sorghum* by Wan et al, PlantPhysiol. 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569,834, 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Bio/Technology 6:923 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; 2$^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

Inducible expression of chimeric genes in most plant cells makes the ZmCAS1 promoter of the instant invention especially useful when inducible expression of a target heterologous nucleic acid fragment is required.

Another general application of the ZmCAS1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the ZmCAS1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the ZmCAS1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:

(a) transforming a plant cell with the recombinant expression construct of described herein;
(b) induction of the inducible promoter by chemical or stress treatment on the cell of (a)
(c) growing fertile mature plants from the transformed plant cell of step (a); and,
(d) selecting plants containing the transformed plant cell wherein the expression of the heterologous nucleic acid fragment is increased or decreased.

Transformation and selection can be accomplished using methods well-known to those skilled in the art including, but not limited to, the methods described herein.

Non-limiting examples of compositions and methods disclosed herein are as follows:

1. An isolated polynucleotide comprising:
   a) a nucleotide sequence comprising the sequence set forth in SEQ ID NO:9 or SEQ ID NO:10, or a full-length complement thereof;
   b) a nucleotide sequence comprising a functional fragment of SEQ ID NO:10, or a full-length complement thereof;
   c) a nucleotide sequence comprising a sequence having at least 85% sequence identity, based on the BLASTN method of alignment, when compared to the nucleotide sequence of (a) or (b);
   d) a nucleotide sequence which hybridizes to SEQ ID NO:9 under highly stringent conditions of a wash of 0.1 SSC, 0.1% (w/v) SDS at 65° C.;
   e) a nucleotide sequence comprising all or a fragment of a 1.7 kb 5' non-coding sequence of a mannitol dehydrogenase; or,
   f) a derivative of one of the nucleotide sequences indicated in (a), (b), (c), (d) or (e) obtained by substitution, addition and/or deletion of one or more nucleotides; and, wherein said nucleotide sequence is an inducible promoter.
2. The isolated polynucleotide of embodiment 1, wherein the nucleotide sequence of c) has at least 90% identity, based on the BLASTN method of alignment, when compared to the sequence set forth in SEQ ID NO:1.
3. The isolated polynucleotide of embodiment 1, wherein the nucleotide sequence of c) has at least 95% identity, based on the BLASTN method of alignment, when compared to the sequence set forth in SEQ ID NO:1.
4. The isolated polynucleotide of embodiment 1, wherein the nucleotide sequence of c) has at least 98% identity, based on the BLASTN method of alignment, when compared to the sequence set forth in SEQ ID NO:1.
5. The isolated polynucleotide of embodiment 1 wherein said inducible promoter is induced by a chemical or stress treatment.
6. The isolated polynucleotide of embodiment 1 wherein said inducible promoter is induced by a safener or heat treatment.
7. The isolated polynucleotide of embodiment 6, wherein the safener is N-(aminocarbonyl)-2-chlorobenzenesulfonamide.
8. The isolated polynucleotide of embodiment 6, wherein said heat treatment comprises a temperature greater than 26° C.
9. A recombinant DNA construct comprising the isolated polynucleotide of embodiment 1 operably linked to at least one heterologous nucleic acid sequence.
10. The recombinant DNA construct of embodiment 9, wherein the heterologous nucleic acid sequence codes for a gene selected from the group consisting of: a double-strand break inducing gene, a recombinase gene, a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat and salt resistance in plants.

11. The recombinant DNA construct of embodiment 9, wherein the heterologous nucleic acid sequence encodes a protein selected from the group consisting of: a double-strand break inducing protein, a recombinase protein, a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

12. A vector comprising the recombinant DNA construct of embodiment 9.

13. A cell comprising the recombinant DNA construct of embodiment 9.

14. The cell of embodiment 13, wherein the cell is a plant cell.

15. The plant cell of embodiment 14 having stably incorporated into its genome the recombinant DNA construct of embodiment 9.

16. A transgenic plant having stably incorporated into its genome the recombinant DNA construct of embodiment 9.

17. The transgenic plant of embodiment 16 wherein said plant is a monocot plant.

18. The transgenic plant of embodiment 17, wherein said monocot is selected from the group comprising: maize, wheat, rice, barley, *sorghum*, millet, sugarcane and rye.

19. The transgenic plant of embodiment 16, wherein said plant is a dicot plant.

20. The transgenic plant of embodiment 19, wherein said dicot is selected from the group comprising: soy, *Brassica* sp., cotton, safflower, tobacco, alfalfa and sunflower.

21. Transgenic seed produced by the transgenic plant of embodiment 16.

22. A plant stably transformed with a recombinant expression construct comprising a plant promoter and a heterologous nucleic acid fragment operably linked to said promoter, wherein said promoter is an inducible promoter and capable of controlling expression of said heterologous nucleic acid fragment in a plant cell, and further wherein said promoter comprises a fragment of SEQ ID NO:10.

23. A method of expressing a coding sequence or a functional RNA in a plant cell comprising:
  a) introducing the recombinant DNA construct of embodiment 9 into a plant cell, wherein the at least one heterologous sequence comprises a coding sequence or a functional RNA;
  b) growing the plant cell of step a);
  c) induction of the inducible promoter by chemical or stress treatment on the plant cell of b); and,
  d) selecting a plant cell displaying expression of the coding sequence or the functional RNA of the recombinant DNA construct.

24. The method of embodiment 23, wherein the chemical is a safener.

25. The method of embodiment 23 wherein the stress treatment is a heat treatment.

26. The method of embodiment 23 further comprising growing the plant cell of d) into a plant.

27. A method of expressing a coding sequence or a functional RNA in anther cells, said method comprising:
  a) introducing the recombinant DNA construct of embodiment 9 into a plant cell, wherein the at least one heterologous sequence comprises a coding sequence or a functional RNA;
  b) growing the plant cell of step a);
  c) induction of the inducible promoter by chemical or stress treatment on the plant cell of b); and,
  d) identification of anther cells displaying expression of the coding sequence or the functional RNA of the recombinant DNA construct.

28. The method of embodiment 23 or embodiment 27 wherein the at least one heterologous sequence is transiently expressed.

29. The method of embodiment 23 or embodiment 27 wherein the at least one heterologous sequence is stably incorporated in the plant cell.

30. A method for altering expression of at least one heterologous nucleic acid fragment in a plant comprising:
  (a) transforming a plant cell with the recombinant expression construct of embodiment 9;
  (b) induction of the inducible promoter by chemical or stress treatment on the cell of (a)
  (c) growing fertile mature plants from the transformed plant cell of step (a); and,
  (d) selecting plants containing the transformed plant cell wherein the expression of the heterologous nucleic acid fragment is increased or decreased.

31. A method of transgenically altering a marketable plant trait, comprising:
  a) introducing a recombinant DNA construct of embodiment 9 into a plant;
  b) induction of the inducible promoter by chemical or stress treatment on the plant of (a);
  c) growing a fertile, mature plant resulting from step b); and
  d) selecting a plant expressing the at least one heterologous nucleotide sequence in at least one plant tissue based on the altered marketable trait.

32. The method of embodiment 31 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

33. An isolated polynucleotide comprising:
  a) a nucleotide sequence comprising all or a functional fragment of SEQ ID NO:19 or SEQ ID NO:22;
  b) a nucleotide sequence comprising a full-length complement of the nucleotide sequence (a); or, c) a nucleotide sequence comprising a sequence having at least 90% sequence identity, based on the BLASTN method of alignment, when compared to the nucleotide sequence of (a) or (b); and, wherein said nucleotide sequence is a promoter.

34. The isolate polynucleotide of embodiment 33 wherein said promoter is an inducible promoter.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter “Sambrook et al., 1989”). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Safener-Inducible cDNAs Expressed in Microspores and/or Tapetum Strategy Design for the Identification of Safener-Inducible cDNAs.

The isolation of conditionally regulated promoters with tissue specificity in plants which are different than the safener induced promoter ZmIN2-2 (Hershey et al. U.S. Pat. No. 5,364,780 Nov. 15, 1994) would enable conditional regulation of genes in microspores and/or the tapetum. Previously, it has been demonstrated that while ZmIN2-2 transcript expression increases in callus, leaf and anther tissues in maize after safener treatment, genes regulated by this promoter do not express in maize tapetal cells (Cigan et al. 2001. Sex. Plant Reprod. 14, 135-142). Immunolocalization studies demonstrated that genes regulated by ZmIN2-2 are present in all anther cell types except the tapetum or microspores. To date, no promoters that respond to CBSU (Chlorobenzenesulfonamide) safener and are specifically expressed in tapetal cells or microspores at the tetrad stage of microsporogenesis have been identified. To enable the isolation of safener-inducible candidate promoters that are expressed in microspores or tapetum, a strategy was designed which takes advantage of two fundamental observations made of plants transformed with the *E. coli* DAM-ethylase gene expressed from the maize anther-specific promoter 5126 (5126:DAM; Unger et al., 2001, Transgenic Res. 10, 409-422). First, cytological examination of tetrad staged anthers from male-sterile plants expressing 5126:DAM revealed abnormal microspores and nearly ablated tapetal cells in otherwise structurally normal appearing anthers. Second, Northern analysis of mRNA isolated from 5126:DAM sterile anthers indicates a loss of two tapetal-specific transcripts, 5126 and MS45, while a transcript not expected to be the tapetal-specific (maize actin), is easily detected (Cigan et al. 2001. Sex. Plant Reprod. 14, 135-142). Therefore, anthers isolated from 5126:DAM sterile plants should be reduced or perhaps completely devoid of tapetal- and/or microspore-specific mRNAs.

In addition, comparison of the ZmIN2-2 transcript expression from RNAs isolated from wild-type male-fertile CBSU-treated plants to RNAs isolated from male-sterile CBSU-treated 5126:DAM plants showed, that in contrast the MS45 and 5126 tapetal-specific mRNAs, the ZmIN2-2 was not reduced in anther RNAs isolated from 5126:DAM CBSU-treated plants (Cigan et al. 2001. Sex. Plant Reprod. 14, 135-142).

A strategy was designed using sterile plants which were reduced or devoid of tapetal- and/or microspore-specific mRNAs. The strategy involved treating maize plants with CBSU and comparing anther mRNA transcript profiles from these treated control plants with treated 5126:DAM plants. Such a strategy did lead to the identification and isolation of mRNAs and, ultimately, promoters which are responsive to the safener and are microspore- or tapetum-expressed as described below.

Toward this end, differential RNA hybridization was used to enrich for maize anther or callus mRNAs that are increased by safener or heat treatment. Subsequently, these mRNAs were used as probes to isolate cDNAs from anther cDNA libraries prepared from CBSU-treated maize plants. These cDNAs were then used to screen mRNAs isolated from male-fertile and male-sterile 5126:DAM control and safener-treated plants as a means to identify transcripts which are induced by CBSU or heat treatment or and expressed in the tapetum or microspores as described below.

Maize Anther cDNA Library Construction from CBSU-Treated Wild-Type Plants and Isolation of Safener Inducible cDNA's.

Figure 1:
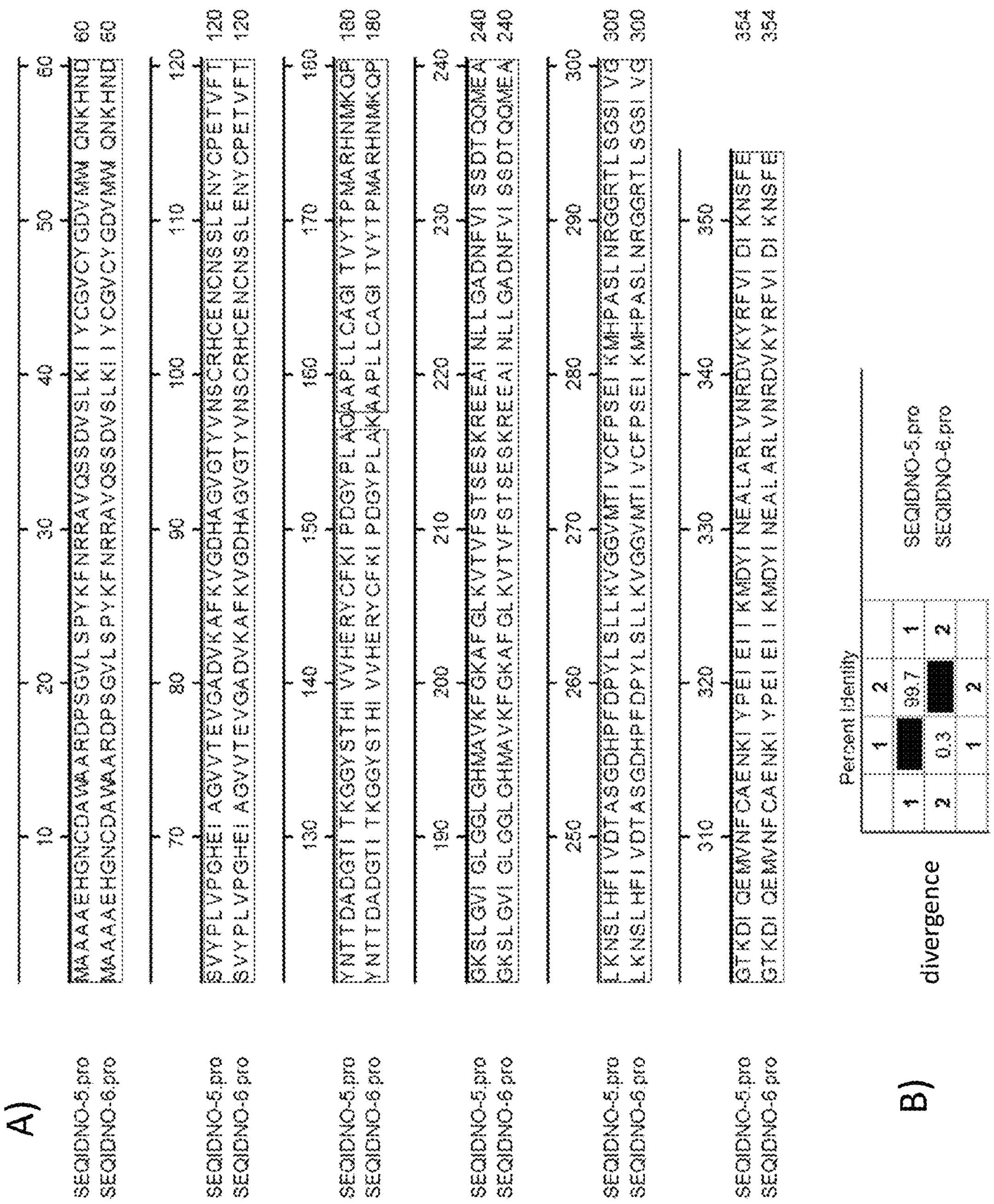

Wild type maize plants were grown to the meiosis stage of microspore development. Plants were watered with 30 mg 2-CBSU and allowed to develop to the quartet and early vacuolate stage of microspore development. PolyA+ anther RNA was isolated from wild type control and CBSU treated plants and stored. A cDNA library was constructed from mRNAs isolated from CBSU-treated plants, arrayed onto nylon filters and stored. A cDNA subtraction library was generated using the Clontech PCR-Select cDNA Subtraction Kit (#K1804-1) following the manufacturer's instructions to enrich for CBSU-specific transcripts. Using this approach anther PolyA+ mRNA from wild-type plants was used to enrich for transcripts found in the anther PolyA+ mRNA from CBSU treated plants. This cDNA subtraction library was subcloned into pSPORT (BRL) vector, colonies plated, picked and sequenced. Among the vector inserts sequenced, two DNA sequences were present at a high proportion, at more than 10% of the inserts sequenced, and referred to as ZmCAS1c-1 (477 bp; SEQ ID NO: 1) and ZmCAS1c-2 (438 bp; SEQ ID NO: 2) (CBSU-Anther-Subtract 1). Both ZmCAS1c-1 and ZmCAS1c-2 had sequence identity to mannitol dehydrogenases from plants. ZmCAS1c-1 and ZmCAS1c-2 DNA fragments were used as hybridization probes to screen the filter arrayed cDNA CBSU-anther library described above to isolate full-length cDNA containing hybridizing clones. Both ZmCAS1c-1 and ZmCAS1c-2 identified identical cDNA clones. One cDNA clone contained a 1354 bp SalI-NotI insert (SEQ ID NO: 3) that was sequenced and identified as a 1338 bp full length cDNA clone referred to ZmCAS1cDNA (SEQ ID NO: 4). ZmCAS1cDNA is capable of encoding a 354 amino acid sequence (SEQ ID NO: 5) with 99.7% identity to a maize mannitol dehydrogenase (GI number 226528549, NP_001147757.1, SEQ ID NO:6; FIG. 1).

Figure 2:
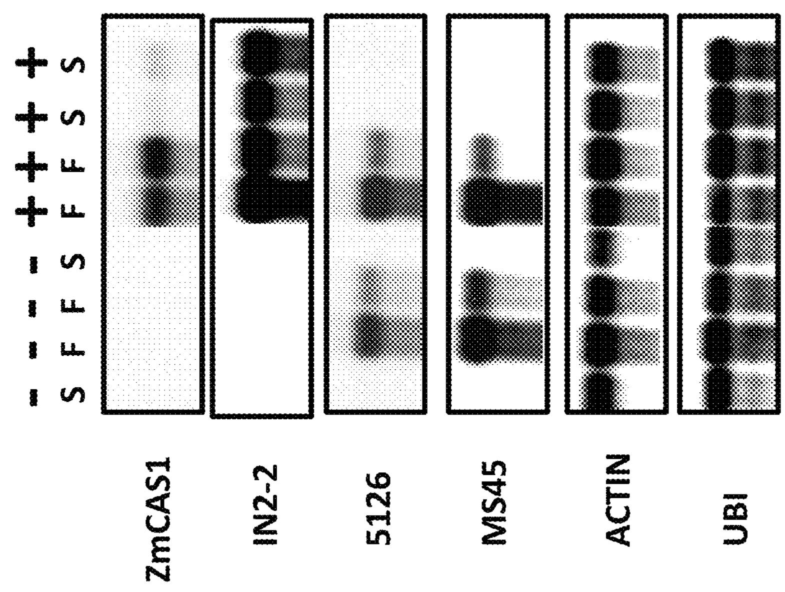

To determine whether the ZmCAS1 cDNA was 1) induced in maize anthers by CBSU-treatment and 2) reduced or absent in tapetum and microspore-ablated maize anthers from CBSU-treated 5126:DAM plants, a 477 bp ZmCAS1c-1 DNA fragment (SEQ ID NO:1), as well as DNA fragments from ZmMS45, Zm5126, ZmActin, and ZmUbiquitin (Cigan et al. 2001. Sex. Plant Reprod. 14, 135-142) were used as a hybridization probes against maize anther mRNAs isolated from male-fertile (F) and male-sterile (S), control (−) or CBSU-treated (+) plants. As shown in FIG. 2, the constitutively expressed maize actin (ACTIN) and ubiquitin (UBI) transcripts were easily detected and did not change their steady-state level across all anther RNA samples and treatments. MS45 and 5126 transcripts were easily detected in anther RNAs from male-fertile plants but absent in anther RNAs from male-sterile plants (FIG. 2) further supporting the observation that these RNAs are localized to the maize tapetum (Cigan et al. 2001. Sex. Plant Reprod. 14, 135-142).

Anther RNAs from control male-fertile (−, F) and control sterile plants (−, S) did not reveal detectable levels of the IN2-2 transcript, while strong hybridization signals were detected in mRNAs from anthers derived from CBSU-treated control male-fertile and male-sterile plants (FIG. 2). In contrast strong hybridization signals for ZmCAS1 are only revealed in mRNAs from anthers derived from male-fertile CBSU-treated plants (+, F). The reduced ZmCAS1 signal observed in mRNAs from anthers of male-sterile CBSU-treated plants (+, S) indicates that this ZmCAS1 transcript was present in cell layers of anthers. This observation indicates that ZmCAS1 tissue specific expression is different from the IN2-2 expression and thus makes the ZmCAS1 promoter a candidate which differs from the IN2-2 promoter in spatial expression in anthers.

When the ZmCAS1 probe was used to hybridize to maize callus or maize leaf treated with CBSU, strong hybridization was observed in mRNAs from callus, leaf and anther (FIG. 3), similar to the IN2-2 probe, suggesting that in addition to expression in anthers, ZmCAS1 transcript is also expressed in callus and leaf in response to safener, CBSU, treatment.

Isolation of the 1.7 kb and Truncated 1.0 kb ZmCAS1 Promoter Fragments

In order to isolate DNA sequences which correspond to the ZmCAS1 promoter, subgenomic SauIIIA genomic phage libraries from the maize line B73 were screened using the 477 bp ZmCAS1c-1 DNA fragment (SEQ ID NO:1) as a hybridization probe. A phage which contained a 4069 bp maize B73 DNA fragment (SEQ ID NO: 7). and hybridized to the ZmCAS1c-1 probe was isolated, plasmid excised and sequenced. DNA sequence analysis of this 4069 bp genomic DNA identified several regions of sequence identity to the ZmCAS1C cDNA. For promoter studies, oligonucleotide directed mutagenesis was used to introduce an RcaI DNA restriction site at nucleotide positions 3447-3452 in SEQ ID NO:7 using the MORPH Site-Specific Plasmid DNA Mutagenesis Kit 5 Prime-3 Prime (Boulder, Colo.) according to the vendors instructions using the oligonucleotide 5'-GCA-GTTCATTCCTCATGACTGCTGCAGCAGAGC-3'(SEQ ID NO:8). A HindIII-RcaI fragment (ZmCAS1HindIII Pro, SEQ ID NO: 15) comprising the truncated 1.0 kb maize ZmCAS1 promoter of SEQ ID NO:9 and a BamHI-RcaI (ZmCAS1 BamPro, SEQ ID NO: 16) fragment comprising the 1.7 kb maize ZmCAS1 promoter of SEQ ID NO:10 were isolated and used for promoter studies in plants.

Figure 4:
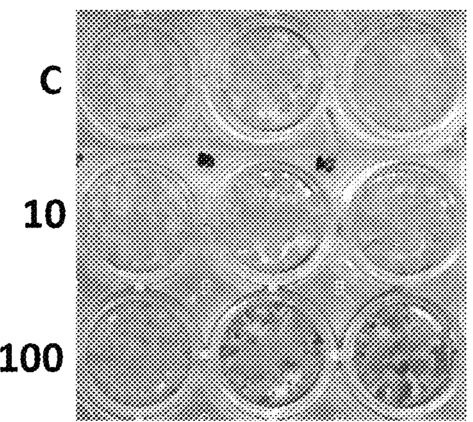
Figure 4:
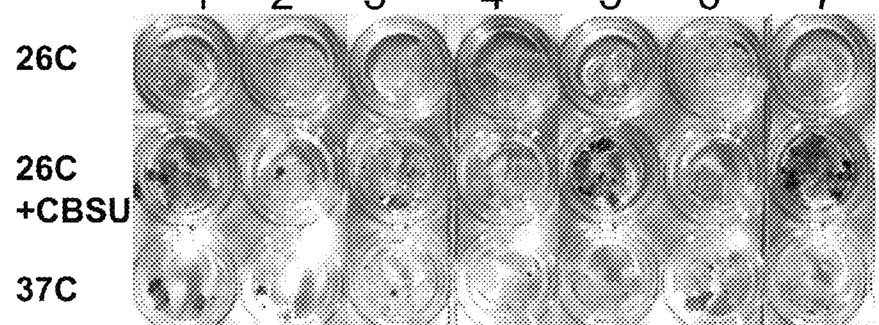

As shown in FIG. 4, Example 2, and other examples described herein, both the 1.7 kb ZmCAS1 promoter (SEQ ID NO:10) and the truncated 1.0 kb ZmCAS1 promoter (SEQ ID NO:9) were active in plant cells and induced by both a safener (CBSU, FIG. 4A, 4B) and/or a heat treatment (FIG. 4B).

Example 2

Increased Expression of GUS and ZmMS45 is Observed in Maize Cells and Plants when these Genes are Placed Under the Transcriptional Control of the ZmCAS1 Promoter in Response to the Safener, CBSU or a Heat Treatment.

*Agrobacterium*-mediated transformation of immature embryos was used to generate integrated copies of PHP16974 (SEQ ID NO:11; ZmCAS1HindIII Pro:GUS/35SPAT) comprising the 1.0 kb ZmCAS1 promoter (SEQ ID NO:9), PHP16975 (SEQ ID NO:12, ZmCAS1BamPro:GUS/35SPAT) comprising the 1.7 kb ZmCAS1 promoter (SEQ ID NO:10) and PHP16972 (SEQ ID NO:13, ZmCAS1HindIII Pro:MS45/35SPAT) comprising the 1.0 kb ZmCAS1 promoter or PHP16973 (SEQ ID NO:14, ZmCAS1BamPro:MS45/35SPAT:) comprising the 1.7 kb ZmCAS1 promoter.

Figure 3:
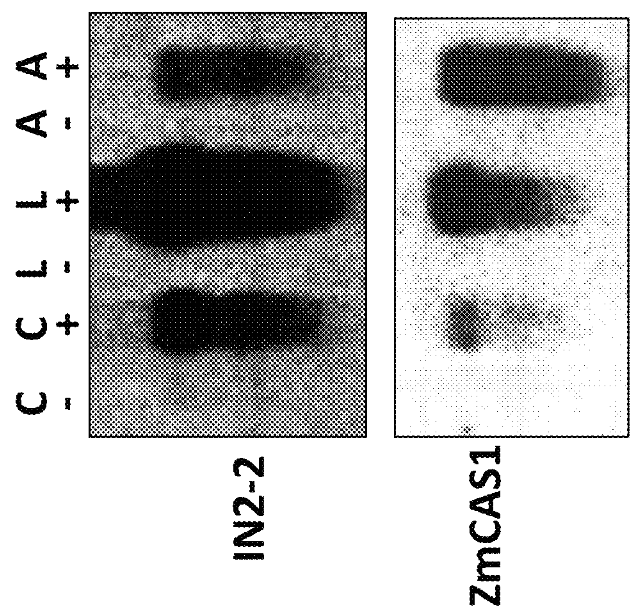

As described in Example 1 and FIG. 3, in addition to expression in anthers, ZmCAS1 transcript was also expressed in callus and leaf tissue in response to safener, CBSU, treatment. Bialophos-resistant callus events were selected for analysis and plant regeneration.

To determine whether the 1.7 kb or the 1.0 kb ZmCAS1 promoter from maize could direct induced expression of the GUS reporter, three bialophos-resistant callus events were placed onto maintenance media and maintenance media containing increasing amounts of the safener CBSU-2 for at room temperature for 18 hours, removed and stained with X-Gluc to detect GUS activity. As shown in FIG. 4A, slight GUS expression is detected in callus grown on maintenance media (FIG. 4A: C). In contrast, low levels of GUS expression are detected in callus grown on 10 mg/l CBSU (FIG. 4A: 10) while strong GUS expression is observed in PHP16975 callus events grown on 100 mg/l CBSU (FIG. 4A: 100). This data indicated that the 1.7 kb ZmCAS1 promoter is active in maize callus and can be induced by safener treatment.

Seven random bialophos-resistant callus events containing PHP16974 which contains a truncated 1.0 kb fragment of the ZmCAS1 promoter driving the GUS reporter were capable of inducible GUS expression when incubated in the presence of 100 mg/liter CBSU at room temperature (FIG. 4B; 26C+CBSU). In a separate experiment, when these 7 callus events were grown on maintenance media without CBSU but incubated for 2 days at 37° C. returned to room temperature and then stained with X-gluc, increased GUS expression was also observed (FIG. 4B; 37C). This data indicated that the truncated 1.0 kb ZmCAS1 promoter is active in maize callus and can be induced by safener and/or heat treatment.

Plants were also regenerated from callus events containing PHP16975 and grown in the greenhouse to approximately the 5 leaf stage. At this stage of development, leaf punches from plants regenerated from the 3 bialophos-resistant events shown in FIG. 5 were collected pre- (C) and post-watering (S) with 30 mg of 2-CBSU to examine GUS expression in leaf in response to application of the safener.

Figure 5:
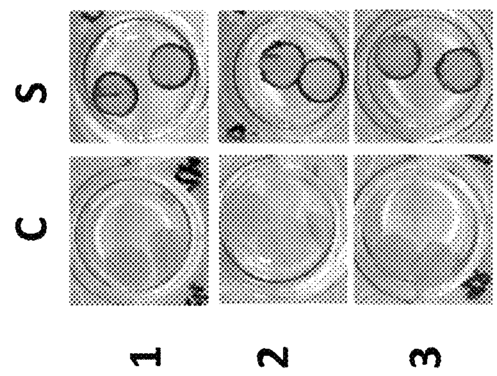
FIG. 5 shows maize leaf punches from three (1, 2, 3) maize plants transformed with PHP16975 and induced with CBSU. Leaf punches from plants regenerated from the 3 bialophos-resistant events were collected pre- (C) and post-watering (S).

As shown in FIG. 5 strong GUS expression was detected in leaf punches 2 days after watering (S) with CBSU across the 3 PHP16975 transformed plants analyzed.). This data further indicates that the 1.7 kb ZmCAS1 promoter is active in maize leaves and can be induced by safener treatment.

Figure 6:
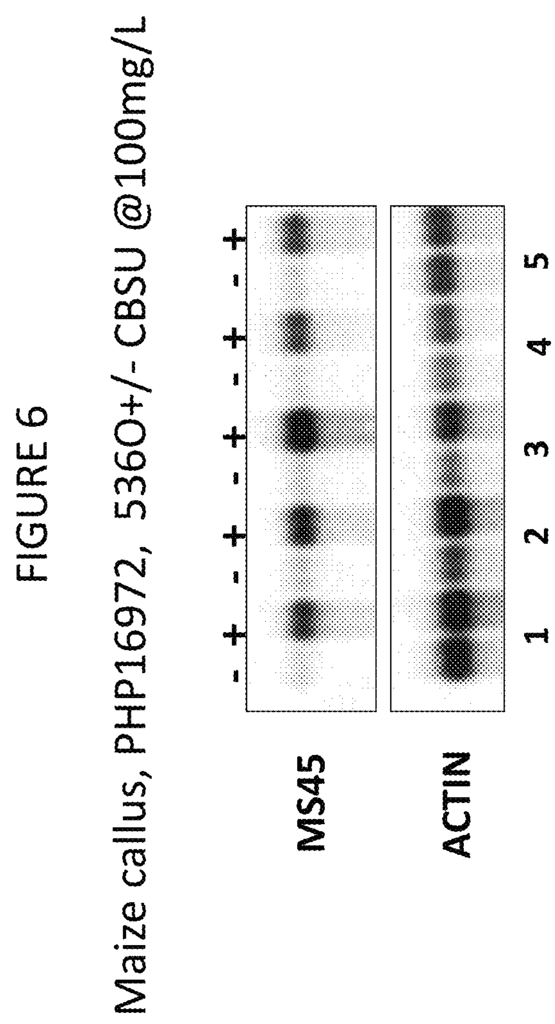
FIG. 6 shows a Northern blot of maize callus RNA from five (1, 2, 3, 4 and 5) events transformed with PHP16972 and treated with (+) or without (−) CBSU.

T-DNA vectors PHP16972 (SEQ ID NO:13, ZmCAS1HindIII Pro: MS45/35S:PAT) and PHP16973 (SEQ ID NO: 14, ZmCAS1 BamPro:MS45/35S:PAT) were used to transform maize callus which was generated to contain a segregating population of MS45/ms45 heterozygous and ms45/ms45 homozygous mutant plants. In order to detect MS45 RNA or protein expression under the control of the 1.0 or 1.7 kb ZmCAS promoter in maize anthers, plants containing a naturally occurring mutation in the maize MS45 gene which results in loss of MS45 RNA and protein were used for these studies. Pollen from MS45/ms45 plants were used to fertilize male-sterile ms45/ms45 plants for the purpose of generating embryos which would be ms45/ms45 as described in Cigan et al 2001. By placing the maize MS45 gene under the control of the ZmCAS1 promoter in these transformation vectors, genes other than GUS could be tested for transcriptional-induction in response to safener in callus, leaf and maize anthers as has been previously demonstrated for ZmIn2-2:MS45 regulated expression (Cigan et al 2001. Sex. Plant Reprod. 14, 135-142). Five random bialophos-resistant callus events containing integrated copies of PHP16972 were placed onto maintenance media (FIG. 5, (−)) and maintenance media containing 100 mg/liter safener CBSU-2 (FIG. 5 (+)) at room temperature for 18 hours, removed and PolyA+ RNA prepared and used for RNA analysis as described (Cigan et al. 2001. Sex. Plant Reprod. 14, 135-142) using the ZmMS45 and ZmActin probes for hybridization analysis. As shown in FIG. 6, strong induction of a hybridization signal corresponding to the MS45 mRNA is detected within RNA transcripts from ms45/ms45 callus grown on CBSU (+). A very low signal was observed when callus was grown in the absence of CBSU. Actin was used as a control probe to show nearly equivalent RNA levels were present in all samples. Multiple plants were regenerated from ms45/ms45 callus events transformed with PHP16973 and grown in the greenhouse. Plants were watered with 30 mg of CBSU at the meiosis stage of microspore development. Leaf and anthers (quartet, early uninucleate microspore stage) were collected 2 days later from control and CBSU-treated plants and whole-cell protein extracts were prepared from 4 leaf punches or 6 anthers as described (Cigan et al 2001). Leaf and anther proteins were electrophoresed on 10% SDS-denaturing polyacrylamide gels, transferred to supported nitrocellulose, and used for Western analysis using antibodies directed against the maize MS45 protein. Examination of leaf extracts from PHP16973 control (C) and treated (+) plants (FIG. 7) demonstrates increased steady-state levels of the MS45 protein in leaf extracts derived from CBSU-treated plants (lanes 3, 5, 7, 9). Increased MS45 protein is also detected in anther extracts (FIG. 8) derived from PHP16973 CBSU treated plants (Lane 2, 4, 7). This data further supports that the ZmCAS1 promoter is active in maize cells such as anthers, callus and leaves when induced by a safener.

Taken together the GUS and MS45 results described herein support that genes can be transcriptionally-induced when placed under the control of either the 1.7 kb or the 1.0 Kb ZmCAS1 promoter in maize cells and plants and transcription can be increased in callus, leaf and anthers in response to application of the safener CBSU and/or heat treatment.

Example 3

Heat Treatment of Rice Plants Transformed with PHP16974 Comprising the Truncated 1.0 kb ZmCAS1 Promoter Driving GUS Expression Results in GUS Expression in Germinating Seedlings.

To determine whether the ZmCAS1 promoter could conditionally regulate expression in response to safener treatment or heat treatment in plant species other than maize, *Agrobacterium*-mediated transformation was used to generate integrated copies of PHP16974 (ZmCAS1HindIII Pro: GUS) comprising the truncated 1.0 kb ZmCAS1 promoter for studies in rice. Scutellum from 10-14 day old germinating seeds (*Oryza sativa* cv. Kitaake) was used for rice transformation experiment (Toki. 1997, PI Mol. Biol Reporter 15:16-21). Bialophos-resistant callus events containing PHP16974 were selected and screened for their ability to respond to safener application. Four independent bialophos-resistant events were grown on maintenance media or maintenance media containing 100 mg/liter CBSU for 24 hours, removed and stained with X-Gluc. As shown FIG. 9, strong GUS expression is observed in PHP16974 callus events when grown on media containing the CBSU safener (FIG. 9). PHP16974 bialophos-resistant events were regenerated into plants. Leaf tissue was collected from these plants and used for DNA hybridization analyses to identify single-copy PHP16974 insertions. These plants were allowed to set selfed seed and were used for subsequent studies to monitor GUS expression under the transcriptional control of the ZmCAS1 promoter. Sixteen seed were selected from 2 single-copy PHP16974 events were sterilized, grown on hormone-free media at 28° C. or 37° C. for 48 hours and allowed to germinate. Germinating seed was then incubated at 28C for 2 additional days and histochemically stained with X-Gluc to detect GUS activity (Reference). As shown in FIGS. 10A and 100, seedlings germinated at 28° C. exhibit very low levels of detectable Gus staining. In contrast, rice seedlings germinated at 37° C. show pronounced blue staining and root and at the base of shoots (FIGS. 10B and 10D). These results are consistent with observations in maize. That is when the GUS gene is regulated by the 1.0 kb ZmCAS1 promoter, incubation at 37C resulted in increased Gus activity even in the absence of safener treatment.

What is claimed is:

1. A recombinant DNA construct comprising the nucleotide sequence set forth in SEQ ID NO:9 or SEQ ID NO:10 operably linked to at least one heterologous nucleic acid sequence, wherein said nucleotide sequence is an inducible promoter.

2. The recombinant DNA construct of claim 1 wherein said inducible promoter is induced by a chemical or stress treatment.

3. The recombinant DNA of claim 1 wherein said inducible promoter is induced by a safener or heat treatment.

4. The recombinant DNA construct of claim 3, wherein the safener is N-(aminocarbonyl)-2-chlorobenzenesulfonamide.

5. The recombinant DNA construct of claim 3, wherein said heat treatment comprises a temperature greater than 26° C.

6. The recombinant DNA construct of claim 1, wherein the heterologous nucleic acid sequence codes for a gene selected from the group consisting of: a double-strand break inducing gene, a recombinase gene, a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance and a gene involved in heat and salt resistance in plants.

7. A vector comprising the recombinant DNA construct of claim 1.

8. A cell comprising the recombinant DNA construct of claim 1.

9. The cell of claim 8, wherein the cell is a plant cell.

10. The plant cell of claim 9 wherein the recombinant DNA construct is stably incorporated into its genome.

11. A transgenic plant having stably incorporated into its genome the recombinant DNA construct of claim 1.

12. The transgenic plant of claim 11 wherein said plant is a monocot plant.

13. The transgenic plant of claim 11, wherein said plant is a dicot plant.

14. A transgenic seed produced by the transgenic plant of claim 11, further comprising said recombinant DNA construct.

15. A method of expressing a coding sequence or a functional RNA in a plant cell comprising:

a) introducing the recombinant DNA construct of claim 1 into a plant cell, wherein the at least one heterologous nucleic acid sequence comprises a coding sequence or a functional RNA;

b) growing the plant cell of step a);

c) induction of the inducible promoter by chemical or stress treatment on the plant cell of b); and, d) selecting a plant cell displaying expression of the coding sequence or the functional RNA of the recombinant DNA construct.

16. The method of claim 15, wherein the chemical is a safener.

17. The method of claim 15 wherein the stress treatment is a heat treatment.

18. The method of claim 15 further comprising growing the plant cell of d) into a plant.

19. A method for altering expression of at least one heterologous nucleic acid sequence in a plant comprising:

(a) transforming a plant cell with the recombinant expression construct of claim 1;

(b) inducing the inducible promoter by chemical or stress treatment on the cell of (a);

(c) growing a fertile mature plant from the transformed plant cell of step (a);

and, (d) selecting a plant containing the transformed plant cell wherein the expression of the at least one heterologous nucleic acid sequence is increased or decreased, when compared to the expression of a cell that is not induced.

* * * * *

SEQUENCE LISTING

```
<160> NUMBER OF SEQ ID NOS: 22

<210> SEQ ID NO 1
<211> LENGTH: 477
<212> TYPE: DNA
<213> ORGANISM: artificial sequence
<220> FEATURE:
<223> OTHER INFORMATION: ZmCAS1C-1 insert
```

<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t

<400> SEQUENCE: 1

```
gtacctccga caatactacc agacaaggtc cgcccaccac ggttgaggct cgcagggtgc     60

atcttgatct cacttggaaa gcacactatt gtcatcacac cgccaacctt aaggagcgag    120

agatacggat cgaatggatg gtcaccagaa gcagtgtcaa ctatgaagtg cagggagttt    180

ttcagggcct ccatctgctg cgtgtctgac gatataacaa agttatctgc tccaaggagg    240

ttaatggctt cttccctctt cgattcgctc gtgctgaaaa ccgtgacctt gagaccaaag    300

gccttaccaa atttgaccgc catgtggcct angccaccga gcccaatgac tcccagcgac    360

ttcccaggct gcttcatgtt gtgccgcgcc attggggtat agacggtgat tccagcacac    420

anaagaagcg ctgcctgcgc cagagggtaa ccatcgggta tcttgaaaca atacctc       477
```

<210> SEQ ID NO 2
<211> LENGTH: 438
<212> TYPE: DNA
<213> ORGANISM: artificial sequence
<220> FEATURE:
<223> OTHER INFORMATION: ZmCAS1C-2insert
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:

<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t

<400> SEQUENCE: 2
gggggnaggg gcttttnnng ganganaatg tnagtggngt atccccccnt tgtgaagggn 60
ccancaacaa tnnttgtgtt gtaaatnaaa aacgnttccg ggnaatnatt ncccnaaaan 120
ccgntncnat tnccccnatn gccggaacaa tttnagttag gtncnaaccc ctgnttggtc 180
accaaccttt gaaaggcctt gacgtctgcg ccaaacctca atcacgaacc caagctntct 240
catgcgcagg aancanagga taaactgagt cgttgtgctt gttctgtatc cacataacgt 300
caccgtaaca caccccgcag tatatgatct tcagcgaaac gtcgctgctt tgcactgccc 360
tgcggttaaa cttgtatggt gagagaaccc agaagggtct ctggccgccc aagcatcgca 420
nttgccacct cgggcgct 438

<210> SEQ ID NO 3
<211> LENGTH: 1354
<212> TYPE: DNA
<213> ORGANISM: artificial seqeunce
<220> FEATURE:
<223> OTHER INFORMATION: ZmCAScDNA insert

<400> SEQUENCE: 3
gtcgacccac gcgtccgcgg acgctgggca gacacagact ccaccacccc gcttcgatct 60
tcttgttgca gctgaaatct gtcagattct gcagttcatt ccaaatggct gctgcagcag 120
agcacggcaa ctgcgatgct tgggcggcca gagacccttc tggggttctc tcaccataca 180
agtttaaccg cagggcagtg caaagcagcg acgtttcgct gaagatcata tactgcgggg 240
tgtgttacgg tgacgttatg tggatacaga acaagcacaa cgactcagtt tatcctctgg 300
ttcctgggca tgagatagct ggggttgtga ctgaggttgg cgcagacgtc aaggccttca 360
aggtgggtga ccacgcaggc gttggaacct acgtgaactc gtgccggcac tgcgagaact 420
gcaacagctc tctggagaac tactgcccag aaacagtttt cacttacaac acaactgatg 480
ctgatgggac catcacaaag gggggctact ccactcacat tgtcgtccat gaaaggtact 540
gcttcaagat acccgatggc taccctctgg cgcaggcagc gcctcttctg tgtgctggaa 600
tcaccgtcta taccccaatg gcgcggcaca acatgaagca gcctgggaag tcgctgggag 660
tcattgggct cggtggccta ggccacatgg cggtcaaatt tggtaaggcc tttggtctca 720
aggtcacggt tttcagcacg agcgaatcga agagggaaga agccattaac ctccttggag 780
cagataactt tgttatatcg tcagacacgc agcagatgga ggccctgaaa aactccctgc 840
acttcatagt tgacactgct tctggtgacc atccattcga tccgtatctc tcgctcctta 900
aggttggcgg tgtgatgaca atagtgtgct ttccaagtga gatcaagatg caccctgcga 960
gcctcaaccg tggtgggcgg accttgtctg gtagtattgt cggaggtaca aaagacatcc 1020
aggagatggt taacttttgc gcggagaaca aaatctatcc agagatcgag atcatcaaga 1080
tggattatat caacgaggct ctcgccaggc ttgttaaccg agacgtgaaa taccgctttg 1140
tcatcgacat caagaactct ttcgagtagc atgctcattc acatgatccc tgtcttcttt 1200
gtcaatgtat gagagataat gagtcgtttc gaataaagcg tagacatgat aaataacaag 1260
tatgcttgtg attgtaaaat cgttctataa ataaatgcgc tgtgttgaac gttaaaaaaa 1320
aaaaaaaaaa aaaaaaaaaa aaaagggcgg ccgc 1354

<210> SEQ ID NO 4
<211> LENGTH: 1338
<212> TYPE: DNA

<213> ORGANISM: Zea mays

<400> SEQUENCE: 4

```
ccacgcgtcc gcggacgctg ggcagacaca gactccacca ccccgcttcg atcttcttgt     60
tgcagctgaa atctgtcaga ttctgcagtt cattccaaat ggctgctgca gcagagcacg    120
gcaactgcga tgcttgggcg gccagagacc cttctggggt tctctcacca tacaagttta    180
accgcagggc agtgcaaagc agcgacgttt cgctgaagat catatactgc ggggtgtgtt    240
acggtgacgt tatgtggata cagaacaagc acaacgactc agtttatcct ctggttcctg    300
ggcatgagat agctggggtt gtgactgagg ttggcgcaga cgtcaaggcc ttcaaggtgg    360
gtgaccacgc aggcgttgga acctacgtga actcgtgccg gcactgcgag aactgcaaca    420
gctctctgga gaactactgc ccagaaacag ttttcactta caacacaact gatgctgatg    480
ggaccatcac aaaggggggc tactccactc acattgtcgt ccatgaaagg tactgcttca    540
agatacccga tggctaccct ctggcgcagg cagcgcctct tctgtgtgct ggaatcaccg    600
tctatacccc aatggcgcgg cacaacatga agcagcctgg gaagtcgctg ggagtcattg    660
ggctcggtgg cctaggccac atggcggtca aatttggtaa ggcctttggt ctcaaggtca    720
cggttttcag cacgagcgaa tcgaagaggg aagaagccat taacctcctt ggagcagata    780
actttgttat atcgtcagac acgcagcaga tggaggccct gaaaaactcc ctgcacttca    840
tagttgacac tgcttctggt gaccatccat tcgatccgta tctctcgctc cttaaggttg    900
gcggtgtgat gacaatagtg tgctttccaa gtgagatcaa gatgcaccct gcgagcctca    960
accgtggtgg gcggaccttg tctggtagta ttgtcggagg tacaaaagac atccaggaga   1020
tggttaactt ttgcgcggag aacaaaatct atccagagat cgagatcatc aagatggatt   1080
atatcaacga ggctctcgcc aggcttgtta accgagacgt gaaataccgc tttgtcatcg   1140
acatcaagaa ctctttcgag tagcatgctc attcacatga tccctgtctt ctttgtcaat   1200
gtatgagaga taatgagtcg tttcgaataa agcgtagaca tgataaataa caagtatgct   1260
tgtgattgta aaatcgttct ataaataaat gcgctgtgtt gaacgttaaa aaaaaaaaaa   1320
aaaaaaaaaa aaaaaaaa                                                 1338
```

<210> SEQ ID NO 5
<211> LENGTH: 354
<212> TYPE: PRT
<213> ORGANISM: Zea mays

<400> SEQUENCE: 5

```
Met Ala Ala Ala Ala Glu His Gly Asn Cys Asp Ala Trp Ala Ala Arg
1               5                   10                  15

Asp Pro Ser Gly Val Leu Ser Pro Tyr Lys Phe Asn Arg Arg Ala Val
            20                  25                  30

Gln Ser Ser Asp Val Ser Leu Lys Ile Ile Tyr Cys Gly Val Cys Tyr
        35                  40                  45

Gly Asp Val Met Trp Ile Gln Asn Lys His Asn Asp Ser Val Tyr Pro
    50                  55                  60

Leu Val Pro Gly His Glu Ile Ala Gly Val Val Thr Glu Val Gly Ala
65                  70                  75                  80

Asp Val Lys Ala Phe Lys Val Gly Asp His Ala Gly Val Gly Thr Tyr
                85                  90                  95

Val Asn Ser Cys Arg His Cys Glu Asn Cys Asn Ser Ser Leu Glu Asn
            100                 105                 110
```

```
Tyr Cys Pro Glu Thr Val Phe Thr Tyr Asn Thr Thr Asp Ala Asp Gly
        115                 120                 125

Thr Ile Thr Lys Gly Gly Tyr Ser Thr His Ile Val Val His Glu Arg
    130                 135                 140

Tyr Cys Phe Lys Ile Pro Asp Gly Tyr Pro Leu Ala Gln Ala Ala Pro
145                 150                 155                 160

Leu Leu Cys Ala Gly Ile Thr Val Tyr Thr Pro Met Ala Arg His Asn
                165                 170                 175

Met Lys Gln Pro Gly Lys Ser Leu Gly Val Ile Gly Leu Gly Gly Leu
            180                 185                 190

Gly His Met Ala Val Lys Phe Gly Lys Ala Phe Gly Leu Lys Val Thr
        195                 200                 205

Val Phe Ser Thr Ser Glu Ser Lys Arg Glu Glu Ala Ile Asn Leu Leu
    210                 215                 220

Gly Ala Asp Asn Phe Val Ile Ser Ser Asp Thr Gln Gln Met Glu Ala
225                 230                 235                 240

Leu Lys Asn Ser Leu His Phe Ile Val Asp Thr Ala Ser Gly Asp His
                245                 250                 255

Pro Phe Asp Pro Tyr Leu Ser Leu Leu Lys Val Gly Gly Val Met Thr
            260                 265                 270

Ile Val Cys Phe Pro Ser Glu Ile Lys Met His Pro Ala Ser Leu Asn
        275                 280                 285

Arg Gly Gly Arg Thr Leu Ser Gly Ser Ile Val Gly Gly Thr Lys Asp
    290                 295                 300

Ile Gln Glu Met Val Asn Phe Cys Ala Glu Asn Lys Ile Tyr Pro Glu
305                 310                 315                 320

Ile Glu Ile Ile Lys Met Asp Tyr Ile Asn Glu Ala Leu Ala Arg Leu
                325                 330                 335

Val Asn Arg Asp Val Lys Tyr Arg Phe Val Ile Asp Ile Lys Asn Ser
            340                 345                 350

Phe Glu


<210> SEQ ID NO 6
<211> LENGTH: 354
<212> TYPE: PRT
<213> ORGANISM: Zea mays

<400> SEQUENCE: 6

Met Ala Ala Ala Ala Glu His Gly Asn Cys Asp Ala Trp Ala Ala Arg
1               5                   10                  15

Asp Pro Ser Gly Val Leu Ser Pro Tyr Lys Phe Asn Arg Arg Ala Val
            20                  25                  30

Gln Ser Ser Asp Val Ser Leu Lys Ile Ile Tyr Cys Gly Val Cys Tyr
        35                  40                  45

Gly Asp Val Met Trp Ile Gln Asn Lys His Asn Asp Ser Val Tyr Pro
    50                  55                  60

Leu Val Pro Gly His Glu Ile Ala Gly Val Val Thr Glu Val Gly Ala
65                  70                  75                  80

Asp Val Lys Ala Phe Lys Val Gly Asp His Ala Gly Val Gly Thr Tyr
                85                  90                  95

Val Asn Ser Cys Arg His Cys Glu Asn Cys Asn Ser Ser Leu Glu Asn
            100                 105                 110

Tyr Cys Pro Glu Thr Val Phe Thr Tyr Asn Thr Thr Asp Ala Asp Gly
        115                 120                 125
```

```
Thr Ile Thr Lys Gly Gly Tyr Ser Thr His Ile Val Val His Glu Arg
    130                 135                 140

Tyr Cys Phe Lys Ile Pro Asp Gly Tyr Pro Leu Ala Lys Ala Ala Pro
145                 150                 155                 160

Leu Leu Cys Ala Gly Ile Thr Val Tyr Thr Pro Met Ala Arg His Asn
                165                 170                 175

Met Lys Gln Pro Gly Lys Ser Leu Gly Val Ile Gly Leu Gly Gly Leu
            180                 185                 190

Gly His Met Ala Val Lys Phe Gly Lys Ala Phe Gly Leu Lys Val Thr
        195                 200                 205

Val Phe Ser Thr Ser Glu Ser Lys Arg Glu Glu Ala Ile Asn Leu Leu
    210                 215                 220

Gly Ala Asp Asn Phe Val Ile Ser Ser Asp Thr Gln Gln Met Glu Ala
225                 230                 235                 240

Leu Lys Asn Ser Leu His Phe Ile Val Asp Thr Ala Ser Gly Asp His
                245                 250                 255

Pro Phe Asp Pro Tyr Leu Ser Leu Leu Lys Val Gly Gly Val Met Thr
            260                 265                 270

Ile Val Cys Phe Pro Ser Glu Ile Lys Met His Pro Ala Ser Leu Asn
        275                 280                 285

Arg Gly Gly Arg Thr Leu Ser Gly Ser Ile Val Gly Gly Thr Lys Asp
    290                 295                 300

Ile Gln Glu Met Val Asn Phe Cys Ala Glu Asn Lys Ile Tyr Pro Glu
305                 310                 315                 320

Ile Glu Ile Ile Lys Met Asp Tyr Ile Asn Glu Ala Leu Ala Arg Leu
                325                 330                 335

Val Asn Arg Asp Val Lys Tyr Arg Phe Val Ile Asp Ile Lys Asn Ser
            340                 345                 350

Phe Glu
```

<210> SEQ ID NO 7
<211> LENGTH: 4069
<212> TYPE: DNA
<213> ORGANISM: Zea mays

<400> SEQUENCE: 7

```
cctcttaagg tcctggtaca tctcctcgat caacggcttc cacagacgaa ccctcgcgtt      60

tatgaaccaa ttcgaaacct ggtacaaacg caaaaccact cgaatccatc attaccccat     120

ctcgccaaaa aagaatcgaa tttgaaacga gtctggtggg atttcgatct gtgcctggtt     180

cctggtgagg ctgctccttg ccgccagcac gtccttctca tggtccttgg gatacctgag     240

cagagcagag cagagcgcga ttctgatcat ggccaacaat gtcgatagac gatttgcgca     300

acaacgtcgc gggacagact tacgggtgca ggaagttctc gaacatccac gccttgagca     360

cggcaacaga cttctctggc agcccgcact ggggccgcca gcactgctgc tcggtgcgcc     420

acagctgctg cgccgaccag tgcttctgta tgaaggcgac tccagctctg ctccacgtcg     480

ccgcccgcgg ccaccgtcac cgacgacgac gactcgcccc agcagctggc cctgctcgcc     540

gtagccatga tctcgccggc gagccaccgc ctcagcccac ggtacatcgc cgacacggcg     600

cggtgcgcga acggcgcgca gatgccaccg ccgcccgggg gcgagtgcat cagggtgttg     660

aacttggctg tcgtgctctg gatcttgtcc aagcactggt tactcgtcca tctgcaaacc     720

atcatccaaa tccaacatgc ttcacaaatc tgctccagaa ttcatataac taatagtgtg     780

aacgaacgag tggtcaccag gaagaactcc aacatgcttc acaaaccatc gtccaactcc     840
```

```
aacctggcat gtggccgacg acgtcgttga gcaaatcctg gaccacggct gcgtaccgcg    900
agcgcaccac caccgcggtg aagtgcagcg ccatccgcga ccgcgaccgc gcccgcggca    960
gctcggtcag ggcggaccgg ctcgctcccg aggagcacta ctccgtcgcg ttcagcgtgc   1020
tgtccgagga agcgatggag ttggagcaca gcgtcggctc gctcgccacc accgccgcgg   1080
acgcgttggc gccactgcag gcggcgagcg ggtagtggag gcctcctgcg tcggagagcc   1140
tggccccggc gaggtggtat gtctcatggg ccggcacggg tactggtccg ccggcgctgg   1200
tccagatacc gtacggcttc ttggacgacg accagaccga catggccccg gattggctgg   1260
ggcaccgcaa gctcgccgcg acgcggctgt cgcagccggc gacgccgtac agctcgtcgt   1320
ccatctcgtc cggcggcgtc ctcccgccgg cacgatcatc tcgcggcggc gcgggggcgt   1380
tagcgaggag ctgggcagct ggctggcgaa ggaggccagc acgatgttgt tcgccgcgta   1440
gtgcgcgccc agatccgccg acgaccgccg tgttgccgag gccgaacccg aagccgccct   1500
ggtcaagaag cacgcagggg tggaagtgcg gcacctcagc gctcataatg ccgccacctc   1560
tgtagcccag gccgaggcgg aggatggatg ggactcgaat ccgggggcgg aggtggagga   1620
cccttccatg gagaccgagc ggggtttagg gatgagcgag catcacatac gccttccatg   1680
gagagcatgg atgcggacgc ggatccgggg cggaagatgg cagggacgcg gattcagggc   1740
ggacgcgctt gccgagggcg cgggggacca cagcgtgcgt tacggggaca gggcgggcat   1800
cgcgaggacg ggtgcgggag cggagccaca tctggtggtg gacgcctact ttgctctctt   1860
atagagtagt aaagattcgt ggaccaaaca acaccctagc ttgtacaaat attcttaggc   1920
agttgctact gatgagagaa aaataacatc actccactgc atttgcgtga tttattgaac   1980
agatcacaat tacatctatt caaatttatt tacctgtacg tgtccgattt ttaggggagg   2040
attttttac ggtattttt ttttaaaaaa ataaatttag gcaacaattt tatagaatcg     2100
agtgctttat ctattatctt ttacaaggca cacgcgtaca ataaggtttg gtcgttcgtg   2160
acttggatag tggttttggt tgcaattccg taattcttgg cataggatac agcccaaccc   2220
agaaaaaaat aatgttgcgg tcagttctgg ctttgagatt cggagtacca cgtggcgtaa   2280
aggcaggccg tgtcttacag atgaataaag gacctgggtc tcacgtgatt ggtttccagt   2340
ttcgtgcatc aagatgtgga attttcaaac tgccgtcgtg tttgtttcgt cacataaaag   2400
ctttttggaa ggctaaggag aggaagccgg cgagaaggag ggggcgtttt acgtgtcact   2460
gtcctgtcgt gttggctgtt gacacgaatc atttcttccg cgcgtgggaa gaagaagatg   2520
cacattagcg gcctgaagta gagatgtcaa tggggaattc cccagcgggg attaactccc   2580
cagacccgta cccatgaaca tagaccggcc cccatccccg aacccgaacc cgacctcggg   2640
tacgaaaatc ctcccatacc cattcccgac cgggtactaa atacccatgg gtatccatac   2700
ccgacccgat tattcaaaaa ttaatgggct ttttatttgt taaccggcgg acgcaatgct   2760
tgggactcta ggttttttta ctttgttgac cggctggcgg ctgggctttt tcctacaggc   2820
ccaaagttgg tcggcagcca ctaggccaca cgtcacaggc agcccacaag taaatgtcgt   2880
tggattgctg gatggtggaa taaaaatcct agatgctaga ttgttctggt tccgggtatt   2940
tttctccatg gctaatcggg tttgggttta gccctcccaa acccgaaccc gccatacccg   3000
atgggtaagg gatttattcc aaatctatac ccatggggat ttgttttaac ccatacctta   3060
accctaatag aggaattccc cacgggtaat cgggtttcgg ggcccattga catctctaga   3120
ctgaaggcgt ccaactcaaa tcattaaaaa gtgttgacgc acgcgctgat gcgccggccg   3180
```

```
cacagcacag gctgcacagc ccgtttaatc agcgatggag ccccggccgt cagccagcca   3240

ggtccggcgt ccgggtctgc gccctgcggc gtcactgctg tcgccaccgt ctccgatggt   3300

cccacatcca tccagcgggc cgcgcgtggt acaaaaggct cttcctcgcc gtcaggtgca   3360

gctgcccaaa caccagacac agactccacc accccgcttc gatcttctgt tgcagctgaa   3420

atctgtcaga ttctgcagtt cattccaaat ggctgctgca gcagagcacg gcaactgcga   3480

tgcttgggcg gccagagacc cttctggggt tctctcacca tacaagttta accgcaggtg   3540

aggtggctcc ccctcctcat ttggtgcaca actcatcatc atcatgtttt tttatcgcct   3600

tttcagaaca ctgctgtctg tcttctcgct atgctagaat tctttggaat agctgccagt   3660

gttgttttcc ttgcctttta catgtacatc atgttttttt tcctgcctgt ggagtgggtt   3720

gatttaaatc actagcaagt caaaaattat ttctaatttc tttcgatctc attaaattca   3780

cacagaacgg gaataaccga acacagccta aaatcgtgaa actgatgcat agcagacggt   3840

agaccatccg taaccgtaca tattcataac gtctactatg ccttctggta ttttttttt    3900

ccagggcagt gcaaagcagc gacgtttcgc tgaagatcat atactgcggg gtgtgttacg   3960

gtgacgttat gtggatacag aacaagcaca acgactcagt ttatcctctg gttcctgggt   4020

aagaacatgt acactgaacc cctagcttag tagagctagg tagggagct               4069
```

<210> SEQ ID NO 8
<211> LENGTH: 33
<212> TYPE: DNA
<213> ORGANISM: artificial sequence
<220> FEATURE:
<223> OTHER INFORMATION: CAS1_RCA_MUTAGENESIS_PRIMER

<400> SEQUENCE: 8

```
gcagttcatt cctcatgact gctgcagcag agc                                  33
```

<210> SEQ ID NO 9
<211> LENGTH: 1049
<212> TYPE: DNA
<213> ORGANISM: Zea mays

<400> SEQUENCE: 9

```
aagctttttg gaaggctaag gagaggaagc cggcgagaag gagggggcgt tttacgtgtc     60

actgtcctgt cgtgttggct gttgacacga atcatttctt ccgcgcgtgg gaagaagaag    120

atgcacatta gcggcctgaa gtagagatgt caatggggaa ttccccagcg gggattaact    180

ccccagaccc gtacccatga acatagaccg gcccccatcc ccgaacccga acccgacctc    240

gggtacgaaa atcctcccat acccattccc gaccgggtac taaataccca tgggtatcca    300

tacccgaccc gattattcaa aaattaatgg gctttttatt tgttaaccgg cggacgcaat    360

gcttgggact ctaggttttt ttactttgtt gaccggctgg cggctgggct ttttcctaca    420

ggcccaaagt tggtcggcag ccactaggcc acacgtcaca ggcagcccac aagtaaatgt    480

cgttggattg ctggatggtg gaataaaaat cctagatgct agattgttct ggttccgggt    540

atttttctcc atggctaatc gggtttgggt ttagccctcc caaacccgaa cccgccatac    600

ccgatgggta agggatttat tccaaatcta tacccatggg gatttgtttt aacccatacc    660

ttaaccctaa tagaggaatt ccccacgggt aatcgggttt cggggcccat tgacatctct    720

agactgaagg cgtccaactc aaatcattaa aaagtgttga cgcacgcgct gatgcgccgg    780

ccgcacagca caggctgcac agcccgttta atcagcgatg gagccccggc cgtcagccag    840

ccaggtccgg cgtccgggtc tgcgccctgc ggcgtcactg ctgtcgccac cgtctccgat    900
```

ggtcccacat ccatccagcg ggccgcgcgt ggtacaaaag gctcttcctc gccgtcaggt 960
gcagctgccc aaacaccaga cacagactcc accaccccgc ttcgatcttc tgttgcagct 1020
gaaatctgtc agattctgca gttcattcc 1049

<210> SEQ ID NO 10
<211> LENGTH: 1746
<212> TYPE: DNA
<213> ORGANISM: Zea mays

<400> SEQUENCE: 10
ggatccgggg cggaagatgg cagggacgcg gattcagggc ggacgcgctt gccgagggcg 60
cgggggacca cagcgtgcgt tacggggaca gggcgggcat cgcgaggacg ggtgcgggag 120
cggagccaca tctggtggtg gacgcctact ttgctctctt atagagtagt aaagattcgt 180
ggaccaaaca acaccctagc ttgtacaaat attcttaggc agttgctact gatgagagaa 240
aaataacatc actccactgc atttgcgtga tttattgaac agatcacaat tacatctatt 300
caaatttatt tacctgtacg tgtccgattt ttaggggagg attttttac ggtatttttt 360 ttttaaaaaa ataaatttag gcaacaattt tatagaatcg agtgctttat ctattatctt 420
ttacaaggca cacgcgtaca ataaggtttg gtcgttcgtg acttggatag tggttttggt 480
tgcaattccg taattcttgg cataggatac agcccaaccc agaaaaaaat aatgttgcgg 540
tcagttctgg ctttgagatt cggagtacca cgtggcgtaa aggcaggccg tgtcttacag 600
atgaataaag gacctgggtc tcacgtgatt ggtttccagt ttcgtgcatc aagatgtgga 660
attttcaaac tgccgtcgtg tttgtttcgt cacataaaag ctttttggaa ggctaaggag 720
aggaagccgg cgagaaggag ggggcgtttt acgtgtcact gtcctgtcgt gttggctgtt 780
gacacgaatc atttcttccg cgcgtgggaa gaagaagatg cacattagcg gcctgaagta 840
gagatgtcaa tggggaattc cccagcgggg attaactccc cagacccgta cccatgaaca 900
tagaccggcc cccatccccg aacccgaacc cgacctcggg tacgaaaatc ctcccatacc 960
cattcccgac cgggtactaa atacccatgg gtatccatac ccgacccgat tattcaaaaa 1020
ttaatgggct ttttatttgt taaccggcgg acgcaatgct tgggactcta ggttttttta 1080
ctttgttgac cggctggcgg ctgggctttt tcctacaggc ccaaagttgg tcggcagcca 1140
ctaggccaca cgtcacaggc agcccacaag taaatgtcgt tggattgctg gatggtggaa 1200
taaaaatcct agatgctaga ttgttctggt tccgggtatt tttctccatg gctaatcggg 1260
tttgggttta gccctcccaa acccgaaccc gccatacccg atgggtaagg gatttattcc 1320
aaatctatac ccatggggat ttgttttaac ccatacctta accctaatag aggaattccc 1380
cacgggtaat cgggtttcgg ggcccattga catctctaga ctgaaggcgt ccaactcaaa 1440
tcattaaaaa gtgttgacgc acgcgctgat gcgccggccg cacagcacag gctgcacagc 1500
ccgtttaatc agcgatggag ccccggccgt cagccagcca ggtccggcgt ccgggtctgc 1560
gccctgcggc gtcactgctg tcgccaccgt ctccgatggt cccacatcca tccagcgggc 1620
cgcgcgtggt acaaaaggct cttcctcgcc gtcaggtgca gctgcccaaa caccagacac 1680
agactccacc accccgcttc gatcttctgt tgcagctgaa atctgtcaga ttctgcagtt 1740
cattcc 1746

<210> SEQ ID NO 11
<211> LENGTH: 47747
<212> TYPE: DNA

<213> ORGANISM: artificial sequence
<220> FEATURE:
<223> OTHER INFORMATION: PHP16974 ZmCAS1HindIII Pro:GUS/35SPAT

<400> SEQUENCE: 11

```
tctagagctc gttcctcgag gaacggtacc tgcggggaag cttacaataa tgtgtgttgt     60
taagtcttgt tgcctgtcat cgtctgactg actttcgtca taaatcccgg cctccgtaac    120
ccagctttgg gcaagctcac ggatttgatc cggcggaacg ggaatatcga gatgccgggc    180
tgaacgctgc agttccagct ttccctttcg ggacaggtac tccagctgat tgattatctg    240
ctgaagggtc ttggttccac ctcctggcac aatgcgaatg attacttgag cgcgatcggg    300
catccaattt tctcccgtca ggtgcgtggt caagtgctac aaggcacctt tcagtaacga    360
gcgaccgtcg atccgtcgcc gggatacgga caaaatggag cgcagtagtc catcgagggc    420
ggcgaaagcc tcgccaaaag caatacgttc atctcgcaca gcctccagat ccgatcgagg    480
gtcttcggcg taggcagata gaagcatgga tacattgctt gagagtattc cgatggactg    540
aagtatggct tccatctttt ctcgtgtgtc tgcatctatt tcgagaaagc ccccgatgcg    600
gcgcaccgca acgcgaattg ccatactatc cgaaagtccc agcaggcgcg cttgatagga    660
aaaggtttca tactcggccg atcgcagacg ggcactcacg accttgaacc cttcaacttt    720
cagggatcga tgctggttga tggtagtctc actcgacgtg gctctggtgt gttttgacat    780
agcttcctcc aaagaaagcg gaaggtctgg atactccagc acgaaatgtg cccgggtaga    840
cggatggaag tctagccctg ctcaatatga aatcaacagt acatttacag tcaatactga    900
atatacttgc tacatttgca attgtcttat aacgaatgtg aaataaaaat agtgtaacaa    960
cgcttttact catcgataat cacaaaaaca tttatacgaa caaaaataca aatgcactcc   1020
ggtttcacag gataggcggg atcagaatat gcaacttttg acgttttgtt ctttcaaagg   1080
gggtgctggc aaaaccaccg cactcatggg cctttgcgct gctttggcaa atgacggtaa   1140
acgagtggcc ctctttgatg ccgacgaaaa ccggcctctg acgcgatgga gagaaaacgc   1200
cttacaaagc agtactggga tcctcgctgt gaagtctatt ccgccgacga aatgcccctt   1260
cttgaagcag cctatgaaaa tgccgagctc gaaggatttg attatgcgtt ggccgatacg   1320
cgtggcggct cgagcgagct caacaacaca atcatcgcta gctcaaacct gcttctgatc   1380
cccaccatgc taacgccgct cgacatcgat gaggcactat ctacctaccg ctacgtcatc   1440
gagctgctgt tgagtgaaaa tttggcaatt cctacagctg ttttgcgcca acgcgtcccg   1500
gtcggccgat tgacaacatc gcaacgcagg atgtcagaga cgctagagag ccttccagtt   1560
gtaccgtctc ccatgcatga aagagatgca tttgccgcga tgaaagaacg cggcatgttg   1620
catcttacat tactaaacac gggaactgat ccgacgatgc gcctcataga gaggaatctt   1680
cggattgcga tggaggaagt cgtggtcatt tcgaaactga tcagcaaaat cttggaggct   1740
tgaagatggc aattcgcaag cccgcattgt cggtcggcga agcacggcgg cttgctggtg   1800
ctcgacccga gatccaccat cccaacccga cacttgttcc ccagaagctg gacctccagc   1860
acttgcctga aaaagccgac gagaaagacc agcaacgtga gcctctcgtc gccgatcaca   1920
tttacagtcc cgatcgacaa cttaagctaa ctgtggatgc ccttagtcca cctccgtccc   1980
cgaaaaagct ccaggttttt ctttcagcgc gaccgcccgc gcctcaagtg tcgaaaacat   2040
atgacaacct cgttcggcaa tacagtccct cgaagtcgct acaaatgatt ttaaggcgcg   2100
cgttggacga tttcgaaagc atgctggcag atggatcatt tcgcgtggcc ccgaaaagtt   2160
atccgatccc ttcaactaca gaaaaatccg ttctcgttca gacctcacgc atgttcccgg   2220
```

```
ttgcgttgct cgaggtcgct cgaagtcatt ttgatccgtt ggggttggag accgctcgag   2280
ctttcggcca caagctggct accgccgcgc tcgcgtcatt ctttgctgga gagaagccat   2340
cgagcaattg gtgaagaggg acctatcgga acccctcacc aaatattgag tgtaggtttg   2400
aggccgctgg ccgcgtcctc agtcaccttt tgagccagat aattaagagc caaatgcaat   2460
tggctcaggc tgccatcgtc cccccgtgcg aaacctgcac gtccgcgtca aagaaataac   2520
cggcacctct tgctgttttt atcagttgag ggcttgacgg atccgcctca agtttgcggc   2580
gcagccgcaa aatgagaaca tctatactcc tgtcgtaaac ctcctcgtcg cgtactcgac   2640
tggcaatgag aagttgctcg cgcgatagaa cgtcgcgggg tttctctaaa aacgcgagga   2700
gaagattgaa ctcacctgcc gtaagtttca cctcaccgcc agcttcggac atcaagcgac   2760
gttgcctgag attaagtgtc cagtcagtaa aacaaaaaga ccgtcggtct ttggagcgga   2820
caacgttggg gcgcacgcgc aaggcaaccc gaatgcgtgc aagaaactct ctcgtactaa   2880
acggcttagc gataaaatca cttgctccta gctcgagtgc aacaacttta tccgtctcct   2940
caaggcggtc gccactgata attatgattg gaatatcaga ctttgccgcc agatttcgaa   3000
cgatctcaag cccatcttca cgacctaaat ttagatcaac aaccacgaca tcgaccgtcg   3060
cggaagagag tactctagtg aactgggtgc tgtcggctac cgcggtcact ttgaaggcgt   3120
ggatcgtaag gtattcgata ataagatgcc gcatagcgac atcgtcatcg ataagaagaa   3180
cgtgtttcaa cggctcacct ttcaatctaa aatctgaacc cttgttcaca gcgcttgaga   3240
aattttcacg tgaaggatgt acaatcatct ccagctaaat gggcagttcg tcagaattgc   3300
ggctgaccgc ggatgacgaa aatgcgaacc aagtatttca attttatgac aaaagttctc   3360
aatcgttgtt acaagtgaaa cgcttcgagg ttacagctac tattgattaa ggagatcgcc   3420
tatggtctcg ccccggcgtc gtgcgtccgc cgcgagccag atctcgccta cttcataaac   3480
gtcctcatag gcacggaatg gaatgatgac atcgatcgcc gtagagagca tgtcaatcag   3540
tgtgcgatct tccaagctag caccttgggc gctacttttg acaagggaaa acagtttctt   3600
gaatccttgg attggattcg cgccgtgtat tgttgaaatc gatcccggat gtcccgagac   3660
gacttcactc agataagccc atgctgcatc gtcgcgcatc tcgccaagca atatccggtc   3720
cggccgcata cgcagacttg cttggagcaa gtgctcggcg ctcacagcac ccagcccagc   3780
accgttcttg gagtagagta gtctaacatg attatcgtgt ggaatgacga gttcgagcgt   3840
atcttctatg gtgattagcc tttcctgggg ggggatggcg ctgatcaagg tcttgctcat   3900
tgttgtcttg ccgcttccgg tagggccaca tagcaacatc gtcagtcggc tgacgacgca   3960
tgcgtgcaga aacgcttcca aatccccgtt gtcaaaatgc tgaaggatag cttcatcatc   4020
ctgattttgg cgtttccttc gtgtctgcca ctggttccac ctcgaagcat cataacggga   4080
ggagacttct ttaagaccag aaacacgcga gcttggccgt cgaatggtca agctgacggt   4140
gcccgaggga acggtcggcg gcagacagat ttgtagtcgt tcaccaccag gaagttcagt   4200
ggcgcagagg gggttacgtg gtccgacatc ctgctttctc agcgcgcccg ctaaaatagc   4260
gatatcttca agatcatcat aagagacggg caaaggcatc ttggtaaaaa tgccggcttg   4320
gcgcacaaat gcctctccag gtcgattgat cgcaatttct tcagtcttcg ggtcatcgag   4380
ccattccaaa atcggcttca gaagaaagcg tagttgcgga tccacttcca tttacaatgt   4440
atcctatctc taagcggaaa tttgaattca ttaagagcgg cggttcctcc cccgcgtggc   4500
gccgccagtc aggcggagct ggtaaacacc aaagaaatcg aggtcccgtg ctacgaaaat   4560
```

-continued

```
ggaaacggtg tcaccctgat tcttcttcag ggttggcggt atgttgatgg ttgccttaag   4620
ggctgtctca gttgtctgct caccgttatt ttgaaagctg ttgaagctca tcccgccacc   4680
cgagctgccg gcgtaggtgc tagctgcctg gaaggcgcct tgaacaacac tcaagagcat   4740
agctccgcta aaacgctgcc agaagtggct gtcgaccgag cccggcaatc ctgagcgacc   4800
gagttcgtcc gcgcttggcg atgttaacga gatcatcgca tggtcaggtg tctcggcgcg   4860
atcccacaac acaaaaacgc gcccatctcc ctgttgcaag ccacgctgta tttcgccaac   4920
aacggtggtg ccacgatcaa gaagcacgat attgttcgtt gttccacgaa tatcctgagg   4980
caagacacac tttacatagc ctgccaaatt tgtgtcgatt gcggtttgca agatgcacgg   5040
aattattgtc ccttgcgtta ccataaaatc ggggtgcggc aagagcgtgg cgctgctggg   5100
ctgcagctcg gtgggtttca tacgtatcga caaatcgttc tcgccggaca cttcgccatt   5160
cggcaaggag ttgtcgtcac gcttgccttc ttgtcttcgg cccgtgtcgc cctgaatggc   5220
gcgtttgctg accccttgat cgccgctgct atatgcaaaa atcggtgttt cttccggccg   5280
tggctcatgc cgctccggtt cgcccctcgg cggtagagga gcagcaggct gaacagcctc   5340
ttgaaccgct ggaggatccg gcggcacctc aatcggagct ggatgaaatg gcttggtgtt   5400
tgttgcgatc aaagttgacg gcgatgcgtt ctcattcacc ttcttttggc gcccacctag   5460
ccaaatgagg cttaatgata acgcgagaac gacacctccg acgatcaatt tctgagaccc   5520
cgaaagacgc cggcgatgtt tgtcggagac cagggatcca gatgcatcaa cctcatgtgc   5580
cgcttgctga ctatcgttat tcatcccttc gccccccttca ggacgcgttt cacatcgggc   5640
ctcaccgtgc ccgtttgcgg cctttggcca acgggatcgt aagcggtgtt ccagatacat   5700
agtactgtgt ggccatccct cagacgccaa cctcgggaaa ccgaagaaat ctcgacatcg   5760
ctccctttaa ctgaatagtt ggcaacagct tccttgccat caggattgat ggtgtagatg   5820
gagggtatgc gtacattgcc cggaaagtgg aataccgtcg taaatccatt gtcgaagact   5880
tcgagtggca acagcgaacg atcgccttgg gcgacgtagt gccaattact gtccgccgca   5940
ccaagggctg tgacaggctg atccaataaa ttctcagctt tccgttgata ttgtgcttcc   6000
gcgtgtagtc tgtccacaac agccttctgt tgtgcctccc ttcgccgagc cgccgcatcg   6060
tcggcggggt aggcgaattg gacgctgtaa tagagatcgg gctgctcttt atcgaggtgg   6120
gacagagtct tggaacttat actgaaaaca taacggcgca tcccggagtc gcttgcggtt   6180
agcacgatta ctggctgagg cgtgaggacc tggcttgcct tgaaaaatag ataatttccc   6240
cgcggtaggg ctgctagatc tttgctattt gaaacggcaa ccgctgtcac cgtttcgttc   6300
gtggcgaatg ttacgaccaa agtagctcca accgccgtcg agaggcgcac cacttgatcg   6360
ggattgtaag ccaaataacg catgcgcgga tctagcttgc ccgccattgg agtgtcttca   6420
gcctccgcac cagtcgcagc ggcaaataaa catgctaaaa tgaaaagtgc ttttctgatc   6480
atggttcgct gtggcctacg tttgaaacgg tatcttccga tgtctgatag gaggtgacaa   6540
ccagacctgc cgggttggtt agtctcaatc tgccgggcaa gctggtcacc ttttcgtagc   6600
gaactgtcgc ggtccacgta ctcaccacag gcattttgcc gtcaacgacg agggtccttt   6660
tatagcgaat ttgctgcgtg cttggagtta catcatttga agcgatgtgc tcgacctcca   6720
ccctgccgcg tttgccaaga atgacttgag gcgaactggg attgggatag ttgaagaatt   6780
gctggtaatc ctggcgcact gttggggcac tgaagttcga taccaggtcg taggcgtact   6840
gagcggtgtc ggcatcataa ctctcgcgca ggcgaacgta ctcccacaat gaggcgttaa   6900
cgacggcctc ctcttgagtt gcaggcaatc gcgagacaga cacctcgctg tcaacggtgc   6960
```

```
cgtccggccg tatccataga tatacgggca caagcctgct caacggcacc attgtggcta   7020
tagcgaacgc ttgagcaaca tttcccaaaa tcgcgatagc tgcgacagct gcaatgagtt   7080
tggagagacg tcgcgccgat ttcgctcgcg cggtttgaaa ggcttctact tccttatagt   7140
gctcggcaag gctttcgcgc gccactagca tggcatattc aggccccgtc atagcgtcca   7200
cccgaattgc cgagctgaag atctgacgga gtaggctgcc atcgccccac attcagcggg   7260
aagatcgggc ctttgcagct cgctaatgtg tcgtttgtct ggcagccgct caaagcgaca   7320
actaggcaca gcaggcaata cttcatagaa ttctccattg aggcgaattt ttgcgcgacc   7380
tagcctcgct caacctgagc gaagcgacgg tacaagctgc tggcagattg ggttgcgccg   7440
ctccagtaac tgcctccaat gttgccggcg atcgccggca aagcgacaat gagcgcatcc   7500
cctgtcagaa aaaacatatc gagttcgtaa agaccaatga tcttggccgc ggtcgtaccg   7560
gcgaaggtga ttacaccaag cataagggtg agcgcagtcg cttcggttag gatgacgatc   7620
gttgccacga ggtttaagag gagaagcaag agaccgtagg tgataagttg cccgatccac   7680
ttagctgcga tgtcccgcgt gcgatcaaaa atatatccga cgaggatcag aggcccgatc   7740
gcgagaagca ctttcgtgag aattccaacg gcgtcgtaaa ctccgaaggc agaccagagc   7800
gtgccgtaaa ggacccactg tgccccttgg aaagcaagga tgtcctggtc gttcatcgga   7860
ccgatttcgg atgcgatttt ctgaaaaacg gcctgggtca cggcgaacat tgtatccaac   7920
tgtgccggaa cagtctgcag aggcaagccg gttacactaa actgctgaac aaagtttggg   7980
accgtctttt cgaagatgga aaccacatag tcttggtagt tagcctgccc aacaattaga   8040
gcaacaacga tggtgaccgt gatcacccga gtgataccgc tacgggtatc gacttcgccg   8100
cgtatgacta aaataccctg aacaataatc caaagagtga cacaggcgat caatggcgca   8160
ctcaccgcct cctggatagt ctcaagcatc gagtccaagc ctgtcgtgaa ggctacatcg   8220
aagatcgtat gaatggccgt aaacggcgcc ggaatcgtga aattcatcga ttggacctga   8280
acttgactgg tttgtcgcat aatgttggat aaaatgagct cgcattcggc gaggatgcgg   8340
gcggatgaac aaatcgccca gccttagggg agggcaccaa agatgacagc ggtcttttga   8400
tgctccttgc gttgagcggc cgcctcttcc gcctcgtgaa ggccggcctg cgcggtagtc   8460
atcgttaata ggcttgtcgc ctgtacattt tgaatcattg cgtcatggat ctgcttgaga   8520
agcaaaccat tggtcacggt tgcctgcatg atattgcgag atcgggaaag ctgagcagac   8580
gtatcagcat tcgccgtcaa gcgtttgtcc atcgtttcca gattgtcagc cgcaatgcca   8640
gcgctgtttg cggaaccggt gatctgcgat cgcaacaggt ccgcttcagc atcactaccc   8700
acgactgcac gatctgtatc gctggtgatc gcacgtgccg tggtcgacat tggcattcgc   8760
ggcgaaaaca tttcattgtc taggtccttc gtcgaaggat actgattttt ctggttgagc   8820
gaagtcagta gtccagtaac gccgtaggcc gacgtcaaca tcgtaaccat cgctatagtc   8880
tgagtgagat tctccgcagt cgcgagcgca gtcgcgagcg tctcagcctc cgttgccggg   8940
tcgctaacaa caaactgcgc ccgcgcgggc tgaatatata gaaagctgca ggtcaaaact   9000
gttgcaataa gttgcgtcgt cttcatcgtt tcctacctta tcaatcttct gcctcgtggt   9060
gacgggccat gaattcgctg agccagccag atgagttgcc ttcttgtgcc tcgcgtagtc   9120
gagttgcaaa gcgcaccgtg ttggcacgcc ccgaaagcac ggcgacatat tcacgcatat   9180
cccgcagatc aaattcgcag atgacgcttc cactttctcg tttaagaaga aacttacggc   9240
tgccgaccgt catgtcttca cggatcgcct gaaattcctt ttcggtacat ttcagtccat   9300
```

```
cgacataagc cgatcgatct gcggttggtg atggatagaa aatcttcgtc atacattgcg   9360
caaccaagct ggctcctagc ggcgattcca gaacatgctc tggttgctgc gttgccagta   9420
ttagcatccc gttgtttttt cgaacggtca ggaggaattt gtcgacgaca gtcgaaaatt   9480
tagggtttaa caaataggcg cgaaactcat cgcagctcat cacaaaacgg cggccgtcga   9540
tcatggctcc aatccgatgc aggagatatg ctgcagcggg agcgcatact tcctcgtatt   9600
cgagaagatg cgtcatgtcg aagccggtaa tcgacggatc taactttact tcgtcaactt   9660
cgccgtcaaa tgcccagcca agcgcatggc cccggcacca gcgttggagc cgcgctcctg   9720
cgccttcggc gggcccatgc aacaaaaatt cacgtaaccc cgcgattgaa cgcatttgtg   9780
gatcaaacga gagctgacga tggataccac ggaccagacg gcggttctct tccggagaaa   9840
tcccaccccg accatcactc tcgatgagag ccacgatcca ttcgcgcaga aaatcgtgtg   9900
aggctgctgt gttttctagg ccacgcaacg gcgccaaccc gctgggtgtg cctctgtgaa   9960
gtgccaaata tgttcctcct gtggcgcgaa ccagcaattc gccaccccgg tccttgtcaa  10020
agaacacgac cgtacctgca cggtcgacca tgctctgttc gagcatggct agaacaaaca  10080
tcatgagcgt cgtcttaccc ctcccgatag gcccgaatat tgccgtcatg ccaacatcgt  10140
gctcatgcgg gatatagtcg aaaggcgttc cgccattggt acgaaatcgg gcaatcgcgt  10200
tgccccagtg gcctgagctg gcgccctctg gaaagttttc gaaagagaca aaccctgcga  10260
aattgcgtga agtgattgcg ccagggcgtg tgcgccactt aaaattcccc ggcaattggg  10320
accaataggc cgcttccata ccaatacctt cttggacaac cacggcacct gcatccgcca  10380
ttcgtgtccg agcccgcgcg cccctgtccc caagactatt gagatcgtct gcatagacgc  10440
aaaggctcaa atgatgtgag cccataacga attcgttgct cgcaagtgcg tcctcagcct  10500
cggataattt gccgatttga gtcacggctt tatcgccgga actcagcatc tggctcgatt  10560
tgaggctaag tttcgcgtgc gcttgcgggc gagtcaggaa cgaaaaactc tgcgtgagaa  10620
caagtggaaa atcgagggat agcagcgcgt tgagcatgcc cggccgtgtt tttgcagggt  10680
attcgcgaaa cgaatagatg gatccaacgt aactgtcttt tggcgttctg atctcgagtc  10740
ctcgcttgcc gcaaatgact ctgtcggtat aaatcgaagc gccgagtgag ccgctgacga  10800
ccggaaccgg tgtgaaccga ccagtcatga tcaaccgtag cgcttcgcca atttcggtga  10860
agagcacacc ctgcttctcg cggatgccaa gacgatgcag gccatacgct ttaagagagc  10920
cagcgacaac atgccaaaga tcttccatgt tcctgatctg gcccgtgaga tcgttttccc  10980
tttttccgct tagcttggtg aacctcctct ttaccttccc taaagccgcc tgtgggtaga  11040
caatcaacgt aaggaagtgt tcattgcgga ggagttggcc ggagagcacg cgctgttcaa  11100
aagcttcgtt caggctagcg gcgaaaacac tacggaagtg tcgcggcgcc gatgatggca  11160
cgtcggcatg acgtacgagg tgagcatata ttgacacatg atcatcagcg atattgcgca  11220
acagcgtgtt gaacgcacga caacgcgcat tgcgcatttc agtttcctca agctcgaatg  11280
caacgccatc aattctcgca atggtcatga tcgatccgtc ttcaagaagg acgatatggt  11340
cgctgaggtg gccaatataa gggagataga tctcaccgga tctttcggtc gttccactcg  11400
cgccgagcat cacaccattc ctctccctcg tgggggaacc ctaattggat ttgggctaac  11460
agtagcgccc ccccaaactg cactatcaat gcttcttccc gcggtccgca aaaatagcag  11520
gacgacgctc gccgcattgt agtctcgctc cacgatgagc cgggctgcaa accataacgg  11580
cacgagaacg acttcgtaga gcgggttctg aacgataacg atgacaaagc cggcgaacat  11640
catgaataac cctgccaatg tcagtggcac cccaagaaac aatgcgggcc gtgtggctgc  11700
```

```
gaggtaaagg gtcgattctt ccaaacgatc agccatcaac taccgccagt gagcgtttgg  11760
ccgaggaagc tcgccccaaa catgataaca atgccgccga cgacgccggc aaccagccca  11820
agcgaagccc gcccgaacat ccaggagatc ccgatagcga caatgccgag aacagcgagt  11880
gactggccga acggaccaag gataaacgtg catatattgt taaccattgt ggcggggtca  11940
gtgccgccac ccgcagattg cgctgcggcg ggtccggatg aggaaatgct ccatgcaatt  12000
gcaccgcaca agcttggggc gcagctcgat atcacgcgca tcatcgcatt cgagagcgag  12060
aggcgattta gatgtaaacg gtatctctca aagcatcgca tcaatgcgca cctccttagt  12120
ataagtcgaa taagacttga ttgtcgtctg cggatttgcc gttgtcctgg tgtggcggtg  12180
gcggagcgat taaaccgcca gcgccatcct cctgcgagcg gcgctgatat gacccccaaa  12240
catcccacgt ctcttcggat tttagcgcct cgtgatcgtc ttttggaggc tcgattaacg  12300
cgggcaccag cgattgagca gctgtttcaa cttttcgcac gtagccgttt gcaaaaccgc  12360
cgatgaaatt accggtgttg taagcggaga tcgcccgacg aagcgcaaat tgcttctcgt  12420
caatcgtttc gccgcctgca taacgacttt tcagcatgtt tgcagcggca gataatgatg  12480
tgcacgcctg gagcgcaccg tcaggtgtca gaccgagcat agaaaaattt cgagagttta  12540
tttgcatgag gccaacatcc agcgaatgcc gtgcatcgag acggtgcctg acgacttggg  12600
ttgcttggct gtgatcttgc cagtgaagcg tttcgccggt cgtgttgtca tgaatcgcta  12660
aaggatcaaa gcgactctcc accttagcta tcgccgcaag cgtagatgtc gcaactgatg  12720
gggcacactt gcgagcaaca tggtcaaact cagcagatga gagtggcgtg gcaaggctcg  12780
acgaacagaa ggagaccatc aaggcaagag aaagcgaccc cgatctctta agcatacctt  12840
atctccttag ctcgcaacta acaccgcctc tcccgttgga agaagtgcgt tgttttatgt  12900
tgaagattat cgggagggtc ggttactcga aaattttcaa ttgcttcttt atgatttcaa  12960
ttgaagcgag aaacctcgcc cggcgtcttg gaacgcaaca tggaccgaga accgcgcatc  13020
catgactaag caaccggatc gacctattca ggccgcagtt ggtcaggtca ggctcagaac  13080
gaaaatgctc ggcgaggtta cgctgtctgt aaacccattc gatgaacggg aagcttcctt  13140
ccgattgctc ttggcaggaa tattggccca tgcctgcttg cgctttgcaa atgctcttat  13200
cgcgttggta tcatatgcct tgtccgccag cagaaacgca ctctaagcga ttatttgtaa  13260
aaatgtttcg gtcatgcggc ggtcatgggc ttgacccgct gtcagcgcaa gacggatcgg  13320
tcaaccgtcg gcatcgacaa cagcgtgaat cttggtggtc aaaccgccac gggaacgtcc  13380
catacagcca tcgtcttgat cccgctgttt cccgtcgccg catgttggtg gacgcggaca  13440
caggaactgt caatcatgac gacattctat cgaaagcctt ggaaatcaca ctcagaatat  13500
gatcccagac gtctgcctca cgccatcgta caaagcgatt gtagcaggtt gtacaggaac  13560
cgtatcgatc aggaacgtct gcccagggcg ggcccgtccg gaagcgccac aagatgacat  13620
tgatcacccg cgtcaacgcg cggcacgcga cgcggcttat ttgggaacaa aggactgaac  13680
aacagtccat tcgaaatcgg tgacatcaaa gcggggacgg gttatcagtg gcctccaagt  13740
caagcctcaa tgaatcaaaa tcagaccgat ttgcaaacct gatttatgag tgtgcggcct  13800
aaatgatgaa atcgtccttc tagatcgcct ccgtggtgta gcaacacctc gcagtatcgc  13860
cgtgctgacc ttggccaggg aattgactgg caagggtgct ttcacatgac cgctcttttg  13920
gccgcgatag atgatttcgt tgctgctttg ggcacgtaga aggagagaag tcatatcgga  13980
gaaattcctc ctggcgcgag agcctgctct atcgcgacgg catcccactg tcgggaacag  14040
```

```
accggatcat tcacgaggcg aaagtcgtca acacatgcgt tataggcatc ttcccttgaa  14100
ggatgatctt gttgctgcca atctggaggt gcggcagccg caggcagatg cgatctcagc  14160
gcaacttgcg gcaaaacatc tcactcacct gaaaaccact agcgagtctc gcgatcagac  14220
gaaggccttt tacttaacga cacaatatcc gatgtctgca tcacaggcgt cgctatccca  14280
gtcaatacta aagcggtgca ggaactaaag attactgatg acttaggcgt gccacgaggc  14340
ctgagacgac gcgcgtagac agttttttga aatcattatc aaagtgatgg cctccgctga  14400
agcctatcac ctctgcgccg gtctgtcgga gagatgggca agcattatta cggtcttcgc  14460
gcccgtacat gcattggacg attgcagggt caatggatct gagatcatcc agaggattgc  14520
cgcccttacc ttccgtttcg agttggagcc agcccctaaa tgagacgaca tagtcgactt  14580
gatgtgacaa tgccaagaga gagatttgct taacccgatt tttttgctca agcgtaagcc  14640
tattgaagct tgccggcatg acgtccgcgc cgaaagaata tcctacaagt aaaacattct  14700
gcacaccgaa atgcttggtg tagacatcga ttatgtgacc aagatcctta gcagtttcgc  14760
ttggggaccg ctccgaccag aaataccgaa gtgaactgac gccaatgaca ggaatccctt  14820
ccgtctgcag ataggtacca tcgatagatc tgctgcctcg cgcgtttcgg tgatgacggt  14880
gaaaacctct gacacatgca gctcccggag acggtcacag cttgtctgta agcggatgcc  14940
gggagcagac aagcccgtca gggcgcgtca gcgggtgttg gcgggtgtcg gggcgcagcc  15000
atgacccagt cacgtagcga tagcggagtg tatactggct taactatgcg gcatcagagc  15060
agattgtact gagagtgcac catatgcggt gtgaaatacc gcacagatgc gtaaggagaa  15120
aataccgcat caggcgctct tccgcttcct cgctcactga ctcgctgcgc tcggtcgttc  15180
ggctgcggcg agcggtatca gctcactcaa aggcggtaat acggttatcc acagaatcag  15240
gggataacgc aggaaagaac atgtgagcaa aaggccagca aaaggccagg aaccgtaaaa  15300
aggccgcgtt gctggcgttt ttccataggc tccgcccccc tgacgagcat cacaaaaatc  15360
gacgctcaag tcagaggtgg cgaaacccga caggactata aagataccag gcgtttcccc  15420
ctggaagctc cctcgtgcgc tctcctgttc cgaccctgcc gcttaccgga tacctgtccg  15480
cctttctccc ttcgggaagc gtggcgcttt ctcatagctc acgctgtagg tatctcagtt  15540
cggtgtaggt cgttcgctcc aagctgggct gtgtgcacga accccccgtt cagcccgacc  15600
gctgcgcctt atccggtaac tatcgtcttg agtccaaccc ggtaagacac gacttatcgc  15660
cactggcagc agccactggt aacaggatta gcagagcgag gtatgtaggc ggtgctacag  15720
agttcttgaa gtggtggcct aactacggct acactagaag gacagtattt ggtatctgcg  15780
ctctgctgaa gccagttacc ttcggaaaaa gagttggtag ctcttgatcc ggcaaacaaa  15840
ccaccgctgg tagcggtggt ttttttgttt gcaagcagca gattacgcgc agaaaaaaag  15900
gatctcaaga agatcctttg atcttttcta cggggtctga cgctcagtgg aacgaaaact  15960
cacgttaagg gattttggtc atgagattat caaaaaggat cttcacctag atccttttaa  16020
attaaaaatg aagttttaaa tcaatctaaa gtatatatga gtaaacttgg tctgacagtt  16080
accaatgctt aatcagtgag gcacctatct cagcgatctg tctatttcgt tcatccatag  16140
ttgcctgact ccccgtcgtg tagataacta cgatacggga gggcttacca tctggcccca  16200
gtgctgcaat gataccgcga gacccacgct caccggctcc agatttatca gcaataaacc  16260
agccagccgg aagggccgag cgcagaagtg gtcctgcaac tttatccgcc tccatccagt  16320
ctattaattg ttgccgggaa gctagagtaa gtagttcgcc agttaatagt ttgcgcaacg  16380
ttgttgccat tgctgcaggg gggggggggg ggggggactt ccattgttca ttccacggac  16440
```

```
aaaaacagag aaaggaaacg acagaggcca aaaagcctcg ctttcagcac ctgtcgtttc  16500
ctttcttttc agagggtatt ttaaataaaa acattaagtt atgacgaaga agaacggaaa  16560
cgccttaaac cggaaaattt tcataaatag cgaaaacccg cgaggtcgcc gccccgtaac  16620
ctgtcggatc accggaaagg acccgtaaag tgataatgat tatcatctac atatcacaac  16680
gtgcgtggag gccatcaaac cacgtcaaat aatcaattat gacgcaggta tcgtattaat  16740
tgatctgcat caacttaacg taaaaacaac ttcagacaat acaaatcagc gacactgaat  16800
acggggcaac ctcatgtccc cccccccccc cccccctgcag ggcatcgtgg tgtcacgctc  16860
gtcgtttggt atggcttcat tcagctccgg ttcccaacga tcaaggcgag ttacatgatc  16920
ccccatgttg tgcaaaaaag cggttagctc cttcggtcct ccgatcgttg tcagaagtaa  16980
gttggccgca gtgttatcac tcatggttat ggcagcactg cataattctc ttactgtcat  17040
gccatccgta agatgctttt ctgtgactgg tgagtactca accaagtcat tctgagaata  17100
gtgtatgcgg cgaccgagtt gctcttgccc ggcgtcaaca cgggataata ccgcgccaca  17160
tagcagaact ttaaaagtgc tcatcattgg aaaacgttct tcggggcgaa aactctcaag  17220
gatcttaccg ctgttgagat ccagttcgat gtaacccact cgtgcaccca actgatcttc  17280
agcatctttt actttcacca gcgtttctgg gtgagcaaaa acaggaaggc aaaatgccgc  17340
aaaaaaggga ataagggcga cacggaaatg ttgaatactc atactcttcc tttttcaata  17400
ttattgaagc atttatcagg gttattgtct catgagcgga tacatatttg aatgtattta  17460
gaaaaataaa caaatagggg ttccgcgcac atttccccga aaagtgccac ctgacgtcta  17520
agaaaccatt attatcatga cattaaccta taaaaatagg cgtatcacga ggccctttcg  17580
tcttcaagaa ttggtcgacg atcttgctgc gttcggatat tttcgtggag ttcccgccac  17640
agacccggat tgaaggcgag atccagcaac tcgcgccaga tcatcctgtg acggaacttt  17700
ggcgcgtgat gactggccag gacgtcggcc gaaagagcga caagcagatc acgcttttcg  17760
acagcgtcgg atttgcgatc gaggattttt cggcgctgcg ctacgtccgc gaccgcgttg  17820
agggatcaag ccacagcagc ccactcgacc ttctagccga cccagacgag ccaagggatc  17880
tttttggaat gctgctccgt cgtcaggctt tccgacgttt gggtggttga acagaagtca  17940
ttatcgtacg gaatgccaag cactcccgag gggaaccctg tggttggcat gcacatacaa  18000
atggacgaac ggataaacct tttcacgccc ttttaaatat ccgttattct aataaacgct  18060
cttttctctt aggtttaccc gccaatatat cctgtcaaac actgatagtt taaactgaag  18120
gcgggaaacg acaatctgat catgagcgga gaattaaggg agtcacgtta tgacccccgc  18180
cgatgacgcg ggacaagccg ttttacgttt ggaactgaca gaaccgcaac gttgaaggag  18240
ccactcagcc caagcttttt ggaaggctaa ggagaggaag ccggcgagaa ggagggggcg  18300
ttttacgtgt cactgtcctg tcgtgttggc tgttgacacg aatcatttct tccgcgcgtg  18360
ggaagaagaa gatgcacatt agcggcctga agtagagatg tcaatgggga attccccagc  18420
ggggattaac tccccagacc cgtacccatg aacatagacc ggcccccatc cccgaacccg  18480
aacccgacct cgggtacgaa aatcctccca tacccattcc cgaccgggta ctaaataccc  18540
atgggtatcc atacccgacc cgattattca aaaattaatg ggctttttat ttgttaaccg  18600
gcggacgcaa tgcttgggac tctaggtttt tttactttgt tgaccggctg gcggctgggc  18660
tttttcctac aggcccaaag ttggtcggca gccactaggc cacacgtcac aggcagccca  18720
caagtaaatg tcgttggatt gctggatggt ggaataaaaa tcctagatgc tagattgttc  18780
```

```
tggttccggg tatttttctc catggctaat cgggtttggg tttagccctc ccaaacccga  18840
acccgccata cccgatgggt aagggattta ttccaaatct atacccatgg ggatttgttt  18900
taacccatac cttaacccta atagaggaat tccccacggg taatcgggtt tcggggccca  18960
ttgacatctc tagactgaag gcgtccaact caaatcatta aaaagtgttg acgcacgcgc  19020
tgatgcgccg gccgcacagc acaggctgca cagcccgttt aatcagcgat ggagccccgg  19080
ccgtcagcca gccaggtccg gcgtccgggt ctgcgccctg cggcgtcact gctgtcgcca  19140
ccgtctccga tggtcccaca tccatccagc gggccgcgcg tggtacaaaa ggctcttcct  19200
cgccgtcagg tgcagctgcc caaacaccag acacagactc caccaccccg cttcgatctt  19260
ctgttgcagc tgaaatctgt cagattctgc agttcattcc tcatggtccg tcctgtagaa  19320
accccaaccc gtgaaatcaa aaaactcgac ggcctgtggg cattcagtct ggatcgcgaa  19380
aactgtggaa ttgatcagcg ttggtgggaa agcgcgttac aagaaagccg ggcaattgct  19440
gtgccaggca gttttaacga tcagttcgcc gatgcagata ttcgtaatta tgcgggcaac  19500
gtctggtatc agcgcgaagt ctttataccg aaaggttggg caggccagcg tatcgtgctg  19560
cgtttcgatg cggtcactca ttacggcaaa gtgtgggtca ataatcagga agtgatggag  19620
catcagggcg gctatacgcc atttgaagcc gatgtcacgc cgtatgttat tgccgggaaa  19680
agtgtacgta tcaccgtttg tgtgaacaac gaactgaact ggcagactat cccgccggga  19740
atggtgatta ccgacgaaaa cggcaagaaa aagcagtctt acttccatga tttctttaac  19800
tatgccggaa tccatcgcag cgtaatgctc tacaccacgc cgaacacctg ggtggacgat  19860
atcaccgtgg tgacgcatgt cgcgcaagac tgtaaccacg cgtctgttga ctgccaggtg  19920
gtggccaatg gtgatgtcag cgttgaactg cgtgatgcgg atcaacaggt ggttgcaact  19980
ggacaaggca ctagcgggac tttgcaagtg gtgaatccgc acctctgcca accgggtgaa  20040
ggttatctct atgaactgtg cgtcacagcc aaaagccaga cagagtgtga tatctacccg  20100
cttcgcgtcg gcatccggtc agtggcagtg aagggccaac agttcctgat taaccacaaa  20160
ccgttctact ttactggctt tggtcgtcat gaagatgcgg acttacgtgg caaaggattc  20220
gataacgtgc tgatggtgca cgaccacgca ttaatggact ggattggggc caactcctac  20280
cgtacctcgc attaccctta cgctgaagag atgctcgact gggcagatga acatggcatc  20340
gtggtgattg atgaaactgc tgctgtcggc tttaacctct ctttaggcat tggtttcgaa  20400
gcgggcaaca agccgaaaga actgtacagc gaagaggcag tcaacgggga aactcagcaa  20460
gcgcacttac aggcgattaa agagctgata gcgcgtgaca aaaaccaccc aagcgtggtg  20520
atgtggagta ttgccaacga accggatacc cgtccgcaag tgcacgggaa tatttcgcca  20580
ctggcggaag caacgcgtaa actcgacccg acgcgtccga tcacctgcgt caatgtaatg  20640
ttctgcgacg ctcacaccga taccatcagc gatctctttg atgtgctgtg cctgaaccgt  20700
tattacggat ggtatgtcca aagcggcgat ttggaaacgg cagagaaggt actggaaaaa  20760
gaacttctgg cctggcagga gaaactgcat cagccgatta tcatcaccga atacggcgtg  20820
gatacgttag ccgggctgca ctcaatgtac accgacatgt ggagtgaaga gtatcagtgt  20880
gcatggctgg atatgtatca ccgcgtcttt gatcgcgtca gcgccgtcgt cggtgaacag  20940
gtatggaatt tcgccgattt tgcgacctcg caaggcatat tgcgcgttgg cggtaacaag  21000
aaagggatct tcactcgcga ccgcaaaccg aagtcggcgg cttttctgct gcaaaaacgc  21060
tggactggca tgaacttcgg tgaaaaaccg cagcagggag gcaaacaatg aatcaacaac  21120
tctcctggcg caccatcgtc ggctacagcc tcggtgacgt ggggcaacct agacttgtcc  21180
```

```
atcttctgga ttggccaact taattaatgt atgaaataaa aggatgcaca catagtgaca  21240
tgctaatcac tataatgtgg gcatcaaagt tgtgtgttat gtgtaattac tagttatctg  21300
aataaaagag aaagagatca tccatatttc ttatcctaaa tgaatgtcac gtgtctttat  21360
aattctttga tgaaccagat gcatttcatt aaccaaatcc atatacatat aaatattaat  21420
catatataat taatatcaat tgggttagca aaacaaatct agtctaggtg tgttttgcga  21480
attgcggccc catggagtca aagattcaaa tagaggacct aacagaactc gccgtaaaga  21540
ctggcgaaca gttcatacag agtctcttac gactcaatga caagaagaaa atcttcgtca  21600
acatggtgga gcacgacacg cttgtctact ccaaaaatat caaagataca gtctcagaag  21660
accaaagggc aattgagact tttcaacaaa gggtaatatc cggaaacctc ctcggattcc  21720
attgcccagc tatctgtcac tttattgtga agatagtgga aaaggaaggt ggctcctaca  21780
aatgccatca ttgcgataaa ggaaaggcca tcgttgaaga tgcctctgcc gacagtggtc  21840
ccaaagatgg acccccaccc acgaggagca tcgtggaaaa agaagacgtt ccaaccacgt  21900
cttcaaagca agtggattga tgtgatatct ccactgacgt aagggatgac gcacaatccc  21960
actatccttc gcaagaccct tcctctatat aaggaagttc atttcatttg gagaggacag  22020
ggtacccggg gatccaccat gtctccggag aggagaccag ttgagattag gccagctaca  22080
gcagctgata tggccgcggt ttgtgatatc gttaaccatt acattgagac gtctacagtg  22140
aactttagga cagagccaca aacaccacaa gagtggattg atgatctaga gaggttgcaa  22200
gatagatacc cttggttggt tgctgaggtt gagggtgttg tggctggtat tgcttacgct  22260
gggccctgga aggctaggaa cgcttacgat tggacagttg agagtactgt ttacgtgtca  22320
cataggcatc aaaggttggg cctaggatcc acattgtaca cacatttgct taagtctatg  22380
gaggcgcaag gttttaagtc tgtggttgct gttataggcc ttccaaacga tccatctgtt  22440
aggttgcatg aggctttggg atacacagcc cggggtacat tgcgcgcagc tggatacaag  22500
catggtggat ggcatgatgt tggtttttgg caaagggatt ttgagttgcc agctcctcca  22560
aggccagtta ggccagttac ccagatctga gtcgacctgc aggcatgccg ctgaaatcac  22620
cagtctctct ctacaaatct atctctctct ataataatgt gtgagtagtt cccagataag  22680
ggaattaggg ttcttatagg gtttcgctca tgtgttgagc atataagaaa cccttagtat  22740
gtatttgtat ttgtaaaata cttctatcaa taaaatttct aattcctaaa accaaaatcc  22800
agtgggtacc gagctcgaat tcagtacatt aaaaacgtcc gcaatgtgtt attaagttgt  22860
ctaagcgtca atttgtttac accacaatat atcctgccac cagccagcca acagctcccc  22920
gaccggcagc tcggcacaaa atcaccactc gatacaggca gcccatcagt ccgggacggc  22980
gtcagcggga gagccgttgt aaggcggcag actttgctca tgttaccgat gctattcgga  23040
agaacggcaa ctaagctgcc gggtttgaaa cacggatgat ctcgcggagg gtagcatgtt  23100
gattgtaacg atgacagagc gttgctgcct gtgatcaaat atcatctccc tcgcagagat  23160
ccgaattatc agccttctta ttcatttctc gcttaaccgt gacaggctgt cgatcttgag  23220
aactatgccg acataatagg aaatcgctgg ataaagccgc tgaggaagct gagtggcgct  23280
atttctttag aagtgaacgt tgacgatcgt cgaccgtacc ccgatgaatt aattcggacg  23340
tacgttctga acacagctgg atacttactt gggcgattgt catacatgac atcaacaatg  23400
tacccgtttg tgtaaccgtc tcttggaggt tcgtatgaca ctagtggttc ccctcagctt  23460
gcgactagat gttgaggcct aacattttat tagagagcag gctagttgct tagatacatg  23520
```

```
atcttcaggc cgttatctgt cagggcaagc gaaaattggc catttatgac gaccaatgcc  23580
ccgcagaagc tcccatcttt gccgccatag acgccgcgcc cccttttgg ggtgtagaac  23640
atccttttgc cagatgtgga aaagaagttc gttgtcccat tgttggcaat gacgtagtag  23700
ccggcgaaag tgcgagaccc atttgcgcta tatataagcc tacgatttcc gttgcgacta  23760
ttgtcgtaat tggatgaact attatcgtag ttgctctcag agttgtcgta atttgatgga  23820
ctattgtcgt aattgcttat ggagttgtcg tagttgcttg gagaaatgtc gtagttggat  23880
ggggagtagt catagggaag acgagcttca tccactaaaa caattggcag gtcagcaagt  23940
gcctgccccg atgccatcgc aagtacgagg cttagaacca ccttcaacag atcgcgcata  24000
gtcttcccca gctctctaac gcttgagtta agccgcgccg cgaagcggcg tcggcttgaa  24060
cgaattgtta gacattattt gccgactacc ttggtgatct cgcctttcac gtagtgaaca  24120
aattcttcca actgatctgc gcgcgaggcc aagcgatctt cttgtccaag ataagcctgc  24180
ctagcttcaa gtatgacggg ctgatactgg gccggcaggc gctccattgc ccagtcggca  24240
gcgacatcct tcggcgcgat tttgccggtt actgcgctgt accaaatgcg ggacaacgta  24300
agcactacat ttcgctcatc gccagcccag tcgggcggcg agttccatag cgttaaggtt  24360
tcatttagcg cctcaaatag atcctgttca ggaaccggat caaagagttc ctccgccgct  24420
ggacctacca aggcaacgct atgttctctt gcttttgtca gcaagatagc cagatcaatg  24480
tcgatcgtgg ctggctcgaa gatacctgca agaatgtcat tgcgctgcca ttctccaaat  24540
tgcagttcgc gcttagctgg ataacgccac ggaatgatgt cgtcgtgcac aacaatggtg  24600
acttctacag cgcggagaat ctcgctctct ccaggggaag ccgaagtttc caaaaggtcg  24660
ttgatcaaag ctcgccgcgt tgtttcatca agccttacgg tcaccgtaac cagcaaatca  24720
atatcactgt gtggcttcag gccgccatcc actgcggagc cgtacaaatg tacggccagc  24780
aacgtcggtt cgagatggcg ctcgatgacg ccaactacct ctgatagttg agtcgatact  24840
tcggcgatca ccgcttccct catgatgttt aactcctgaa ttaagccgcg ccgcgaagcg  24900
gtgtcggctt gaatgaattg ttaggcgtca tcctgtgctc ccgagaacca gtaccagtac  24960
atcgctgttt cgttcgagac ttgaggtcta gttttatacg tgaacaggtc aatgccgccg  25020
agagtaaagc cacattttgc gtacaaattg caggcaggta cattgttcgt ttgtgtctct  25080
aatcgtatgc caaggagctg tctgcttagt gcccactttt tcgcaaattc gatgagactg  25140
tgcgcgactc ctttgcctcg gtgcgtgtgc gacacaacaa tgtgttcgat agaggctaga  25200
tcgttccatg ttgagttgag ttcaatcttc ccgacaagct cttggtcgat gaatgcgcca  25260
tagcaagcag agtcttcatc agagtcatca tccgagatgt aatccttccg gtaggggctc  25320
acacttctgg tagatagttc aaagccttgg tcggataggt gcacatcgaa cacttcacga  25380
acaatgaaat ggttctcagc atccaatgtt tccgccacct gctcagggat caccgaaatc  25440
ttcatatgac gcctaacgcc tggcacagcg gatcgcaaac ctggcgcggc ttttggcaca  25500
aaaggcgtga caggtttgcg aatccgttgc tgccacttgt taaccctttt gccagatttg  25560
gtaactataa tttatgttag aggcgaagtc ttgggtaaaa actggcctaa aattgctggg  25620
gatttcagga aagtaaacat caccttccgg ctcgatgtct attgtagata tatgtagtgt  25680
atctacttga tcgggggatc tgctgcctcg cgcgtttcgg tgatgacggt gaaaacctct  25740
gacacatgca gctcccggag acggtcacag cttgtctgta agcggatgcc gggagcagac  25800
aagcccgtca gggcgcgtca gcgggtgttg gcgggtgtcg gggcgcagcc atgacccagt  25860
cacgtagcga tagcggagtg tatactggct taactatgcg gcatcagagc agattgtact  25920
```

```
gagagtgcac catatgcggt gtgaaatacc gcacagatgc gtaaggagaa aataccgcat  25980
caggcgctct tccgcttcct cgctcactga ctcgctgcgc tcggtcgttc ggctgcggcg  26040
agcggtatca gctcactcaa aggcggtaat acggttatcc acagaatcag gggataacgc  26100
aggaaagaac atgtgagcaa aaggccagca aaaggccagg aaccgtaaaa aggccgcgtt  26160
gctggcgttt ttccataggc tccgcccccc tgacgagcat cacaaaaatc gacgctcaag  26220
tcagaggtgg cgaaacccga caggactata aagataccag gcgtttcccc ctggaagctc  26280
cctcgtgcgc tctcctgttc cgaccctgcc gcttaccgga tacctgtccg cctttctccc  26340
ttcgggaagc gtggcgcttt ctcatagctc acgctgtagg tatctcagtt cggtgtaggt  26400
cgttcgctcc aagctgggct gtgtgcacga accccccgtt cagcccgacc gctgcgcctt  26460
atccggtaac tatcgtcttg agtccaaccc ggtaagacac gacttatcgc cactggcagc  26520
agccactggt aacaggatta gcagagcgag gtatgtaggc ggtgctacag agttcttgaa  26580
gtggtggcct aactacggct acactagaag gacagtattt ggtatctgcg ctctgctgaa  26640
gccagttacc ttcggaaaaa gagttggtag ctcttgatcc ggcaaacaaa ccaccgctgg  26700
tagcggtggt ttttttgttt gcaagcagca gattacgcgc agaaaaaaag gatctcaaga  26760
agatcctttg atcttttcta cggggtctga cgctcagtgg aacgaaaact cacgttaagg  26820
gattttggtc atgagattat caaaaaggat cttcacctag atccttttaa attaaaaatg  26880
aagttttaaa tcaatctaaa gtatatatga gtaaacttgg tctgacagtt accaatgctt  26940
aatcagtgag gcacctatct cagcgatctg tctatttcgt tcatccatag ttgcctgact  27000
ccccgtcgtg tagataacta cgatacggga gggcttacca tctggcccca gtgctgcaat  27060
gataccgcga gacccacgct caccggctcc agatttatca gcaataaacc agccagccgg  27120
aagggccgag cgcagaagtg gtcctgcaac tttatccgcc tccatccagt ctattaattg  27180
ttgccgggaa gctagagtaa gtagttcgcc agttaatagt ttgcgcaacg ttgttgccat  27240
tgctgcaggg gggggggggg ggggggactt ccattgttca ttccacggac aaaaacagag  27300
aaaggaaacg acagaggcca aaaagcctcg ctttcagcac ctgtcgtttc ctttcttttc  27360
agagggtatt ttaaataaaa acattaagtt atgacgaaga agaacggaaa cgccttaaac  27420
cggaaaattt tcataaatag cgaaaacccg cgaggtcgcc gccccgtaac ctgtcggatc  27480
accggaaagg acccgtaaag tgataatgat tatcatctac atatcacaac gtgcgtggag  27540
gccatcaaac cacgtcaaat aatcaattat gacgcaggta tcgtattaat tgatctgcat  27600
caacttaacg taaaaacaac ttcagacaat acaaatcagc gacactgaat acggggcaac  27660
ctcatgtccc cccccccccc cccccctgcag gcatcgtggt gtcacgctcg tcgtttggta  27720
tggcttcatt cagctccggt tcccaacgat caaggcgagt tacatgatcc cccatgttgt  27780
gcaaaaaagc ggttagctcc ttcggtcctc cgatcgttgt cagaagtaag ttggccgcag  27840
tgttatcact catggttatg gcagcactgc ataattctct tactgtcatg ccatccgtaa  27900
gatgcttttc tgtgactggt gagtactcaa ccaagtcatt ctgagaatag tgtatgcggc  27960
gaccgagttg ctcttgcccg gcgtcaacac gggataatac cgcgccacat agcagaactt  28020
taaaagtgct catcattgga aaacgttctt cggggcgaaa actctcaagg atcttaccgc  28080
tgttgagatc cagttcgatg taacccactc gtgcacccaa ctgatcttca gcatctttta  28140
ctttcaccag cgtttctggg tgagcaaaaa caggaaggca aaatgccgca aaaaagggaa  28200
taagggcgac acggaaatgt tgaatactca tactcttcct ttttcaatat tattgaagca  28260
```

```
tttatcaggg ttattgtctc atgagcggat acatatttga atgtatttag aaaaataaac  28320
aaataggggt tccgcgcaca tttccccgaa aagtgccacc tgacgtctaa gaaaccatta  28380
ttatcatgac attaacctat aaaaataggc gtatcacgag gccctttcgt cttcaagaat  28440
tcggagcttt tgccattctc accggattca gtcgtcactc atggtgattt ctcacttgat  28500
aaccttattt ttgacgaggg gaaattaata ggttgtattg atgttggacg agtcggaatc  28560
gcagaccgat accaggatct tgccatccta tggaactgcc tcggtgagtt ttctccttca  28620
ttacagaaac ggctttttca aaaatatggt attgataatc ctgatatgaa taaattgcag  28680
tttcatttga tgctcgatga gtttttctaa tcagaattgg ttaattggtt gtaacactgg  28740
cagagcatta cgctgacttg acgggacggc ggctttgttg aataaatcga acttttgctg  28800
agttgaagga tcagatcacg catcttcccg acaacgcaga ccgttccgtg gcaaagcaaa  28860
agttcaaaat caccaactgg tccacctaca acaaagctct catcaaccgt ggctccctca  28920
ctttctggct ggatgatggg gcgattcagg cctggtatga gtcagcaaca ccttcttcac  28980
gaggcagacc tcagcgccag aaggccgcca gagaggccga gcgcggccgt gaggcttgga  29040
cgctagggca gggcatgaaa aagcccgtag cgggctgcta cgggcgtctg acgcggtgga  29100
aagggggagg ggatgttgtc tacatggctc tgctgtagtg agtgggttgc gctccggcag  29160
cggtcctgat caatcgtcac cctttctcgg tccttcaacg ttcctgacaa cgagcctcct  29220
tttcgccaat ccatcgacaa tcaccgcgag tccctgctcg aacgctgcgt ccggaccggc  29280
ttcgtcgaag gcgtctatcg cggcccgcaa cagcggcgag agcggagcct gttcaacggt  29340
gccgccgcgc tcgccggcat cgctgtcgcc ggcctgctcc tcaagcacgg ccccaacagt  29400
gaagtagctg attgtcatca gcgcattgac ggcgtccccg gccgaaaaac ccgcctcgca  29460
gaggaagcga agctgcgcgt cggccgtttc catctgcggt gcgcccggtc gcgtgccggc  29520
atggatgcgc gcgccatcgc ggtaggcgag cagcgcctgc ctgaagctgc gggcattccc  29580
gatcagaaat gagcgccagt cgtcgtcggc tctcggcacc gaatgcgtat gattctccgc  29640
cagcatggct tcggccagtg cgtcgagcag cgcccgcttg ttcctgaagt gccagtaaag  29700
cgccggctgc tgaaccccca accgttccgc cagtttgcgt gtcgtcagac cgtctacgcc  29760
gacctcgttc aacaggtcca gggcggcacg gatcactgta ttcggctgca actttgtcat  29820
gcttgacact ttatcactga taaacataat atgtccacca acttatcagt gataaagaat  29880
ccgcgcgttc aatcggacca gcggaggctg gtccggaggc cagacgtgaa acccaacata  29940
cccctgatcg taattctgag cactgtcgcg ctcgacgctg tcggcatcgg cctgattatg  30000
ccggtgctgc cgggcctcct gcgcgatctg gttcactcga acgacgtcac cgcccactat  30060
ggcattctgc tggcgctgta tgcgttggtg caatttgcct gcgcacctgt gctgggcgcg  30120
ctgtcggatc gtttcgggcg gcggccaatc ttgctcgtct cgctggccgg cgccactgtc  30180
gactacgcca tcatggcgac agcgcctttc ctttgggttc tctatatcgg gcggatcgtg  30240
gccggcatca ccggggcgac tggggcggta gccggcgctt atattgccga tatcactgat  30300
ggcgatgagc gcgcgcggca cttcggcttc atgagcgcct gtttcgggtt cgggatggtc  30360
gcgggacctg tgctcggtgg gctgatgggc ggtttctccc cccacgctcc gttcttcgcc  30420
gcggcagcct tgaacggcct caatttcctg acgggctgtt tccttttgcc ggagtcgcac  30480
aaaggcgaac gccggccgtt acgccgggag gctctcaacc cgctcgcttc gttccggtgg  30540
gcccggggca tgaccgtcgt cgccgccctg atggcggtct tcttcatcat gcaacttgtc  30600
ggacaggtgc cggccgcgct ttgggtcatt ttcggcgagg atcgctttca ctgggacgcg  30660
```

```
accacgatcg gcatttcgct tgccgcattt ggcattctgc attcactcgc ccaggcaatg  30720
atcaccggcc ctgtagccgc ccggctcggc gaaaggcggg cactcatgct cggaatgatt  30780
gccgacggca caggctacat cctgcttgcc ttcgcgacac ggggatggat ggcgttcccg  30840
atcatggtcc tgcttgcttc gggtggcatc ggaatgccgg cgctgcaagc aatgttgtcc  30900
aggcaggtgg atgaggaacg tcaggggcag ctgcaaggct cactggcggc gctcaccagc  30960
ctgacctcga tcgtcggacc cctcctcttc acggcgatct atgcggcttc tataacaacg  31020
tggaacgggt gggcatggat tgcaggcgct gccctctact tgctctgcct gccggcgctg  31080
cgtcgcgggc tttggagcgg cgcagggcaa cgagccgatc gctgatcgtg gaaacgatag  31140
gcctatgcca tgcgggtcaa ggcgacttcc ggcaagctat acgcgcccta ggagtgcggt  31200
tggaacgttg gcccagccag atactcccga tcacgagcag gacgccgatg atttgaagcg  31260
cactcagcgt ctgatccaag aacaaccatc ctagcaacac ggcggtcccc gggctgagaa  31320
agcccagtaa ggaaacaact gtaggttcga gtcgcgagat cccccggaac caaaggaagt  31380
aggttaaacc cgctccgatc aggccgagcc acgccaggcc gagaacattg gttcctgtag  31440
gcatcgggat tggcggatca aacactaaag ctactggaac gagcagaagt cctccggccg  31500
ccagttgcca ggcggtaaag gtgagcagag gcacgggagg ttgccacttg cgggtcagca  31560
cggttccgaa cgccatggaa accgcccccg ccaggcccgc tgcgacgccg acaggatcta  31620
gcgctgcgtt tggtgtcaac accaacagcg ccacgcccgc agttccgcaa atagccccca  31680
ggaccgccat caatcgtatc gggctaccta gcagagcggc agagatgaac acgaccatca  31740
gcggctgcac agcgcctacc gtcgccgcga ccccgcccgg caggcggtag accgaaataa  31800
acaacaagct ccagaatagc gaaatattaa gtgcgccgag gatgaagatg cgcatccacc  31860
agattcccgt tggaatctgt cggacgatca tcacgagcaa taaacccgcc ggcaacgccc  31920
gcagcagcat accggcgacc cctcggcctc gctgttcggg ctccacgaaa acgccggaca  31980
gatgcgcctt gtgagcgtcc ttggggccgt cctcctgttt gaagaccgac agcccaatga  32040
tctcgccgtc gatgtaggcg ccgaatgcca cggcatctcg caaccgttca gcgaacgcct  32100
ccatgggctt tttctcctcg tgctcgtaaa cggacccgaa catctctgga gctttcttca  32160
gggccgacaa tcggatctcg cggaaatcct gcacgtcggc cgctccaagc cgtcgaatct  32220
gagccttaat cacaattgtc aattttaatc ctctgtttat cggcagttcg tagagcgcgc  32280
cgtgcgtccc gagcgatact gagcgaagca agtgcgtcga gcagtgcccg cttgttcctg  32340
aaatgccagt aaagcgctgg ctgctgaacc cccagccgga actgacccca caaggcccta  32400
gcgtttgcaa tgcaccaggt catcattgac ccaggcgtgt tccaccaggc cgctgcctcg  32460
caactcttcg caggcttcgc cgacctgctc gcgccacttc ttcacgcggg tggaatccga  32520
tccgcacatg aggcggaagg tttccagctt gagcgggtac ggctcccggt gcgagctgaa  32580
atagtcgaac atccgtcggg ccgtcggcga cagcttgcgg tacttctccc atatgaattt  32640
cgtgtagtgg tcgccagcaa acagcacgac gatttcctcg tcgatcagga cctggcaacg  32700
ggacgttttc ttgccacggt ccaggacgcg gaagcggtgc agcagcgaca ccgattccag  32760
gtgcccaacg cggtcggacg tgaagcccat cgccgtcgcc tgtaggcgcg acaggcattc  32820
ctcggccttc gtgtaatacc ggccattgat cgaccagccc aggtcctggc aaagctcgta  32880
gaacgtgaag gtgatcggct cgccgatagg ggtgcgcttc gcgtactcca acacctgctg  32940
ccacaccagt tcgtcatcgt cggcccgcag ctcgacgccg gtgtaggtga tcttcacgtc  33000
```

```
cttgttgacg tggaaaatga ccttgttttg cagcgcctcg cgcgggattt tcttgttgcg  33060
cgtggtgaac agggcagagc gggccgtgtc gtttggcatc gctcgcatcg tgtccggcca  33120
cggcgcaata tcgaacaagg aaagctgcat ttccttgatc tgctgcttcg tgtgtttcag  33180
caacgcggcc tgcttggcct cgctgacctg ttttgccagg tcctcgccgg cggtttttcg  33240
cttcttggtc gtcatagttc ctcgcgtgtc gatggtcatc gacttcgcca aacctgccgc  33300
ctcctgttcg agacgacgcg aacgctccac ggcggccgat ggcgcgggca gggcaggggg  33360
agccagttgc acgctgtcgc gctcgatctt ggccgtagct tgctggacca tcgagccgac  33420
ggactggaag gtttcgcggg gcgcacgcat gacggtgcgg cttgcgatgg tttcggcatc  33480
ctcggcggaa aaccccgcgt cgatcagttc ttgcctgtat gccttccggt caaacgtccg  33540
attcattcac cctccttgcg ggattgcccc gactcacgcc ggggcaatgt gcccttattc  33600
ctgatttgac ccgcctggtg ccttggtgtc cagataatcc accttatcgg caatgaagtc  33660
ggtcccgtag accgtctggc cgtccttctc gtacttggta ttccgaatct tgccctgcac  33720
gaataccagc gaccccttgc ccaaatactt gccgtgggcc tcggcctgag agccaaaaca  33780
cttgatgcgg aagaagtcgg tgcgctcctg cttgtcgccg gcatcgttgc gccactcttc  33840
attaaccgct atatcgaaaa ttgcttgcgg cttgttagaa ttgccatgac gtacctcggt  33900
gtcacgggta agattaccga taaactggaa ctgattatgg ctcatatcga aagtctcctt  33960
gagaaaggag actctagttt agctaaacat tggttccgct gtcaagaact ttagcggcta  34020
aaattttgcg ggccgcgacc aaaggtgcga ggggcggctt ccgctgtgta caaccagata  34080
tttttcacca acatccttcg tctgctcgat gagcggggca tgacgaaaca tgagctgtcg  34140
gagagggcag ggtttcaat ttcgtttttta tcagacttaa ccaacggtaa ggccaacccc  34200
tcgttgaagg tgatggaggc cattgccgac gccctggaaa ctcccctacc tcttctcctg  34260
gagtccaccg accttgaccg cgaggcactc gcggagattg cgggtcatcc tttcaagagc  34320
agcgtgccgc ccggatacga acgcatcagt gtggttttgc cgtcacataa ggcgtttatc  34380
gtaaagaaat ggggcgacga cacccgaaaa aagctgcgtg gaaggctctg acgccaaggg  34440
ttagggcttg cacttccttc tttagccgct aaaacggccc cttctctgcg ggccgtcggc  34500
tcgcgcatca tatcgacatc ctcaacggaa gccgtgccgc gaatggcatc gggcgggtgc  34560
gctttgacag ttgttttcta tcagaacccc tacgtcgtgc ggttcgatta gctgtttgtc  34620
ttgcaggcta aacactttcg gtatatcgtt tgcctgtgcg ataatgttgc taatgatttg  34680
ttgcgtaggg gttactgaaa agtgagcggg aaagaagagt ttcagaccat caaggagcgg  34740
gccaagcgca agctggaacg cgacatgggt gcggacctgt tggccgcgct caacgacccg  34800
aaaaccgttg aagtcatgct caacgcggac ggcaaggtgt ggcacgaacg ccttggcgag  34860
ccgatgcggt acatctgcga catgcggccc agccagtcgc aggcgattat agaaacggtg  34920
gccggattcc acggcaaaga ggtcacgcgg cattcgccca tcctggaagg cgagttcccc  34980
ttggatggca gccgctttgc cggccaattg ccgccggtcg tggccgcgcc aacctttgcg  35040
atccgcaagc gcgcggtcgc catcttcacg ctggaacagt acgtcgaggc gggcatcatg  35100
acccgcgagc aatacgaggt cattaaaagc gccgtcgcgg cgcatcgaaa catcctcgtc  35160
attggcggta ctggctcggg caagaccacg ctcgtcaacg cgatcatcaa tgaaatggtc  35220
gccttcaacc cgtctgagcg cgtcgtcatc atcgaggaca ccggcgaaat ccagtgcgcc  35280
gcagagaacg ccgtccaata ccacaccagc atcgacgtct cgatgacgct gctgctcaag  35340
acaacgctgc gtatgcgccc cgaccgcatc ctggtcggtg aggtacgtgg ccccgaagcc  35400
```

```
cttgatctgt tgatggcctg gaacaccggg catgaaggag gtgccgccac cctgcacgca  35460
aacaacccca aagcgggcct gagccggctc gccatgctta tcagcatgca cccggattca  35520
ccgaaaccca ttgagccgct gattggcgag gcggttcatg tggtcgtcca tatcgccagg  35580
acccctagcg gccgtcgagt gcaagaaatt ctcgaagttc ttggttacga gaacggccag  35640
tacatcacca aaaccctgta aggagtattt ccaatgacaa cggctgttcc gttccgtctg  35700
accatgaatc gcggcatttt gttctacctt gccgtgttct tcgttctcgc tctcgcgtta  35760
tccgcgcatc cggcgatggc ctcggaaggc accggcggca gcttgccata tgagagctgg  35820
ctgacgaacc tgcgcaactc cgtaaccggc ccggtggcct tcgcgctgtc catcatcggc  35880
atcgtcgtcg ccggcggcgt gctgatcttc ggcggcgaac tcaacgcctt cttccgaacc  35940
ctgatcttcc tggttctggt gatggcgctg ctggtcggcg cgcagaacgt gatgagcacc  36000
ttcttcggtc gtggtgccga aatcgcggcc ctcggcaacg gggcgctgca ccaggtgcaa  36060
gtcgcggcgg cggatgccgt gcgtgcggta gcggctggac ggctcgccta atcatggctc  36120
tgcgcacgat ccccatccgt cgcgcaggca accgagaaaa cctgttcatg ggtggtgatc  36180
gtgaactggt gatgttctcg ggcctgatgg cgtttgcgct gattttcagc gcccaagagc  36240
tgcgggccac cgtggtcggt ctgatcctgt ggttcggggc gctctatgcg ttccgaatca  36300
tggcgaaggc cgatccgaag atgcggttcg tgtacctgcg tcaccgccgg tacaagccgt  36360
attacccggc ccgctcgacc ccgttccgcg agaacaccaa tagccaaggg aagcaatacc  36420
gatgatccaa gcaattgcga ttgcaatcgc gggcctcggc gcgcttctgt tgttcatcct  36480
ctttgcccgc atccgcgcgg tcgatgccga actgaaactg aaaaagcatc gttccaagga  36540
cgccggcctg gccgatctgc tcaactacgc cgctgtcgtc gatgacggcg taatcgtggg  36600
caagaacggc agctttatgg ctgcctggct gtacaagggc gatgacaacg caagcagcac  36660
cgaccagcag cgcgaagtag tgtccgcccg catcaaccag gccctcgcgg gcctgggaag  36720
tgggtggatg atccatgtgg acgccgtgcg gcgtcctgct ccgaactacg cggagcgggg  36780
cctgtcggcg ttccctgacc gtctgacggc agcgattgaa gaagagcgct cggtcttgcc  36840
ttgctcgtcg gtgatgtact tcaccagctc cgcgaagtcg ctcttcttga tggagcgcat  36900
ggggacgtgc ttggcaatca cgcgcacccc ccggccgttt tagcggctaa aaaagtcatg  36960
gctctgccct cgggcggacc acgcccatca tgaccttgcc aagctcgtcc tgcttctctt  37020
cgatcttcgc cagcagggcg aggatcgtgg catcaccgaa ccgcgccgtg cgcgggtcgt  37080
cggtgagcca gagtttcagc aggccgccca ggcggcccag gtcgccattg atgcgggcca  37140
gctcgcggac gtgctcatag tccacgacgc ccgtgatttt gtagccctgg ccgacggcca  37200
gcaggtaggc cgacaggctc atgccggccg ccgccgcctt ttcctcaatc gctcttcgtt  37260
cgtctggaag gcagtacacc ttgataggtg ggctgccctt cctggttggc ttggtttcat  37320
cagccatccg cttgccctca tctgttacgc cggcggtagc cggccagcct cgcagagcag  37380
gattcccgtt gagcaccgcc aggtgcgaat aagggacagt gaagaaggaa cacccgctcg  37440
cgggtgggcc tacttcacct atcctgcccg gctgacgccg ttggatacac caaggaaagt  37500
ctacacgaac cctttggcaa aatcctgtat atcgtgcgaa aaaggatgga tataccgaaa  37560
aaatcgctat aatgaccccg aagcagggtt atgcagcgga aaagcgctgc ttccctgctg  37620
ttttgtggaa tatctaccga ctggaaacag gcaaatgcag gaaattactg aactgagggg  37680
acaggcgaga gacgatgcca aagagctaca ccgacgagct ggccgagtgg gttgaatccc  37740
```

```
gcgcggccaa gaagcgccgg cgtgatgagg ctgcggttgc gttcctggcg gtgagggcgg  37800
atgtcgaggc ggcgttagcg tccggctatg cgctcgtcac catttgggag cacatgcggg  37860
aaacggggaa ggtcaagttc tcctacgaga cgttccgctc gcacgccagg cggcacatca  37920
aggccaagcc cgccgatgtg cccgcaccgc aggccaaggc tgcggaaccc gcgccggcac  37980
ccaagacgcc ggagccacgg cggccgaagc agggggcaa ggctgaaaag ccggcccccg  38040
ctgcggcccc gaccggcttc accttcaacc caacaccgga caaaaaggat ctactgtaat  38100
ggcgaaaatt cacatggttt tgcagggcaa gggcggggtc ggcaagtcgg ccatcgccgc  38160
gatcattgcg cagtacaaga tggacaaggg gcagacaccc ttgtgcatcg acaccgaccc  38220
ggtgaacgcg acgttcgagg gctacaaggc cctgaacgtc cgccggctga acatcatggc  38280
cggcgacgaa attaactcgc gcaacttcga caccctggtc gagctgattg cgccgaccaa  38340
ggatgacgtg gtgatcgaca acggtgccag ctcgttcgtg cctctgtcgc attacctcat  38400
cagcaaccag gtgccggctc tgctgcaaga aatggggcat gagctggtca tccataccgt  38460
cgtcaccggc ggccaggctc tcctggacac ggtgagcggc ttcgcccagc tcgccagcca  38520
gttcccggcc gaagcgcttt tcgtggtctg gctgaacccg tattgggggc ctatcgagca  38580
tgagggcaag agctttgagc agatgaaggc gtacacggcc aacaaggccc gcgtgtcgtc  38640
catcatccag attccggccc tcaaggaaga aacctacggc cgcgatttca gcgacatgct  38700
gcaagagcgg ctgacgttcg accaggcgct ggccgatgaa tcgctcacga tcatgacgcg  38760
gcaacgcctc aagatcgtgc ggcgcggcct gtttgaacag ctcgacgcgg cggccgtgct  38820
atgagcgacc agattgaaga gctgatccgg gagattgcgg ccaagcacgg catcgccgtc  38880
ggccgcgacg acccggtgct gatcctgcat accatcaacg cccggctcat ggccgacagt  38940
gcggccaagc aagaggaaat ccttgccgcg ttcaaggaag agctggaagg gatcgcccat  39000
cgttggggcg aggacgccaa ggccaaagcg gagcggatgc tgaacgcggc cctggcggcc  39060
agcaaggacg caatggcgaa ggtaatgaag gacagcgccg cgcaggcggc cgaagcgatc  39120
cgcagggaaa tcgacgacgg ccttggccgc cagctcgcgg ccaaggtcgc ggacgcgcgg  39180
cgcgtggcga tgatgaacat gatcgccggc ggcatggtgt tgttcgcggc cgccctggtg  39240
gtgtgggcct cgttatgaat cgcagaggcg cagatgaaaa agcccggcgt tgccgggctt  39300
tgtttttgcg ttagctgggc ttgtttgaca ggcccaagct ctgactgcgc ccgcgctcgc  39360
gctcctgggc ctgtttcttc tcctgctcct gcttgcgcat cagggcctgg tgccgtcggg  39420
ctgcttcacg catcgaatcc cagtcgccgg ccagctcggg atgctccgcg cgcatcttgc  39480
gcgtcgccag ttcctcgatc ttgggcgcgt gaatgcccat gccttccttg atttcgcgca  39540
ccatgtccag ccgcgtgtgc agggtctgca agcgggcttg ctgttgggcc tgctgctgct  39600
gccaggcggc ctttgtacgc ggcagggaca gcaagccggg ggcattggac tgtagctgct  39660
gcaaacgcgc ctgctgacgg tctacgagct gttctaggcg gtcctcgatg cgctccacct  39720
ggtcatgctt tgcctgcacg tagagcgcaa gggtctgctg gtaggtctgc tcgatgggcg  39780
cggattctaa gagggcctgc tgttccgtct cggcctcctg ggccgcctgt agcaaatcct  39840
cgccgctgtt gccgctggac tgctttactg ccggggactg ctgttgccct gctcgcgccg  39900
tcgtcgcagt tcggcttgcc cccactcgat tgactgcttc atttcgagcc gcagcgatgc  39960
gatctcggat tgcgtcaacg gacggggcag cgcggaggtg tccggcttct ccttgggtga  40020
gtcggtcgat gccatagcca aaggtttcct tccaaaatgc gtccattgct ggaccgtgtt  40080
tctcattgat gcccgcaagc atcttcggct tgaccgccag gtcaagcgcg ccttcatggg  40140
```

```
cggtcatgac ggacgccgcc atgaccttgc cgccgttgtt ctcgatgtag ccgcgtaatg  40200
aggcaatggt gccgcccatc gtcagcgtgt catcgacaac gatgtacttc tggccgggga  40260
tcacctcccc ctcgaaagtc gggttgaacg ccaggcgatg atctgaaccg gctccggttc  40320
gggcgacctt ctcccgctgc acaatgtccg tttcgacctc aaggccaagg cggtcggcca  40380
gaacgaccgc catcatggcc ggaatcttgt tgttccccgc cgcctcgacg gcgaggactg  40440
gaacgatgcg gggcttgtcg tcgccgatca gcgtcttgag ctgggcaaca gtgtcgtccg  40500
aaatcaggcg ctcgaccaaa ttaagcgccg cttccgcgtc gccctgcttc gcagcctggt  40560
attcaggctc gttggtcaaa gaaccaaggt cgccgttgcg aaccaccttc gggaagtctc  40620
cccacggtgc gcgctcggct ctgctgtagc tgctcaagac gcctcccttt ttagccgcta  40680
aaactctaac gagtgcgccc gcgactcaac ttgacgcttt cggcacttac ctgtgccttg  40740
ccacttgcgt cataggtgat gcttttcgca ctcccgattt caggtacttt atcgaaatct  40800
gaccgggcgt gcattacaaa gttcttcccc acctgttggt aaatgctgcc gctatctgcg  40860
tggacgatgc tgccgtcgtg gcgctgcgac ttatcggcct tttgggccat atagatgttg  40920
taaatgccag gtttcagggc cccggcttta tctaccttct ggttcgtcca tgcgccttgg  40980
ttctcggtct ggacaattct ttgcccattc atgaccagga ggcggtgttt cattgggtga  41040
ctcctgacgg ttgcctctgg tgttaaacgt gtcctggtcg cttgccggct aaaaaaaagc  41100
cgacctcggc agttcgaggc cggctttccc tagagccggg cgcgtcaagg ttgttccatc  41160
tattttagtg aactgcgttc gatttatcag ttactttcct cccgctttgt gtttcctccc  41220
actcgtttcc gcgtctagcc gacccctcaa catagcggcc tcttcttggg ctgcctttgc  41280
ctcttgccgc gcttcgtcac gctcggcttg caccgtcgta aagcgctcgg cctgcctggc  41340
cgcctcttgc gccgccaact tcctttgctc ctggtgggcc tcggcgtcgg cctgcgcctt  41400
cgctttcacc gctgccaact ccgtgcgcaa actctccgct tcgcgcctgg tggcgtcgcg  41460
ctcgccgcga agcgcctgca tttcctggtt ggccgcgtcc agggtcttgc ggctctcttc  41520
tttgaatgcg cgggcgtcct ggtgagcgta gtccagctcg gcgcgcagct cctgcgctcg  41580
acgctccacc tcgtcggccc gctgcgtcgc cagcgcggcc cgctgctcgg ctcctgccag  41640
ggcggtgcgt gcttcggcca gggcttgccg ctggcgtgcg gccagctcgg ccgcctcggc  41700
ggcctgctgc tctagcaatg taacgcgcgc ctgggcttct tccagctcgc gggcctgcgc  41760
ctcgaaggcg tcggccagct ccccgcgcac ggcttccaac tcgttgcgct cacgatccca  41820
gccggcttgc gctgcctgca acgattcatt ggcaagggcc tgggcggctt gccagagggc  41880
ggccacggcc tggttgccgg cctgctgcac cgcgtccggc acctggactg ccagcggggc  41940
ggcctgcgcc gtgcgctggc gtcgccattc gcgcatgccg gcgctggcgt cgttcatgtt  42000
gacgcgggcg gccttacgca ctgcatccac ggtcgggaag ttctcccggt cgccttgctc  42060
gaacagctcg tccgcagccg caaaaatgcg gtcgcgcgtc tctttgttca gttccatgtt  42120
ggctccggta attggtaaga ataataatac tcttacctac cttatcagcg caagagttta  42180
gctgaacagt tctcgactta acggcaggtt ttttagcggc tgaagggcag gcaaaaaaag  42240
ccccgcacgg tcggcggggg caaagggtca gcgggaaggg gattagcggg cgtcgggctt  42300
cttcatgcgt cggggccgcg cttcttggga tggagcacga cgaagcgcgc acgcgcatcg  42360
tcctcggccc tatcggcccg cgtcgcggtc aggaacttgt cgcgcgctag gtcctccctg  42420
gtgggcacca ggggcatgaa ctcggcctgc tcgatgtagg tccactccat gaccgcatcg  42480
```

-continued

```
cagtcgaggc cgcgttcctt caccgtctct tgcaggtcgc ggtacgcccg ctcgttgagc  42540
ggctggtaac gggccaattg gtcgtaaatg gctgtcggcc atgagcggcc tttcctgttg  42600
agccagcagc cgacgacgaa gccggcaatg caggcccctg gcacaaccag gccgacgccg  42660
ggggcagggg atggcagcag ctcgccaacc aggaaccccg ccgcgatgat gccgatgccg  42720
gtcaaccagc ccttgaaact atccggcccc gaaacacccc tgcgcattgc ctggatgctg  42780
cgccggatag cttgcaacat caggagccgt ttcttttgtt cgtcagtcat ggtccgccct  42840
caccagttgt tcgtatcggt gtcggacgaa ctgaaatcgc aagagctgcc ggtatcggtc  42900
cagccgctgt ccgtgtcgct gctgccgaag cacggcgagg ggtccgcgaa cgccgcagac  42960
ggcgtatccg gccgcagcgc atcgcccagc atggccccgg tcagcgagcc gccggccagg  43020
tagcccagca tggtgctgtt ggtcgccccg gccaccaggg ccgacgtgac gaaatcgccg  43080
tcattccctc tggattgttc gctgctcggc ggggcagtgc gccgcgccgg cggcgtcgtg  43140
gatggctcgg gttggctggc ctgcgacggc cggcgaaagg tgcgcagcag ctcgttatcg  43200
accggctgcg gcgtcggggc cgccgccttg cgctgcggtc ggtgttcctt cttcggctcg  43260
cgcagcttga acagcatgat cgcggaaacc agcagcaacg ccgcgcctac gcctcccgcg  43320
atgtagaaca gcatcggatt cattcttcgg tcctccttgt agcggaaccg ttgtctgtgc  43380
ggcgcgggtg gcccgcgccg ctgtctttgg ggatcagccc tcgatgagcg cgaccagttt  43440
cacgtcggca aggttcgcct cgaactcctg gccgtcgtcc tcgtacttca accaggcata  43500
gccttccgcc ggcggccgac ggttgaggat aaggcgggca gggcgctcgt cgtgctcgac  43560
ctggacgatg gcctttttca gcttgtccgg gtccggctcc ttcgcgccct tttccttggc  43620
gtccttaccg tcctggtcgc cgtcctcgcc gtcctggccg tcgccggcct ccgcgtcacg  43680
ctcggcatca gtctggccgt tgaaggcatc gacggtgttg ggatcgcggc ccttctcgtc  43740
caggaactcg cgcagcagct tgaccgtgcc gcgcgtgatt tcctgggtgt cgtcgtcaag  43800
ccacgcctcg acttcctccg ggcgcttctt gaaggccgtc accagctcgt tcaccacggt  43860
cacgtcgcgc acgcggccgg tgttgaacgc atcggcgatc ttctccggca ggtccagcag  43920
cgtgacgtgc tgggtgatga acgccggcga cttgccgatt tccttggcga tatcgccttt  43980
cttcttgccc ttcgccagct cgcggccaat gaagtcggca atttcgcgcg gggtcagctc  44040
gttgcgttgc aggttctcga taacctggtc ggcttcgttg tagtcgttgt cgatgaacgc  44100
cgggatggac ttcttgccgg cccacttcga gccacggtag cggcgggcgc cgtgattgat  44160
gatatagcgg cccggctgct cctggttctc gcgcaccgaa atgggtgact tcaccccgcg  44220
ctctttgatc gtggcaccga tttccgcgat gctctccggg gaaaagccgg ggttgtcggc  44280
cgtccgcggc tgatgcggat cttcgtcgat caggtccagg tccagctcga tagggccgga  44340
accgccctga gacgccgcag gagcgtccag gaggctcgac aggtcgccga tgctatccaa  44400
ccccaggccg gacggctgcg ccgcgcctgc ggcttcctga gcggccgcag cggtgttttt  44460
cttggtggtc ttggcttgag ccgcagtcat tgggaaatct ccatcttcgt gaacacgtaa  44520
tcagccaggg cgcgaacctc tttcgatgcc ttgcgcgcgg ccgttttctt gatcttccag  44580
accggcacac cggatgcgag ggcatcggcg atgctgctgc gcaggccaac ggtggccgga  44640
atcatcatct tggggtacgc ggccagcagc tcggcttggt ggcgcgcgtg gcgcggattc  44700
cgcgcatcga ccttgctggg caccatgcca aggaattgca gcttggcgtt cttctggcgc  44760
acgttcgcaa tggtcgtgac catcttcttg atgccctgga tgctgtacgc ctcaagctcg  44820
atgggggaca gcacatagtc ggccgcgaag agggcggccg ccaggccgac gccaagggtc  44880
```

```
ggggccgtgt cgatcaggca cacgtcgaag ccttggttcg ccagggcctt gatgttcgcc  44940
ccgaacagct cgcgggcgtc gtccagcgac agccgttcgg cgttcgccag taccgggttg  45000
gactcgatga gggcgaggcg cgcggcctgg ccgtcgccgg ctgcgggtgc ggtttcggtc  45060
cagccgccgg cagggacagc gccgaacagc ttgcttgcat gcaggccggt agcaaagtcc  45120
ttgagcgtgt aggacgcatt gccctggggg tccaggtcga tcacggcaac ccgcaagccg  45180
cgctcgaaaa agtcgaaggc aagatgcaca agggtcgaag tcttgccgac gccgcctttc  45240
tggttggccg tgaccaaagt tttcatcgtt tggtttcctg ttttttcttg gcgtccgctt  45300
cccacttccg gacgatgtac gcctgatgtt ccggcagaac cgccgttacc cgcgcgtacc  45360
cctcgggcaa gttcttgtcc tcgaacgcgg cccacacgcg atgcaccgct tgcgacactg  45420
cgcccctggt cagtcccagc gacgttgcga acgtcgcctg tggcttccca tcgactaaga  45480
cgccccgcgc tatctcgatg gtctgctgcc ccacttccag cccctggatc gcctcctgga  45540
actggctttc ggtaagccgt ttcttcatgg ataacaccca taatttgctc cgcgccttgg  45600
ttgaacatag cggtgacagc cgccagcaca tgagagaagt ttagctaaac atttctcgca  45660
cgtcaacacc tttagccgct aaaactcgtc cttggcgtaa caaaacaaaa gcccggaaac  45720
cgggctttcg tctcttgccg cttatggctc tgcacccggc tccatcacca acaggtcgcg  45780
cacgcgcttc actcggttgc ggatcgacac tgccagccca acaaagccgg ttgccgccgc  45840
cgccaggatc gcgccgatga tgccggccac accggccatc gcccaccagg tcgccgcctt  45900
ccggttccat tcctgctggt actgcttcgc aatgctggac ctcggctcac cataggctga  45960
ccgctcgatg gcgtatgccg cttctcccct tggcgtaaaa cccagcgccg caggcggcat  46020
tgccatgctg cccgccgctt tcccgaccac gacgcgcgca ccaggcttgc ggtccagacc  46080
ttcggccacg gcgagctgcg caaggacata atcagccgcc gacttggctc cacgcgcctc  46140
gatcagctct tgcactcgcg cgaaatcctt ggcctccacg gccgccatga atcgcgcacg  46200
cggcgaaggc tccgcagggc cggcgtcgtg atcgccgccg agaatgccct tcaccaagtt  46260
cgacgacacg aaaatcatgc tgacggctat caccatcatg cagacggatc gcacgaaccc  46320
gctgaattga acacgagcac ggcacccgcg accactatgc caagaatgcc caaggtaaaa  46380
attgccggcc ccgccatgaa gtccgtgaat gccccgacgg ccgaagtgaa gggcaggccg  46440
ccacccaggc cgccgccctc actgcccggc acctggtcgc tgaatgtcga tgccagcacc  46500
tgcggcacgt caatgcttcc gggcgtcgcg ctcgggctga tcgcccatcc cgttactgcc  46560
ccgatcccgg caatggcaag gactgccagc gctgccattt ttggggtgag gccgttcgcg  46620
gccgaggggc gcagcccctg gggggatggg aggcccgcgt tagcgggccg ggagggttcg  46680
agaagggggg gcacccccct tcggcgtgcg cggtcacgcg cacagggcgc agccctggtt  46740
aaaaacaagg tttataaata ttggtttaaa agcaggttaa aagacaggtt agcggtggcc  46800
gaaaaacggg cggaaaccct tgcaaatgct ggattttctg cctgtggaca gcccctcaaa  46860
tgtcaatagg tgcgcccctc atctgtcagc actctgcccc tcaagtgtca aggatcgcgc  46920
ccctcatctg tcagtagtcg cgcccctcaa gtgtcaatac cgcagggcac ttatccccag  46980
gcttgtccac atcatctgtg ggaaactcgc gtaaaatcag gcgttttcgc cgatttgcga  47040
ggctggccag ctccacgtcg ccggccgaaa tcgagcctgc ccctcatctg tcaacgccgc  47100
gccgggtgag tcggcccctc aagtgtcaac gtccgcccct catctgtcag tgagggccaa  47160
gttttccgcg aggtatccac aacgccggcg gccgcggtgt ctcgcacacg gcttcgacgg  47220
```

```
cgtttctggc gcgtttgcag ggccatagac ggccgccagc ccagcggcga gggcaaccag  47280
cccggtgagc gtcggaaagg cgctggaagc cccgtagcga cgcggagagg ggcgagacaa  47340
gccaagggcg caggctcgat gcgcagcacg acatagccgg ttctcgcaag gacgagaatt  47400
tccctgcggt gcccctcaag tgtcaatgaa agtttccaac gcgagccatt cgcgagagcc  47460
ttgagtccac gctagatgag agctttgttg taggtggacc agttggtgat tttgaacttt  47520
tgctttgcca cggaacggtc tgcgttgtcg ggaagatgcg tgatctgatc cttcaactca  47580
gcaaaagttc gatttattca acaaagccac gttgtgtctc aaaatctctg atgttacatt  47640
gcacaagata aaaatatatc atcatgaaca ataaaactgt ctgcttacat aaacagtaat  47700
acaaggggtg ttatgagcca tattcaacgg gaaacgtctt gctcgac              47747
```

<210> SEQ ID NO 12
<211> LENGTH: 48474
<212> TYPE: DNA
<213> ORGANISM: artificial sequence
<220> FEATURE:
<223> OTHER INFORMATION: PHP16975 ZmCAS1BamPro:GUS/35SPAT

<400> SEQUENCE: 12

```
tctagagctc gttcctcgag gaacggtacc tgcggggaag cttacaataa tgtgtgttgt     60
taagtcttgt tgcctgtcat cgtctgactg actttcgtca taaatcccgg cctccgtaac    120
ccagctttgg gcaagctcac ggatttgatc cggcggaacg ggaatatcga gatgccgggc    180
tgaacgctgc agttccagct ttccctttcg ggacaggtac tccagctgat tgattatctg    240
ctgaagggtc ttggttccac ctcctggcac aatgcgaatg attacttgag cgcgatcggg    300
catccaattt tctcccgtca ggtgcgtggt caagtgctac aaggcacctt tcagtaacga    360
gcgaccgtcg atccgtcgcc gggatacgga caaaatggag cgcagtagtc catcgagggc    420
ggcgaaagcc tcgccaaaag caatacgttc atctcgcaca gcctccagat ccgatcgagg    480
gtcttcggcg taggcagata gaagcatgga tacattgctt gagagtattc cgatggactg    540
aagtatggct tccatctttt ctcgtgtgtc tgcatctatt tcgagaaagc cccgatgcg     600
gcgcaccgca acgcgaattg ccatactatc cgaaagtccc agcaggcgcg cttgatagga    660
aaaggtttca tactcggccg atcgcagacg ggcactcacg accttgaacc cttcaacttt    720
cagggatcga tgctggttga tggtagtctc actcgacgtg gctctggtgt gttttgacat    780
agcttcctcc aaagaaagcg gaaggtctgg atactccagc acgaaatgtg cccgggtaga    840
cggatggaag tctagccctg ctcaatatga aatcaacagt acatttacag tcaatactga    900
atatacttgc tacatttgca attgtcttat aacgaatgtg aaataaaaat agtgtaacaa    960
cgcttttact catcgataat cacaaaaaca tttatacgaa caaaaataca aatgcactcc   1020
ggtttcacag gataggcggg atcagaatat gcaacttttg acgttttgtt ctttcaaagg   1080
gggtgctggc aaaaccaccg cactcatggg cctttgcgct gctttggcaa atgacggtaa   1140
acgagtggcc ctctttgatg ccgacgaaaa ccggcctctg acgcgatgga gagaaaacgc   1200
cttacaaagc agtactggga tcctcgctgt gaagtctatt ccgccgacga aatgcccctt   1260
cttgaagcag cctatgaaaa tgccgagctc gaaggatttg attatgcgtt ggccgatacg   1320
cgtggcggct cgagcgagct caacaacaca atcatcgcta gctcaaacct gcttctgatc   1380
cccaccatgc taacgccgct cgacatcgat gaggcactat ctacctaccg ctacgtcatc   1440
gagctgctgt tgagtgaaaa tttggcaatt cctacagctg ttttgcgcca acgcgtcccg   1500
gtcggccgat tgacaacatc gcaacgcagg atgtcagaga cgctagagag ccttccagtt   1560
```

```
gtaccgtctc ccatgcatga aagagatgca tttgccgcga tgaaagaacg cggcatgttg   1620
catcttacat tactaaacac gggaactgat ccgacgatgc gcctcataga gaggaatctt   1680
cggattgcga tggaggaagt cgtggtcatt tcgaaactga tcagcaaaat cttggaggct   1740
tgaagatggc aattcgcaag cccgcattgt cggtcggcga agcacggcgg cttgctggtg   1800
ctcgacccga gatccaccat cccaacccga cacttgttcc ccagaagctg gacctccagc   1860
acttgcctga aaaagccgac gagaaagacc agcaacgtga gcctctcgtc gccgatcaca   1920
tttacagtcc cgatcgacaa cttaagctaa ctgtggatgc ccttagtcca cctccgtccc   1980
cgaaaaagct ccaggttttt ctttcagcgc gaccgcccgc gcctcaagtg tcgaaaacat   2040
atgacaacct cgttcggcaa tacagtccct cgaagtcgct acaaatgatt ttaaggcgcg   2100
cgttggacga tttcgaaagc atgctggcag atggatcatt tcgcgtggcc ccgaaaagtt   2160
atccgatccc ttcaactaca gaaaaatccg ttctcgttca gacctcacgc atgttcccgg   2220
ttgcgttgct cgaggtcgct cgaagtcatt ttgatccgtt ggggttggag accgctcgag   2280
ctttcggcca caagctggct accgccgcgc tcgcgtcatt ctttgctgga gagaagccat   2340
cgagcaattg gtgaagaggg acctatcgga acccctcacc aaatattgag tgtaggtttg   2400
aggccgctgg ccgcgtcctc agtcaccttt tgagccagat aattaagagc caaatgcaat   2460
tggctcaggc tgccatcgtc cccccgtgcg aaacctgcac gtccgcgtca aagaaataac   2520
cggcacctct tgctgttttt atcagttgag ggcttgacgg atccgcctca agtttgcggc   2580
gcagccgcaa aatgagaaca tctatactcc tgtcgtaaac ctcctcgtcg cgtactcgac   2640
tggcaatgag aagttgctcg cgcgatagaa cgtcgcgggg tttctctaaa aacgcgagga   2700
gaagattgaa ctcacctgcc gtaagtttca cctcaccgcc agcttcggac atcaagcgac   2760
gttgcctgag attaagtgtc cagtcagtaa aacaaaaaga ccgtcggtct ttggagcgga   2820
caacgttggg gcgcacgcgc aaggcaaccc gaatgcgtgc aagaaactct ctcgtactaa   2880
acggcttagc gataaaatca cttgctccta gctcgagtgc aacaacttta tccgtctcct   2940
caaggcggtc gccactgata attatgattg gaatatcaga ctttgccgcc agatttcgaa   3000
cgatctcaag cccatcttca cgacctaaat ttagatcaac aaccacgaca tcgaccgtcg   3060
cggaagagag tactctagtg aactgggtgc tgtcggctac cgcggtcact ttgaaggcgt   3120
ggatcgtaag gtattcgata ataagatgcc gcatagcgac atcgtcatcg ataagaagaa   3180
cgtgtttcaa cggctcacct ttcaatctaa aatctgaacc cttgttcaca gcgcttgaga   3240
aattttcacg tgaaggatgt acaatcatct ccagctaaat gggcagttcg tcagaattgc   3300
ggctgaccgc ggatgacgaa aatgcgaacc aagtatttca attttatgac aaaagttctc   3360
aatcgttgtt acaagtgaaa cgcttcgagg ttacagctac tattgattaa ggagatcgcc   3420
tatggtctcg ccccggcgtc gtgcgtccgc cgcgagccag atctcgccta cttcataaac   3480
gtcctcatag gcacggaatg gaatgatgac atcgatcgcc gtagagagca tgtcaatcag   3540
tgtgcgatct tccaagctag caccttgggc gctacttttg acaagggaaa acagtttctt   3600
gaatccttgg attggattcg cgccgtgtat tgttgaaatc gatcccggat gtcccgagac   3660
gacttcactc agataagccc atgctgcatc gtcgcgcatc tcgccaagca atatccggtc   3720
cggccgcata cgcagacttg cttggagcaa gtgctcggcg ctcacagcac ccagcccagc   3780
accgttcttg gagtagagta gtctaacatg attatcgtgt ggaatgacga gttcgagcgt   3840
atcttctatg gtgattagcc tttcctgggg ggggatggcg ctgatcaagg tcttgctcat   3900
```

-continued

```
tgttgtcttg ccgcttccgg tagggccaca tagcaacatc gtcagtcggc tgacgacgca   3960
tgcgtgcaga aacgcttcca aatccccgtt gtcaaaatgc tgaaggatag cttcatcatc   4020
ctgattttgg cgtttccttc gtgtctgcca ctggttccac ctcgaagcat cataacggga   4080
ggagacttct ttaagaccag aaacacgcga gcttggccgt cgaatggtca agctgacggt   4140
gcccgaggga acggtcggcg gcagacagat ttgtagtcgt tcaccaccag gaagttcagt   4200
ggcgcagagg gggttacgtg gtccgacatc ctgctttctc agcgcgcccg ctaaaatagc   4260
gatatcttca agatcatcat aagagacggg caaaggcatc ttggtaaaaa tgccggcttg   4320
gcgcacaaat gcctctccag gtcgattgat cgcaatttct tcagtcttcg ggtcatcgag   4380
ccattccaaa atcggcttca gaagaaagcg tagttgcgga tccacttcca tttacaatgt   4440
atcctatctc taagcggaaa tttgaattca ttaagagcgg cggttcctcc cccgcgtggc   4500
gccgccagtc aggcggagct ggtaaacacc aaagaaatcg aggtcccgtg ctacgaaaat   4560
ggaaacggtg tcaccctgat tcttcttcag ggttggcggt atgttgatgg ttgccttaag   4620
ggctgtctca gttgtctgct caccgttatt ttgaaagctg ttgaagctca tcccgccacc   4680
cgagctgccg gcgtaggtgc tagctgcctg gaaggcgcct tgaacaacac tcaagagcat   4740
agctccgcta aaacgctgcc agaagtggct gtcgaccgag cccggcaatc ctgagcgacc   4800
gagttcgtcc gcgcttggcg atgttaacga gatcatcgca tggtcaggtg tctcggcgcg   4860
atcccacaac acaaaaacgc gcccatctcc ctgttgcaag ccacgctgta tttcgccaac   4920
aacggtggtg ccacgatcaa gaagcacgat attgttcgtt gttccacgaa tatcctgagg   4980
caagacacac tttacatagc ctgccaaatt tgtgtcgatt gcggtttgca agatgcacgg   5040
aattattgtc ccttgcgtta ccataaaatc ggggtgcggc aagagcgtgg cgctgctggg   5100
ctgcagctcg gtgggtttca tacgtatcga caaatcgttc tcgccggaca cttcgccatt   5160
cggcaaggag ttgtcgtcac gcttgccttc ttgtcttcgg cccgtgtcgc cctgaatggc   5220
gcgtttgctg accccttgat cgccgctgct atatgcaaaa atcggtgttt cttccggccg   5280
tggctcatgc cgctccggtt cgcccctcgg cggtagagga gcagcaggct gaacagcctc   5340
ttgaaccgct ggaggatccg gcggcacctc aatcggagct ggatgaaatg gcttggtgtt   5400
tgttgcgatc aaagttgacg gcgatgcgtt ctcattcacc ttcttttggc gcccacctag   5460
ccaaatgagg cttaatgata acgcgagaac gacacctccg acgatcaatt tctgagaccc   5520
cgaaagacgc cggcgatgtt tgtcggagac cagggatcca gatgcatcaa cctcatgtgc   5580
cgcttgctga ctatcgttat tcatcccttc gccccccttca ggacgcgttt cacatcgggc   5640
ctcaccgtgc ccgtttgcgg cctttggcca acgggatcgt aagcggtgtt ccagatacat   5700
agtactgtgt ggccatccct cagacgccaa cctcgggaaa ccgaagaaat ctcgacatcg   5760
ctccctttaa ctgaatagtt ggcaacagct tccttgccat caggattgat ggtgtagatg   5820
gagggtatgc gtacattgcc cggaaagtgg aataccgtcg taaatccatt gtcgaagact   5880
tcgagtggca acagcgaacg atcgccttgg gcgacgtagt gccaattact gtccgccgca   5940
ccaagggctg tgacaggctg atccaataaa ttctcagctt tccgttgata ttgtgcttcc   6000
gcgtgtagtc tgtccacaac agccttctgt tgtgcctccc ttcgccgagc cgccgcatcg   6060
tcggcggggt aggcgaattg gacgctgtaa tagagatcgg gctgctcttt atcgaggtgg   6120
gacagagtct tggaacttat actgaaaaca taacggcgca tcccggagtc gcttgcggtt   6180
agcacgatta ctggctgagg cgtgaggacc tggcttgcct tgaaaaatag ataatttccc   6240
cgcggtaggg ctgctagatc tttgctattt gaaacggcaa ccgctgtcac cgtttcgttc   6300
```

```
gtggcgaatg ttacgaccaa agtagctcca accgccgtcg agaggcgcac cacttgatcg   6360
ggattgtaag ccaaataacg catgcgcgga tctagcttgc ccgccattgg agtgtcttca   6420
gcctccgcac cagtcgcagc ggcaaataaa catgctaaaa tgaaaagtgc ttttctgatc   6480
atggttcgct gtggcctacg tttgaaacgg tatcttccga tgtctgatag gaggtgacaa   6540
ccagacctgc cgggttggtt agtctcaatc tgccgggcaa gctggtcacc ttttcgtagc   6600
gaactgtcgc ggtccacgta ctcaccacag gcattttgcc gtcaacgacg agggtccttt   6660
tatagcgaat ttgctgcgtg cttggagtta catcatttga agcgatgtgc tcgacctcca   6720
ccctgccgcg tttgccaaga atgacttgag gcgaactggg attgggatag ttgaagaatt   6780
gctggtaatc ctggcgcact gttggggcac tgaagttcga taccaggtcg taggcgtact   6840
gagcggtgtc ggcatcataa ctctcgcgca ggcgaacgta ctcccacaat gaggcgttaa   6900
cgacggcctc ctcttgagtt gcaggcaatc gcgagacaga cacctcgctg tcaacggtgc   6960
cgtccggccg tatccataga tatacgggca caagcctgct caacggcacc attgtggcta   7020
tagcgaacgc ttgagcaaca tttcccaaaa tcgcgatagc tgcgacagct gcaatgagtt   7080
tggagagacg tcgcgccgat ttcgctcgcg cggtttgaaa ggcttctact tccttatagt   7140
gctcggcaag gctttcgcgc gccactagca tggcatattc aggccccgtc atagcgtcca   7200
cccgaattgc cgagctgaag atctgacgga gtaggctgcc atcgccccac attcagcggg   7260
aagatcgggc ctttgcagct cgctaatgtg tcgtttgtct ggcagccgct caaagcgaca   7320
actaggcaca gcaggcaata cttcatagaa ttctccattg aggcgaattt ttgcgcgacc   7380
tagcctcgct caacctgagc gaagcgacgg tacaagctgc tggcagattg ggttgcgccg   7440
ctccagtaac tgcctccaat gttgccggcg atcgccggca aagcgacaat gagcgcatcc   7500
cctgtcagaa aaaacatatc gagttcgtaa agaccaatga tcttggccgc ggtcgtaccg   7560
gcgaaggtga ttacaccaag cataagggtg agcgcagtcg cttcggttag gatgacgatc   7620
gttgccacga ggtttaagag gagaagcaag agaccgtagg tgataagttg cccgatccac   7680
ttagctgcga tgtcccgcgt gcgatcaaaa atatatccga cgaggatcag aggcccgatc   7740
gcgagaagca ctttcgtgag aattccaacg gcgtcgtaaa ctccgaaggc agaccagagc   7800
gtgccgtaaa ggacccactg tgccccttgg aaagcaagga tgtcctggtc gttcatcgga   7860
ccgatttcgg atgcgatttt ctgaaaaacg gcctgggtca cggcgaacat tgtatccaac   7920
tgtgccggaa cagtctgcag aggcaagccg gttacactaa actgctgaac aaagtttggg   7980
accgtctttt cgaagatgga aaccacatag tcttggtagt tagcctgccc aacaattaga   8040
gcaacaacga tggtgaccgt gatcacccga gtgataccgc tacgggtatc gacttcgccg   8100
cgtatgacta aaataccctg aacaataatc caaagagtga cacaggcgat caatggcgca   8160
ctcaccgcct cctggatagt ctcaagcatc gagtccaagc ctgtcgtgaa ggctacatcg   8220
aagatcgtat gaatggccgt aaacggcgcc ggaatcgtga aattcatcga ttggacctga   8280
acttgactgg tttgtcgcat aatgttggat aaaatgagct cgcattcggc gaggatgcgg   8340
gcggatgaac aaatcgccca gccttagggg agggcaccaa agatgacagc ggtcttttga   8400
tgctccttgc gttgagcggc cgcctcttcc gcctcgtgaa ggccggcctg cgcggtagtc   8460
atcgttaata ggcttgtcgc ctgtacattt tgaatcattg cgtcatggat ctgcttgaga   8520
agcaaaccat tggtcacggt tgcctgcatg atattgcgag atcgggaaag ctgagcagac   8580
gtatcagcat tcgccgtcaa gcgtttgtcc atcgtttcca gattgtcagc cgcaatgcca   8640
```

```
gcgctgtttg cggaaccggt gatctgcgat cgcaacaggt ccgcttcagc atcactaccc   8700
acgactgcac gatctgtatc gctggtgatc gcacgtgccg tggtcgacat tggcattcgc   8760
ggcgaaaaca tttcattgtc taggtccttc gtcgaaggat actgattttt ctggttgagc   8820
gaagtcagta gtccagtaac gccgtaggcc gacgtcaaca tcgtaaccat cgctatagtc   8880
tgagtgagat tctccgcagt cgcgagcgca gtcgcgagcg tctcagcctc cgttgccggg   8940
tcgctaacaa caaactgcgc ccgcgcgggc tgaatatata gaaagctgca ggtcaaaact   9000
gttgcaataa gttgcgtcgt cttcatcgtt tcctacctta tcaatcttct gcctcgtggt   9060
gacgggccat gaattcgctg agccagccag atgagttgcc ttcttgtgcc tcgcgtagtc   9120
gagttgcaaa gcgcaccgtg ttggcacgcc ccgaaagcac ggcgacatat tcacgcatat   9180
cccgcagatc aaattcgcag atgacgcttc cactttctcg tttaagaaga aacttacggc   9240
tgccgaccgt catgtcttca cggatcgcct gaaattcctt ttcggtacat ttcagtccat   9300
cgacataagc cgatcgatct gcggttggtg atggatagaa aatcttcgtc atacattgcg   9360
caaccaagct ggctcctagc ggcgattcca gaacatgctc tggttgctgc gttgccagta   9420
ttagcatccc gttgtttttt cgaacggtca ggaggaattt gtcgacgaca gtcgaaaatt   9480
tagggtttaa caaataggcg cgaaactcat cgcagctcat cacaaaacgg cggccgtcga   9540
tcatggctcc aatccgatgc aggagatatg ctgcagcggg agcgcatact tcctcgtatt   9600
cgagaagatg cgtcatgtcg aagccggtaa tcgacggatc taactttact tcgtcaactt   9660
cgccgtcaaa tgcccagcca agcgcatggc ccggcacca gcgttggagc cgcgctcctg   9720
cgccttcggc gggcccatgc aacaaaaatt cacgtaaccc cgcgattgaa cgcatttgtg   9780
gatcaaacga gagctgacga tggataccac ggaccagacg gcggttctct tccggagaaa   9840
tcccaccccg accatcactc tcgatgagag ccacgatcca ttcgcgcaga aaatcgtgtg   9900
aggctgctgt gttttctagg ccacgcaacg gcgccaaccc gctgggtgtg cctctgtgaa   9960
gtgccaaata tgttcctcct gtggcgcgaa ccagcaattc gccaccccgg tccttgtcaa  10020
agaacacgac cgtacctgca cggtcgacca tgctctgttc gagcatggct agaacaaaca  10080
tcatgagcgt cgtcttaccc ctcccgatag gcccgaatat tgccgtcatg ccaacatcgt  10140
gctcatgcgg gatatagtcg aaaggcgttc cgccattggt acgaaatcgg gcaatcgcgt  10200
tgccccagtg gcctgagctg gcgccctctg gaaagttttc gaaagagaca aaccctgcga  10260
aattgcgtga agtgattgcg ccagggcgtg tgcgccactt aaaattcccc ggcaattggg  10320
accaataggc cgcttccata ccaatacctt cttggacaac cacggcacct gcatccgcca  10380
ttcgtgtccg agcccgcgcg cccctgtccc caagactatt gagatcgtct gcatagacgc  10440
aaaggctcaa atgatgtgag cccataacga attcgttgct cgcaagtgcg tcctcagcct  10500
cggataattt gccgatttga gtcacggctt tatcgccgga actcagcatc tggctcgatt  10560
tgaggctaag tttcgcgtgc gcttgcgggc gagtcaggaa cgaaaaactc tgcgtgagaa  10620
caagtggaaa atcgagggat agcagcgcgt tgagcatgcc cggccgtgtt tttgcagggt  10680
attcgcgaaa cgaatagatg gatccaacgt aactgtcttt tggcgttctg atctcgagtc  10740
ctcgcttgcc gcaaatgact ctgtcggtat aaatcgaagc gccgagtgag ccgctgacga  10800
ccggaaccgg tgtgaaccga ccagtcatga tcaaccgtag cgcttcgcca atttcggtga  10860
agagcacacc ctgcttctcg cggatgccaa gacgatgcag gccatacgct ttaagagagc  10920
cagcgacaac atgccaaaga tcttccatgt tcctgatctg gcccgtgaga tcgttttccc  10980
tttttccgct tagcttggtg aacctcctct ttaccttccc taaagccgcc tgtgggtaga  11040
```

```
caatcaacgt aaggaagtgt tcattgcgga ggagttggcc ggagagcacg cgctgttcaa  11100
aagcttcgtt caggctagcg gcgaaaacac tacggaagtg tcgcggcgcc gatgatggca  11160
cgtcggcatg acgtacgagg tgagcatata ttgacacatg atcatcagcg atattgcgca  11220
acagcgtgtt gaacgcacga caacgcgcat tgcgcatttc agtttcctca agctcgaatg  11280
caacgccatc aattctcgca atggtcatga tcgatccgtc ttcaagaagg acgatatggt  11340
cgctgaggtg gccaatataa gggagataga tctcaccgga tctttcggtc gttccactcg  11400
cgccgagcat cacaccattc ctctccctcg tgggggaacc ctaattggat ttgggctaac  11460
agtagcgccc ccccaaactg cactatcaat gcttcttccc gcggtccgca aaaatagcag  11520
gacgacgctc gccgcattgt agtctcgctc cacgatgagc cgggctgcaa accataacgg  11580
cacgagaacg acttcgtaga gcgggttctg aacgataacg atgacaaagc cggcgaacat  11640
catgaataac cctgccaatg tcagtggcac cccaagaaac aatgcgggcc gtgtggctgc  11700
gaggtaaagg gtcgattctt ccaaacgatc agccatcaac taccgccagt gagcgtttgg  11760
ccgaggaagc tcgccccaaa catgataaca atgccgccga cgacgccggc aaccagccca  11820
agcgaagccc gcccgaacat ccaggagatc ccgatagcga caatgccgag aacagcgagt  11880
gactggccga acggaccaag gataaacgtg catatattgt taaccattgt ggcggggtca  11940
gtgccgccac ccgcagattg cgctgcggcg ggtccggatg aggaaatgct ccatgcaatt  12000
gcaccgcaca agcttggggc gcagctcgat atcacgcgca tcatcgcatt cgagagcgag  12060
aggcgattta gatgtaaacg gtatctctca aagcatcgca tcaatgcgca cctccttagt  12120
ataagtcgaa taagacttga ttgtcgtctg cggatttgcc gttgtcctgg tgtggcggtg  12180
gcggagcgat taaaccgcca gcgccatcct cctgcgagcg gcgctgatat gacccccaaa  12240
catcccacgt ctcttcggat tttagcgcct cgtgatcgtc ttttggaggc tcgattaacg  12300
cgggcaccag cgattgagca gctgtttcaa cttttcgcac gtagccgttt gcaaaaccgc  12360
cgatgaaatt accggtgttg taagcggaga tcgcccgacg aagcgcaaat tgcttctcgt  12420
caatcgtttc gccgcctgca taacgacttt tcagcatgtt tgcagcggca gataatgatg  12480
tgcacgcctg gagcgcaccg tcaggtgtca gaccgagcat agaaaaattt cgagagttta  12540
tttgcatgag gccaacatcc agcgaatgcc gtgcatcgag acggtgcctg acgacttggg  12600
ttgcttggct gtgatcttgc cagtgaagcg tttcgccggt cgtgttgtca tgaatcgcta  12660
aaggatcaaa gcgactctcc accttagcta tcgccgcaag cgtagatgtc gcaactgatg  12720
gggcacactt gcgagcaaca tggtcaaact cagcagatga gagtggcgtg gcaaggctcg  12780
acgaacagaa ggagaccatc aaggcaagag aaagcgaccc cgatctctta agcatacctt  12840
atctccttag ctcgcaacta acaccgcctc tcccgttgga agaagtgcgt tgttttatgt  12900
tgaagattat cgggagggtc ggttactcga aaattttcaa ttgcttcttt atgatttcaa  12960
ttgaagcgag aaacctcgcc cggcgtcttg gaacgcaaca tggaccgaga accgcgcatc  13020
catgactaag caaccggatc gacctattca ggccgcagtt ggtcaggtca ggctcagaac  13080
gaaaatgctc ggcgaggtta cgctgtctgt aaacccattc gatgaacggg aagcttcctt  13140
ccgattgctc ttggcaggaa tattggccca tgcctgcttg cgctttgcaa atgctcttat  13200
cgcgttggta tcatatgcct tgtccgccag cagaaacgca ctctaagcga ttatttgtaa  13260
aaatgtttcg gtcatgcggc ggtcatgggc ttgacccgct gtcagcgcaa gacggatcgg  13320
tcaaccgtcg gcatcgacaa cagcgtgaat cttggtggtc aaaccgccac gggaacgtcc  13380
```

```
catacagcca tcgtcttgat cccgctgttt cccgtcgccg catgttggtg gacgcggaca  13440
caggaactgt caatcatgac gacattctat cgaaagcctt ggaaatcaca ctcagaatat  13500
gatcccagac gtctgcctca cgccatcgta caaagcgatt gtagcaggtt gtacaggaac  13560
cgtatcgatc aggaacgtct gcccagggcg ggcccgtccg gaagcgccac aagatgacat  13620
tgatcacccg cgtcaacgcg cggcacgcga cgcggcttat ttgggaacaa aggactgaac  13680
aacagtccat tcgaaatcgg tgacatcaaa gcggggacgg gttatcagtg gcctccaagt  13740
caagcctcaa tgaatcaaaa tcagaccgat ttgcaaacct gatttatgag tgtgcggcct  13800
aaatgatgaa atcgtccttc tagatcgcct ccgtggtgta gcaacacctc gcagtatcgc  13860
cgtgctgacc ttggccaggg aattgactgg caagggtgct ttcacatgac cgctcttttg  13920
gccgcgatag atgatttcgt tgctgctttg ggcacgtaga aggagagaag tcatatcgga  13980
gaaattcctc ctggcgcgag agcctgctct atcgcgacgg catcccactg tcgggaacag  14040
accggatcat tcacgaggcg aaagtcgtca acacatgcgt tataggcatc ttcccttgaa  14100
ggatgatctt gttgctgcca atctggaggt gcggcagccg caggcagatg cgatctcagc  14160
gcaacttgcg gcaaaacatc tcactcacct gaaaaccact agcgagtctc gcgatcagac  14220
gaaggccttt tacttaacga cacaatatcc gatgtctgca tcacaggcgt cgctatccca  14280
gtcaatacta aagcggtgca ggaactaaag attactgatg acttaggcgt gccacgaggc  14340
ctgagacgac gcgcgtagac agtttttga aatcattatc aaagtgatgg cctccgctga  14400
agcctatcac ctctgcgccg gtctgtcgga gagatgggca agcattatta cggtcttcgc  14460
gcccgtacat gcattggacg attgcagggt caatggatct gagatcatcc agaggattgc  14520
cgcccttacc ttccgtttcg agttggagcc agcccctaaa tgagacgaca tagtcgactt  14580
gatgtgacaa tgccaagaga gagatttgct taacccgatt tttttgctca agcgtaagcc  14640
tattgaagct tgccggcatg acgtccgcgc cgaaagaata tcctacaagt aaaacattct  14700
gcacaccgaa atgcttggtg tagacatcga ttatgtgacc aagatcctta gcagtttcgc  14760
ttggggaccg ctccgaccag aaataccgaa gtgaactgac gccaatgaca ggaatccctt  14820
ccgtctgcag ataggtacca tcgatagatc tgctgcctcg cgcgtttcgg tgatgacggt  14880
gaaaacctct gacacatgca gctcccggag acggtcacag cttgtctgta agcggatgcc  14940
gggagcagac aagcccgtca gggcgcgtca gcgggtgttg gcgggtgtcg gggcgcagcc  15000
atgacccagt cacgtagcga tagcggagtg tatactggct taactatgcg gcatcagagc  15060
agattgtact gagagtgcac catatgcggt gtgaaatacc gcacagatgc gtaaggagaa  15120
aataccgcat caggcgctct tccgcttcct cgctcactga ctcgctgcgc tcggtcgttc  15180
ggctgcggcg agcggtatca gctcactcaa aggcggtaat acggttatcc acagaatcag  15240
gggataacgc aggaaagaac atgtgagcaa aaggccagca aaaggccagg aaccgtaaaa  15300
aggccgcgtt gctggcgttt ttccataggc tccgcccccc tgacgagcat cacaaaaatc  15360
gacgctcaag tcagaggtgg cgaaacccga caggactata aagataccag gcgtttcccc  15420
ctggaagctc cctcgtgcgc tctcctgttc cgaccctgcc gcttaccgga tacctgtccg  15480
cctttctccc ttcgggaagc gtggcgcttt ctcatagctc acgctgtagg tatctcagtt  15540
cggtgtaggt cgttcgctcc aagctgggct gtgtgcacga accccccgtt cagcccgacc  15600
gctgcgcctt atccggtaac tatcgtcttg agtccaaccc ggtaagacac gacttatcgc  15660
cactggcagc agccactggt aacaggatta gcagagcgag gtatgtaggc ggtgctacag  15720
agttcttgaa gtggtggcct aactacggct acactagaag gacagtattt ggtatctgcg  15780
```

```
ctctgctgaa gccagttacc ttcggaaaaa gagttggtag ctcttgatcc ggcaaacaaa  15840
ccaccgctgg tagcggtggt ttttttgttt gcaagcagca gattacgcgc agaaaaaaag  15900
gatctcaaga agatcctttg atcttttcta cggggtctga cgctcagtgg aacgaaaact  15960
cacgttaagg gattttggtc atgagattat caaaaaggat cttcacctag atccttttaa  16020
attaaaaatg aagttttaaa tcaatctaaa gtatatatga gtaaacttgg tctgacagtt  16080
accaatgctt aatcagtgag gcacctatct cagcgatctg tctatttcgt tcatccatag  16140
ttgcctgact ccccgtcgtg tagataacta cgatacggga gggcttacca tctggcccca  16200
gtgctgcaat gataccgcga gacccacgct caccggctcc agatttatca gcaataaacc  16260
agccagccgg aagggccgag cgcagaagtg gtcctgcaac tttatccgcc tccatccagt  16320
ctattaattg ttgccgggaa gctagagtaa gtagttcgcc agttaatagt ttgcgcaacg  16380
ttgttgccat tgctgcaggg gggggggggg gggggacttc ccattgttca ttccacggac  16440
aaaaacagag aaaggaaacg acagaggcca aaaagcctcg ctttcagcac ctgtcgtttc  16500
ctttcttttc agagggtatt ttaaataaaa acattaagtt atgacgaaga agaacggaaa  16560
cgccttaaac cggaaaattt tcataaatag cgaaaacccg cgaggtcgcc gccccgtaac  16620
ctgtcggatc accggaaagg acccgtaaag tgataatgat tatcatctac atatcacaac  16680
gtgcgtggag gccatcaaac cacgtcaaat aatcaattat gacgcaggta tcgtattaat  16740
tgatctgcat caacttaacg taaaaacaac ttcagacaat acaaatcagc gacactgaat  16800
acggggcaac ctcatgtccc cccccccccc cccccctgcag ggcatcgtgg tgtcacgctc  16860
gtcgtttggt atggcttcat tcagctccgg ttcccaacga tcaaggcgag ttacatgatc  16920
ccccatgttg tgcaaaaaag cggttagctc cttcggtcct ccgatcgttg tcagaagtaa  16980
gttggccgca gtgttatcac tcatggttat ggcagcactg cataattctc ttactgtcat  17040
gccatccgta agatgctttt ctgtgactgg tgagtactca accaagtcat tctgagaata  17100
gtgtatgcgg cgaccgagtt gctcttgccc ggcgtcaaca cgggataata ccgcgccaca  17160
tagcagaact ttaaaagtgc tcatcattgg aaaacgttct tcggggcgaa aactctcaag  17220
gatcttaccg ctgttgagat ccagttcgat gtaacccact cgtgcaccca actgatcttc  17280
agcatctttt actttcacca gcgtttctgg gtgagcaaaa acaggaaggc aaaatgccgc  17340
aaaaaaggga ataagggcga cacggaaatg ttgaatactc atactcttcc tttttcaata  17400
ttattgaagc atttatcagg gttattgtct catgagcgga tacatatttg aatgtattta  17460
gaaaaataaa caaatagggg ttccgcgcac atttccccga aaagtgccac ctgacgtcta  17520
agaaaccatt attatcatga cattaaccta taaaaatagg cgtatcacga ggccctttcg  17580
tcttcaagaa ttggtcgacg atcttgctgc gttcggatat tttcgtggag ttcccgccac  17640
agacccggat tgaaggcgag atccagcaac tcgcgccaga tcatcctgtg acggaacttt  17700
ggcgcgtgat gactggccag gacgtcggcc gaaagagcga caagcagatc acgcttttcg  17760
acagcgtcgg atttgcgatc gaggattttt cggcgctgcg ctacgtccgc gaccgcgttg  17820
agggatcaag ccacagcagc ccactcgacc ttctagccga cccagacgag ccaagggatc  17880
tttttggaat gctgctccgt cgtcaggctt tccgacgttt gggtggttga acagaagtca  17940
ttatcgtacg gaatgccaag cactcccgag gggaaccctg tggttggcat gcacatacaa  18000
atggacgaac ggataaacct tttcacgccc ttttaaatat ccgttattct aataaacgct  18060
cttttctctt aggtttaccc gccaatatat cctgtcaaac actgatagtt taaactgaag  18120
```

-continued

```
gcgggaaacg acaatctgat catgagcgga gaattaaggg agtcacgtta tgacccccgc  18180
cgatgacgcg ggacaagccg ttttacgttt ggaactgaca gaaccgcaac gttgaaggag  18240
ccactcagcc caagcttgat atcgaattcc tgcagcccgg gggatccggg gcggaagatg  18300
gcagggacgc ggattcaggg cggacgcgct tgccgagggc gcgggggacc acagcgtgcg  18360
ttacggggac agggcgggca tcgcgaggac gggtgcggga gcggagccac atctggtggt  18420
ggacgcctac tttgctctct tatagagtag taaagattcg tggaccaaac aacaccctag  18480
cttgtacaaa tattcttagg cagttgctac tgatgagaga aaaataacat cactccactg  18540
catttgcgtg atttattgaa cagatcacaa ttacatctat tcaaatttat ttacctgtac  18600
gtgtccgatt tttaggggag gatttttta cggtatttt tttttaaaaa aataaattta  18660
ggcaacaatt ttatagaatc gagtgcttta tctattatct tttacaaggc acacgcgtac  18720
aataaggttt ggtcgttcgt gacttggata gtggttttgg ttgcaattcc gtaattcttg  18780
gcataggata cagcccaacc cagaaaaaaa taatgttgcg gtcagttctg gctttgagat  18840
tcggagtacc acgtggcgta aaggcaggcc gtgtcttaca gatgaataaa ggacctgggt  18900
ctcacgtgat tggtttccag tttcgtgcat caagatgtgg aattttcaaa ctgccgtcgt  18960
gtttgtttcg tcacataaaa gctttttgga aggctaagga gaggaagccg gcgagaagga  19020
gggggcgttt tacgtgtcac tgtcctgtcg tgttggctgt tgacacgaat catttcttcc  19080
gcgcgtggga agaagaagat gcacattagc ggcctgaagt agagatgtca atggggaatt  19140
ccccagcggg gattaactcc ccagacccgt acccatgaac atagaccggc ccccatcccc  19200
gaacccgaac ccgacctcgg gtacgaaaat cctcccatac ccattcccga ccgggtacta  19260
aatacccatg ggtatccata cccgacccga ttattcaaaa attaatgggc tttttatttg  19320
ttaaccggcg gacgcaatgc ttgggactct aggtttttt actttgttga ccggctggcg  19380
gctgggcttt ttcctacagg cccaaagttg gtcggcagcc actaggccac acgtcacagg  19440
cagcccacaa gtaaatgtcg ttggattgct ggatggtgga ataaaaatcc tagatgctag  19500
attgttctgg ttccgggtat ttttctccat ggctaatcgg gtttgggttt agccctccca  19560
aacccgaacc cgccataccc gatgggtaag ggatttattc caaatctata cccatgggga  19620
tttgttttaa cccatacctt aaccctaata gaggaattcc ccacgggtaa tcgggtttcg  19680
gggcccattg acatctctag actgaaggcg tccaactcaa atcattaaaa agtgttgacg  19740
cacgcgctga tgcgccggcc gcacagcaca ggctgcacag cccgtttaat cagcgatgga  19800
gccccggccg tcagccagcc aggtccggcg tccgggtctg cgccctgcgg cgtcactgct  19860
gtcgccaccg tctccgatgg tcccacatcc atccagcggg ccgcgcgtgg tacaaaaggc  19920
tcttcctcgc cgtcaggtgc agctgcccaa acaccagaca cagactccac caccccgctt  19980
cgatcttctg ttgcagctga aatctgtcag attctgcagt tcattcctca tggtccgtcc  20040
tgtagaaacc ccaacccgtg aaatcaaaaa actcgacggc ctgtgggcat tcagtctgga  20100
tcgcgaaaac tgtggaattg atcagcgttg gtgggaaagc gcgttacaag aaagccgggc  20160
aattgctgtg ccaggcagtt ttaacgatca gttcgccgat gcagatattc gtaattatgc  20220
gggcaacgtc tggtatcagc gcgaagtctt tataccgaaa ggttgggcag gccagcgtat  20280
cgtgctgcgt ttcgatgcgg tcactcatta cggcaaagtg tgggtcaata atcaggaagt  20340
gatggagcat cagggcggct atacgccatt tgaagccgat gtcacgccgt atgttattgc  20400
cgggaaaagt gtacgtatca ccgtttgtgt gaacaacgaa ctgaactggc agactatccc  20460
gccgggaatg gtgattaccg acgaaaacgg caagaaaaag cagtcttact tccatgattt  20520
```

```
ctttaactat gccggaatcc atcgcagcgt aatgctctac accacgccga acacctgggt  20580
ggacgatatc accgtggtga cgcatgtcgc gcaagactgt aaccacgcgt ctgttgactg  20640
ccaggtggtg gccaatggtg atgtcagcgt tgaactgcgt gatgcggatc aacaggtggt  20700
tgcaactgga caaggcacta gcgggacttt gcaagtggtg aatccgcacc tctgccaacc  20760
gggtgaaggt tatctctatg aactgtgcgt cacagccaaa agccagacag agtgtgatat  20820
ctacccgctt cgcgtcggca tccggtcagt ggcagtgaag ggccaacagt tcctgattaa  20880
ccacaaaccg ttctacttta ctggctttgg tcgtcatgaa gatgcggact tacgtggcaa  20940
aggattcgat aacgtgctga tggtgcacga ccacgcatta atggactgga ttggggccaa  21000
ctcctaccgt acctcgcatt acccttacgc tgaagagatg ctcgactggg cagatgaaca  21060
tggcatcgtg gtgattgatg aaactgctgc tgtcggcttt aacctctctt taggcattgg  21120
tttcgaagcg ggcaacaagc cgaaagaact gtacagcgaa gaggcagtca acggggaaac  21180
tcagcaagcg cacttacagg cgattaaaga gctgatagcg cgtgacaaaa accacccaag  21240
cgtggtgatg tggagtattg ccaacgaacc ggatacccgt ccgcaagtgc acgggaatat  21300
ttcgccactg gcggaagcaa cgcgtaaact cgacccgacg cgtccgatca cctgcgtcaa  21360
tgtaatgttc tgcgacgctc acaccgatac catcagcgat ctctttgatg tgctgtgcct  21420
gaaccgttat tacggatggt atgtccaaag cggcgatttg gaaacggcag agaaggtact  21480
ggaaaaagaa cttctggcct ggcaggagaa actgcatcag ccgattatca tcaccgaata  21540
cggcgtggat acgttagccg ggctgcactc aatgtacacc gacatgtgga gtgaagagta  21600
tcagtgtgca tggctggata tgtatcaccg cgtctttgat cgcgtcagcg ccgtcgtcgg  21660
tgaacaggta tggaatttcg ccgattttgc gacctcgcaa ggcatattgc gcgttggcgg  21720
taacaagaaa gggatcttca ctcgcgaccg caaaccgaag tcggcggctt ttctgctgca  21780
aaaacgctgg actggcatga acttcggtga aaaaccgcag cagggaggca aacaatgaat  21840
caacaactct cctggcgcac catcgtcggc tacagcctcg gtgacgtggg gcaacctaga  21900
cttgtccatc ttctggattg gccaacttaa ttaatgtatg aaataaaagg atgcacacat  21960
agtgacatgc taatcactat aatgtgggca tcaaagttgt gtgttatgtg taattactag  22020
ttatctgaat aaaagagaaa gagatcatcc atatttctta tcctaaatga atgtcacgtg  22080
tctttataat tctttgatga accagatgca tttcattaac caaatccata tacatataaa  22140
tattaatcat atataattaa tatcaattgg gttagcaaaa caaatctagt ctaggtgtgt  22200
tttgcgaatt gcggccccat ggagtcaaag attcaaatag aggacctaac agaactcgcc  22260
gtaaagactg gcgaacagtt catacagagt ctcttacgac tcaatgacaa gaagaaaatc  22320
ttcgtcaaca tggtggagca cgacacgctt gtctactcca aaaatatcaa agatacagtc  22380
tcagaagacc aaagggcaat tgagactttt caacaaaggg taatatccgg aaacctcctc  22440
ggattccatt gcccagctat ctgtcacttt attgtgaaga tagtggaaaa ggaaggtggc  22500
tcctacaaat gccatcattg cgataaagga aaggccatcg ttgaagatgc ctctgccgac  22560
agtggtccca aagatggacc cccacccacg aggagcatcg tggaaaaaga agacgttcca  22620
accacgtctt caaagcaagt ggattgatgt gatatctcca ctgacgtaag ggatgacgca  22680
caatcccact atccttcgca agacccttcc tctatataag gaagttcatt tcatttggag  22740
aggacagggt acccggggat ccaccatgtc tccggagagg agaccagttg agattaggcc  22800
agctacagca gctgatatgg ccgcggtttg tgatatcgtt aaccattaca ttgagacgtc  22860
```

```
tacagtgaac tttaggacag agccacaaac accacaagag tggattgatg atctagagag  22920
gttgcaagat agataccctt ggttggttgc tgaggttgag ggtgttgtgg ctggtattgc  22980
ttacgctggg ccctggaagg ctaggaacgc ttacgattgg acagttgaga gtactgttta  23040
cgtgtcacat aggcatcaaa ggttgggcct aggatccaca ttgtacacac atttgcttaa  23100
gtctatggag gcgcaaggtt ttaagtctgt ggttgctgtt ataggccttc caaacgatcc  23160
atctgttagg ttgcatgagg ctttgggata cacagcccgg ggtacattgc gcgcagctgg  23220
atacaagcat ggtggatggc atgatgttgg tttttggcaa agggattttg agttgccagc  23280
tcctccaagg ccagttaggc cagttaccca gatctgagtc gacctgcagg catgccgctg  23340
aaatcaccag tctctctcta caaatctatc tctctctata ataatgtgtg agtagttccc  23400
agataaggga attagggttc ttatagggtt tcgctcatgt gttgagcata taagaaaccc  23460
ttagtatgta tttgtatttg taaaatactt ctatcaataa aatttctaat tcctaaaacc  23520
aaaatccagt gggtaccgag ctcgaattca gtacattaaa aacgtccgca atgtgttatt  23580
aagttgtcta agcgtcaatt tgtttacacc acaatatatc ctgccaccag ccagccaaca  23640
gctccccgac cggcagctcg gcacaaaatc accactcgat acaggcagcc catcagtccg  23700
ggacggcgtc agcgggagag ccgttgtaag gcggcagact ttgctcatgt taccgatgct  23760
attcggaaga acggcaacta agctgccggg tttgaaacac ggatgatctc gcggagggta  23820
gcatgttgat tgtaacgatg acagagcgtt gctgcctgtg atcaaatatc atctccctcg  23880
cagagatccg aattatcagc cttcttattc atttctcgct taaccgtgac aggctgtcga  23940
tcttgagaac tatgccgaca taataggaaa tcgctggata aagccgctga ggaagctgag  24000
tggcgctatt tctttagaag tgaacgttga cgatcgtcga ccgtaccccg atgaattaat  24060
tcggacgtac gttctgaaca cagctggata cttacttggg cgattgtcat acatgacatc  24120
aacaatgtac ccgtttgtgt aaccgtctct tggaggttcg tatgacacta gtggttcccc  24180
tcagcttgcg actagatgtt gaggcctaac attttattag agagcaggct agttgcttag  24240
atacatgatc ttcaggccgt tatctgtcag ggcaagcgaa aattggccat ttatgacgac  24300
caatgccccg cagaagctcc catctttgcc gccatagacg ccgcgccccc cttttggggt  24360
gtagaacatc cttttgccag atgtggaaaa gaagttcgtt gtcccattgt tggcaatgac  24420
gtagtagccg gcgaaagtgc gagacccatt tgcgctatat ataagcctac gatttccgtt  24480
gcgactattg tcgtaattgg atgaactatt atcgtagttg ctctcagagt tgtcgtaatt  24540
tgatggacta ttgtcgtaat tgcttatgga gttgtcgtag ttgcttggag aaatgtcgta  24600
gttggatggg gagtagtcat agggaagacg agcttcatcc actaaaacaa ttggcaggtc  24660
agcaagtgcc tgccccgatg ccatcgcaag tacgaggctt agaaccacct tcaacagatc  24720
gcgcatagtc ttccccagct ctctaacgct tgagttaagc cgcgccgcga agcggcgtcg  24780
gcttgaacga attgttagac attatttgcc gactaccttg gtgatctcgc ctttcacgta  24840
gtgaacaaat tcttccaact gatctgcgcg cgaggccaag cgatcttctt gtccaagata  24900
agcctgccta gcttcaagta tgacgggctg atactgggcc ggcaggcgct ccattgccca  24960
gtcggcagcg acatccttcg gcgcgatttt gccggttact gcgctgtacc aaatgcggga  25020
caacgtaagc actacatttc gctcatcgcc agcccagtcg ggcggcgagt tccatagcgt  25080
taaggtttca tttagcgcct caaatagatc ctgttcagga accggatcaa agagttcctc  25140
cgccgctgga cctaccaagg caacgctatg ttctcttgct tttgtcagca agatagccag  25200
atcaatgtcg atcgtggctg gctcgaagat acctgcaaga atgtcattgc gctgccattc  25260
```

```
tccaaattgc agttcgcgct tagctggata acgccacgga atgatgtcgt cgtgcacaac  25320
aatggtgact tctacagcgc ggagaatctc gctctctcca ggggaagccg aagtttccaa  25380
aaggtcgttg atcaaagctc gccgcgttgt ttcatcaagc cttacggtca ccgtaaccag  25440
caaatcaata tcactgtgtg gcttcaggcc gccatccact gcggagccgt acaaatgtac  25500
ggccagcaac gtcggttcga gatggcgctc gatgacgcca actacctctg atagttgagt  25560
cgatacttcg gcgatcaccg cttccctcat gatgtttaac tcctgaatta agccgcgccg  25620
cgaagcggtg tcggcttgaa tgaattgtta ggcgtcatcc tgtgctcccg agaaccagta  25680
ccagtacatc gctgtttcgt tcgagacttg aggtctagtt ttatacgtga acaggtcaat  25740
gccgccgaga gtaaagccac attttgcgta caaattgcag gcaggtacat tgttcgtttg  25800
tgtctctaat cgtatgccaa ggagctgtct gcttagtgcc cactttttcg caaattcgat  25860
gagactgtgc gcgactcctt tgcctcggtg cgtgtgcgac acaacaatgt gttcgataga  25920
ggctagatcg ttccatgttg agttgagttc aatcttcccg acaagctctt ggtcgatgaa  25980
tgcgccatag caagcagagt cttcatcaga gtcatcatcc gagatgtaat ccttccggta  26040
ggggctcaca cttctggtag atagttcaaa gccttggtcg gataggtgca catcgaacac  26100
ttcacgaaca atgaaatggt tctcagcatc caatgtttcc gccacctgct cagggatcac  26160
cgaaatcttc atatgacgcc taacgcctgg cacagcggat cgcaaacctg gcgcggcttt  26220
tggcacaaaa ggcgtgacag gtttgcgaat ccgttgctgc cacttgttaa ccctttttgcc  26280
agatttggta actataattt atgttagagg cgaagtcttg ggtaaaaact ggcctaaaat  26340
tgctggggat ttcaggaaag taaacatcac cttccggctc gatgtctatt gtagatatat  26400
gtagtgtatc tacttgatcg gggatctgc tgcctcgcgc gtttcggtga tgacggtgaa  26460
aacctctgac acatgcagct cccggagacg gtcacagctt gtctgtaagc ggatgccggg  26520
agcagacaag cccgtcaggg cgcgtcagcg ggtgttggcg ggtgtcgggg cgcagccatg  26580
acccagtcac gtagcgatag cggagtgtat actggcttaa ctatgcggca tcagagcaga  26640
ttgtactgag agtgcaccat atgcggtgtg aaataccgca cagatgcgta aggagaaaat  26700
accgcatcag gcgctcttcc gcttcctcgc tcactgactc gctgcgctcg gtcgttcggc  26760
tgcggcgagc ggtatcagct cactcaaagg cggtaatacg gttatccaca gaatcagggg  26820
ataacgcagg aaagaacatg tgagcaaaag gccagcaaaa ggccaggaac cgtaaaaagg  26880
ccgcgttgct ggcgtttttc cataggctcc gcccccctga cgagcatcac aaaaatcgac  26940
gctcaagtca gaggtggcga aacccgacag gactataaag ataccaggcg tttccccctg  27000
gaagctccct cgtgcgctct cctgttccga ccctgccgct taccggatac ctgtccgcct  27060
ttctcccttc gggaagcgtg gcgctttctc atagctcacg ctgtaggtat ctcagttcgg  27120
tgtaggtcgt tcgctccaag ctgggctgtg tgcacgaacc ccccgttcag cccgaccgct  27180
gcgccttatc cggtaactat cgtcttgagt ccaacccggt aagacacgac ttatcgccac  27240
tggcagcagc cactggtaac aggattagca gagcgaggta tgtaggcggt gctacagagt  27300
tcttgaagtg gtggcctaac tacggctaca ctagaaggac agtatttggt atctgcgctc  27360
tgctgaagcc agttaccttc ggaaaaagag ttggtagctc ttgatccggc aaacaaacca  27420
ccgctggtag cggtggtttt tttgtttgca agcagcagat tacgcgcaga aaaaaaggat  27480
ctcaagaaga tcctttgatc ttttctacgg ggtctgacgc tcagtggaac gaaaactcac  27540
gttaagggat tttggtcatg agattatcaa aaggatcttc cacctagatc cttttaaatt  27600
```

```
aaaaatgaag ttttaaatca atctaaagta tatatgagta aacttggtct gacagttacc  27660
aatgcttaat cagtgaggca cctatctcag cgatctgtct atttcgttca tccatagttg  27720
cctgactccc cgtcgtgtag ataactacga tacgggaggg cttaccatct ggccccagtg  27780
ctgcaatgat accgcgagac ccacgctcac cggctccaga tttatcagca ataaaccagc  27840
cagccggaag ggccgagcgc agaagtggtc ctgcaacttt atccgcctcc atccagtcta  27900
ttaattgttg ccgggaagct agagtaagta gttcgccagt taatagtttg cgcaacgttg  27960
ttgccattgc tgcagggggg gggggggggg gggacttcca ttgttcattc cacggacaaa  28020
aacagagaaa ggaaacgaca gaggccaaaa agcctcgctt tcagcacctg tcgtttcctt  28080
tcttttcaga gggtatttta aataaaaaca ttaagttatg acgaagaaga acggaaacgc  28140
cttaaaccgg aaaattttca taaatagcga aaacccgcga ggtcgccgcc ccgtaacctg  28200
tcggatcacc ggaaaggacc cgtaaagtga taatgattat catctacata tcacaacgtg  28260
cgtggaggcc atcaaaccac gtcaaataat caattatgac gcaggtatcg tattaattga  28320
tctgcatcaa cttaacgtaa aaacaacttc agacaataca aatcagcgac actgaatacg  28380
gggcaacctc atgtcccccc cccccccccc cctgcaggca tcgtggtgtc acgctcgtcg  28440
tttggtatgg cttcattcag ctccggttcc caacgatcaa ggcgagttac atgatccccc  28500
atgttgtgca aaaaagcggt tagctccttc ggtcctccga tcgttgtcag aagtaagttg  28560
gccgcagtgt tatcactcat ggttatggca gcactgcata attctcttac tgtcatgcca  28620
tccgtaagat gcttttctgt gactggtgag tactcaacca agtcattctg agaatagtgt  28680
atgcggcgac cgagttgctc ttgcccggcg tcaacacggg ataataccgc gccacatagc  28740
agaactttaa aagtgctcat cattggaaaa cgttcttcgg ggcgaaaact ctcaaggatc  28800
ttaccgctgt tgagatccag ttcgatgtaa cccactcgtg cacccaactg atcttcagca  28860
tcttttactt tcaccagcgt ttctgggtga gcaaaaacag gaaggcaaaa tgccgcaaaa  28920
aagggaataa gggcgacacg gaaatgttga atactcatac tcttcctttt tcaatattat  28980
tgaagcattt atcagggtta ttgtctcatg agcggataca tatttgaatg tatttagaaa  29040
aataaacaaa taggggttcc gcgcacattt ccccgaaaag tgccacctga cgtctaagaa  29100
accattatta tcatgacatt aacctataaa aataggcgta tcacgaggcc ctttcgtctt  29160
caagaattcg gagcttttgc cattctcacc ggattcagtc gtcactcatg gtgatttctc  29220
acttgataac cttatttttg acgaggggaa attaataggt tgtattgatg ttggacgagt  29280
cggaatcgca gaccgatacc aggatcttgc catcctatgg aactgcctcg gtgagttttc  29340
tccttcatta cagaaacggc tttttcaaaa atatggtatt gataatcctg atatgaataa  29400
attgcagttt catttgatgc tcgatgagtt tttctaatca gaattggtta attggttgta  29460
acactggcag agcattacgc tgacttgacg ggacggcggc tttgttgaat aaatcgaact  29520
tttgctgagt tgaaggatca gatcacgcat cttcccgaca acgcagaccg ttccgtggca  29580
aagcaaaagt tcaaaatcac caactggtcc acctacaaca aagctctcat caaccgtggc  29640
tccctcactt tctggctgga tgatggggcg attcaggcct ggtatgagtc agcaacacct  29700
tcttcacgag gcagacctca gcgccagaag gccgccagag aggccgagcg cggccgtgag  29760
gcttggacgc tagggcaggg catgaaaaag cccgtagcgg gctgctacgg gcgtctgacg  29820
cggtggaaag gggggagggga tgttgtctac atggctctgc tgtagtgagt gggttgcgct  29880
ccggcagcgg tcctgatcaa tcgtcaccct ttctcggtcc ttcaacgttc ctgacaacga  29940
gcctcctttt cgccaatcca tcgacaatca ccgcgagtcc ctgctcgaac gctgcgtccg  30000
```

```
gaccggcttc gtcgaaggcg tctatcgcgg cccgcaacag cggcgagagc ggagcctgtt  30060
caacggtgcc gccgcgctcg ccggcatcgc tgtcgccggc ctgctcctca agcacggccc  30120
caacagtgaa gtagctgatt gtcatcagcg cattgacggc gtccccggcc gaaaaacccg  30180
cctcgcagag gaagcgaagc tgcgcgtcgg ccgtttccat ctgcggtgcg cccggtcgcg  30240
tgccggcatg gatgcgcgcg ccatcgcggt aggcgagcag cgcctgcctg aagctgcggg  30300
cattcccgat cagaaatgag cgccagtcgt cgtcggctct cggcaccgaa tgcgtatgat  30360
tctccgccag catggcttcg gccagtgcgt cgagcagcgc ccgcttgttc ctgaagtgcc  30420
agtaaagcgc cggctgctga acccccaacc gttccgccag tttgcgtgtc gtcagaccgt  30480
ctacgccgac ctcgttcaac aggtccaggg cggcacggat cactgtattc ggctgcaact  30540
ttgtcatgct tgacacttta tcactgataa acataatatg tccaccaact tatcagtgat  30600
aaagaatccg cgcgttcaat cggaccagcg gaggctggtc cggaggccag acgtgaaacc  30660
caacataccc ctgatcgtaa ttctgagcac tgtcgcgctc gacgctgtcg gcatcggcct  30720
gattatgccg gtgctgccgg gcctcctgcg cgatctggtt cactcgaacg acgtcaccgc  30780
ccactatggc attctgctgg cgctgtatgc gttggtgcaa tttgcctgcg cacctgtgct  30840
gggcgcgctg tcggatcgtt tcgggcggcg gccaatcttg ctcgtctcgc tggccggcgc  30900
cactgtcgac tacgccatca tggcgacagc gcctttcctt tgggttctct atatcgggcg  30960
gatcgtggcc ggcatcaccg ggcgactgg ggcggtagcc ggcgcttata ttgccgatat  31020
cactgatggc gatgagcgcg cgcggcactt cggcttcatg agcgcctgtt tcgggttcgg  31080
gatggtcgcg ggacctgtgc tcggtgggct gatgggcggt ttctcccccc acgctccgtt  31140
cttcgccgcg gcagccttga acggcctcaa tttcctgacg ggctgtttcc ttttgccgga  31200
gtcgcacaaa ggcgaacgcc ggccgttacg ccgggaggct ctcaacccgc tcgcttcgtt  31260
ccggtgggcc cggggcatga ccgtcgtcgc cgccctgatg gcggtcttct tcatcatgca  31320
acttgtcgga caggtgccgg ccgcgctttg ggtcattttc ggcgaggatc gctttcactg  31380
ggacgcgacc acgatcggca tttcgcttgc cgcatttggc attctgcatt cactcgccca  31440
ggcaatgatc accggccctg tagccgcccg gctcggcgaa aggcgggcac tcatgctcgg  31500
aatgattgcc gacggcacag gctacatcct gcttgccttc gcgacacggg gatggatggc  31560
gttcccgatc atggtcctgc ttgcttcggg tggcatcgga atgccggcgc tgcaagcaat  31620
gttgtccagg caggtggatg aggaacgtca ggggcagctg caaggctcac tggcggcgct  31680
caccagcctg acctcgatcg tcggacccct cctcttcacg gcgatctatg cggcttctat  31740
aacaacgtgg aacgggtggg catggattgc aggcgctgcc ctctacttgc tctgcctgcc  31800
ggcgctgcgt cgcgggcttt ggagcggcgc agggcaacga gccgatcgct gatcgtggaa  31860
acgataggcc tatgccatgc gggtcaaggc gacttccggc aagctatacg cgccctagga  31920
gtgcggttgg aacgttggcc cagccagata ctcccgatca cgagcaggac gccgatgatt  31980
tgaagcgcac tcagcgtctg atccaagaac aaccatccta gcaacacggc ggtccccggg  32040
ctgagaaagc ccagtaagga aacaactgta ggttcgagtc gcgagatccc ccggaaccaa  32100
aggaagtagg ttaaacccgc tccgatcagg ccgagccacg ccaggccgag aacattggtt  32160
cctgtaggca tcgggattgg cggatcaaac actaaagcta ctggaacgag cagaagtcct  32220
ccggccgcca gttgccaggc ggtaaaggtg agcagaggca cgggaggttg ccacttgcgg  32280
gtcagcacgg ttccgaacgc catggaaacc gcccccgcca ggcccgctgc gacgccgaca  32340
```

```
ggatctagcg ctgcgtttgg tgtcaacacc aacagcgcca cgcccgcagt tccgcaaata  32400
gcccccagga ccgccatcaa tcgtatcggg ctacctagca gagcggcaga gatgaacacg  32460
accatcagcg gctgcacagc gcctaccgtc gccgcgaccc cgcccggcag gcggtagacc  32520
gaaataaaca acaagctcca gaatagcgaa atattaagtg cgccgaggat gaagatgcgc  32580
atccaccaga ttcccgttgg aatctgtcgg acgatcatca cgagcaataa acccgccggc  32640
aacgcccgca gcagcatacc ggcgacccct cggcctcgct gttcgggctc cacgaaaacg  32700
ccggacagat gcgccttgtg agcgtccttg gggccgtcct cctgtttgaa gaccgacagc  32760
ccaatgatct cgccgtcgat gtaggcgccg aatgccacgg catctcgcaa ccgttcagcg  32820
aacgcctcca tgggcttttt ctcctcgtgc tcgtaaacgg acccgaacat ctctggagct  32880
ttcttcaggg ccgacaatcg gatctcgcgg aaatcctgca cgtcggccgc tccaagccgt  32940
cgaatctgag ccttaatcac aattgtcaat tttaatcctc tgtttatcgg cagttcgtag  33000
agcgcgccgt gcgtcccgag cgatactgag cgaagcaagt gcgtcgagca gtgcccgctt  33060
gttcctgaaa tgccagtaaa gcgctggctg ctgaaccccc agccggaact gaccccacaa  33120
ggccctagcg tttgcaatgc accaggtcat cattgaccca ggcgtgttcc accaggccgc  33180
tgcctcgcaa ctcttcgcag gcttcgccga cctgctcgcg ccacttcttc acgcgggtgg  33240
aatccgatcc gcacatgagg cggaaggttt ccagcttgag cgggtacggc tcccggtgcg  33300
agctgaaata gtcgaacatc cgtcgggccg tcggcgacag cttgcggtac ttctcccata  33360
tgaatttcgt gtagtggtcg ccagcaaaca gcacgacgat ttcctcgtcg atcaggacct  33420
ggcaacggga cgttttcttg ccacggtcca ggacgcggaa gcggtgcagc agcgacaccg  33480
attccaggtg cccaacgcgg tcggacgtga agcccatcgc cgtcgcctgt aggcgcgaca  33540
ggcattcctc ggccttcgtg taataccggc cattgatcga ccagcccagg tcctggcaaa  33600
gctcgtagaa cgtgaaggtg atcggctcgc cgataggggt gcgcttcgcg tactccaaca  33660
cctgctgcca caccagttcg tcatcgtcgg cccgcagctc gacgccggtg taggtgatct  33720
tcacgtcctt gttgacgtgg aaaatgacct tgttttgcag cgcctcgcgc gggattttct  33780
tgttgcgcgt ggtgaacagg gcagagcggg ccgtgtcgtt tggcatcgct cgcatcgtgt  33840
ccggccacgg cgcaatatcg aacaaggaaa gctgcatttc cttgatctgc tgcttcgtgt  33900
gtttcagcaa cgcggcctgc ttggcctcgc tgacctgttt tgccaggtcc tcgccggcgg  33960
tttttcgctt cttggtcgtc atagttcctc gcgtgtcgat ggtcatcgac ttcgccaaac  34020
ctgccgcctc ctgttcgaga cgacgcgaac gctccacggc ggccgatggc gcgggcaggg  34080
caggggggagc cagttgcacg ctgtcgcgct cgatcttggc cgtagcttgc tggaccatcg  34140
agccgacgga ctggaaggtt tcgcggggcg cacgcatgac ggtgcggctt gcgatggttt  34200
cggcatcctc ggcggaaaac cccgcgtcga tcagttcttg cctgtatgcc ttccggtcaa  34260
acgtccgatt cattcaccct ccttgcggga ttgccccgac tcacgccggg gcaatgtgcc  34320
cttattcctg atttgacccg cctggtgcct tggtgtccag ataatccacc ttatcggcaa  34380
tgaagtcggt cccgtagacc gtctggccgt ccttctcgta cttggtattc cgaatcttgc  34440
cctgcacgaa taccagcgac cccttgccca aatacttgcc gtgggcctcg gcctgagagc  34500
caaaacactt gatgcggaag aagtcggtgc gctcctgctt gtcgccggca tcgttgcgcc  34560
actcttcatt aaccgctata tcgaaaattg cttgcggctt gttagaattg ccatgacgta  34620
cctcggtgtc acgggtaaga ttaccgataa actggaactg attatggctc atatcgaaag  34680
tctccttgag aaaggagact ctagtttagc taaacattgg ttccgctgtc aagaacttta  34740
```

```
gcggctaaaa ttttgcgggc cgcgaccaaa ggtgcgaggg gcggcttccg ctgtgtacaa  34800
ccagatattt ttcaccaaca tccttcgtct gctcgatgag cggggcatga cgaaacatga  34860
gctgtcggag agggcagggg tttcaatttc gtttttatca gacttaacca acggtaaggc  34920
caacccctcg ttgaaggtga tggaggccat tgccgacgcc ctggaaactc ccctacctct  34980
tctcctggag tccaccgacc ttgaccgcga ggcactcgcg gagattgcgg gtcatccttt  35040
caagagcagc gtgccgcccg gatacgaacg catcagtgtg gttttgccgt cacataaggc  35100
gtttatcgta aagaaatggg gcgacgacac ccgaaaaaag ctgcgtggaa ggctctgacg  35160
ccaagggtta gggcttgcac ttccttcttt agccgctaaa acggcccctt ctctgcgggc  35220
cgtcggctcg cgcatcatat cgacatcctc aacggaagcc gtgccgcgaa tggcatcggg  35280
cgggtgcgct ttgacagttg ttttctatca gaacccctac gtcgtgcggt tcgattagct  35340
gtttgtcttg caggctaaac actttcggta tatcgtttgc ctgtgcgata atgttgctaa  35400
tgatttgttg cgtaggggtt actgaaaagt gagcgggaaa gaagagtttc agaccatcaa  35460
ggagcgggcc aagcgcaagc tggaacgcga catgggtgcg gacctgttgg ccgcgctcaa  35520
cgacccgaaa accgttgaag tcatgctcaa cgcggacggc aaggtgtggc acgaacgcct  35580
tggcgagccg atgcggtaca tctgcgacat gcggcccagc cagtcgcagg cgattataga  35640
aacggtggcc ggattccacg gcaaagaggt cacgcggcat tcgcccatcc tggaaggcga  35700
gttcccccttg gatggcagcc gctttgccgg ccaattgccg ccggtcgtgg ccgcgccaac  35760
ctttgcgatc cgcaagcgcg cggtcgccat cttcacgctg gaacagtacg tcgaggcggg  35820
catcatgacc cgcgagcaat acgaggtcat taaaagcgcc gtcgcggcgc atcgaaacat  35880
cctcgtcatt ggcggtactg gctcgggcaa gaccacgctc gtcaacgcga tcatcaatga  35940
aatggtcgcc ttcaacccgt ctgagcgcgt cgtcatcatc gaggacaccg gcgaaatcca  36000
gtgcgccgca gagaacgccg tccaatacca caccagcatc gacgtctcga tgacgctgct  36060
gctcaagaca acgctgcgta tgcgccccga ccgcatcctg gtcggtgagg tacgtggccc  36120
cgaagccctt gatctgttga tggcctggaa caccgggcat gaaggaggtg ccgccaccct  36180
gcacgcaaac aaccccaaag cgggcctgag ccggctcgcc atgcttatca gcatgcaccc  36240
ggattcaccg aaacccattg agccgctgat tggcgaggcg gttcatgtgg tcgtccatat  36300
cgccaggacc cctagcggcc gtcgagtgca agaaattctc gaagttcttg gttacgagaa  36360
cggccagtac atcaccaaaa ccctgtaagg agtatttcca atgacaacgg ctgttccgtt  36420
ccgtctgacc atgaatcgcg gcattttgtt ctaccttgcc gtgttcttcg ttctcgctct  36480
cgcgttatcc gcgcatccgg cgatggcctc ggaaggcacc ggcggcagct tgccatatga  36540
gagctggctg acgaacctgc gcaactccgt aaccggcccg gtggccttcg cgctgtccat  36600
catcggcatc gtcgtcgccg gcggcgtgct gatcttcggc ggcgaactca acgccttctt  36660
ccgaaccctg atcttcctgg ttctggtgat ggcgctgctg gtcggcgcgc agaacgtgat  36720
gagcaccttc ttcggtcgtg gtgccgaaat cgcggccctc ggcaacgggg cgctgcacca  36780
ggtgcaagtc gcggcggcgg atgccgtgcg tgcggtagcg gctggacggc tcgcctaatc  36840
atggctctgc gcacgatccc catccgtcgc gcaggcaacc gagaaaacct gttcatgggt  36900
ggtgatcgtg aactggtgat gttctcgggc ctgatggcgt ttgcgctgat tttcagcgcc  36960
caagagctgc gggccaccgt ggtcggtctg atcctgtggt tcggggcgct ctatgcgttc  37020
cgaatcatgg cgaaggccga tccgaagatg cggttcgtgt acctgcgtca ccgccggtac  37080
```

```
aagccgtatt acccggcccg ctcgaccccg ttccgcgaga acaccaatag ccaagggaag  37140
caataccgat gatccaagca attgcgattg caatcgcggg cctcggcgcg cttctgttgt  37200
tcatcctctt tgcccgcatc cgcgcggtcg atgccgaact gaaactgaaa aagcatcgtt  37260
ccaaggacgc cggcctggcc gatctgctca actacgccgc tgtcgtcgat gacggcgtaa  37320
tcgtgggcaa gaacggcagc tttatggctg cctggctgta caagggcgat gacaacgcaa  37380
gcagcaccga ccagcagcgc gaagtagtgt ccgcccgcat caaccaggcc ctcgcgggcc  37440
tgggaagtgg gtggatgatc catgtggacg ccgtgcggcg tcctgctccg aactacgcgg  37500
agcggggcct gtcggcgttc cctgaccgtc tgacggcagc gattgaagaa gagcgctcgg  37560
tcttgccttg ctcgtcggtg atgtacttca ccagctccgc gaagtcgctc ttcttgatgg  37620
agcgcatggg gacgtgcttg gcaatcacgc gcaccccccg gccgttttag cggctaaaaa  37680
agtcatggct ctgccctcgg gcggaccacg cccatcatga ccttgccaag ctcgtcctgc  37740
ttctcttcga tcttcgccag cagggcgagg atcgtggcat caccgaaccg cgccgtgcgc  37800
gggtcgtcgg tgagccagag tttcagcagg ccgcccaggc ggcccaggtc gccattgatg  37860
cgggccagct cgcggacgtg ctcatagtcc acgacgcccg tgattttgta gccctggccg  37920
acggccagca ggtaggccga caggctcatg ccggccgccg ccgccttttc ctcaatcgct  37980
cttcgttcgt ctggaaggca gtacaccttg ataggtgggc tgcccttcct ggttggcttg  38040
gtttcatcag ccatccgctt gccctcatct gttacgccgg cggtagccgg ccagcctcgc  38100
agagcaggat tcccgttgag caccgccagg tgcgaataag ggacagtgaa gaaggaacac  38160
ccgctcgcgg gtgggcctac ttcacctatc ctgcccggct gacgccgttg gatacaccaa  38220
ggaaagtcta cacgaaccct ttggcaaaat cctgtatatc gtgcgaaaaa ggatggatat  38280
accgaaaaaa tcgctataat gaccccgaag cagggttatg cagcggaaaa gcgctgcttc  38340
cctgctgttt tgtggaatat ctaccgactg gaaacaggca aatgcaggaa attactgaac  38400
tgaggggaca ggcgagagac gatgccaaag agctacaccg acgagctggc cgagtgggtt  38460
gaatcccgcg cggccaagaa gcgccggcgt gatgaggctg cggttgcgtt cctggcggtg  38520
agggcggatg tcgaggcggc gttagcgtcc ggctatgcgc tcgtcaccat ttgggagcac  38580
atgcgggaaa cggggaaggt caagttctcc tacgagacgt tccgctcgca cgccaggcgg  38640
cacatcaagg ccaagcccgc cgatgtgccc gcaccgcagg ccaaggctgc ggaacccgcg  38700
ccggcaccca agacgccgga gccacggcgg ccgaagcagg ggggcaaggc tgaaaagccg  38760
gcccccgctg cggccccgac cggcttcacc ttcaacccaa caccggacaa aaaggatcta  38820
ctgtaatggc gaaaattcac atggttttgc agggcaaggg cggggtcggc aagtcggcca  38880
tcgccgcgat cattgcgcag tacaagatgg acaaggggca gacacccttg tgcatcgaca  38940
ccgacccggt gaacgcgacg ttcgagggct acaaggccct gaacgtccgc cggctgaaca  39000
tcatggccgg cgacgaaatt aactcgcgca acttcgacac cctggtcgag ctgattgcgc  39060
cgaccaagga tgacgtggtg atcgacaacg gtgccagctc gttcgtgcct ctgtcgcatt  39120
acctcatcag caaccaggtg ccggctctgc tgcaagaaat ggggcatgag ctggtcatcc  39180
ataccgtcgt caccggcggc caggctctcc tggacacggt gagcggcttc gcccagctcg  39240
ccagccagtt cccggccgaa gcgcttttcg tggtctggct gaacccgtat tgggggccta  39300
tcgagcatga gggcaagagc tttgagcaga tgaaggcgta cacggccaac aaggcccgcg  39360
tgtcgtccat catccagatt ccggccctca aggaagaaac ctacggccgc gatttcagcg  39420
acatgctgca agagcggctg acgttcgacc aggcgctggc cgatgaatcg ctcacgatca  39480
```

```
tgacgcggca acgcctcaag atcgtgcggc gcggcctgtt tgaacagctc gacgcggcgg  39540
ccgtgctatg agcgaccaga ttgaagagct gatccgggag attgcggcca agcacggcat  39600
cgccgtcggc cgcgacgacc cggtgctgat cctgcatacc atcaacgccc ggctcatggc  39660
cgacagtgcg gccaagcaag aggaaatcct tgccgcgttc aaggaagagc tggaagggat  39720
cgcccatcgt tggggcgagg acgccaaggc caaagcggag cggatgctga acgcggccct  39780
ggcggccagc aaggacgcaa tggcgaaggt aatgaaggac agcgccgcgc aggcggccga  39840
agcgatccgc agggaaatcg acgacggcct tggccgccag ctcgcggcca aggtcgcgga  39900
cgcgcggcgc gtggcgatga tgaacatgat cgccggcggc atggtgttgt tcgcggccgc  39960
cctggtggtg tgggcctcgt tatgaatcgc agaggcgcag atgaaaaagc ccggcgttgc  40020
cgggctttgt ttttgcgtta gctgggcttg tttgacaggc ccaagctctg actgcgcccg  40080
cgctcgcgct cctgggcctg tttcttctcc tgctcctgct tgcgcatcag ggcctggtgc  40140
cgtcgggctg cttcacgcat cgaatcccag tcgccggcca gctcgggatg ctccgcgcgc  40200
atcttgcgcg tcgccagttc ctcgatcttg ggcgcgtgaa tgcccatgcc ttccttgatt  40260
tcgcgcacca tgtccagccg cgtgtgcagg gtctgcaagc gggcttgctg ttgggcctgc  40320
tgctgctgcc aggcggcctt tgtacgcggc agggacagca agccgggggc attggactgt  40380
agctgctgca aacgcgcctg ctgacggtct acgagctgtt ctaggcggtc ctcgatgcgc  40440
tccacctggt catgctttgc ctgcacgtag agcgcaaggg tctgctggta ggtctgctcg  40500
atgggcgcgg attctaagag ggcctgctgt tccgtctcgg cctcctgggc cgcctgtagc  40560
aaatcctcgc cgctgttgcc gctggactgc tttactgccg gggactgctg ttgccctgct  40620
cgcgccgtcg tcgcagttcg gcttgccccc actcgattga ctgcttcatt tcgagccgca  40680
gcgatgcgat ctcggattgc gtcaacggac ggggcagcgc ggaggtgtcc ggcttctcct  40740
tgggtgagtc ggtcgatgcc atagccaaag gtttccttcc aaaatgcgtc cattgctgga  40800
ccgtgtttct cattgatgcc cgcaagcatc ttcggcttga ccgccaggtc aagcgcgcct  40860
tcatgggcgg tcatgacgga cgccgccatg accttgccgc cgttgttctc gatgtagccg  40920
cgtaatgagg caatggtgcc gcccatcgtc agcgtgtcat cgacaacgat gtacttctgg  40980
ccggggatca cctccccctc gaaagtcggg ttgaacgcca ggcgatgatc tgaaccggct  41040
ccggttcggg cgaccttctc ccgctgcaca atgtccgttt cgacctcaag gccaaggcgg  41100
tcggccagaa cgaccgccat catggccgga atcttgttgt tccccgccgc ctcgacggcg  41160
aggactggaa cgatgcgggg cttgtcgtcg ccgatcagcg tcttgagctg ggcaacagtg  41220
tcgtccgaaa tcaggcgctc gaccaaatta agcgccgctt ccgcgtcgcc ctgcttcgca  41280
gcctggtatt caggctcgtt ggtcaaagaa ccaaggtcgc cgttgcgaac caccttcggg  41340
aagtctcccc acggtgcgcg ctcggctctg ctgtagctgc tcaagacgcc tccctttta  41400
gccgctaaaa ctctaacgag tgcgcccgcg actcaacttg acgctttcgg cacttacctg  41460
tgccttgcca cttgcgtcat aggtgatgct tttcgcactc ccgatttcag gtactttatc  41520
gaaatctgac cgggcgtgca ttacaaagtt cttccccacc tgttggtaaa tgctgccgct  41580
atctgcgtgg acgatgctgc cgtcgtggcg ctgcgactta tcggcctttt gggccatata  41640
gatgttgtaa atgccaggtt tcagggcccc ggctttatct accttctggt tcgtccatgc  41700
gccttggttc tcggtctgga caattctttg cccattcatg accaggaggc ggtgtttcat  41760
tgggtgactc ctgacggttg cctctggtgt taaacgtgtc ctggtcgctt gccggctaaa  41820
```

```
aaaaagccga cctcggcagt tcgaggccgg ctttccctag agccgggcgc gtcaaggttg  41880
ttccatctat tttagtgaac tgcgttcgat ttatcagtta ctttcctccc gctttgtgtt  41940
tcctcccact cgtttccgcg tctagccgac ccctcaacat agcggcctct tcttgggctg  42000
cctttgcctc ttgccgcgct tcgtcacgct cggcttgcac cgtcgtaaag cgctcggcct  42060
gcctggccgc ctcttgcgcc gccaacttcc tttgctcctg gtgggcctcg gcgtcggcct  42120
gcgccttcgc tttcaccgct gccaactccg tgcgcaaact ctccgcttcg cgcctggtgg  42180
cgtcgcgctc gccgcgaagc gcctgcattt cctggttggc cgcgtccagg gtcttgcggc  42240
tctcttcttt gaatgcgcgg gcgtcctggt gagcgtagtc cagctcggcg cgcagctcct  42300
gcgctcgacg ctccacctcg tcggcccgct gcgtcgccag cgcggcccgc tgctcggctc  42360
ctgccagggc ggtgcgtgct tcggccaggg cttgccgctg gcgtgcggcc agctcggccg  42420
cctcggcggc ctgctgctct agcaatgtaa cgcgcgcctg ggcttcttcc agctcgcggg  42480
cctgcgcctc gaaggcgtcg gccagctccc cgcgcacggc ttccaactcg ttgcgctcac  42540
gatcccagcc ggcttgcgct gcctgcaacg attcattggc aagggcctgg gcggcttgcc  42600
agagggcggc cacggcctgg ttgccggcct gctgcaccgc gtccggcacc tggactgcca  42660
gcggggcggc ctgcgccgtg cgctggcgtc gccattcgcg catgccggcg ctggcgtcgt  42720
tcatgttgac gcgggcggcc ttacgcactg catccacggt cgggaagttc tcccggtcgc  42780
cttgctcgaa cagctcgtcc gcagccgcaa aaatgcggtc gcgcgtctct ttgttcagtt  42840
ccatgttggc tccggtaatt ggtaagaata ataatactct tacctacctt atcagcgcaa  42900
gagtttagct gaacagttct cgacttaacg gcaggttttt tagcggctga agggcaggca  42960
aaaaaagccc cgcacggtcg gcgggggcaa agggtcagcg ggaaggggat tagcgggcgt  43020
cgggcttctt catgcgtcgg ggccgcgctt cttgggatgg agcacgacga agcgcgcacg  43080
cgcatcgtcc tcggccctat cggcccgcgt cgcggtcagg aacttgtcgc gcgctaggtc  43140
ctccctggtg ggcaccaggg gcatgaactc ggcctgctcg atgtaggtcc actccatgac  43200
cgcatcgcag tcgaggccgc gttccttcac cgtctcttgc aggtcgcggt acgcccgctc  43260
gttgagcggc tggtaacggg ccaattggtc gtaaatggct gtcggccatg agcggccttt  43320
cctgttgagc cagcagccga cgacgaagcc ggcaatgcag gcccctggca caaccaggcc  43380
gacgccgggg gcaggggatg gcagcagctc gccaaccagg aaccccgccg cgatgatgcc  43440
gatgccggtc aaccagccct tgaaactatc cggccccgaa acacccctgc gcattgcctg  43500
gatgctgcgc cggatagctt gcaacatcag gagccgtttc ttttgttcgt cagtcatggt  43560
ccgccctcac cagttgttcg tatcggtgtc ggacgaactg aaatcgcaag agctgccggt  43620
atcggtccag ccgctgtccg tgtcgctgct gccgaagcac ggcgaggggt ccgcgaacgc  43680
cgcagacggc gtatccggcc gcagcgcatc gcccagcatg gccccggtca gcgagccgcc  43740
ggccaggtag cccagcatgg tgctgttggt cgccccggcc accagggccg acgtgacgaa  43800
atcgccgtca ttccctctgg attgttcgct gctcggcggg gcagtgcgcc gcgccggcgg  43860
cgtcgtggat ggctcgggtt ggctggcctg cgacggccgg cgaaaggtgc gcagcagctc  43920
gttatcgacc ggctgcggcg tcggggccgc cgccttgcgc tgcggtcggt gttccttctt  43980
cggctcgcgc agcttgaaca gcatgatcgc ggaaaccagc agcaacgccg cgcctacgcc  44040
tcccgcgatg tagaacagca tcggattcat tcttcggtcc tccttgtagc ggaaccgttg  44100
tctgtgcggc gcgggtggcc cgcgccgctg tctttgggga tcagccctcg atgagcgcga  44160
ccagtttcac gtcggcaagg ttcgcctcga actcctggcc gtcgtcctcg tacttcaacc  44220
```

```
aggcatagcc ttccgccggc ggccgacggt tgaggataag gcgggcaggg cgctcgtcgt  44280
gctcgacctg gacgatggcc tttttcagct tgtccgggtc cggctccttc gcgccctttt  44340
ccttggcgtc cttaccgtcc tggtcgccgt cctcgccgtc ctggccgtcg ccggcctccg  44400
cgtcacgctc ggcatcagtc tggccgttga aggcatcgac ggtgttggga tcgcggccct  44460
tctcgtccag gaactcgcgc agcagcttga ccgtgccgcg cgtgatttcc tgggtgtcgt  44520
cgtcaagcca cgcctcgact tcctccgggc gcttcttgaa ggccgtcacc agctcgttca  44580
ccacggtcac gtcgcgcacg cggccggtgt tgaacgcatc ggcgatcttc tccggcaggt  44640
ccagcagcgt gacgtgctgg gtgatgaacg ccggcgactt gccgatttcc ttggcgatat  44700
cgcctttctt cttgcccttc gccagctcgc ggccaatgaa gtcggcaatt tcgcgcgggg  44760
tcagctcgtt gcgttgcagg ttctcgataa cctggtcggc ttcgttgtag tcgttgtcga  44820
tgaacgccgg gatggacttc ttgccggccc acttcgagcc acggtagcgg cgggcgccgt  44880
gattgatgat atagcggccc ggctgctcct ggttctcgcg caccgaaatg ggtgacttca  44940
ccccgcgctc tttgatcgtg gcaccgattt ccgcgatgct ctccggggaa aagccggggt  45000
tgtcggccgt ccgcggctga tgcggatctt cgtcgatcag gtccaggtcc agctcgatag  45060
ggccggaacc gccctgagac gccgcaggag cgtccaggag gctcgacagg tcgccgatgc  45120
tatccaaccc caggccggac ggctgcgccg cgcctgcggc ttcctgagcg gccgcagcgg  45180
tgtttttctt ggtggtcttg gcttgagccg cagtcattgg gaaatctcca tcttcgtgaa  45240
cacgtaatca gccagggcgc gaacctcttt cgatgccttg cgcgcggccg ttttcttgat  45300
cttccagacc ggcacaccgg atgcgagggc atcggcgatg ctgctgcgca ggccaacggt  45360
ggccggaatc atcatcttgg ggtacgcggc cagcagctcg gcttggtggc gcgcgtggcg  45420
cggattccgc gcatcgacct tgctgggcac catgccaagg aattgcagct tggcgttctt  45480
ctggcgcacg ttcgcaatgg tcgtgaccat cttcttgatg ccctggatgc tgtacgcctc  45540
aagctcgatg ggggacagca catagtcggc cgcgaagagg gcggccgcca ggccgacgcc  45600
aagggtcggg gccgtgtcga tcaggcacac gtcgaagcct tggttcgcca gggccttgat  45660
gttcgccccg aacagctcgc gggcgtcgtc cagcgacagc cgttcggcgt tcgccagtac  45720
cgggttggac tcgatgaggg cgaggcgcgc ggcctggccg tcgccggctg cgggtgcggt  45780
ttcggtccag ccgccggcag ggacagcgcc gaacagcttg cttgcatgca ggccggtagc  45840
aaagtccttg agcgtgtagg acgcattgcc ctgggggtcc aggtcgatca cggcaacccg  45900
caagccgcgc tcgaaaaagt cgaaggcaag atgcacaagg gtcgaagtct tgccgacgcc  45960
gcctttctgg ttggccgtga ccaaagtttt catcgtttgg tttcctgttt tttcttggcg  46020
tccgcttccc acttccggac gatgtacgcc tgatgttccg gcagaaccgc cgttacccgc  46080
gcgtacccct cgggcaagtt cttgtcctcg aacgcggccc acacgcgatg caccgcttgc  46140
gacactgcgc ccctggtcag tcccagcgac gttgcgaacg tcgcctgtgg cttcccatcg  46200
actaagacgc cccgcgctat ctcgatggtc tgctgcccca cttccagccc ctggatcgcc  46260
tcctggaact ggctttcggt aagccgtttc ttcatggata acacccataa tttgctccgc  46320
gccttggttg aacatagcgg tgacagccgc cagcacatga gagaagttta gctaaacatt  46380
tctcgcacgt caacaccttt agccgctaaa actcgtcctt ggcgtaacaa aacaaaagcc  46440
cggaaaccgg gctttcgtct cttgccgctt atggctctgc acccggctcc atcaccaaca  46500
ggtcgcgcac gcgcttcact cggttgcgga tcgacactgc cagcccaaca aagccggttg  46560
```

ccgccgccgc caggatcgcg ccgatgatgc cggccacacc ggccatcgcc caccaggtcg 46620
ccgccttccg gttccattcc tgctggtact gcttcgcaat gctggacctc ggctcaccat 46680
aggctgaccg ctcgatggcg tatgccgctt ctccccttgg cgtaaaaccc agcgccgcag 46740
gcggcattgc catgctgccc gccgctttcc cgaccacgac gcgcgcacca ggcttgcggt 46800
ccagaccttc ggccacggcg agctgcgcaa ggacataatc agccgccgac ttggctccac 46860
gcgcctcgat cagctcttgc actcgcgcga aatccttggc ctccacggcc gccatgaatc 46920
gcgcacgcgg cgaaggctcc gcagggccgg cgtcgtgatc gccgccgaga atgcccttca 46980
ccaagttcga cgacacgaaa atcatgctga cggctatcac catcatgcag acggatcgca 47040
cgaacccgct gaattgaaca cgagcacggc acccgcgacc actatgccaa gaatgcccaa 47100
ggtaaaaatt gccggccccg ccatgaagtc cgtgaatgcc ccgacggccg aagtgaaggg 47160
caggccgcca cccaggccgc cgccctcact gcccggcacc tggtcgctga atgtcgatgc 47220
cagcacctgc ggcacgtcaa tgcttccggg cgtcgcgctc gggctgatcg cccatcccgt 47280
tactgccccg atcccggcaa tggcaaggac tgccagcgct gccatttttg gggtgaggcc 47340
gttcgcggcc gaggggcgca gcccctgggg ggatgggagg cccgcgttag cgggccggga 47400
gggttcgaga aggggggca cccccttcg gcgtgcgcgg tcacgcgcac agggcgcagc 47460
cctggttaaa aacaaggttt ataaatattg gtttaaaagc aggttaaaag acaggttagc 47520
ggtggccgaa aaacgggcgg aaacccttgc aaatgctgga ttttctgcct gtggacagcc 47580
cctcaaatgt caataggtgc gcccctcatc tgtcagcact ctgcccctca agtgtcaagg 47640
atcgcgcccc tcatctgtca gtagtcgcgc ccctcaagtg tcaataccgc agggcactta 47700
tccccaggct tgtccacatc atctgtggga aactcgcgta aaatcaggcg ttttcgccga 47760
tttgcgaggc tggccagctc cacgtcgccg gccgaaatcg agcctgcccc tcatctgtca 47820
acgccgcgcc gggtgagtcg gcccctcaag tgtcaacgtc cgcccctcat ctgtcagtga 47880
gggccaagtt ttccgcgagg tatccacaac gccggcggcc gcggtgtctc gcacacggct 47940
tcgacggcgt ttctggcgcg tttgcagggc catagacggc cgccagccca gcggcgaggg 48000
caaccagccc ggtgagcgtc ggaaaggcgc tggaagcccc gtagcgacgc ggagaggggc 48060
gagacaagcc aagggcgcag gctcgatgcg cagcacgaca tagccggttc tcgcaaggac 48120
gagaatttcc ctgcggtgcc cctcaagtgt caatgaaagt ttccaacgcg agccattcgc 48180
gagagccttg agtccacgct agatgagagc tttgttgtag gtggaccagt tggtgatttt 48240
gaacttttgc tttgccacgg aacggtctgc gttgtcggga agatgcgtga tctgatcctt 48300
caactcagca aaagttcgat ttattcaaca aagccacgtt gtgtctcaaa atctctgatg 48360
ttacattgca caagataaaa atatatcatc atgaacaata aaactgtctg cttacataaa 48420
cagtaataca aggggtgtta tgagccatat tcaacgggaa acgtcttgct cgac 48474

<210> SEQ ID NO 13
<211> LENGTH: 47505
<212> TYPE: DNA
<213> ORGANISM: artificial sequence
<220> FEATURE:
<223> OTHER INFORMATION: PHP16972 (ZmCAS1HindIII Pro:MS45/35SPAT)

<400> SEQUENCE: 13
tctagagctc gttcctcgag gaacggtacc tgcggggaag cttacaataa tgtgtgttgt 60
taagtcttgt tgcctgtcat cgtctgactg actttcgtca taaatcccgg cctccgtaac 120
ccagctttgg gcaagctcac ggatttgatc cggcggaacg ggaatatcga gatgccgggc 180

```
tgaacgctgc agttccagct ttccctttcg ggacaggtac tccagctgat tgattatctg    240
ctgaagggtc ttggttccac ctcctggcac aatgcgaatg attacttgag cgcgatcggg    300
catccaattt tctcccgtca ggtgcgtggt caagtgctac aaggcacctt tcagtaacga    360
gcgaccgtcg atccgtcgcc gggatacgga caaaatggag cgcagtagtc catcgagggc    420
ggcgaaagcc tcgccaaaag caatacgttc atctcgcaca gcctccagat ccgatcgagg    480
gtcttcggcg taggcagata gaagcatgga tacattgctt gagagtattc cgatggactg    540
aagtatggct tccatctttt ctcgtgtgtc tgcatctatt tcgagaaagc cccgatgcg    600
gcgcaccgca acgcgaattg ccatactatc cgaaagtccc agcaggcgcg cttgatagga    660
aaaggtttca tactcggccg atcgcagacg ggcactcacg accttgaacc cttcaacttt    720
cagggatcga tgctggttga tggtagtctc actcgacgtg gctctggtgt gttttgacat    780
agcttcctcc aaagaaagcg gaaggtctgg atactccagc acgaaatgtg cccgggtaga    840
cggatggaag tctagccctg ctcaatatga aatcaacagt acatttacag tcaatactga    900
atatacttgc tacatttgca attgtcttat aacgaatgtg aaataaaaat agtgtaacaa    960
cgcttttact catcgataat cacaaaaaca tttatacgaa caaaaataca aatgcactcc   1020
ggtttcacag gataggcggg atcagaatat gcaacttttg acgttttgtt ctttcaaagg   1080
gggtgctggc aaaaccaccg cactcatggg cctttgcgct gctttggcaa atgacggtaa   1140
acgagtggcc ctctttgatg ccgacgaaaa ccggcctctg acgcgatgga gagaaaacgc   1200
cttacaaagc agtactggga tcctcgctgt gaagtctatt ccgccgacga aatgcccctt   1260
cttgaagcag cctatgaaaa tgccgagctc gaaggatttg attatgcgtt ggccgatacg   1320
cgtggcggct cgagcgagct caacaacaca atcatcgcta gctcaaacct gcttctgatc   1380
cccaccatgc taacgccgct cgacatcgat gaggcactat ctacctaccg ctacgtcatc   1440
gagctgctgt tgagtgaaaa tttggcaatt cctacagctg ttttgcgcca acgcgtcccg   1500
gtcggccgat tgacaacatc gcaacgcagg atgtcagaga cgctagagag ccttccagtt   1560
gtaccgtctc ccatgcatga aagagatgca tttgccgcga tgaaagaacg cggcatgttg   1620
catcttacat tactaaacac gggaactgat ccgacgatgc gcctcataga gaggaatctt   1680
cggattgcga tggaggaagt cgtggtcatt tcgaaactga tcagcaaaat cttggaggct   1740
tgaagatggc aattcgcaag cccgcattgt cggtcggcga agcacggcgg cttgctggtg   1800
ctcgacccga gatccaccat cccaacccga cacttgttcc ccagaagctg gacctccagc   1860
acttgcctga aaaagccgac gagaaagacc agcaacgtga gcctctcgtc gccgatcaca   1920
tttacagtcc cgatcgacaa cttaagctaa ctgtggatgc ccttagtcca cctccgtccc   1980
cgaaaaagct ccaggttttt ctttcagcgc gaccgcccgc gcctcaagtg tcgaaaacat   2040
atgacaacct cgttcggcaa tacagtccct cgaagtcgct acaaatgatt ttaaggcgcg   2100
cgttggacga tttcgaaagc atgctggcag atggatcatt tcgcgtggcc ccgaaaagtt   2160
atccgatccc ttcaactaca gaaaaatccg ttctcgttca gacctcacgc atgttcccgg   2220
ttgcgttgct cgaggtcgct cgaagtcatt ttgatccgtt ggggttggag accgctcgag   2280
ctttcggcca caagctggct accgccgcgc tcgcgtcatt ctttgctgga gagaagccat   2340
cgagcaattg gtgaagaggg acctatcgga acccctcacc aaatattgag tgtaggtttg   2400
aggccgctgg ccgcgtcctc agtcaccttt tgagccagat aattaagagc caaatgcaat   2460
tggctcaggc tgccatcgtc cccccgtgcg aaacctgcac gtccgcgtca aagaaataac   2520
```

```
cggcacctct tgctgttttt atcagttgag ggcttgacgg atccgcctca agtttgcggc   2580
gcagccgcaa aatgagaaca tctatactcc tgtcgtaaac ctcctcgtcg cgtactcgac   2640
tggcaatgag aagttgctcg cgcgatagaa cgtcgcgggg tttctctaaa aacgcgagga   2700
gaagattgaa ctcacctgcc gtaagtttca cctcaccgcc agcttcggac atcaagcgac   2760
gttgcctgag attaagtgtc cagtcagtaa aacaaaaaga ccgtcggtct ttggagcgga   2820
caacgttggg gcgcacgcgc aaggcaaccc gaatgcgtgc aagaaactct ctcgtactaa   2880
acggcttagc gataaaatca cttgctccta gctcgagtgc aacaacttta tccgtctcct   2940
caaggcggtc gccactgata attatgattg gaatatcaga ctttgccgcc agatttcgaa   3000
cgatctcaag cccatcttca cgacctaaat ttagatcaac aaccacgaca tcgaccgtcg   3060
cggaagagag tactctagtg aactgggtgc tgtcggctac cgcggtcact ttgaaggcgt   3120
ggatcgtaag gtattcgata ataagatgcc gcatagcgac atcgtcatcg ataagaagaa   3180
cgtgtttcaa cggctcacct ttcaatctaa aatctgaacc cttgttcaca gcgcttgaga   3240
aattttcacg tgaaggatgt acaatcatct ccagctaaat gggcagttcg tcagaattgc   3300
ggctgaccgc ggatgacgaa aatgcgaacc aagtatttca attttatgac aaaagttctc   3360
aatcgttgtt acaagtgaaa cgcttcgagg ttacagctac tattgattaa ggagatcgcc   3420
tatggtctcg ccccggcgtc gtgcgtccgc cgcgagccag atctcgccta cttcataaac   3480
gtcctcatag gcacggaatg gaatgatgac atcgatcgcc gtagagagca tgtcaatcag   3540
tgtgcgatct tccaagctag caccttgggc gctacttttg acaagggaaa acagtttctt   3600
gaatccttgg attggattcg cgccgtgtat tgttgaaatc gatcccggat gtcccgagac   3660
gacttcactc agataagccc atgctgcatc gtcgcgcatc tcgccaagca atatccggtc   3720
cggccgcata cgcagacttg cttggagcaa gtgctcggcg ctcacagcac ccagcccagc   3780
accgttcttg gagtagagta gtctaacatg attatcgtgt ggaatgacga gttcgagcgt   3840
atcttctatg gtgattagcc tttcctgggg ggggatggcg ctgatcaagg tcttgctcat   3900
tgttgtcttg ccgcttccgg tagggccaca tagcaacatc gtcagtcggc tgacgacgca   3960
tgcgtgcaga aacgcttcca aatccccgtt gtcaaaatgc tgaaggatag cttcatcatc   4020
ctgattttgg cgtttccttc gtgtctgcca ctggttccac ctcgaagcat cataacggga   4080
ggagacttct ttaagaccag aaacacgcga gcttggccgt cgaatggtca agctgacggt   4140
gcccgaggga acggtcggcg gcagacagat ttgtagtcgt tcaccaccag gaagttcagt   4200
ggcgcagagg gggttacgtg gtccgacatc ctgctttctc agcgcgcccg ctaaaatagc   4260
gatatcttca agatcatcat aagagacggg caaaggcatc ttggtaaaaa tgccggcttg   4320
gcgcacaaat gcctctccag gtcgattgat cgcaatttct tcagtcttcg ggtcatcgag   4380
ccattccaaa atcggcttca gaagaaagcg tagttgcgga tccacttcca tttacaatgt   4440
atcctatctc taagcggaaa tttgaattca ttaagagcgg cggttcctcc cccgcgtggc   4500
gccgccagtc aggcggagct ggtaaacacc aaagaaatcg aggtcccgtg ctacgaaaat   4560
ggaaacggtg tcaccctgat tcttcttcag ggttggcggt atgttgatgg ttgccttaag   4620
ggctgtctca gttgtctgct caccgttatt ttgaaagctg ttgaagctca tcccgccacc   4680
cgagctgccg gcgtaggtgc tagctgcctg gaaggcgcct tgaacaacac tcaagagcat   4740
agctccgcta aaacgctgcc agaagtggct gtcgaccgag cccggcaatc ctgagcgacc   4800
gagttcgtcc gcgcttggcg atgttaacga gatcatcgca tggtcaggtg tctcggcgcg   4860
atcccacaac acaaaaacgc gcccatctcc ctgttgcaag ccacgctgta tttcgccaac   4920
```

```
aacggtggtg ccacgatcaa gaagcacgat attgttcgtt gttccacgaa tatcctgagg   4980
caagacacac tttacatagc ctgccaaatt tgtgtcgatt gcggtttgca agatgcacgg   5040
aattattgtc ccttgcgtta ccataaaatc ggggtgcggc aagagcgtgg cgctgctggg   5100
ctgcagctcg gtgggtttca tacgtatcga caaatcgttc tcgccggaca cttcgccatt   5160
cggcaaggag ttgtcgtcac gcttgccttc ttgtcttcgg cccgtgtcgc cctgaatggc   5220
gcgtttgctg accccttgat cgccgctgct atatgcaaaa atcggtgttt cttccggccg   5280
tggctcatgc cgctccggtt cgcccctcgg cggtagagga gcagcaggct gaacagcctc   5340
ttgaaccgct ggaggatccg gcggcacctc aatcggagct ggatgaaatg gcttggtgtt   5400
tgttgcgatc aaagttgacg gcgatgcgtt ctcattcacc ttcttttggc gcccacctag   5460
ccaaatgagg cttaatgata acgcgagaac gacacctccg acgatcaatt tctgagaccc   5520
cgaaagacgc cggcgatgtt tgtcggagac cagggatcca gatgcatcaa cctcatgtgc   5580
cgcttgctga ctatcgttat tcatcccttc gccccttca ggacgcgttt cacatcgggc   5640
ctcaccgtgc ccgtttgcgg cctttggcca acgggatcgt aagcggtgtt ccagatacat   5700
agtactgtgt ggccatccct cagacgccaa cctcgggaaa ccgaagaaat ctcgacatcg   5760
ctccctttaa ctgaatagtt ggcaacagct tccttgccat caggattgat ggtgtagatg   5820
gagggtatgc gtacattgcc cggaaagtgg aataccgtcg taaatccatt gtcgaagact   5880
tcgagtggca acagcgaacg atcgccttgg gcgacgtagt gccaattact gtccgccgca   5940
ccaagggctg tgacaggctg atccaataaa ttctcagctt tccgttgata ttgtgcttcc   6000
gcgtgtagtc tgtccacaac agccttctgt tgtgcctccc ttcgccgagc cgccgcatcg   6060
tcggcggggt aggcgaattg gacgctgtaa tagagatcgg gctgctcttt atcgaggtgg   6120
gacagagtct tggaacttat actgaaaaca taacggcgca tcccggagtc gcttgcggtt   6180
agcacgatta ctggctgagg cgtgaggacc tggcttgcct tgaaaaatag ataatttccc   6240
cgcggtaggg ctgctagatc tttgctattt gaaacggcaa ccgctgtcac cgtttcgttc   6300
gtggcgaatg ttacgaccaa agtagctcca accgccgtcg agaggcgcac cacttgatcg   6360
ggattgtaag ccaaataacg catgcgcgga tctagcttgc ccgccattgg agtgtcttca   6420
gcctccgcac cagtcgcagc ggcaaataaa catgctaaaa tgaaaagtgc ttttctgatc   6480
atggttcgct gtggcctacg tttgaaacgg tatcttccga tgtctgatag gaggtgacaa   6540
ccagacctgc cgggttggtt agtctcaatc tgccgggcaa gctggtcacc ttttcgtagc   6600
gaactgtcgc ggtccacgta ctcaccacag gcattttgcc gtcaacgacg agggtccttt   6660
tatagcgaat ttgctgcgtg cttggagtta catcatttga agcgatgtgc tcgacctcca   6720
ccctgccgcg tttgccaaga atgacttgag gcgaactggg attgggatag ttgaagaatt   6780
gctggtaatc ctggcgcact gttggggcac tgaagttcga taccaggtcg taggcgtact   6840
gagcggtgtc ggcatcataa ctctcgcgca ggcgaacgta ctcccacaat gaggcgttaa   6900
cgacggcctc ctcttgagtt gcaggcaatc gcgagacaga cacctcgctg tcaacggtgc   6960
cgtccggccg tatccataga tatacgggca caagcctgct caacggcacc attgtggcta   7020
tagcgaacgc ttgagcaaca tttcccaaaa tcgcgatagc tgcgacagct gcaatgagtt   7080
tggagagacg tcgcgccgat ttcgctcgcg cggtttgaaa ggcttctact tccttatagt   7140
gctcggcaag gctttcgcgc gccactagca tggcatattc aggccccgtc atagcgtcca   7200
cccgaattgc cgagctgaag atctgacgga gtaggctgcc atcgccccac attcagcggg   7260
```

```
aagatcgggc ctttgcagct cgctaatgtg tcgtttgtct ggcagccgct caaagcgaca   7320
actaggcaca gcaggcaata cttcatagaa ttctccattg aggcgaattt ttgcgcgacc   7380
tagcctcgct caacctgagc gaagcgacgg tacaagctgc tggcagattg ggttgcgccg   7440
ctccagtaac tgcctccaat gttgccggcg atcgccggca aagcgacaat gagcgcatcc   7500
cctgtcagaa aaaacatatc gagttcgtaa agaccaatga tcttggccgc ggtcgtaccg   7560
gcgaaggtga ttacaccaag cataagggtg agcgcagtcg cttcggttag gatgacgatc   7620
gttgccacga ggtttaagag gagaagcaag agaccgtagg tgataagttg cccgatccac   7680
ttagctgcga tgtcccgcgt gcgatcaaaa atatatccga cgaggatcag aggcccgatc   7740
gcgagaagca ctttcgtgag aattccaacg gcgtcgtaaa ctccgaaggc agaccagagc   7800
gtgccgtaaa ggacccactg tgccccttgg aaagcaagga tgtcctggtc gttcatcgga   7860
ccgatttcgg atgcgatttt ctgaaaaacg gcctgggtca cggcgaacat tgtatccaac   7920
tgtgccggaa cagtctgcag aggcaagccg gttacactaa actgctgaac aaagtttggg   7980
accgtctttt cgaagatgga aaccacatag tcttggtagt tagcctgccc aacaattaga   8040
gcaacaacga tggtgaccgt gatcacccga gtgataccgc tacgggtatc gacttcgccg   8100
cgtatgacta aaataccctg aacaataatc caaagagtga cacaggcgat caatggcgca   8160
ctcaccgcct cctggatagt ctcaagcatc gagtccaagc ctgtcgtgaa ggctacatcg   8220
aagatcgtat gaatggccgt aaacggcgcc ggaatcgtga aattcatcga ttggacctga   8280
acttgactgg tttgtcgcat aatgttggat aaaatgagct cgcattcggc gaggatgcgg   8340
gcggatgaac aaatcgccca gccttagggg agggcaccaa agatgacagc ggtcttttga   8400
tgctccttgc gttgagcggc cgcctcttcc gcctcgtgaa ggccggcctg cgcggtagtc   8460
atcgttaata ggcttgtcgc ctgtacattt tgaatcattg cgtcatggat ctgcttgaga   8520
agcaaaccat tggtcacggt tgcctgcatg atattgcgag atcgggaaag ctgagcagac   8580
gtatcagcat tcgccgtcaa gcgtttgtcc atcgtttcca gattgtcagc cgcaatgcca   8640
gcgctgtttg cggaaccggt gatctgcgat cgcaacaggt ccgcttcagc atcactaccc   8700
acgactgcac gatctgtatc gctggtgatc gcacgtgccg tggtcgacat tggcattcgc   8760
ggcgaaaaca tttcattgtc taggtccttc gtcgaaggat actgattttt ctggttgagc   8820
gaagtcagta gtccagtaac gccgtaggcc gacgtcaaca tcgtaaccat cgctatagtc   8880
tgagtgagat tctccgcagt cgcgagcgca gtcgcgagcg tctcagcctc cgttgccggg   8940
tcgctaacaa caaactgcgc ccgcgcgggc tgaatatata gaaagctgca ggtcaaaact   9000
gttgcaataa gttgcgtcgt cttcatcgtt tcctacctta tcaatcttct gcctcgtggt   9060
gacgggccat gaattcgctg agccagccag atgagttgcc ttcttgtgcc tcgcgtagtc   9120
gagttgcaaa gcgcaccgtg ttggcacgcc ccgaaagcac ggcgacatat tcacgcatat   9180
cccgcagatc aaattcgcag atgacgcttc cactttctcg tttaagaaga aacttacggc   9240
tgccgaccgt catgtcttca cggatcgcct gaaattcctt ttcggtacat ttcagtccat   9300
cgacataagc cgatcgatct gcggttggtg atggatagaa aatcttcgtc atacattgcg   9360
caaccaagct ggctcctagc ggcgattcca gaacatgctc tggttgctgc gttgccagta   9420
ttagcatccc gttgtttttt cgaacggtca ggaggaattt gtcgacgaca gtcgaaaatt   9480
tagggtttaa caaataggcg cgaaactcat cgcagctcat cacaaaacgg cggccgtcga   9540
tcatggctcc aatccgatgc aggagatatg ctgcagcggg agcgcatact tcctcgtatt   9600
cgagaagatg cgtcatgtcg aagccggtaa tcgacggatc taactttact tcgtcaactt   9660
```

```
cgccgtcaaa tgcccagcca agcgcatggc cccggcacca gcgttggagc cgcgctcctg    9720
cgccttcggc gggcccatgc aacaaaaatt cacgtaaccc cgcgattgaa cgcatttgtg    9780
gatcaaacga gagctgacga tggataccac ggaccagacg gcggttctct tccggagaaa    9840
tcccaccccg accatcactc tcgatgagag ccacgatcca ttcgcgcaga aaatcgtgtg    9900
aggctgctgt gttttctagg ccacgcaacg gcgccaaccc gctgggtgtg cctctgtgaa    9960
gtgccaaata tgttcctcct gtggcgcgaa ccagcaattc gccaccccgg tccttgtcaa   10020
agaacacgac cgtacctgca cggtcgacca tgctctgttc gagcatggct agaacaaaca   10080
tcatgagcgt cgtcttaccc ctcccgatag gcccgaatat tgccgtcatg ccaacatcgt   10140
gctcatgcgg gatatagtcg aaaggcgttc cgccattggt acgaaatcgg gcaatcgcgt   10200
tgccccagtg gcctgagctg gcgccctctg gaaagttttc gaaagagaca aaccctgcga   10260
aattgcgtga agtgattgcg ccagggcgtg tgcgccactt aaaattcccc ggcaattggg   10320
accaataggc cgcttccata ccaatacctt cttggacaac cacggcacct gcatccgcca   10380
ttcgtgtccg agcccgcgcg cccctgtccc caagactatt gagatcgtct gcatagacgc   10440
aaaggctcaa atgatgtgag cccataacga attcgttgct cgcaagtgcg tcctcagcct   10500
cggataattt gccgatttga gtcacggctt tatcgccgga actcagcatc tggctcgatt   10560
tgaggctaag tttcgcgtgc gcttgcgggc gagtcaggaa cgaaaaactc tgcgtgagaa   10620
caagtggaaa atcgagggat agcagcgcgt tgagcatgcc cggccgtgtt tttgcagggt   10680
attcgcgaaa cgaatagatg gatccaacgt aactgtcttt tggcgttctg atctcgagtc   10740
ctcgcttgcc gcaaatgact ctgtcggtat aaatcgaagc gccgagtgag ccgctgacga   10800
ccggaaccgg tgtgaaccga ccagtcatga tcaaccgtag cgcttcgcca atttcggtga   10860
agagcacacc ctgcttctcg cggatgccaa gacgatgcag gccatacgct ttaagagagc   10920
cagcgacaac atgccaaaga tcttccatgt tcctgatctg gcccgtgaga tcgttttccc   10980
tttttccgct tagcttggtg aacctcctct ttaccttccc taaagccgcc tgtgggtaga   11040
caatcaacgt aaggaagtgt tcattgcgga ggagttggcc ggagagcacg cgctgttcaa   11100
aagcttcgtt caggctagcg gcgaaaacac tacggaagtg tcgcggcgcc gatgatggca   11160
cgtcggcatg acgtacgagg tgagcatata ttgacacatg atcatcagcg atattgcgca   11220
acagcgtgtt gaacgcacga caacgcgcat tgcgcatttc agtttcctca agctcgaatg   11280
caacgccatc aattctcgca atggtcatga tcgatccgtc ttcaagaagg acgatatggt   11340
cgctgaggtg gccaatataa gggagataga tctcaccgga tctttcggtc gttccactcg   11400
cgccgagcat cacaccattc ctctccctcg tgggggaacc ctaattggat ttgggctaac   11460
agtagcgccc ccccaaactg cactatcaat gcttcttccc gcggtccgca aaaatagcag   11520
gacgacgctc gccgcattgt agtctcgctc cacgatgagc cgggctgcaa accataacgg   11580
cacgagaacg acttcgtaga gcgggttctg aacgataacg atgacaaagc cggcgaacat   11640
catgaataac cctgccaatg tcagtggcac cccaagaaac aatgcgggcc gtgtggctgc   11700
gaggtaaagg gtcgattctt ccaaacgatc agccatcaac taccgccagt gagcgtttgg   11760
ccgaggaagc tcgccccaaa catgataaca atgccgccga cgacgccggc aaccagccca   11820
agcgaagccc gcccgaacat ccaggagatc ccgatagcga caatgccgag aacagcgagt   11880
gactggccga acggaccaag gataaacgtg catatattgt taaccattgt ggcggggtca   11940
gtgccgccac ccgcagattg cgctgcggcg ggtccggatg aggaaatgct ccatgcaatt   12000
```

```
gcaccgcaca agcttggggc gcagctcgat atcacgcgca tcatcgcatt cgagagcgag  12060
aggcgattta gatgtaaacg gtatctctca aagcatcgca tcaatgcgca cctccttagt  12120
ataagtcgaa taagacttga ttgtcgtctg cggatttgcc gttgtcctgg tgtggcggtg  12180
gcggagcgat taaaccgcca gcgccatcct cctgcgagcg gcgctgatat gacccccaaa  12240
catcccacgt ctcttcggat tttagcgcct cgtgatcgtc ttttggaggc tcgattaacg  12300
cgggcaccag cgattgagca gctgtttcaa cttttcgcac gtagccgttt gcaaaaccgc  12360
cgatgaaatt accggtgttg taagcggaga tcgcccgacg aagcgcaaat tgcttctcgt  12420
caatcgtttc gccgcctgca taacgacttt tcagcatgtt tgcagcggca gataatgatg  12480
tgcacgcctg gagcgcaccg tcaggtgtca gaccgagcat agaaaaattt cgagagttta  12540
tttgcatgag gccaacatcc agcgaatgcc gtgcatcgag acggtgcctg acgacttggg  12600
ttgcttggct gtgatcttgc cagtgaagcg tttcgccggt cgtgttgtca tgaatcgcta  12660
aaggatcaaa gcgactctcc accttagcta tcgccgcaag cgtagatgtc gcaactgatg  12720
gggcacactt gcgagcaaca tggtcaaact cagcagatga gagtggcgtg gcaaggctcg  12780
acgaacagaa ggagaccatc aaggcaagag aaagcgaccc cgatctctta agcatacctt  12840
atctccttag ctcgcaacta acaccgcctc tcccgttgga agaagtgcgt tgttttatgt  12900
tgaagattat cgggagggtc ggttactcga aaattttcaa ttgcttcttt atgatttcaa  12960
ttgaagcgag aaacctcgcc cggcgtcttg gaacgcaaca tggaccgaga accgcgcatc  13020
catgactaag caaccggatc gacctattca ggccgcagtt ggtcaggtca ggctcagaac  13080
gaaaatgctc ggcgaggtta cgctgtctgt aaacccattc gatgaacggg aagcttcctt  13140
ccgattgctc ttggcaggaa tattggccca tgcctgcttg cgctttgcaa atgctcttat  13200
cgcgttggta tcatatgcct tgtccgccag cagaaacgca ctctaagcga ttatttgtaa  13260
aaatgtttcg gtcatgcggc ggtcatgggc ttgacccgct gtcagcgcaa gacggatcgg  13320
tcaaccgtcg gcatcgacaa cagcgtgaat cttggtggtc aaaccgccac gggaacgtcc  13380
catacagcca tcgtcttgat cccgctgttt cccgtcgccg catgttggtg gacgcggaca  13440
caggaactgt caatcatgac gacattctat cgaaagcctt ggaaatcaca ctcagaatat  13500
gatcccagac gtctgcctca cgccatcgta caaagcgatt gtagcaggtt gtacaggaac  13560
cgtatcgatc aggaacgtct gcccagggcg ggcccgtccg gaagcgccac aagatgacat  13620
tgatcacccg cgtcaacgcg cggcacgcga cgcggcttat ttgggaacaa aggactgaac  13680
aacagtccat tcgaaatcgg tgacatcaaa gcggggacgg gttatcagtg gcctccaagt  13740
caagcctcaa tgaatcaaaa tcagaccgat ttgcaaacct gatttatgag tgtgcggcct  13800
aaatgatgaa atcgtccttc tagatcgcct ccgtggtgta gcaacacctc gcagtatcgc  13860
cgtgctgacc ttggccaggg aattgactgg caagggtgct ttcacatgac cgctcttttg  13920
gccgcgatag atgatttcgt tgctgctttg ggcacgtaga aggagagaag tcatatcgga  13980
gaaattcctc ctggcgcgag agcctgctct atcgcgacgg catcccactg tcgggaacag  14040
accggatcat tcacgaggcg aaagtcgtca acacatgcgt tataggcatc ttcccttgaa  14100
ggatgatctt gttgctgcca atctggaggt gcggcagccg caggcagatg cgatctcagc  14160
gcaacttgcg gcaaaacatc tcactcacct gaaaaccact agcgagtctc gcgatcagac  14220
gaaggccttt tacttaacga cacaatatcc gatgtctgca tcacaggcgt cgctatccca  14280
gtcaatacta aagcggtgca ggaactaaag attactgatg acttaggcgt gccacgaggc  14340
ctgagacgac gcgcgtagac agttttttga aatcattatc aaagtgatgg cctccgctga  14400
```

```
agcctatcac ctctgcgccg gtctgtcgga gagatgggca agcattatta cggtcttcgc  14460
gcccgtacat gcattggacg attgcagggt caatggatct gagatcatcc agaggattgc  14520
cgcccttacc ttccgtttcg agttggagcc agcccctaaa tgagacgaca tagtcgactt  14580
gatgtgacaa tgccaagaga gagatttgct taacccgatt tttttgctca agcgtaagcc  14640
tattgaagct tgccggcatg acgtccgcgc cgaaagaata tcctacaagt aaaacattct  14700
gcacaccgaa atgcttggtg tagacatcga ttatgtgacc aagatcctta gcagtttcgc  14760
ttggggaccg ctccgaccag aaataccgaa gtgaactgac gccaatgaca ggaatccctt  14820
ccgtctgcag ataggtacca tcgatagatc tgctgcctcg cgcgtttcgg tgatgacggt  14880
gaaaacctct gacacatgca gctcccggag acggtcacag cttgtctgta agcggatgcc  14940
gggagcagac aagcccgtca gggcgcgtca gcgggtgttg gcgggtgtcg gggcgcagcc  15000
atgacccagt cacgtagcga tagcggagtg tatactggct taactatgcg gcatcagagc  15060
agattgtact gagagtgcac catatgcggt gtgaaatacc gcacagatgc gtaaggagaa  15120
aataccgcat caggcgctct tccgcttcct cgctcactga ctcgctgcgc tcggtcgttc  15180
ggctgcggcg agcggtatca gctcactcaa aggcggtaat acggttatcc acagaatcag  15240
gggataacgc aggaaagaac atgtgagcaa aaggccagca aaaggccagg aaccgtaaaa  15300
aggccgcgtt gctggcgttt ttccataggc tccgcccccc tgacgagcat cacaaaaatc  15360
gacgctcaag tcagaggtgg cgaaacccga caggactata aagataccag gcgtttcccc  15420
ctggaagctc cctcgtgcgc tctcctgttc cgaccctgcc gcttaccgga tacctgtccg  15480
cctttctccc ttcgggaagc gtggcgcttt ctcatagctc acgctgtagg tatctcagtt  15540
cggtgtaggt cgttcgctcc aagctgggct gtgtgcacga accccccgtt cagcccgacc  15600
gctgcgcctt atccggtaac tatcgtcttg agtccaaccc ggtaagacac gacttatcgc  15660
cactggcagc agccactggt aacaggatta gcagagcgag gtatgtaggc ggtgctacag  15720
agttcttgaa gtggtggcct aactacggct acactagaag gacagtattt ggtatctgcg  15780
ctctgctgaa gccagttacc ttcggaaaaa gagttggtag ctcttgatcc ggcaaacaaa  15840
ccaccgctgg tagcggtggt ttttttgttt gcaagcagca gattacgcgc agaaaaaaag  15900
gatctcaaga agatcctttg atcttttcta cggggtctga cgctcagtgg aacgaaaact  15960
cacgttaagg gattttggtc atgagattat caaaaaggat cttcacctag atccttttaa  16020
attaaaaatg aagttttaaa tcaatctaaa gtatatatga gtaaacttgg tctgacagtt  16080
accaatgctt aatcagtgag gcacctatct cagcgatctg tctatttcgt tcatccatag  16140
ttgcctgact ccccgtcgtg tagataacta cgatacggga gggcttacca tctggcccca  16200
gtgctgcaat gataccgcga gacccacgct caccggctcc agatttatca gcaataaacc  16260
agccagccgg aagggccgag cgcagaagtg gtcctgcaac tttatccgcc tccatccagt  16320
ctattaattg ttgccgggaa gctagagtaa gtagttcgcc agttaatagt ttgcgcaacg  16380
ttgttgccat tgctgcaggg gggggggggg ggggggactt ccattgttca ttccacggac  16440
aaaaacagag aaaggaaacg acagaggcca aaaagcctcg ctttcagcac ctgtcgtttc  16500
ctttcttttc agagggtatt ttaaataaaa acattaagtt atgacgaaga agaacggaaa  16560
cgccttaaac cggaaaattt tcataaatag cgaaaacccg cgaggtcgcc gccccgtaac  16620
ctgtcggatc accggaaagg acccgtaaag tgataatgat tatcatctac atatcacaac  16680
gtgcgtggag gccatcaaac cacgtcaaat aatcaattat gacgcaggta tcgtattaat  16740
```

```
tgatctgcat caacttaacg taaaaacaac ttcagacaat acaaatcagc gacactgaat  16800
acggggcaac ctcatgtccc cccccccccc cccccctgcag ggcatcgtgg tgtcacgctc  16860
gtcgtttggt atggcttcat tcagctccgg ttcccaacga tcaaggcgag ttacatgatc  16920
ccccatgttg tgcaaaaaag cggttagctc cttcggtcct ccgatcgttg tcagaagtaa  16980
gttggccgca gtgttatcac tcatggttat ggcagcactg cataattctc ttactgtcat  17040
gccatccgta agatgctttt ctgtgactgg tgagtactca accaagtcat tctgagaata  17100
gtgtatgcgg cgaccgagtt gctcttgccc ggcgtcaaca cgggataata ccgcgccaca  17160
tagcagaact ttaaaagtgc tcatcattgg aaaacgttct tcggggcgaa aactctcaag  17220
gatcttaccg ctgttgagat ccagttcgat gtaacccact cgtgcaccca actgatcttc  17280
agcatctttt actttcacca gcgtttctgg gtgagcaaaa acaggaaggc aaaatgccgc  17340
aaaaaaggga ataagggcga cacggaaatg ttgaatactc atactcttcc tttttcaata  17400
ttattgaagc atttatcagg gttattgtct catgagcgga tacatatttg aatgtattta  17460
gaaaaataaa caaatagggg ttccgcgcac atttccccga aaagtgccac ctgacgtcta  17520
agaaaccatt attatcatga cattaaccta taaaaatagg cgtatcacga ggccctttcg  17580
tcttcaagaa ttggtcgacg atcttgctgc gttcggatat tttcgtggag ttcccgccac  17640
agacccggat tgaaggcgag atccagcaac tcgcgccaga tcatcctgtg acggaacttt  17700
ggcgcgtgat gactggccag gacgtcggcc gaaagagcga caagcagatc acgcttttcg  17760
acagcgtcgg atttgcgatc gaggattttt cggcgctgcg ctacgtccgc gaccgcgttg  17820
agggatcaag ccacagcagc ccactcgacc ttctagccga cccagacgag ccaagggatc  17880
tttttggaat gctgctccgt cgtcaggctt tccgacgttt gggtggttga acagaagtca  17940
ttatcgtacg gaatgccaag cactcccgag gggaaccctg tggttggcat gcacatacaa  18000
atggacgaac ggataaacct tttcacgccc ttttaaatat ccgttattct aataaacgct  18060
cttttctctt aggtttaccc gccaatatat cctgtcaaac actgatagtt taaactgaag  18120
gcgggaaacg acaatctgat catgagcgga gaattaaggg agtcacgtta tgacccccgc  18180
cgatgacgcg ggacaagccg ttttacgttt ggaactgaca gaaccgcaac gttgaaggag  18240
ccactcagcc caagcttttt ggaaggctaa ggagaggaag ccggcgagaa ggagggggcg  18300
ttttacgtgt cactgtcctg tcgtgttggc tgttgacacg aatcatttct tccgcgcgtg  18360
ggaagaagaa gatgcacatt agcggcctga agtagagatg tcaatgggga attccccagc  18420
ggggattaac tccccagacc cgtacccatg aacatagacc ggcccccatc cccgaacccg  18480
aacccgacct cgggtacgaa aatcctccca tacccattcc cgaccgggta ctaaataccc  18540
atgggtatcc atacccgacc cgattattca aaaattaatg ggcttttttat ttgttaaccg  18600
gcggacgcaa tgcttgggac tctaggtttt tttactttgt tgaccggctg gcggctgggc  18660
tttttcctac aggcccaaag ttggtcggca gccactaggc cacacgtcac aggcagccca  18720
caagtaaatg tcgttggatt gctggatggt ggaataaaaa tcctagatgc tagattgttc  18780
tggttccggg tatttttctc catggctaat cgggtttggg tttagccctc ccaaacccga  18840
acccgccata cccgatgggt aagggattta ttccaaatct atacccatgg ggatttgttt  18900
taacccatac cttaacccta atagaggaat tccccacggg taatcgggtt tcggggccca  18960
ttgacatctc tagactgaag gcgtccaact caaatcatta aaaagtgttg acgcacgcgc  19020
tgatgcgccg gccgcacagc acaggctgca cagcccgttt aatcagcgat ggagccccgg  19080
ccgtcagcca gccaggtccg gcgtccgggt ctgcgccctg cggcgtcact gctgtcgcca  19140
```

```
ccgtctccga tggtcccaca tccatccagc gggccgcgcg tggtacaaaa ggctcttcct  19200
cgccgtcagg tgcagctgcc caaacaccag acacagactc caccaccccg cttcgatctt  19260
ctgttgcagc tgaaatctgt cagattctgc agttcattcc tcatggagaa gaggaacctg  19320
cagtggcggc gagggcgtga tggcatcgtg cagtaccctc acctcttctt cgcggccctg  19380
gcgctggccc tcctagtcgc ggaccgttcg gcctcagtcc gctggccgag gtcgactacc  19440
ggccggtgaa gcacgagctc gcgccgtacg gggaggtcat gggcagctgg cccagagaca  19500
atgccagccg gctcaggcgc gggaggctgg agttcgtcgg cgaggtgttc gggccggagt  19560
ctatcgagtt cgatctccag ggccgcgggc cgtacgccgg cctcgccgac ggccgcgtcg  19620
tgcggtggat gggcgaggag gccgggtggg agacgttcgc cggtcatgaa tcctgactgg  19680
taagtgctcg atatgcctcc ggcgtccact cgttacagtg ctataatata gtagtactaa  19740
gatattttga tctgattttt tgcattcttg ggagaaacgt catgcaaaat ttgttgtttc  19800
ttggcaaagg tcagaagaag tctgtgccaa tggagtgaac tcaacgacga ggaagcagca  19860
cgagaaggag gagttctgcg gcggccgctc ggcctgaggt tccacgggga gaccggcgag  19920
ctctacgtcg ccgacgcgta ctacggtctc atggtcgttg gccagagcgg cggcgtggcg  19980
tcctccgtcg cgagggaagc cgacggggac cccatccggt tcgcgaacga cctcgatgtg  20040
cacaggaatg gatccgtatt cttcactgac acgagcatga gatacagcag aaagtgagca  20100
aagcagcgta acaatccggc ttctcatttt caaacgcctc tgtattctct gctgaaagag  20160
tagctcacca gacaagagct gaatttgcag ggaccatctg aacatcctgt tagaaggaga  20220
aggcaccggg aggctgctca ggtatgatcc agaaacaagc ggtgtccatg tcgtgctcaa  20280
ggggctggtg ttcccaaacg gcgtgcagat ctcagaggac catcagtttc ttctcttctc  20340
cgagacaaca aactgcaggt aacaaaaata ctatctgacg atgctcatga ttctaccgta  20400
tccatagtca tgaacacaaa ccacacgaat ctggccttga ccaggataat gaggtactgg  20460
ctggaaggcc caagagcggg cgaggtagag gtgttcgcga acctgccggg cttccccgac  20520
aacgtgcgct ccaacggcag gggccagttc tgggtggcga tcgactgctg ccggaccgag  20580
gaggtgttcc caagagcgtg gctccggacc ctgtacttca agttcccgct gtcgctcaag  20640
gtgctcactt ggaaggccgc caggaggatg cacacggtgc tcgcgctcct cgacggcgaa  20700
gggcgcgtcg tggaggtgct cgaggaccgg ggccacgagg tgatgaagct ggtgagcgag  20760
gtgcgggagg tgggccgcaa gctgtggatc ggaaccgtgg cgcacaacca catcgccacc  20820
atcccctacc ctttagagga ctaaccatga tctatgctgt ttcaatgcct cctaatctgt  20880
gtacgtctat aaatgtctaa tgcagctcat ggttgtaatc ttgtttgtgt ttggcaaatt  20940
ggcataataa tggacagatt caatgggcat tggtgctgta gtcgcatcac actaattgaa  21000
tgggatcatg ttgagctctc actttgctac aatttgctcc agcttgtacg gttgtaccct  21060
cttgctcgtc tatagtaagg gccatctaaa aaaaactcaa attagatctg caatacaagt  21120
atgattgggc cgaatttgga ttgtcacggg tccgcgaccg cgaattgggc tccggtttga  21180
tttagccgac atagtagtga ccgacccgag ccggccggcg agaccaaacc gagcggacgc  21240
ccgccatgca tggagtcaaa gattcaaata gaggacctaa cagaactcgc cgtaaagact  21300
ggcgaacagt tcatacagag tctcttacga ctcaatgaca agaagaaaat cttcgtcaac  21360
atggtggagc acgacacgct tgtctactcc aaaaatatca aagatacagt ctcagaagac  21420
caaagggcaa ttgagacttt tcaacaaagg gtaatatccg gaaacctcct cggattccat  21480
```

```
tgcccagcta tctgtcactt tattgtgaag atagtggaaa aggaaggtgg ctcctacaaa  21540
tgccatcatt gcgataaagg aaaggccatc gttgaagatg cctctgccga cagtggtccc  21600
aaagatggac ccccacccac gaggagcatc gtggaaaaag aagacgttcc aaccacgtct  21660
tcaaagcaag tggattgatg tgatatctcc actgacgtaa gggatgacgc acaatcccac  21720
tatccttcgc aagacccttc ctctatataa ggaagttcat ttcatttgga gaggacaggg  21780
tacccgggga tccaccatgt ctccggagag gagaccagtt gagattaggc cagctacagc  21840
agctgatatg gccgcggttt gtgatatcgt taaccattac attgagacgt ctacagtgaa  21900
ctttaggaca gagccacaaa caccacaaga gtggattgat gatctagaga ggttgcaaga  21960
tagataccct tggttggttg ctgaggttga gggtgttgtg gctggtattg cttacgctgg  22020
gccctggaag gctaggaacg cttacgattg gacagttgag agtactgttt acgtgtcaca  22080
taggcatcaa aggttgggcc taggatccac attgtacaca catttgctta agtctatgga  22140
ggcgcaaggt tttaagtctg tggttgctgt tataggcctt ccaaacgatc catctgttag  22200
gttgcatgag gctttgggat acacagcccg gggtacattg cgcgcagctg gatacaagca  22260
tggtggatgg catgatgttg gtttttggca aagggatttt gagttgccag ctcctccaag  22320
gccagttagg ccagttaccc agatctgagt cgacctgcag gcatgccgct gaaatcacca  22380
gtctctctct acaaatctat ctctctctat aataatgtgt gagtagttcc cagataaggg  22440
aattagggtt cttatagggt ttcgctcatg tgttgagcat ataagaaacc cttagtatgt  22500
atttgtattt gtaaaatact tctatcaata aaatttctaa ttcctaaaac caaaatccag  22560
tgggtaccga gctcgaattc agtacattaa aaacgtccgc aatgtgttat taagttgtct  22620
aagcgtcaat ttgtttacac cacaatatat cctgccacca gccagccaac agctccccga  22680
ccggcagctc ggcacaaaat caccactcga tacaggcagc ccatcagtcc gggacggcgt  22740
cagcgggaga gccgttgtaa ggcggcagac tttgctcatg ttaccgatgc tattcggaag  22800
aacggcaact aagctgccgg gtttgaaaca cggatgatct cgcggagggt agcatgttga  22860
ttgtaacgat gacagagcgt tgctgcctgt gatcaaatat catctccctc gcagagatcc  22920
gaattatcag ccttcttatt catttctcgc ttaaccgtga caggctgtcg atcttgagaa  22980
ctatgccgac ataataggaa atcgctggat aaagccgctg aggaagctga gtggcgctat  23040
ttctttagaa gtgaacgttg acgatcgtcg accgtacccc gatgaattaa ttcggacgta  23100
cgttctgaac acagctggat acttacttgg gcgattgtca tacatgacat caacaatgta  23160
cccgtttgtg taaccgtctc ttggaggttc gtatgacact agtggttccc ctcagcttgc  23220
gactagatgt tgaggcctaa cattttatta gagagcaggc tagttgctta gatacatgat  23280
cttcaggccg ttatctgtca gggcaagcga aaattggcca tttatgacga ccaatgcccc  23340
gcagaagctc ccatctttgc cgccatagac gccgcgcccc ccttttgggg tgtagaacat  23400
ccttttgcca gatgtggaaa agaagttcgt tgtcccattg ttggcaatga cgtagtagcc  23460
ggcgaaagtg cgagacccat ttgcgctata tataagccta cgatttccgt tgcgactatt  23520
gtcgtaattg gatgaactat tatcgtagtt gctctcagag ttgtcgtaat ttgatggact  23580
attgtcgtaa ttgcttatgg agttgtcgta gttgcttgga gaaatgtcgt agttggatgg  23640
ggagtagtca tagggaagac gagcttcatc cactaaaaca attggcaggt cagcaagtgc  23700
ctgccccgat gccatcgcaa gtacgaggct tagaaccacc ttcaacagat cgcgcatagt  23760
cttccccagc tctctaacgc ttgagttaag ccgcgccgcg aagcggcgtc ggcttgaacg  23820
aattgttaga cattatttgc cgactacctt ggtgatctcg cctttcacgt agtgaacaaa  23880
```

```
ttcttccaac tgatctgcgc gcgaggccaa gcgatcttct tgtccaagat aagcctgcct  23940
agcttcaagt atgacgggct gatactgggc cggcaggcgc tccattgccc agtcggcagc  24000
gacatccttc ggcgcgattt tgccggttac tgcgctgtac caaatgcggg acaacgtaag  24060
cactacattt cgctcatcgc cagcccagtc gggcggcgag ttccatagcg ttaaggtttc  24120
atttagcgcc tcaaatagat cctgttcagg aaccggatca aagagttcct ccgccgctgg  24180
acctaccaag gcaacgctat gttctcttgc ttttgtcagc aagatagcca gatcaatgtc  24240
gatcgtggct ggctcgaaga tacctgcaag aatgtcattg cgctgccatt ctccaaattg  24300
cagttcgcgc ttagctggat aacgccacgg aatgatgtcg tcgtgcacaa caatggtgac  24360
ttctacagcg cggagaatct cgctctctcc aggggaagcc gaagtttcca aaaggtcgtt  24420
gatcaaagct cgccgcgttg tttcatcaag ccttacggtc accgtaacca gcaaatcaat  24480
atcactgtgt ggcttcaggc cgccatccac tgcggagccg tacaaatgta cggccagcaa  24540
cgtcggttcg agatggcgct cgatgacgcc aactacctct gatagttgag tcgatacttc  24600
ggcgatcacc gcttccctca tgatgtttaa ctcctgaatt aagccgcgcc gcgaagcggt  24660
gtcggcttga atgaattgtt aggcgtcatc ctgtgctccc gagaaccagt accagtacat  24720
cgctgtttcg ttcgagactt gaggtctagt tttatacgtg aacaggtcaa tgccgccgag  24780
agtaaagcca cattttgcgt acaaattgca ggcaggtaca ttgttcgttt gtgtctctaa  24840
tcgtatgcca aggagctgtc tgcttagtgc ccactttttc gcaaattcga tgagactgtg  24900
cgcgactcct ttgcctcggt gcgtgtgcga cacaacaatg tgttcgatag aggctagatc  24960
gttccatgtt gagttgagtt caatcttccc gacaagctct tggtcgatga atgcgccata  25020
gcaagcagag tcttcatcag agtcatcatc cgagatgtaa tccttccggt aggggctcac  25080
acttctggta gatagttcaa agccttggtc ggataggtgc acatcgaaca cttcacgaac  25140
aatgaaatgg ttctcagcat ccaatgtttc cgccacctgc tcagggatca ccgaaatctt  25200
catatgacgc ctaacgcctg gcacagcgga tcgcaaacct ggcgcggctt ttggcacaaa  25260
aggcgtgaca ggtttgcgaa tccgttgctg ccacttgtta accccttttgc cagatttggt  25320
aactataatt tatgttagag gcgaagtctt gggtaaaaac tggcctaaaa ttgctgggga  25380
tttcaggaaa gtaaacatca ccttccggct cgatgtctat tgtagatata tgtagtgtat  25440
ctacttgatc gggggatctg ctgcctcgcg cgtttcggtg atgacggtga aaacctctga  25500
cacatgcagc tcccggagac ggtcacagct tgtctgtaag cggatgccgg gagcagacaa  25560
gcccgtcagg gcgcgtcagc gggtgttggc gggtgtcggg gcgcagccat gacccagtca  25620
cgtagcgata gcggagtgta tactggctta actatgcggc atcagagcag attgtactga  25680
gagtgcacca tatgcggtgt gaaataccgc acagatgcgt aaggagaaaa taccgcatca  25740
ggcgctcttc cgcttcctcg ctcactgact cgctgcgctc ggtcgttcgg ctgcggcgag  25800
cggtatcagc tcactcaaag gcggtaatac ggttatccac agaatcaggg gataacgcag  25860
gaaagaacat gtgagcaaaa ggccagcaaa aggccaggaa ccgtaaaaag gccgcgttgc  25920
tggcgttttt ccataggctc cgcccccctg acgagcatca caaaaatcga cgctcaagtc  25980
agaggtggcg aaacccgaca ggactataaa gataccaggc gtttccccct ggaagctccc  26040
tcgtgcgctc tcctgttccg accctgccgc ttaccggata cctgtccgcc tttctccctt  26100
cgggaagcgt ggcgctttct catagctcac gctgtaggta tctcagttcg gtgtaggtcg  26160
ttcgctccaa gctgggctgt gtgcacgaac cccccgttca gcccgaccgc tgcgccttat  26220
```

```
ccggtaacta tcgtcttgag tccaacccgg taagacacga cttatcgcca ctggcagcag  26280
ccactggtaa caggattagc agagcgaggt atgtaggcgg tgctacagag ttcttgaagt  26340
ggtggcctaa ctacggctac actagaagga cagtatttgg tatctgcgct ctgctgaagc  26400
cagttacctt cggaaaaaga gttggtagct cttgatccgg caaacaaacc accgctggta  26460
gcggtggttt ttttgtttgc aagcagcaga ttacgcgcag aaaaaaagga tctcaagaag  26520
atcctttgat cttttctacg gggtctgacg ctcagtggaa cgaaaactca cgttaaggga  26580
ttttggtcat gagattatca aaaaggatct tcacctagat ccttttaaat taaaaatgaa  26640
gttttaaatc aatctaaagt atatatgagt aaacttggtc tgacagttac caatgcttaa  26700
tcagtgaggc acctatctca gcgatctgtc tatttcgttc atccatagtt gcctgactcc  26760
ccgtcgtgta gataactacg atacgggagg gcttaccatc tggccccagt gctgcaatga  26820
taccgcgaga cccacgctca ccggctccag atttatcagc aataaaccag ccagccggaa  26880
gggccgagcg cagaagtggt cctgcaactt tatccgcctc catccagtct attaattgtt  26940
gccgggaagc tagagtaagt agttcgccag ttaatagttt gcgcaacgtt gttgccattg  27000
ctgcaggggg gggggggggg ggggacttcc attgttcatt ccacggacaa aaacagagaa  27060
aggaaacgac agaggccaaa aagcctcgct ttcagcacct gtcgtttcct ttcttttcag  27120
agggtatttt aaataaaaac attaagttat gacgaagaag aacggaaacg ccttaaaccg  27180
gaaaattttc ataaatagcg aaaacccgcg aggtcgccgc cccgtaacct gtcggatcac  27240
cggaaaggac ccgtaaagtg ataatgatta tcatctacat atcacaacgt gcgtggaggc  27300
catcaaacca cgtcaaataa tcaattatga cgcaggtatc gtattaattg atctgcatca  27360
acttaacgta aaaacaactt cagacaatac aaatcagcga cactgaatac ggggcaacct  27420
catgtccccc cccccccccc ccctgcaggc atcgtggtgt cacgctcgtc gtttggtatg  27480
gcttcattca gctccggttc ccaacgatca aggcgagtta catgatcccc catgttgtgc  27540
aaaaaagcgg ttagctcctt cggtcctccg atcgttgtca gaagtaagtt ggccgcagtg  27600
ttatcactca tggttatggc agcactgcat aattctctta ctgtcatgcc atccgtaaga  27660
tgcttttctg tgactggtga gtactcaacc aagtcattct gagaatagtg tatgcggcga  27720
ccgagttgct cttgcccggc gtcaacacgg gataataccg cgccacatag cagaacttta  27780
aaagtgctca tcattggaaa acgttcttcg gggcgaaaac tctcaaggat cttaccgctg  27840
ttgagatcca gttcgatgta acccactcgt gcacccaact gatcttcagc atcttttact  27900
ttcaccagcg tttctgggtg agcaaaaaca ggaaggcaaa atgccgcaaa aaagggaata  27960
agggcgacac ggaaatgttg aatactcata ctcttccttt ttcaatatta ttgaagcatt  28020
tatcagggtt attgtctcat gagcggatac atatttgaat gtatttagaa aaataaacaa  28080
ataggggttc cgcgcacatt tccccgaaaa gtgccacctg acgtctaaga aaccattatt  28140
atcatgacat taacctataa aaataggcgt atcacgaggc cctttcgtct tcaagaattc  28200
ggagcttttg ccattctcac cggattcagt cgtcactcat ggtgatttct cacttgataa  28260
ccttattttt gacgagggga aattaatagg ttgtattgat gttggacgag tcggaatcgc  28320
agaccgatac caggatcttg ccatcctatg gaactgcctc ggtgagtttt ctccttcatt  28380
acagaaacgg ctttttcaaa aatatggtat tgataatcct gatatgaata aattgcagtt  28440
tcatttgatg ctcgatgagt ttttctaatc agaattggtt aattggttgt aacactggca  28500
gagcattacg ctgacttgac gggacggcgg ctttgttgaa taaatcgaac ttttgctgag  28560
ttgaaggatc agatcacgca tcttcccgac aacgcagacc gttccgtggc aaagcaaaag  28620
```

```
ttcaaaatca ccaactggtc cacctacaac aaagctctca tcaaccgtgg ctccctcact  28680
ttctggctgg atgatggggc gattcaggcc tggtatgagt cagcaacacc ttcttcacga  28740
ggcagacctc agcgccagaa ggccgccaga gaggccgagc gcggccgtga ggcttggacg  28800
ctagggcagg gcatgaaaaa gcccgtagcg ggctgctacg ggcgtctgac gcggtggaaa  28860
gggggagggg atgttgtcta catggctctg ctgtagtgag tgggttgcgc tccggcagcg  28920
gtcctgatca atcgtcaccc tttctcggtc cttcaacgtt cctgacaacg agcctccttt  28980
tcgccaatcc atcgacaatc accgcgagtc cctgctcgaa cgctgcgtcc ggaccggctt  29040
cgtcgaaggc gtctatcgcg gcccgcaaca gcggcgagag cggagcctgt tcaacggtgc  29100
cgccgcgctc gccggcatcg ctgtcgccgg cctgctcctc aagcacggcc ccaacagtga  29160
agtagctgat tgtcatcagc gcattgacgg cgtccccggc cgaaaaaccc gcctcgcaga  29220
ggaagcgaag ctgcgcgtcg gccgtttcca tctgcggtgc gcccggtcgc gtgccggcat  29280
ggatgcgcgc gccatcgcgg taggcgagca gcgcctgcct gaagctgcgg gcattcccga  29340
tcagaaatga gcgccagtcg tcgtcggctc tcggcaccga atgcgtatga ttctccgcca  29400
gcatggcttc ggccagtgcg tcgagcagcg cccgcttgtt cctgaagtgc cagtaaagcg  29460
ccggctgctg aacccccaac cgttccgcca gtttgcgtgt cgtcagaccg tctacgccga  29520
cctcgttcaa caggtccagg gcggcacgga tcactgtatt cggctgcaac tttgtcatgc  29580
ttgacacttt atcactgata aacataatat gtccaccaac ttatcagtga taaagaatcc  29640
gcgcgttcaa tcggaccagc ggaggctggt ccggaggcca gacgtgaaac ccaacatacc  29700
cctgatcgta attctgagca ctgtcgcgct cgacgctgtc ggcatcggcc tgattatgcc  29760
ggtgctgccg ggcctcctgc gcgatctggt tcactcgaac gacgtcaccg cccactatgg  29820
cattctgctg gcgctgtatg cgttggtgca atttgcctgc gcacctgtgc tgggcgcgct  29880
gtcggatcgt ttcgggcggc ggccaatctt gctcgtctcg ctggccggcg ccactgtcga  29940
ctacgccatc atggcgacag cgcctttcct ttgggttctc tatatcgggc ggatcgtggc  30000
cggcatcacc ggggcgactg gggcggtagc cggcgcttat attgccgata tcactgatgg  30060
cgatgagcgc gcgcggcact tcggcttcat gagcgcctgt ttcgggttcg ggatggtcgc  30120
gggacctgtg ctcggtgggc tgatgggcgg tttctccccc cacgctccgt tcttcgccgc  30180
ggcagccttg aacggcctca atttcctgac gggctgtttc cttttgccgg agtcgcacaa  30240
aggcgaacgc cggccgttac gccgggaggc tctcaacccg ctcgcttcgt tccggtgggc  30300
ccggggcatg accgtcgtcg ccgccctgat ggcggtcttc ttcatcatgc aacttgtcgg  30360
acaggtgccg gccgcgcttt gggtcatttt cggcgaggat cgctttcact gggacgcgac  30420
cacgatcggc atttcgcttg ccgcatttgg cattctgcat tcactcgccc aggcaatgat  30480
caccggccct gtagccgccc ggctcggcga aaggcgggca ctcatgctcg gaatgattgc  30540
cgacggcaca ggctacatcc tgcttgcctt cgcgacacgg ggatggatgg cgttcccgat  30600
catggtcctg cttgcttcgg gtggcatcgg aatgccggcg ctgcaagcaa tgttgtccag  30660
gcaggtggat gaggaacgtc aggggcagct gcaaggctca ctggcggcgc tcaccagcct  30720
gacctcgatc gtcggacccc tcctcttcac ggcgatctat gcggcttcta taacaacgtg  30780
gaacgggtgg gcatggattg caggcgctgc cctctacttg ctctgcctgc cggcgctgcg  30840
tcgcgggctt tggagcggcg cagggcaacg agccgatcgc tgatcgtgga aacgataggc  30900
ctatgccatg cgggtcaagg cgacttccgg caagctatac gcgccctagg agtgcggttg  30960
```

```
gaacgttggc ccagccagat actcccgatc acgagcagga cgccgatgat ttgaagcgca  31020
ctcagcgtct gatccaagaa caaccatcct agcaacacgg cggtccccgg gctgagaaag  31080
cccagtaagg aaacaactgt aggttcgagt cgcgagatcc cccggaacca aaggaagtag  31140
gttaaacccg ctccgatcag gccgagccac gccaggccga gaacattggt tcctgtaggc  31200
atcgggattg gcggatcaaa cactaaagct actggaacga gcagaagtcc tccggccgcc  31260
agttgccagg cggtaaaggt gagcagaggc acgggaggtt gccacttgcg ggtcagcacg  31320
gttccgaacg ccatggaaac cgcccccgcc aggcccgctg cgacgccgac aggatctagc  31380
gctgcgtttg gtgtcaacac caacagcgcc acgcccgcag ttccgcaaat agcccccagg  31440
accgccatca atcgtatcgg gctacctagc agagcggcag agatgaacac gaccatcagc  31500
ggctgcacag cgcctaccgt cgccgcgacc ccgcccggca ggcggtagac cgaaataaac  31560
aacaagctcc agaatagcga aatattaagt gcgccgagga tgaagatgcg catccaccag  31620
attcccgttg gaatctgtcg gacgatcatc acgagcaata aacccgccgg caacgcccgc  31680
agcagcatac cggcgacccc tcggcctcgc tgttcgggct ccacgaaaac gccggacaga  31740
tgcgccttgt gagcgtcctt ggggccgtcc tcctgtttga agaccgacag cccaatgatc  31800
tcgccgtcga tgtaggcgcc gaatgccacg gcatctcgca accgttcagc gaacgcctcc  31860
atgggctttt tctcctcgtg ctcgtaaacg gacccgaaca tctctggagc tttcttcagg  31920
gccgacaatc ggatctcgcg gaaatcctgc acgtcggccg ctccaagccg tcgaatctga  31980
gccttaatca caattgtcaa ttttaatcct ctgtttatcg gcagttcgta gagcgcgccg  32040
tgcgtcccga gcgatactga gcgaagcaag tgcgtcgagc agtgcccgct tgttcctgaa  32100
atgccagtaa agcgctggct gctgaacccc cagccggaac tgaccccaca aggccctagc  32160
gtttgcaatg caccaggtca tcattgaccc aggcgtgttc caccaggccg ctgcctcgca  32220
actcttcgca ggcttcgccg acctgctcgc gccacttctt cacgcgggtg gaatccgatc  32280
cgcacatgag gcggaaggtt tccagcttga gcgggtacgg ctcccggtgc gagctgaaat  32340
agtcgaacat ccgtcgggcc gtcggcgaca gcttgcggta cttctcccat atgaatttcg  32400
tgtagtggtc gccagcaaac agcacgacga tttcctcgtc gatcaggacc tggcaacggg  32460
acgttttctt gccacggtcc aggacgcgga agcggtgcag cagcgacacc gattccaggt  32520
gcccaacgcg gtcggacgtg aagcccatcg ccgtcgcctg taggcgcgac aggcattcct  32580
cggccttcgt gtaataccgg ccattgatcg accagcccag gtcctggcaa agctcgtaga  32640
acgtgaaggt gatcggctcg ccgatagggg tgcgcttcgc gtactccaac acctgctgcc  32700
acaccagttc gtcatcgtcg gcccgcagct cgacgccggt gtaggtgatc ttcacgtcct  32760
tgttgacgtg gaaaatgacc ttgttttgca gcgcctcgcg cgggatttc ttgttgcgcg  32820
tggtgaacag ggcagagcgg gccgtgtcgt ttggcatcgc tcgcatcgtg tccggccacg  32880
gcgcaatatc gaacaaggaa agctgcattt ccttgatctg ctgcttcgtg tgtttcagca  32940
acgcggcctg cttggcctcg ctgacctgtt ttgccaggtc ctcgccggcg gtttttcgct  33000
tcttggtcgt catagttcct cgcgtgtcga tggtcatcga cttcgccaaa cctgccgcct  33060
cctgttcgag acgacgcgaa cgctccacgg cggccgatgg cgcgggcagg gcagggggag  33120
ccagttgcac gctgtcgcgc tcgatcttgg ccgtagcttg ctggaccatc gagccgacgg  33180
actggaaggt ttcgcggggc gcacgcatga cggtgcggct tgcgatggtt tcggcatcct  33240
cggcggaaaa ccccgcgtcg atcagttctt gcctgtatgc cttccggtca aacgtccgat  33300
tcattcaccc tccttgcggg attgccccga ctcacgccgg ggcaatgtgc ccttattcct  33360
```

```
gatttgaccc gcctggtgcc ttggtgtcca gataatccac cttatcggca atgaagtcgg  33420
tcccgtagac cgtctggccg tccttctcgt acttggtatt ccgaatcttg ccctgcacga  33480
ataccagcga ccccttgccc aaatacttgc cgtgggcctc ggcctgagag ccaaaacact  33540
tgatgcggaa gaagtcggtg cgctcctgct tgtcgccggc atcgttgcgc cactcttcat  33600
taaccgctat atcgaaaatt gcttgcggct tgttagaatt gccatgacgt acctcggtgt  33660
cacgggtaag attaccgata aactggaact gattatggct catatcgaaa gtctccttga  33720
gaaaggagac tctagtttag ctaaacattg gttccgctgt caagaacttt agcggctaaa  33780
attttgcggg ccgcgaccaa aggtgcgagg ggcggcttcc gctgtgtaca accagatatt  33840
tttcaccaac atccttcgtc tgctcgatga gcggggcatg acgaaacatg agctgtcgga  33900
gagggcaggg gtttcaattt cgtttttatc agacttaacc aacggtaagg ccaacccctc  33960
gttgaaggtg atggaggcca ttgccgacgc cctggaaact cccctacctc ttctcctgga  34020
gtccaccgac cttgaccgcg aggcactcgc ggagattgcg ggtcatcctt tcaagagcag  34080
cgtgccgccc ggatacgaac gcatcagtgt ggttttgccg tcacataagg cgtttatcgt  34140
aaagaaatgg ggcgacgaca cccgaaaaaa gctgcgtgga aggctctgac gccaagggtt  34200
agggcttgca cttccttctt tagccgctaa aacggcccct tctctgcggg ccgtcggctc  34260
gcgcatcata tcgacatcct caacggaagc cgtgccgcga atggcatcgg gcgggtgcgc  34320
tttgacagtt gttttctatc agaaccccta cgtcgtgcgg ttcgattagc tgtttgtctt  34380
gcaggctaaa cactttcggt atatcgtttg cctgtgcgat aatgttgcta atgatttgtt  34440
gcgtaggggt tactgaaaag tgagcgggaa agaagagttt cagaccatca aggagcgggc  34500
caagcgcaag ctggaacgcg acatgggtgc ggacctgttg gccgcgctca acgacccgaa  34560
aaccgttgaa gtcatgctca acgcggacgg caaggtgtgg cacgaacgcc ttggcgagcc  34620
gatgcggtac atctgcgaca tgcggcccag ccagtcgcag gcgattatag aaacggtggc  34680
cggattccac ggcaaagagg tcacgcggca ttcgcccatc ctggaaggcg agttcccctt  34740
ggatggcagc cgctttgccg gccaattgcc gccggtcgtg gccgcgccaa cctttgcgat  34800
ccgcaagcgc gcggtcgcca tcttcacgct ggaacagtac gtcgaggcgg gcatcatgac  34860
ccgcgagcaa tacgaggtca ttaaaagcgc cgtcgcggcg catcgaaaca tcctcgtcat  34920
tggcggtact ggctcgggca agaccacgct cgtcaacgcg atcatcaatg aaatggtcgc  34980
cttcaacccg tctgagcgcg tcgtcatcat cgaggacacc ggcgaaatcc agtgcgccgc  35040
agagaacgcc gtccaatacc acaccagcat cgacgtctcg atgacgctgc tgctcaagac  35100
aacgctgcgt atgcgccccg accgcatcct ggtcggtgag gtacgtggcc ccgaagccct  35160
tgatctgttg atggcctgga acaccgggca tgaaggaggt gccgccaccc tgcacgcaaa  35220
caaccccaaa gcgggcctga gccggctcgc catgcttatc agcatgcacc cggattcacc  35280
gaaacccatt gagccgctga ttggcgaggc ggttcatgtg gtcgtccata tcgccaggac  35340
ccctagcggc cgtcgagtgc aagaaattct cgaagttctt ggttacgaga acggccagta  35400
catcaccaaa accctgtaag gagtatttcc aatgacaacg gctgttccgt tccgtctgac  35460
catgaatcgc ggcattttgt tctaccttgc cgtgttcttc gttctcgctc tcgcgttatc  35520
cgcgcatccg gcgatggcct cggaaggcac cggcggcagc ttgccatatg agagctggct  35580
gacgaacctg cgcaactccg taaccggccc ggtggccttc gcgctgtcca tcatcggcat  35640
cgtcgtcgcc ggcggcgtgc tgatcttcgg cggcgaactc aacgccttct tccgaaccct  35700
```

```
gatcttcctg gttctggtga tggcgctgct ggtcggcgcg cagaacgtga tgagcacctt  35760
cttcggtcgt ggtgccgaaa tcgcggccct cggcaacggg gcgctgcacc aggtgcaagt  35820
cgcggcggcg gatgccgtgc gtgcggtagc ggctggacgg ctcgcctaat catggctctg  35880
cgcacgatcc ccatccgtcg cgcaggcaac cgagaaaacc tgttcatggg tggtgatcgt  35940
gaactggtga tgttctcggg cctgatggcg tttgcgctga ttttcagcgc ccaagagctg  36000
cgggccaccg tggtcggtct gatcctgtgg ttcggggcgc tctatgcgtt ccgaatcatg  36060
gcgaaggccg atccgaagat gcggttcgtg tacctgcgtc accgccggta caagccgtat  36120
tacccggccc gctcgacccc gttccgcgag aacaccaata gccaagggaa gcaataccga  36180
tgatccaagc aattgcgatt gcaatcgcgg gcctcggcgc gcttctgttg ttcatcctct  36240
ttgcccgcat ccgcgcggtc gatgccgaac tgaaactgaa aaagcatcgt tccaaggacg  36300
ccggcctggc cgatctgctc aactacgccg ctgtcgtcga tgacggcgta atcgtgggca  36360
agaacggcag ctttatggct gcctggctgt acaagggcga tgacaacgca agcagcaccg  36420
accagcagcg cgaagtagtg tccgcccgca tcaaccaggc cctcgcgggc ctgggaagtg  36480
ggtggatgat ccatgtggac gccgtgcggc gtcctgctcc gaactacgcg gagcggggcc  36540
tgtcggcgtt ccctgaccgt ctgacggcag cgattgaaga agagcgctcg gtcttgcctt  36600
gctcgtcggt gatgtacttc accagctccg cgaagtcgct cttcttgatg gagcgcatgg  36660
ggacgtgctt ggcaatcacg cgcacccccc ggccgtttta gcggctaaaa aagtcatggc  36720
tctgccctcg ggcggaccac gcccatcatg accttgccaa gctcgtcctg cttctcttcg  36780
atcttcgcca gcagggcgag gatcgtggca tcaccgaacc gcgccgtgcg cgggtcgtcg  36840
gtgagccaga gtttcagcag gccgcccagg cggcccaggt cgccattgat gcgggccagc  36900
tcgcggacgt gctcatagtc cacgacgccc gtgattttgt agccctggcc gacggccagc  36960
aggtaggccg acaggctcat gccggccgcc gccgcctttt cctcaatcgc tcttcgttcg  37020
tctggaaggc agtacacctt gataggtggg ctgcccttcc tggttggctt ggtttcatca  37080
gccatccgct tgccctcatc tgttacgccg gcggtagccg gccagcctcg cagagcagga  37140
ttcccgttga gcaccgccag gtgcgaataa gggacagtga agaaggaaca cccgctcgcg  37200
ggtgggccta cttcacctat cctgcccggc tgacgccgtt ggatacacca aggaaagtct  37260
acacgaaccc tttggcaaaa tcctgtatat cgtgcgaaaa aggatggata taccgaaaaa  37320
atcgctataa tgaccccgaa gcagggttat gcagcggaaa agcgctgctt ccctgctgtt  37380
ttgtggaata tctaccgact ggaaacaggc aaatgcagga aattactgaa ctgaggggac  37440
aggcgagaga cgatgccaaa gagctacacc gacgagctgg ccgagtgggt tgaatcccgc  37500
gcggccaaga agcgccggcg tgatgaggct gcggttgcgt tcctggcggt gagggcggat  37560
gtcgaggcgg cgttagcgtc cggctatgcg ctcgtcacca tttgggagca catgcgggaa  37620
acggggaagg tcaagttctc ctacgagacg ttccgctcgc acgccaggcg gcacatcaag  37680
gccaagcccg ccgatgtgcc cgcaccgcag gccaaggctg cggaacccgc gccggcaccc  37740
aagacgccgg agccacggcg gccgaagcag gggggcaagg ctgaaaagcc ggcccccgct  37800
gcggccccga ccggcttcac cttcaaccca acaccggaca aaaaggatct actgtaatgg  37860
cgaaaattca catggttttg cagggcaagg gcggggtcgg caagtcggcc atcgccgcga  37920
tcattgcgca gtacaagatg gacaaggggc agacaccctt gtgcatcgac accgacccgg  37980
tgaacgcgac gttcgagggc tacaaggccc tgaacgtccg ccggctgaac atcatggccg  38040
gcgacgaaat taactcgcgc aacttcgaca ccctggtcga gctgattgcg ccgaccaagg  38100
```

```
atgacgtggt gatcgacaac ggtgccagct cgttcgtgcc tctgtcgcat tacctcatca  38160
gcaaccaggt gccggctctg ctgcaagaaa tggggcatga gctggtcatc cataccgtcg  38220
tcaccggcgg ccaggctctc ctggacacgg tgagcggctt cgcccagctc gccagccagt  38280
tcccggccga agcgcttttc gtggtctggc tgaacccgta ttgggggcct atcgagcatg  38340
agggcaagag ctttgagcag atgaaggcgt acacggccaa caaggcccgc gtgtcgtcca  38400
tcatccagat tccggccctc aaggaagaaa cctacggccg cgatttcagc gacatgctgc  38460
aagagcggct gacgttcgac caggcgctgg ccgatgaatc gctcacgatc atgacgcggc  38520
aacgcctcaa gatcgtgcgg cgcggcctgt ttgaacagct cgacgcggcg gccgtgctat  38580
gagcgaccag attgaagagc tgatccggga gattgcggcc aagcacggca tcgccgtcgg  38640
ccgcgacgac ccggtgctga tcctgcatac catcaacgcc cggctcatgg ccgacagtgc  38700
ggccaagcaa gaggaaatcc ttgccgcgtt caaggaagag ctggaaggga tcgcccatcg  38760
ttggggcgag gacgccaagg ccaaagcgga gcggatgctg aacgcggccc tggcggccag  38820
caaggacgca atggcgaagg taatgaagga cagcgccgcg caggcggccg aagcgatccg  38880
cagggaaatc gacgacggcc ttggccgcca gctcgcggcc aaggtcgcgg acgcgcggcg  38940
cgtggcgatg atgaacatga tcgccggcgg catggtgttg ttcgcggccg ccctggtggt  39000
gtgggcctcg ttatgaatcg cagaggcgca gatgaaaaag cccggcgttg ccgggctttg  39060
tttttgcgtt agctgggctt gtttgacagg cccaagctct gactgcgccc gcgctcgcgc  39120
tcctgggcct gtttcttctc ctgctcctgc ttgcgcatca gggcctggtg ccgtcgggct  39180
gcttcacgca tcgaatccca gtcgccggcc agctcgggat gctccgcgcg catcttgcgc  39240
gtcgccagtt cctcgatctt gggcgcgtga atgcccatgc cttccttgat ttcgcgcacc  39300
atgtccagcc gcgtgtgcag ggtctgcaag cgggcttgct gttgggcctg ctgctgctgc  39360
caggcggcct ttgtacgcgg cagggacagc aagccggggg cattggactg tagctgctgc  39420
aaacgcgcct gctgacggtc tacgagctgt tctaggcggt cctcgatgcg ctccacctgg  39480
tcatgctttg cctgcacgta gagcgcaagg gtctgctggt aggtctgctc gatgggcgcg  39540
gattctaaga gggcctgctg ttccgtctcg gcctcctggg ccgcctgtag caaatcctcg  39600
ccgctgttgc cgctggactg ctttactgcc ggggactgct gttgccctgc tcgcgccgtc  39660
gtcgcagttc ggcttgcccc cactcgattg actgcttcat ttcgagccgc agcgatgcga  39720
tctcggattg cgtcaacgga cggggcagcg cggaggtgtc cggcttctcc ttgggtgagt  39780
cggtcgatgc catagccaaa ggtttccttc caaaatgcgt ccattgctgg accgtgtttc  39840
tcattgatgc ccgcaagcat cttcggcttg accgccaggt caagcgcgcc ttcatgggcg  39900
gtcatgacgg acgccgccat gaccttgccg ccgttgttct cgatgtagcc gcgtaatgag  39960
gcaatggtgc cgcccatcgt cagcgtgtca tcgacaacga tgtacttctg gccggggatc  40020
acctccccct cgaaagtcgg gttgaacgcc aggcgatgat ctgaaccggc tccggttcgg  40080
gcgaccttct cccgctgcac aatgtccgtt tcgacctcaa ggccaaggcg gtcggccaga  40140
acgaccgcca tcatggccgg aatcttgttg ttccccgccg cctcgacggc gaggactgga  40200
acgatgcggg gcttgtcgtc gccgatcagc gtcttgagct gggcaacagt gtcgtccgaa  40260
atcaggcgct cgaccaaatt aagcgccgct tccgcgtcgc cctgcttcgc agcctggtat  40320
tcaggctcgt tggtcaaaga accaaggtcg ccgttgcgaa ccaccttcgg gaagtctccc  40380
cacggtgcgc gctcggctct gctgtagctg ctcaagacgc ctcccttttt agccgctaaa  40440
```

actctaacga gtgcgcccgc gactcaactt gacgctttcg gcacttacct gtgccttgcc 40500
acttgcgtca taggtgatgc ttttcgcact cccgatttca ggtactttat cgaaatctga 40560
ccgggcgtgc attacaaagt tcttccccac ctgttggtaa atgctgccgc tatctgcgtg 40620
gacgatgctg ccgtcgtggc gctgcgactt atcggccttt tgggccatat agatgttgta 40680
aatgccaggt ttcagggccc cggctttatc taccttctgg ttcgtccatg cgccttggtt 40740
ctcggtctgg acaattcttt gcccattcat gaccaggagg cggtgtttca ttgggtgact 40800
cctgacggtt gcctctggtg ttaaacgtgt cctggtcgct tgccggctaa aaaaaagccg 40860
acctcggcag ttcgaggccg gctttcccta gagccgggcg cgtcaaggtt gttccatcta 40920
ttttagtgaa ctgcgttcga tttatcagtt actttcctcc cgctttgtgt ttcctcccac 40980
tcgtttccgc gtctagccga cccctcaaca tagcggcctc ttcttgggct gcctttgcct 41040
cttgccgcgc ttcgtcacgc tcggcttgca ccgtcgtaaa gcgctcggcc tgcctggccg 41100
cctcttgcgc cgccaacttc ctttgctcct ggtgggcctc ggcgtcggcc tgcgccttcg 41160
ctttcaccgc tgccaactcc gtgcgcaaac tctccgcttc gcgcctggtg gcgtcgcgct 41220
cgccgcgaag cgcctgcatt tcctggttgg ccgcgtccag ggtcttgcgg ctctcttctt 41280
tgaatgcgcg ggcgtcctgg tgagcgtagt ccagctcggc gcgcagctcc tgcgctcgac 41340
gctccacctc gtcggcccgc tgcgtcgcca gcgcggcccg ctgctcggct cctgccaggg 41400
cggtgcgtgc ttcggccagg gcttgccgct ggcgtgcggc cagctcggcc gcctcggcgg 41460
cctgctgctc tagcaatgta acgcgcgcct gggcttcttc cagctcgcgg gcctgcgcct 41520
cgaaggcgtc ggccagctcc ccgcgcacgg cttccaactc gttgcgctca cgatcccagc 41580
cggcttgcgc tgcctgcaac gattcattgg caagggcctg ggcggcttgc cagagggcgg 41640
ccacggcctg gttgccggcc tgctgcaccg cgtccggcac ctggactgcc agcggggcgg 41700
cctgcgccgt gcgctggcgt cgccattcgc gcatgccggc gctggcgtcg ttcatgttga 41760
cgcgggcggc cttacgcact gcatccacgg tcgggaagtt ctcccggtcg ccttgctcga 41820
acagctcgtc cgcagccgca aaaatgcggt cgcgcgtctc tttgttcagt tccatgttgg 41880
ctccggtaat tggtaagaat aataatactc ttacctacct tatcagcgca agagtttagc 41940
tgaacagttc tcgacttaac ggcaggtttt ttagcggctg aagggcaggc aaaaaaagcc 42000
ccgcacggtc ggcgggggca aagggtcagc gggaagggga ttagcgggcg tcgggcttct 42060
tcatgcgtcg gggccgcgct tcttgggatg gagcacgacg aagcgcgcac gcgcatcgtc 42120
ctcggcccta tcggcccgcg tcgcggtcag gaacttgtcg cgcgctaggt cctccctggt 42180
gggcaccagg ggcatgaact cggcctgctc gatgtaggtc cactccatga ccgcatcgca 42240
gtcgaggccg cgttccttca ccgtctcttg caggtcgcgg tacgcccgct cgttgagcgg 42300
ctggtaacgg gccaattggt cgtaaatggc tgtcggccat gagcggcctt tcctgttgag 42360
ccagcagccg acgacgaagc cggcaatgca ggcccctggc acaaccaggc cgacgccggg 42420
ggcaggggat ggcagcagct cgccaaccag gaaccccgcc gcgatgatgc cgatgccggt 42480
caaccagccc ttgaaactat ccggccccga aacacccctg cgcattgcct ggatgctgcg 42540
ccggatagct tgcaacatca ggagccgttt cttttgttcg tcagtcatgg tccgccctca 42600
ccagttgttc gtatcggtgt cggacgaact gaaatcgcaa gagctgccgg tatcggtcca 42660
gccgctgtcc gtgtcgctgc tgccgaagca cggcgagggg tccgcgaacg ccgcagacgg 42720
cgtatccggc cgcagcgcat cgcccagcat ggccccggtc agcgagccgc cggccaggta 42780
gcccagcatg gtgctgttgg tcgccccggc caccagggcc gacgtgacga aatcgccgtc 42840

```
attccctctg gattgttcgc tgctcggcgg ggcagtgcgc cgcgccggcg gcgtcgtgga  42900
tggctcgggt tggctggcct gcgacggccg gcgaaaggtg cgcagcagct cgttatcgac  42960
cggctgcggc gtcggggccg ccgccttgcg ctgcggtcgg tgttccttct tcggctcgcg  43020
cagcttgaac agcatgatcg cggaaaccag cagcaacgcc gcgcctacgc ctcccgcgat  43080
gtagaacagc atcggattca ttcttcggtc ctccttgtag cggaaccgtt gtctgtgcgg  43140
cgcgggtggc ccgcgccgct gtctttgggg atcagccctc gatgagcgcg accagtttca  43200
cgtcggcaag gttcgcctcg aactcctggc cgtcgtcctc gtacttcaac caggcatagc  43260
cttccgccgg cggccgacgg ttgaggataa ggcgggcagg gcgctcgtcg tgctcgacct  43320
ggacgatggc ctttttcagc ttgtccgggt ccggctcctt cgcgcccttt tccttggcgt  43380
ccttaccgtc ctggtcgccg tcctcgccgt cctggccgtc gccggcctcc gcgtcacgct  43440
cggcatcagt ctggccgttg aaggcatcga cggtgttggg atcgcggccc ttctcgtcca  43500
ggaactcgcg cagcagcttg accgtgccgc gcgtgatttc ctgggtgtcg tcgtcaagcc  43560
acgcctcgac ttcctccggg cgcttcttga aggccgtcac cagctcgttc accacggtca  43620
cgtcgcgcac gcggccggtg ttgaacgcat cggcgatctt ctccggcagg tccagcagcg  43680
tgacgtgctg ggtgatgaac gccggcgact tgccgatttc cttggcgata tcgcctttct  43740
tcttgccctt cgccagctcg cggccaatga agtcggcaat ttcgcgcggg gtcagctcgt  43800
tgcgttgcag gttctcgata acctggtcgg cttcgttgta gtcgttgtcg atgaacgccg  43860
ggatggactt cttgccggcc cacttcgagc cacggtagcg gcgggcgccg tgattgatga  43920
tatagcggcc cggctgctcc tggttctcgc gcaccgaaat gggtgacttc accccgcgct  43980
ctttgatcgt ggcaccgatt tccgcgatgc tctccgggga aaagccgggg ttgtcggccg  44040
tccgcggctg atgcggatct tcgtcgatca ggtccaggtc cagctcgata gggccggaac  44100
cgccctgaga cgccgcagga gcgtccagga ggctcgacag gtcgccgatg ctatccaacc  44160
ccaggccgga cggctgcgcc gcgcctgcgg cttcctgagc ggccgcagcg gtgtttttct  44220
tggtggtctt ggcttgagcc gcagtcattg ggaaatctcc atcttcgtga acacgtaatc  44280
agccagggcg cgaacctctt tcgatgcctt gcgcgcggcc gttttcttga tcttccagac  44340
cggcacaccg gatgcgaggg catcggcgat gctgctgcgc aggccaacgg tggccggaat  44400
catcatcttg ggtacgcgg ccagcagctc ggcttggtgg cgcgcgtggc gcggattccg  44460
cgcatcgacc ttgctgggca ccatgccaag gaattgcagc ttggcgttct tctggcgcac  44520
gttcgcaatg gtcgtgacca tcttcttgat gccctggatg ctgtacgcct caagctcgat  44580
gggggacagc acatagtcgg ccgcgaagag ggcggccgcc aggccgacgc caagggtcgg  44640
ggccgtgtcg atcaggcaca cgtcgaagcc ttggttcgcc agggccttga tgttcgcccc  44700
gaacagctcg cgggcgtcgt ccagcgacag ccgttcggcg ttcgccagta ccgggttgga  44760
ctcgatgagg gcgaggcgcg cggcctggcc gtcgccggct gcgggtgcgg tttcggtcca  44820
gccgccggca gggacagcgc cgaacagctt gcttgcatgc aggccggtag caaagtcctt  44880
gagcgtgtag gacgcattgc cctgggggtc caggtcgatc acggcaaccc gcaagccgcg  44940
ctcgaaaaag tcgaaggcaa gatgcacaag ggtcgaagtc ttgccgacgc cgcctttctg  45000
gttggccgtg accaaagttt tcatcgtttg gtttcctgtt ttttcttggc gtccgcttcc  45060
cacttccgga cgatgtacgc ctgatgttcc ggcagaaccg ccgttacccg cgcgtacccc  45120
tcgggcaagt tcttgtcctc gaacgcggcc cacacgcgat gcaccgcttg cgacactgcg  45180
```

```
ccccctggtca gtcccagcga cgttgcgaac gtcgcctgtg gcttcccatc gactaagacg  45240
ccccgcgcta tctcgatggt ctgctgcccc acttccagcc cctggatcgc ctcctggaac  45300
tggctttcgg taagccgttt cttcatggat aacacccata atttgctccg cgccttggtt  45360
gaacatagcg gtgacagccg ccagcacatg agagaagttt agctaaacat ttctcgcacg  45420
tcaacacctt tagccgctaa aactcgtcct tggcgtaaca aaacaaaagc ccggaaaccg  45480
ggctttcgtc tcttgccgct tatggctctg cacccggctc catcaccaac aggtcgcgca  45540
cgcgcttcac tcggttgcgg atcgacactg ccagcccaac aaagccggtt gccgccgccg  45600
ccaggatcgc gccgatgatg ccggccacac cggccatcgc ccaccaggtc gccgccttcc  45660
ggttccattc ctgctggtac tgcttcgcaa tgctggacct cggctcacca taggctgacc  45720
gctcgatggc gtatgccgct tctccccttg gcgtaaaacc cagcgccgca ggcggcattg  45780
ccatgctgcc cgccgctttc ccgaccacga cgcgcgcacc aggcttgcgg tccagacctt  45840
cggccacggc gagctgcgca aggacataat cagccgccga cttggctcca cgcgcctcga  45900
tcagctcttg cactcgcgcg aaatccttgg cctccacggc cgccatgaat cgcgcacgcg  45960
gcgaaggctc cgcagggccg gcgtcgtgat cgccgccgag aatgcccttc accaagttcg  46020
acgacacgaa aatcatgctg acggctatca ccatcatgca gacggatcgc acgaacccgc  46080
tgaattgaac acgagcacgg cacccgcgac cactatgcca agaatgccca aggtaaaaat  46140
tgccggcccc gccatgaagt ccgtgaatgc cccgacggcc gaagtgaagg gcaggccgcc  46200
acccaggccg ccgccctcac tgcccggcac ctggtcgctg aatgtcgatg ccagcacctg  46260
cggcacgtca atgcttccgg gcgtcgcgct cgggctgatc gcccatcccg ttactgcccc  46320
gatcccggca atggcaagga ctgccagcgc tgccattttt ggggtgaggc cgttcgcggc  46380
cgaggggcgc agcccctggg gggatgggag gcccgcgtta gcgggccggg agggttcgag  46440
aaggggggc acccccttc ggcgtgcgcg gtcacgcgca cagggcgcag ccctggttaa  46500
aaacaaggtt tataaatatt ggtttaaaag caggttaaaa gacaggttag cggtggccga  46560
aaaacgggcg gaaacccttg caaatgctgg attttctgcc tgtggacagc ccctcaaatg  46620
tcaataggtg cgcccctcat ctgtcagcac tctgcccctc aagtgtcaag gatcgcgccc  46680
ctcatctgtc agtagtcgcg cccctcaagt gtcaataccg cagggcactt atccccaggc  46740
ttgtccacat catctgtggg aaactcgcgt aaaatcaggc gttttcgccg atttgcgagg  46800
ctggccagct ccacgtcgcc ggccgaaatc gagcctgccc ctcatctgtc aacgccgcgc  46860
cgggtgagtc ggcccctcaa gtgtcaacgt ccgcccctca tctgtcagtg agggccaagt  46920
tttccgcgag gtatccacaa cgccggcggc cgcggtgtct cgcacacggc ttcgacggcg  46980
tttctggcgc gtttgcaggg ccatagacgg ccgccagccc agcggcgagg gcaaccagcc  47040
cggtgagcgt cggaaaggcg ctggaagccc cgtagcgacg cggagagggg cgagacaagc  47100
caagggcgca ggctcgatgc gcagcacgac atagccggtt ctcgcaagga cgagaatttc  47160
cctgcggtgc ccctcaagtg tcaatgaaag tttccaacgc gagccattcg cgagagcctt  47220
gagtccacgc tagatgagag ctttgttgta ggtggaccag ttggtgattt tgaacttttg  47280
ctttgccacg gaacggtctg cgttgtcggg aagatgcgtg atctgatcct tcaactcagc  47340
aaaagttcga tttattcaac aaagccacgt tgtgtctcaa aatctctgat gttacattgc  47400
acaagataaa aatatatcat catgaacaat aaaactgtct gcttacataa acagtaatac  47460
aaggggtgtt atgagccata ttcaacggga aacgtcttgc tcgac                 47505
```

<210> SEQ ID NO 14
<211> LENGTH: 48232
<212> TYPE: DNA
<213> ORGANISM: artificial sequence
<220> FEATURE:
<223> OTHER INFORMATION: PHP16973 (ZmCAS1BamPro:MS45/35SPAT)

<400> SEQUENCE: 14
tctagagctc gttcctcgag gaacggtacc tgcggggaag cttacaataa tgtgtgttgt 60
taagtcttgt tgcctgtcat cgtctgactg actttcgtca taaatcccgg cctccgtaac 120
ccagctttgg gcaagctcac ggatttgatc cggcggaacg ggaatatcga gatgccgggc 180
tgaacgctgc agttccagct ttccctttcg ggacaggtac tccagctgat tgattatctg 240
ctgaagggtc ttggttccac ctcctggcac aatgcgaatg attacttgag cgcgatcggg 300
catccaattt tctcccgtca ggtgcgtggt caagtgctac aaggcacctt tcagtaacga 360
gcgaccgtcg atccgtcgcc gggatacgga caaaatggag cgcagtagtc catcgagggc 420
ggcgaaagcc tcgccaaaag caatacgttc atctcgcaca gcctccagat ccgatcgagg 480
gtcttcggcg taggcagata gaagcatgga tacattgctt gagagtattc cgatggactg 540
aagtatggct tccatctttt ctcgtgtgtc tgcatctatt tcgagaaagc cccgatgcg 600 gcgcaccgca acgcgaattg ccatactatc cgaaagtccc agcaggcgcg cttgatagga 660
aaaggtttca tactcggccg atcgcagacg ggcactcacg accttgaacc cttcaacttt 720
cagggatcga tgctggttga tggtagtctc actcgacgtg gctctggtgt gttttgacat 780
agcttcctcc aaagaaagcg gaaggtctgg atactccagc acgaaatgtg cccgggtaga 840
cggatggaag tctagccctg ctcaatatga aatcaacagt acatttacag tcaatactga 900
atatacttgc tacatttgca attgtcttat aacgaatgtg aaataaaaat agtgtaacaa 960
cgcttttact catcgataat cacaaaaaca tttatacgaa caaaaataca aatgcactcc 1020
ggtttcacag gataggcggg atcagaatat gcaacttttg acgttttgtt ctttcaaagg 1080
gggtgctggc aaaaccaccg cactcatggg cctttgcgct gctttggcaa atgacggtaa 1140
acgagtggcc ctctttgatg ccgacgaaaa ccggcctctg acgcgatgga gagaaaacgc 1200
cttacaaagc agtactggga tcctcgctgt gaagtctatt ccgccgacga aatgcccctt 1260
cttgaagcag cctatgaaaa tgccgagctc gaaggatttg attatgcgtt ggccgatacg 1320
cgtggcggct cgagcgagct caacaacaca atcatcgcta gctcaaacct gcttctgatc 1380
cccaccatgc taacgccgct cgacatcgat gaggcactat ctacctaccg ctacgtcatc 1440
gagctgctgt tgagtgaaaa tttggcaatt cctacagctg ttttgcgcca acgcgtcccg 1500
gtcggccgat tgacaacatc gcaacgcagg atgtcagaga cgctagagag ccttccagtt 1560
gtaccgtctc ccatgcatga aagagatgca tttgccgcga tgaaagaacg cggcatgttg 1620
catcttacat tactaaacac gggaactgat ccgacgatgc gcctcataga gaggaatctt 1680
cggattgcga tggaggaagt cgtggtcatt tcgaaactga tcagcaaaat cttggaggct 1740
tgaagatggc aattcgcaag cccgcattgt cggtcggcga agcacggcgg cttgctggtg 1800
ctcgacccga gatccaccat cccaacccga cacttgttcc ccagaagctg gacctccagc 1860
acttgcctga aaagccgac gagaaagacc agcaacgtga gcctctcgtc gccgatcaca 1920
tttacagtcc cgatcgacaa cttaagctaa ctgtggatgc ccttagtcca cctccgtccc 1980
cgaaaaagct ccaggttttt ctttcagcgc gaccgcccgc gcctcaagtg tcgaaaacat 2040
atgacaacct cgttcggcaa tacagtccct cgaagtcgct acaaatgatt ttaaggcgcg 2100

```
cgttggacga tttcgaaagc atgctggcag atggatcatt tcgcgtggcc ccgaaaagtt   2160
atccgatccc ttcaactaca gaaaaatccg ttctcgttca gacctcacgc atgttcccgg   2220
ttgcgttgct cgaggtcgct cgaagtcatt ttgatccgtt ggggttggag accgctcgag   2280
ctttcggcca caagctggct accgccgcgc tcgcgtcatt ctttgctgga gagaagccat   2340
cgagcaattg gtgaagaggg acctatcgga acccctcacc aaatattgag tgtaggtttg   2400
aggccgctgg ccgcgtcctc agtcaccttt tgagccagat aattaagagc caaatgcaat   2460
tggctcaggc tgccatcgtc cccccgtgcg aaacctgcac gtccgcgtca aagaaataac   2520
cggcacctct tgctgttttt atcagttgag ggcttgacgg atccgcctca agtttgcggc   2580
gcagccgcaa aatgagaaca tctatactcc tgtcgtaaac ctcctcgtcg cgtactcgac   2640
tggcaatgag aagttgctcg cgcgatagaa cgtcgcgggg tttctctaaa aacgcgagga   2700
gaagattgaa ctcacctgcc gtaagtttca cctcaccgcc agcttcggac atcaagcgac   2760
gttgcctgag attaagtgtc cagtcagtaa aacaaaaaga ccgtcggtct ttggagcgga   2820
caacgttggg gcgcacgcgc aaggcaaccc gaatgcgtgc aagaaactct ctcgtactaa   2880
acggcttagc gataaaatca cttgctccta gctcgagtgc aacaacttta tccgtctcct   2940
caaggcggtc gccactgata attatgattg gaatatcaga ctttgccgcc agatttcgaa   3000
cgatctcaag cccatcttca cgacctaaat ttagatcaac aaccacgaca tcgaccgtcg   3060
cggaagagag tactctagtg aactgggtgc tgtcggctac cgcggtcact ttgaaggcgt   3120
ggatcgtaag gtattcgata ataagatgcc gcatagcgac atcgtcatcg ataagaagaa   3180
cgtgtttcaa cggctcacct ttcaatctaa aatctgaacc cttgttcaca gcgcttgaga   3240
aattttcacg tgaaggatgt acaatcatct ccagctaaat gggcagttcg tcagaattgc   3300
ggctgaccgc ggatgacgaa aatgcgaacc aagtatttca attttatgac aaaagttctc   3360
aatcgttgtt acaagtgaaa cgcttcgagg ttacagctac tattgattaa ggagatcgcc   3420
tatggtctcg ccccggcgtc gtgcgtccgc cgcgagccag atctcgccta cttcataaac   3480
gtcctcatag gcacggaatg gaatgatgac atcgatcgcc gtagagagca tgtcaatcag   3540
tgtgcgatct tccaagctag caccttgggc gctacttttg acaagggaaa acagtttctt   3600
gaatccttgg attggattcg cgccgtgtat tgttgaaatc gatcccggat gtcccgagac   3660
gacttcactc agataagccc atgctgcatc gtcgcgcatc tcgccaagca atatccggtc   3720
cggccgcata cgcagacttg cttggagcaa gtgctcggcg ctcacagcac ccagcccagc   3780
accgttcttg gagtagagta gtctaacatg attatcgtgt ggaatgacga gttcgagcgt   3840
atcttctatg gtgattagcc tttcctgggg ggggatggcg ctgatcaagg tcttgctcat   3900
tgttgtcttg ccgcttccgg tagggccaca tagcaacatc gtcagtcggc tgacgacgca   3960
tgcgtgcaga aacgcttcca aatccccgtt gtcaaaatgc tgaaggatag cttcatcatc   4020
ctgattttgg cgtttccttc gtgtctgcca ctggttccac ctcgaagcat cataacggga   4080
ggagacttct ttaagaccag aaacacgcga gcttggccgt cgaatggtca agctgacggt   4140
gcccgaggga acggtcggcg gcagacagat ttgtagtcgt tcaccaccag gaagttcagt   4200
ggcgcagagg gggttacgtg gtccgacatc ctgctttctc agcgcgcccg ctaaaatagc   4260
gatatcttca agatcatcat aagagacggg caaaggcatc ttggtaaaaa tgccggcttg   4320
gcgcacaaat gcctctccag gtcgattgat cgcaatttct tcagtcttcg ggtcatcgag   4380
ccattccaaa atcggcttca gaagaaagcg tagttgcgga tccacttcca tttacaatgt   4440
atcctatctc taagcggaaa tttgaattca ttaagagcgg cggttcctcc cccgcgtggc   4500
```

```
gccgccagtc aggcggagct ggtaaacacc aaagaaatcg aggtcccgtg ctacgaaaat   4560
ggaaacggtg tcaccctgat tcttcttcag ggttggcggt atgttgatgg ttgccttaag   4620
ggctgtctca gttgtctgct caccgttatt ttgaaagctg ttgaagctca tcccgccacc   4680
cgagctgccg gcgtaggtgc tagctgcctg gaaggcgcct tgaacaacac tcaagagcat   4740
agctccgcta aaacgctgcc agaagtggct gtcgaccgag cccggcaatc ctgagcgacc   4800
gagttcgtcc gcgcttggcg atgttaacga gatcatcgca tggtcaggtg tctcggcgcg   4860
atcccacaac acaaaaacgc gcccatctcc ctgttgcaag ccacgctgta tttcgccaac   4920
aacggtggtg ccacgatcaa gaagcacgat attgttcgtt gttccacgaa tatcctgagg   4980
caagacacac tttacatagc ctgccaaatt tgtgtcgatt gcggtttgca agatgcacgg   5040
aattattgtc ccttgcgtta ccataaaatc ggggtgcggc aagagcgtgg cgctgctggg   5100
ctgcagctcg gtgggtttca tacgtatcga caaatcgttc tcgccggaca cttcgccatt   5160
cggcaaggag ttgtcgtcac gcttgccttc ttgtcttcgg cccgtgtcgc cctgaatggc   5220
gcgtttgctg accccttgat cgccgctgct atatgcaaaa atcggtgttt cttccggccg   5280
tggctcatgc cgctccggtt cgcccctcgg cggtagagga gcagcaggct gaacagcctc   5340
ttgaaccgct ggaggatccg gcggcacctc aatcggagct ggatgaaatg gcttggtgtt   5400
tgttgcgatc aaagttgacg gcgatgcgtt ctcattcacc ttcttttggc gcccacctag   5460
ccaaatgagg cttaatgata acgcgagaac gacacctccg acgatcaatt tctgagaccc   5520
cgaaagacgc cggcgatgtt tgtcggagac cagggatcca gatgcatcaa cctcatgtgc   5580
cgcttgctga ctatcgttat tcatcccttc gccccttca ggacgcgttt cacatcgggc   5640
ctcaccgtgc ccgtttgcgg cctttggcca acgggatcgt aagcggtgtt ccagatacat   5700
agtactgtgt ggccatccct cagacgccaa cctcgggaaa ccgaagaaat ctcgacatcg   5760
ctccctttaa ctgaatagtt ggcaacagct tccttgccat caggattgat ggtgtagatg   5820
gagggtatgc gtacattgcc cggaaagtgg aataccgtcg taaatccatt gtcgaagact   5880
tcgagtggca acagcgaacg atcgccttgg gcgacgtagt gccaattact gtccgccgca   5940
ccaagggctg tgacaggctg atccaataaa ttctcagctt tccgttgata ttgtgcttcc   6000
gcgtgtagtc tgtccacaac agccttctgt tgtgcctccc ttcgccgagc cgccgcatcg   6060
tcggcggggt aggcgaattg gacgctgtaa tagagatcgg gctgctcttt atcgaggtgg   6120
gacagagtct tggaacttat actgaaaaca taacggcgca tcccggagtc gcttgcggtt   6180
agcacgatta ctggctgagg cgtgaggacc tggcttgcct tgaaaaatag ataatttccc   6240
cgcggtaggg ctgctagatc tttgctattt gaaacggcaa ccgctgtcac cgtttcgttc   6300
gtggcgaatg ttacgaccaa agtagctcca accgccgtcg agaggcgcac cacttgatcg   6360
ggattgtaag ccaaataacg catgcgcgga tctagcttgc ccgccattgg agtgtcttca   6420
gcctccgcac cagtcgcagc ggcaaataaa catgctaaaa tgaaaagtgc ttttctgatc   6480
atggttcgct gtggcctacg tttgaaacgg tatcttccga tgtctgatag gaggtgacaa   6540
ccagacctgc cgggttggtt agtctcaatc tgccgggcaa gctggtcacc ttttcgtagc   6600
gaactgtcgc ggtccacgta ctcaccacag gcattttgcc gtcaacgacg agggtccttt   6660
tatagcgaat ttgctgcgtg cttggagtta catcatttga agcgatgtgc tcgacctcca   6720
ccctgccgcg tttgccaaga atgacttgag gcgaactggg attgggatag ttgaagaatt   6780
gctggtaatc ctggcgcact gttggggcac tgaagttcga taccaggtcg taggcgtact   6840
```

```
gagcggtgtc ggcatcataa ctctcgcgca ggcgaacgta ctcccacaat gaggcgttaa   6900
cgacggcctc ctcttgagtt gcaggcaatc gcgagacaga cacctcgctg tcaacggtgc   6960
cgtccggccg tatccataga tatacgggca caagcctgct caacggcacc attgtggcta   7020
tagcgaacgc ttgagcaaca tttcccaaaa tcgcgatagc tgcgacagct gcaatgagtt   7080
tggagagacg tcgcgccgat ttcgctcgcg cggtttgaaa ggcttctact tccttatagt   7140
gctcggcaag gctttcgcgc gccactagca tggcatattc aggccccgtc atagcgtcca   7200
cccgaattgc cgagctgaag atctgacgga gtaggctgcc atcgccccac attcagcggg   7260
aagatcgggc ctttgcagct cgctaatgtg tcgtttgtct ggcagccgct caaagcgaca   7320
actaggcaca gcaggcaata cttcatagaa ttctccattg aggcgaattt ttgcgcgacc   7380
tagcctcgct caacctgagc gaagcgacgg tacaagctgc tggcagattg ggttgcgccg   7440
ctccagtaac tgcctccaat gttgccggcg atcgccggca aagcgacaat gagcgcatcc   7500
cctgtcagaa aaaacatatc gagttcgtaa agaccaatga tcttggccgc ggtcgtaccg   7560
gcgaaggtga ttacaccaag cataagggtg agcgcagtcg cttcggttag gatgacgatc   7620
gttgccacga ggtttaagag gagaagcaag agaccgtagg tgataagttg cccgatccac   7680
ttagctgcga tgtcccgcgt gcgatcaaaa atatatccga cgaggatcag aggcccgatc   7740
gcgagaagca ctttcgtgag aattccaacg gcgtcgtaaa ctccgaaggc agaccagagc   7800
gtgccgtaaa ggacccactg tgccccttgg aaagcaagga tgtcctggtc gttcatcgga   7860
ccgatttcgg atgcgatttt ctgaaaaacg gcctgggtca cggcgaacat tgtatccaac   7920
tgtgccggaa cagtctgcag aggcaagccg gttacactaa actgctgaac aaagtttggg   7980
accgtctttt cgaagatgga aaccacatag tcttggtagt tagcctgccc aacaattaga   8040
gcaacaacga tggtgaccgt gatcacccga gtgataccgc tacgggtatc gacttcgccg   8100
cgtatgacta aaataccctg aacaataatc caaagagtga cacaggcgat caatggcgca   8160
ctcaccgcct cctggatagt ctcaagcatc gagtccaagc ctgtcgtgaa ggctacatcg   8220
aagatcgtat gaatggccgt aaacggcgcc ggaatcgtga aattcatcga ttggacctga   8280
acttgactgg tttgtcgcat aatgttggat aaaatgagct cgcattcggc gaggatgcgg   8340
gcggatgaac aaatcgccca gccttagggg agggcaccaa agatgacagc ggtcttttga   8400
tgctccttgc gttgagcggc cgcctcttcc gcctcgtgaa ggccggcctg cgcggtagtc   8460
atcgttaata ggcttgtcgc ctgtacattt tgaatcattg cgtcatggat ctgcttgaga   8520
agcaaaccat tggtcacggt tgcctgcatg atattgcgag atcgggaaag ctgagcagac   8580
gtatcagcat tcgccgtcaa gcgtttgtcc atcgtttcca gattgtcagc cgcaatgcca   8640
gcgctgtttg cggaaccggt gatctgcgat cgcaacaggt ccgcttcagc atcactaccc   8700
acgactgcac gatctgtatc gctggtgatc gcacgtgccg tggtcgacat tggcattcgc   8760
ggcgaaaaca tttcattgtc taggtccttc gtcgaaggat actgattttt ctggttgagc   8820
gaagtcagta gtccagtaac gccgtaggcc gacgtcaaca tcgtaaccat cgctatagtc   8880
tgagtgagat tctccgcagt cgcgagcgca gtcgcgagcg tctcagcctc cgttgccggg   8940
tcgctaacaa caaactgcgc ccgcgcgggc tgaatatata gaaagctgca ggtcaaaact   9000
gttgcaataa gttgcgtcgt cttcatcgtt tcctacctta tcaatcttct gcctcgtggt   9060
gacgggccat gaattcgctg agccagccag atgagttgcc ttcttgtgcc tcgcgtagtc   9120
gagttgcaaa gcgcaccgtg ttggcacgcc ccgaaagcac ggcgacatat tcacgcatat   9180
cccgcagatc aaattcgcag atgacgcttc cactttctcg tttaagaaga aacttacggc   9240
```

```
tgccgaccgt catgtcttca cggatcgcct gaaattcctt ttcggtacat ttcagtccat   9300
cgacataagc cgatcgatct gcggttggtg atggatagaa aatcttcgtc atacattgcg   9360
caaccaagct ggctcctagc ggcgattcca gaacatgctc tggttgctgc gttgccagta   9420
ttagcatccc gttgtttttt cgaacggtca ggaggaattt gtcgacgaca gtcgaaaatt   9480
tagggtttaa caaataggcg cgaaactcat cgcagctcat cacaaaacgg cggccgtcga   9540
tcatggctcc aatccgatgc aggagatatg ctgcagcggg agcgcatact tcctcgtatt   9600
cgagaagatg cgtcatgtcg aagccggtaa tcgacggatc taactttact tcgtcaactt   9660
cgccgtcaaa tgcccagcca agcgcatggc cccggcacca gcgttggagc cgcgctcctg   9720
cgccttcggc gggcccatgc aacaaaaatt cacgtaaccc cgcgattgaa cgcatttgtg   9780
gatcaaacga gagctgacga tggataccac ggaccagacg gcggttctct tccggagaaa   9840
tcccaccccg accatcactc tcgatgagag ccacgatcca ttcgcgcaga aaatcgtgtg   9900
aggctgctgt gttttctagg ccacgcaacg gcgccaaccc gctgggtgtg cctctgtgaa   9960
gtgccaaata tgttcctcct gtggcgcgaa ccagcaattc gccaccccgg tccttgtcaa  10020
agaacacgac cgtacctgca cggtcgacca tgctctgttc gagcatggct agaacaaaca  10080
tcatgagcgt cgtcttaccc ctcccgatag gcccgaatat tgccgtcatg ccaacatcgt  10140
gctcatgcgg gatatagtcg aaaggcgttc cgccattggt acgaaatcgg gcaatcgcgt  10200
tgccccagtg gcctgagctg gcgccctctg gaaagttttc gaaagagaca aaccctgcga  10260
aattgcgtga agtgattgcg ccagggcgtg tgcgccactt aaaattcccc ggcaattggg  10320
accaataggc cgcttccata ccaatacctt cttggacaac cacggcacct gcatccgcca  10380
ttcgtgtccg agcccgcgcg cccctgtccc caagactatt gagatcgtct gcatagacgc  10440
aaaggctcaa atgatgtgag cccataacga attcgttgct cgcaagtgcg tcctcagcct  10500
cggataattt gccgatttga gtcacggctt tatcgccgga actcagcatc tggctcgatt  10560
tgaggctaag tttcgcgtgc gcttgcgggc gagtcaggaa cgaaaaactc tgcgtgagaa  10620
caagtggaaa atcgagggat agcagcgcgt tgagcatgcc cggccgtgtt tttgcagggt  10680
attcgcgaaa cgaatagatg gatccaacgt aactgtcttt tggcgttctg atctcgagtc  10740
ctcgcttgcc gcaaatgact ctgtcggtat aaatcgaagc gccgagtgag ccgctgacga  10800
ccggaaccgg tgtgaaccga ccagtcatga tcaaccgtag cgcttcgcca atttcggtga  10860
agagcacacc ctgcttctcg cggatgccaa gacgatgcag gccatacgct ttaagagagc  10920
cagcgacaac atgccaaaga tcttccatgt tcctgatctg gcccgtgaga tcgttttccc  10980
tttttccgct tagcttggtg aacctcctct ttaccttccc taaagccgcc tgtgggtaga  11040
caatcaacgt aaggaagtgt tcattgcgga ggagttggcc ggagagcacg cgctgttcaa  11100
aagcttcgtt caggctagcg gcgaaaacac tacggaagtg tcgcggcgcc gatgatggca  11160
cgtcggcatg acgtacgagg tgagcatata ttgacacatg atcatcagcg atattgcgca  11220
acagcgtgtt gaacgcacga caacgcgcat tgcgcatttc agtttcctca agctcgaatg  11280
caacgccatc aattctcgca atggtcatga tcgatccgtc ttcaagaagg acgatatggt  11340
cgctgaggtg gccaatataa gggagataga tctcaccgga tctttcggtc gttccactcg  11400
cgccgagcat cacaccattc ctctccctcg tgggggaacc ctaattggat ttgggctaac  11460
agtagcgccc ccccaaactg cactatcaat gcttcttccc gcggtccgca aaaatagcag  11520
gacgacgctc gccgcattgt agtctcgctc cacgatgagc cgggctgcaa accataacgg  11580
```

-continued

```
cacgagaacg acttcgtaga gcgggttctg aacgataacg atgacaaagc cggcgaacat  11640
catgaataac cctgccaatg tcagtggcac cccaagaaac aatgcgggcc gtgtggctgc  11700
gaggtaaagg gtcgattctt ccaaacgatc agccatcaac taccgccagt gagcgtttgg  11760
ccgaggaagc tcgccccaaa catgataaca atgccgccga cgacgccggc aaccagccca  11820
agcgaagccc gcccgaacat ccaggagatc ccgatagcga caatgccgag aacagcgagt  11880
gactggccga acggaccaag gataaacgtg catatattgt taaccattgt ggcggggtca  11940
gtgccgccac ccgcagattg cgctgcggcg ggtccggatg aggaaatgct ccatgcaatt  12000
gcaccgcaca agcttggggc gcagctcgat atcacgcgca tcatcgcatt cgagagcgag  12060
aggcgattta gatgtaaacg gtatctctca aagcatcgca tcaatgcgca cctccttagt  12120
ataagtcgaa taagacttga ttgtcgtctg cggatttgcc gttgtcctgg tgtggcggtg  12180
gcggagcgat taaaccgcca gcgccatcct cctgcgagcg gcgctgatat gacccccaaa  12240
catcccacgt ctcttcggat tttagcgcct cgtgatcgtc ttttggaggc tcgattaacg  12300
cgggcaccag cgattgagca gctgtttcaa cttttcgcac gtagccgttt gcaaaaccgc  12360
cgatgaaatt accggtgttg taagcggaga tcgcccgacg aagcgcaaat tgcttctcgt  12420
caatcgtttc gccgcctgca taacgacttt tcagcatgtt tgcagcggca gataatgatg  12480
tgcacgcctg gagcgcaccg tcaggtgtca gaccgagcat agaaaaattt cgagagttta  12540
tttgcatgag gccaacatcc agcgaatgcc gtgcatcgag acggtgcctg acgacttggg  12600
ttgcttggct gtgatcttgc cagtgaagcg tttcgccggt cgtgttgtca tgaatcgcta  12660
aaggatcaaa gcgactctcc accttagcta tcgccgcaag cgtagatgtc gcaactgatg  12720
gggcacactt gcgagcaaca tggtcaaact cagcagatga gagtggcgtg gcaaggctcg  12780
acgaacagaa ggagaccatc aaggcaagag aaagcgaccc cgatctctta agcatacctt  12840
atctccttag ctcgcaacta acaccgcctc tcccgttgga agaagtgcgt tgttttatgt  12900
tgaagattat cgggagggtc ggttactcga aaattttcaa ttgcttcttt atgatttcaa  12960
ttgaagcgag aaacctcgcc cggcgtcttg gaacgcaaca tggaccgaga accgcgcatc  13020
catgactaag caaccggatc gacctattca ggccgcagtt ggtcaggtca ggctcagaac  13080
gaaaatgctc ggcgaggtta cgctgtctgt aaacccattc gatgaacggg aagcttcctt  13140
ccgattgctc ttggcaggaa tattggccca tgcctgcttg cgctttgcaa atgctcttat  13200
cgcgttggta tcatatgcct tgtccgccag cagaaacgca ctctaagcga ttatttgtaa  13260
aaatgtttcg gtcatgcggc ggtcatgggc ttgacccgct gtcagcgcaa gacggatcgg  13320
tcaaccgtcg gcatcgacaa cagcgtgaat cttggtggtc aaaccgccac gggaacgtcc  13380
catacagcca tcgtcttgat cccgctgttt cccgtcgccg catgttggtg gacgcggaca  13440
caggaactgt caatcatgac gacattctat cgaaagcctt ggaaatcaca ctcagaatat  13500
gatcccagac gtctgcctca cgccatcgta caaagcgatt gtagcaggtt gtacaggaac  13560
cgtatcgatc aggaacgtct gcccagggcg ggcccgtccg gaagcgccac aagatgacat  13620
tgatcacccg cgtcaacgcg cggcacgcga cgcggcttat ttgggaacaa aggactgaac  13680
aacagtccat tcgaaatcgg tgacatcaaa gcggggacgg gttatcagtg gcctccaagt  13740
caagcctcaa tgaatcaaaa tcagaccgat ttgcaaacct gatttatgag tgtgcggcct  13800
aaatgatgaa atcgtccttc tagatcgcct ccgtggtgta gcaacacctc gcagtatcgc  13860
cgtgctgacc ttggccaggg aattgactgg caagggtgct ttcacatgac cgctcttttg  13920
gccgcgatag atgatttcgt tgctgctttg ggcacgtaga aggagagaag tcatatcgga  13980
```

```
gaaattcctc ctggcgcgag agcctgctct atcgcgacgg catcccactg tcgggaacag  14040
accggatcat tcacgaggcg aaagtcgtca acacatgcgt tataggcatc ttcccttgaa  14100
ggatgatctt gttgctgcca atctggaggt gcggcagccg caggcagatg cgatctcagc  14160
gcaacttgcg gcaaaacatc tcactcacct gaaaaccact agcgagtctc gcgatcagac  14220
gaaggccttt tacttaacga cacaatatcc gatgtctgca tcacaggcgt cgctatccca  14280
gtcaatacta aagcggtgca ggaactaaag attactgatg acttaggcgt gccacgaggc  14340
ctgagacgac gcgcgtagac agtttttga aatcattatc aaagtgatgg cctccgctga  14400
agcctatcac ctctgcgccg gtctgtcgga gagatgggca agcattatta cggtcttcgc  14460
gcccgtacat gcattggacg attgcagggt caatggatct gagatcatcc agaggattgc  14520
cgcccttacc ttccgtttcg agttggagcc agcccctaaa tgagacgaca tagtcgactt  14580
gatgtgacaa tgccaagaga gagatttgct taacccgatt tttttgctca agcgtaagcc  14640
tattgaagct tgccggcatg acgtccgcgc cgaaagaata tcctacaagt aaaacattct  14700
gcacaccgaa atgcttggtg tagacatcga ttatgtgacc aagatcctta gcagtttcgc  14760
ttggggaccg ctccgaccag aaataccgaa gtgaactgac gccaatgaca ggaatccctt  14820
ccgtctgcag ataggtacca tcgatagatc tgctgcctcg cgcgtttcgg tgatgacggt  14880
gaaaacctct gacacatgca gctcccggag acggtcacag cttgtctgta agcggatgcc  14940
gggagcagac aagcccgtca gggcgcgtca gcgggtgttg gcgggtgtcg gggcgcagcc  15000
atgacccagt cacgtagcga tagcggagtg tatactggct taactatgcg gcatcagagc  15060
agattgtact gagagtgcac catatgcggt gtgaaatacc gcacagatgc gtaaggagaa  15120
aataccgcat caggcgctct tccgcttcct cgctcactga ctcgctgcgc tcggtcgttc  15180
ggctgcggcg agcggtatca gctcactcaa aggcggtaat acggttatcc acagaatcag  15240
gggataacgc aggaaagaac atgtgagcaa aaggccagca aaaggccagg aaccgtaaaa  15300
aggccgcgtt gctggcgttt ttccataggc tccgcccccc tgacgagcat cacaaaaatc  15360
gacgctcaag tcagaggtgg cgaaacccga caggactata aagataccag gcgtttcccc  15420
ctggaagctc cctcgtgcgc tctcctgttc cgaccctgcc gcttaccgga tacctgtccg  15480
cctttctccc ttcgggaagc gtggcgcttt ctcatagctc acgctgtagg tatctcagtt  15540
cggtgtaggt cgttcgctcc aagctgggct gtgtgcacga accccccgtt cagcccgacc  15600
gctgcgcctt atccggtaac tatcgtcttg agtccaaccc ggtaagacac gacttatcgc  15660
cactggcagc agccactggt aacaggatta gcagagcgag gtatgtaggc ggtgctacag  15720
agttcttgaa gtggtggcct aactacggct acactagaag gacagtattt ggtatctgcg  15780
ctctgctgaa gccagttacc ttcggaaaaa gagttggtag ctcttgatcc ggcaaacaaa  15840
ccaccgctgg tagcggtggt ttttttgttt gcaagcagca gattacgcgc agaaaaaaag  15900
gatctcaaga agatcctttg atcttttcta cggggtctga cgctcagtgg aacgaaaact  15960
cacgttaagg gattttggtc atgagattat caaaaaggat cttcacctag atccttttaa  16020
attaaaaatg aagttttaaa tcaatctaaa gtatatatga gtaaacttgg tctgacagtt  16080
accaatgctt aatcagtgag gcacctatct cagcgatctg tctatttcgt tcatccatag  16140
ttgcctgact ccccgtcgtg tagataacta cgatacggga gggcttacca tctggcccca  16200
gtgctgcaat gataccgcga gacccacgct caccggctcc agatttatca gcaataaacc  16260
agccagccgg aagggccgag cgcagaagtg gtcctgcaac tttatccgcc tccatccagt  16320
```

```
ctattaattg ttgccgggaa gctagagtaa gtagttcgcc agttaatagt ttgcgcaacg  16380
ttgttgccat tgctgcaggg gggggggggg ggggggactt ccattgttca ttccacggac  16440
aaaaacagag aaaggaaacg acagaggcca aaaagcctcg ctttcagcac ctgtcgtttc  16500
ctttcttttc agagggtatt ttaaataaaa acattaagtt atgacgaaga agaacggaaa  16560
cgccttaaac cggaaaattt tcataaatag cgaaaacccg cgaggtcgcc gccccgtaac  16620
ctgtcggatc accggaaagg acccgtaaag tgataatgat tatcatctac atatcacaac  16680
gtgcgtggag gccatcaaac cacgtcaaat aatcaattat gacgcaggta tcgtattaat  16740
tgatctgcat caacttaacg taaaaacaac ttcagacaat acaaatcagc gacactgaat  16800
acggggcaac ctcatgtccc cccccccccc cccccctgcag ggcatcgtgg tgtcacgctc  16860
gtcgtttggt atggcttcat tcagctccgg ttcccaacga tcaaggcgag ttacatgatc  16920
ccccatgttg tgcaaaaaag cggttagctc cttcggtcct ccgatcgttg tcagaagtaa  16980
gttggccgca gtgttatcac tcatggttat ggcagcactg cataattctc ttactgtcat  17040
gccatccgta agatgctttt ctgtgactgg tgagtactca accaagtcat tctgagaata  17100
gtgtatgcgg cgaccgagtt gctcttgccc ggcgtcaaca cgggataata ccgcgccaca  17160
tagcagaact ttaaaagtgc tcatcattgg aaaacgttct tcggggcgaa aactctcaag  17220
gatcttaccg ctgttgagat ccagttcgat gtaacccact cgtgcaccca actgatcttc  17280
agcatctttt actttcacca gcgtttctgg gtgagcaaaa acaggaaggc aaaatgccgc  17340
aaaaaaggga ataagggcga cacggaaatg ttgaatactc atactcttcc tttttcaata  17400
ttattgaagc atttatcagg gttattgtct catgagcgga tacatatttg aatgtattta  17460
gaaaaataaa caaatagggg ttccgcgcac atttccccga aaagtgccac ctgacgtcta  17520
agaaaccatt attatcatga cattaaccta taaaaatagg cgtatcacga ggccctttcg  17580
tcttcaagaa ttggtcgacg atcttgctgc gttcggatat tttcgtggag ttcccgccac  17640
agacccggat tgaaggcgag atccagcaac tcgcgccaga tcatcctgtg acggaacttt  17700
ggcgcgtgat gactggccag gacgtcggcc gaaagagcga caagcagatc acgcttttcg  17760
acagcgtcgg atttgcgatc gaggattttt cggcgctgcg ctacgtccgc gaccgcgttg  17820
agggatcaag ccacagcagc ccactcgacc ttctagccga cccagacgag ccaagggatc  17880
tttttggaat gctgctccgt cgtcaggctt tccgacgttt gggtggttga acagaagtca  17940
ttatcgtacg gaatgccaag cactcccgag gggaaccctg tggttggcat gcacatacaa  18000
atggacgaac ggataaacct tttcacgccc ttttaaatat ccgttattct aataaacgct  18060
cttttctctt aggtttaccc gccaatatat cctgtcaaac actgatagtt taaactgaag  18120
gcgggaaacg acaatctgat catgagcgga gaattaaggg agtcacgtta tgacccccgc  18180
cgatgacgcg ggacaagccg ttttacgttt ggaactgaca gaaccgcaac gttgaaggag  18240
ccactcagcc caagcttgat atcgaattcc tgcagcccgg gggatccggg gcggaagatg  18300
gcagggacgc ggattcaggg cggacgcgct tgccgagggc gcgggggacc acagcgtgcg  18360
ttacggggac agggcgggca tcgcgaggac gggtgcggga gcggagccac atctggtggt  18420
ggacgcctac tttgctctct tatagagtag taaagattcg tggaccaaac aacaccctag  18480
cttgtacaaa tattcttagg cagttgctac tgatgagaga aaaataacat cactccactg  18540
catttgcgtg atttattgaa cagatcacaa ttacatctat tcaaatttat ttacctgtac  18600
gtgtccgatt tttaggggag gatttttta cggtattttt tttttaaaaa aataaattta  18660
ggcaacaatt ttatagaatc gagtgcttta tctattatct tttacaaggc acacgcgtac  18720
```

```
aataaggttt ggtcgttcgt gacttggata gtggttttgg ttgcaattcc gtaattcttg  18780
gcataggata cagcccaacc cagaaaaaaa taatgttgcg gtcagttctg gctttgagat  18840
tcggagtacc acgtggcgta aaggcaggcc gtgtcttaca gatgaataaa ggacctgggt  18900
ctcacgtgat tggtttccag tttcgtgcat caagatgtgg aattttcaaa ctgccgtcgt  18960
gtttgtttcg tcacataaaa gctttttgga aggctaagga gaggaagccg gcgagaagga  19020
gggggcgttt tacgtgtcac tgtcctgtcg tgttggctgt tgacacgaat catttcttcc  19080
gcgcgtggga agaagaagat gcacattagc ggcctgaagt agagatgtca atggggaatt  19140
ccccagcggg gattaactcc ccagacccgt acccatgaac atagaccggc ccccatcccc  19200
gaacccgaac ccgacctcgg gtacgaaaat cctcccatac ccattcccga ccgggtacta  19260
aatacccatg ggtatccata cccgacccga ttattcaaaa attaatgggc tttttatttg  19320
ttaaccggcg gacgcaatgc ttgggactct aggttttttt actttgttga ccggctggcg  19380
gctgggcttt ttcctacagg cccaaagttg gtcggcagcc actaggccac acgtcacagg  19440
cagcccacaa gtaaatgtcg ttggattgct ggatggtgga ataaaaatcc tagatgctag  19500
attgttctgg ttccgggtat ttttctccat ggctaatcgg gtttgggttt agccctccca  19560
aacccgaacc cgccataccc gatgggtaag ggatttattc caaatctata cccatgggga  19620
tttgttttaa cccatacctt aaccctaata gaggaattcc ccacgggtaa tcgggtttcg  19680
gggcccattg acatctctag actgaaggcg tccaactcaa atcattaaaa agtgttgacg  19740
cacgcgctga tgcgccggcc gcacagcaca ggctgcacag cccgtttaat cagcgatgga  19800
gccccggccg tcagccagcc aggtccggcg tccgggtctg cgccctgcgg cgtcactgct  19860
gtcgccaccg tctccgatgg tcccacatcc atccagcggg ccgcgcgtgg tacaaaaggc  19920
tcttcctcgc cgtcaggtgc agctgcccaa acaccagaca cagactccac caccccgctt  19980
cgatcttctg ttgcagctga aatctgtcag attctgcagt tcattcctca tggagaagag  20040
gaacctgcag tggcggcgag ggcgtgatgg catcgtgcag taccctcacc tcttcttcgc  20100
ggccctggcg ctggccctcc tagtcgcgga ccgttcggcc tcagtccgct ggccgaggtc  20160
gactaccggc cggtgaagca cgagctcgcg ccgtacgggg aggtcatggg cagctggccc  20220
agagacaatg ccagccggct caggcgcggg aggctggagt tcgtcggcga ggtgttcggg  20280
ccggagtcta tcgagttcga tctccagggc cgcgggccgt acgccggcct cgccgacggc  20340
cgcgtcgtgc ggtggatggg cgaggaggcc gggtgggaga cgttcgccgg tcatgaatcc  20400
tgactggtaa gtgctcgata tgcctccggc gtccactcgt tacagtgcta taatatagta  20460
gtactaagat attttgatct gattttttgc attcttggga gaaacgtcat gcaaaatttg  20520
ttgtttcttg gcaaaggtca gaagaagtct gtgccaatgg agtgaactca acgacgagga  20580
agcagcacga gaaggaggag ttctgcggcg gccgctcggc ctgaggttcc acggggagac  20640
cggcgagctc tacgtcgccg acgcgtacta cggtctcatg gtcgttggcc agagcggcgg  20700
cgtggcgtcc tccgtcgcga gggaagccga cggggacccc atccggttcg cgaacgacct  20760
cgatgtgcac aggaatggat ccgtattctt cactgacacg agcatgagat acagcagaaa  20820
gtgagcaaag cagcgtaaca atccggcttc tcattttcaa acgcctctgt attctctgct  20880
gaaagagtag ctcaccagac aagagctgaa tttgcaggga ccatctgaac atcctgttag  20940
aaggagaagg caccgggagg ctgctcaggt atgatccaga aacaagcggt gtccatgtcg  21000
tgctcaaggg gctggtgttc ccaaacggcg tgcagatctc agaggaccat cagtttcttc  21060
```

```
tcttctccga gacaacaaac tgcaggtaac aaaaatacta tctgacgatg ctcatgattc  21120
taccgtatcc atagtcatga acacaaacca cacgaatctg gccttgacca ggataatgag  21180
gtactggctg gaaggcccaa gagcgggcga ggtagaggtg ttcgcgaacc tgccgggctt  21240
ccccgacaac gtgcgctcca acggcagggg ccagttctgg gtggcgatcg actgctgccg  21300
gaccgaggag gtgttcccaa gagcgtggct ccggaccctg tacttcaagt tcccgctgtc  21360
gctcaaggtg ctcacttgga aggccgccag gaggatgcac acggtgctcg cgctcctcga  21420
cggcgaaggg cgcgtcgtgg aggtgctcga ggaccggggc cacgaggtga tgaagctggt  21480
gagcgaggtg cgggaggtgg gccgcaagct gtggatcgga accgtggcgc acaaccacat  21540
cgccaccatc ccctaccctt tagaggacta accatgatct atgctgtttc aatgcctcct  21600
aatctgtgta cgtctataaa tgtctaatgc agctcatggt tgtaatcttg tttgtgtttg  21660
gcaaattggc ataataatgg acagattcaa tgggcattgg tgctgtagtc gcatcacact  21720
aattgaatgg gatcatgttg agctctcact ttgctacaat ttgctccagc ttgtacggtt  21780
gtaccctctt gctcgtctat agtaagggcc atctaaaaaa aactcaaatt agatctgcaa  21840
tacaagtatg attgggccga atttggattg tcacgggtcc gcgaccgcga attgggctcc  21900
ggtttgattt agccgacata gtagtgaccg acccgagccg gccggcgaga ccaaaccgag  21960
cggacgcccg ccatgcatgg agtcaaagat tcaaatagag gacctaacag aactcgccgt  22020
aaagactggc gaacagttca tacagagtct cttacgactc aatgacaaga agaaaatctt  22080
cgtcaacatg gtggagcacg acacgcttgt ctactccaaa aatatcaaag atacagtctc  22140
agaagaccaa agggcaattg agacttttca acaaagggta atatccggaa acctcctcgg  22200
attccattgc ccagctatct gtcactttat tgtgaagata gtggaaaagg aaggtggctc  22260
ctacaaatgc catcattgcg ataaaggaaa ggccatcgtt gaagatgcct ctgccgacag  22320
tggtcccaaa gatggacccc cacccacgag gagcatcgtg gaaaaagaag acgttccaac  22380
cacgtcttca aagcaagtgg attgatgtga tatctccact gacgtaaggg atgacgcaca  22440
atcccactat ccttcgcaag acccttcctc tatataagga agttcatttc atttggagag  22500
gacagggtac ccggggatcc accatgtctc cggagaggag accagttgag attaggccag  22560
ctacagcagc tgatatggcc gcggtttgtg atatcgttaa ccattacatt gagacgtcta  22620
cagtgaactt taggacagag ccacaaacac cacaagagtg gattgatgat ctagagaggt  22680
tgcaagatag ataccccttgg ttggttgctg aggttgaggg tgttgtggct ggtattgctt  22740
acgctgggcc ctggaaggct aggaacgctt acgattggac agttgagagt actgtttacg  22800
tgtcacatag gcatcaaagg ttgggcctag gatccacatt gtacacacat ttgcttaagt  22860
ctatggaggc gcaaggtttt aagtctgtgg ttgctgttat aggccttcca aacgatccat  22920
ctgttaggtt gcatgaggct ttgggataca cagcccgggg tacattgcgc gcagctggat  22980
acaagcatgg tggatggcat gatgttggtt tttggcaaag ggattttgag ttgccagctc  23040
ctccaaggcc agttaggcca gttacccaga tctgagtcga cctgcaggca tgccgctgaa  23100
atcaccagtc tctctctaca aatctatctc tctctataat aatgtgtgag tagttcccag  23160
ataagggaat tagggttctt atagggtttc gctcatgtgt tgagcatata agaaaccctt  23220
agtatgtatt tgtatttgta aaatacttct atcaataaaa tttctaattc ctaaaaccaa  23280
aatccagtgg gtaccgagct cgaattcagt acattaaaaa cgtccgcaat gtgttattaa  23340
gttgtctaag cgtcaatttg tttacaccac aatatatcct gccaccagcc agccaacagc  23400
tccccgaccg gcagctcggc acaaaatcac cactcgatac aggcagccca tcagtccggg  23460
```

```
acggcgtcag cgggagagcc gttgtaaggc ggcagacttt gctcatgtta ccgatgctat  23520
tcggaagaac ggcaactaag ctgccgggtt tgaaacacgg atgatctcgc ggagggtagc  23580
atgttgattg taacgatgac agagcgttgc tgcctgtgat caaatatcat ctccctcgca  23640
gagatccgaa ttatcagcct tcttattcat ttctcgctta accgtgacag gctgtcgatc  23700
ttgagaacta tgccgacata ataggaaatc gctggataaa gccgctgagg aagctgagtg  23760
gcgctatttc tttagaagtg aacgttgacg atcgtcgacc gtaccccgat gaattaattc  23820
ggacgtacgt tctgaacaca gctggatact tacttgggcg attgtcatac atgacatcaa  23880
caatgtaccc gtttgtgtaa ccgtctcttg gaggttcgta tgacactagt ggttcccctc  23940
agcttgcgac tagatgttga ggcctaacat tttattagag agcaggctag ttgcttagat  24000
acatgatctt caggccgtta tctgtcaggg caagcgaaaa ttggccattt atgacgacca  24060
atgccccgca gaagctccca tctttgccgc catagacgcc gcgccccccct tttggggtgt  24120
agaacatcct tttgccagat gtggaaaaga agttcgttgt cccattgttg gcaatgacgt  24180
agtagccggc gaaagtgcga gacccatttg cgctatatat aagcctacga tttccgttgc  24240
gactattgtc gtaattggat gaactattat cgtagttgct ctcagagttg tcgtaatttg  24300
atggactatt gtcgtaattg cttatggagt tgtcgtagtt gcttggagaa atgtcgtagt  24360
tggatgggga gtagtcatag ggaagacgag cttcatccac taaaacaatt ggcaggtcag  24420
caagtgcctg ccccgatgcc atcgcaagta cgaggcttag aaccaccttc aacagatcgc  24480
gcatagtctt ccccagctct ctaacgcttg agttaagccg cgccgcgaag cggcgtcggc  24540
ttgaacgaat tgttagacat tatttgccga ctaccttggt gatctcgcct ttcacgtagt  24600
gaacaaattc ttccaactga tctgcgcgcg aggccaagcg atcttcttgt ccaagataag  24660
cctgcctagc ttcaagtatg acgggctgat actgggccgg caggcgctcc attgcccagt  24720
cggcagcgac atccttcggc gcgattttgc cggttactgc gctgtaccaa atgcgggaca  24780
acgtaagcac tacatttcgc tcatcgccag cccagtcggg cggcgagttc catagcgtta  24840
aggtttcatt tagcgcctca aatagatcct gttcaggaac cggatcaaag agttcctccg  24900
ccgctggacc taccaaggca acgctatgtt ctcttgcttt tgtcagcaag atagccagat  24960
caatgtcgat cgtggctggc tcgaagatac ctgcaagaat gtcattgcgc tgccattctc  25020
caaattgcag ttcgcgctta gctggataac gccacggaat gatgtcgtcg tgcacaacaa  25080
tggtgacttc tacagcgcgg agaatctcgc tctctccagg ggaagccgaa gtttccaaaa  25140
ggtcgttgat caaagctcgc cgcgttgttt catcaagcct tacggtcacc gtaaccagca  25200
aatcaatatc actgtgtggc ttcaggccgc catccactgc ggagccgtac aaatgtacgg  25260
ccagcaacgt cggttcgaga tggcgctcga tgacgccaac tacctctgat agttgagtcg  25320
atacttcggc gatcaccgct tccctcatga tgtttaactc ctgaattaag ccgcgccgcg  25380
aagcggtgtc ggcttgaatg aattgttagg cgtcatcctg tgctcccgag aaccagtacc  25440
agtacatcgc tgtttcgttc gagacttgag gtctagtttt atacgtgaac aggtcaatgc  25500
cgccgagagt aaagccacat tttgcgtaca aattgcaggc aggtacattg ttcgtttgtg  25560
tctctaatcg tatgccaagg agctgtctgc ttagtgccca ctttttcgca aattcgatga  25620
gactgtgcgc gactcctttg cctcggtgcg tgtgcgacac aacaatgtgt tcgatagagg  25680
ctagatcgtt ccatgttgag ttgagttcaa tcttcccgac aagctcttgg tcgatgaatg  25740
cgccatagca agcagagtct tcatcagagt catcatccga gatgtaatcc ttccggtagg  25800
```

```
ggctcacact tctggtagat agttcaaagc cttggtcgga taggtgcaca tcgaacactt  25860
cacgaacaat gaaatggttc tcagcatcca atgtttccgc cacctgctca gggatcaccg  25920
aaatcttcat atgacgccta acgcctggca cagcggatcg caaacctggc gcggcttttg  25980
gcacaaaagg cgtgacaggt ttgcgaatcc gttgctgcca cttgttaacc cttttgccag  26040
atttggtaac tataatttat gttagaggcg aagtcttggg taaaaactgg cctaaaattg  26100
ctggggattt caggaaagta aacatcacct tccggctcga tgtctattgt agatatatgt  26160
agtgtatcta cttgatcggg ggatctgctg cctcgcgcgt ttcggtgatg acggtgaaaa  26220
cctctgacac atgcagctcc cggagacggt cacagcttgt ctgtaagcgg atgccgggag  26280
cagacaagcc cgtcagggcg cgtcagcggg tgttggcggg tgtcggggcg cagccatgac  26340
ccagtcacgt agcgatagcg gagtgtatac tggcttaact atgcggcatc agagcagatt  26400
gtactgagag tgcaccatat gcggtgtgaa ataccgcaca gatgcgtaag gagaaaatac  26460
cgcatcaggc gctcttccgc ttcctcgctc actgactcgc tgcgctcggt cgttcggctg  26520
cggcgagcgg tatcagctca ctcaaaggcg gtaatacggt tatccacaga atcaggggat  26580
aacgcaggaa agaacatgtg agcaaaaggc cagcaaaagg ccaggaaccg taaaaaggcc  26640
gcgttgctgg cgtttttcca taggctccgc ccccctgacg agcatcacaa aaatcgacgc  26700
tcaagtcaga ggtggcgaaa cccgacagga ctataaagat accaggcgtt tccccctgga  26760
agctccctcg tgcgctctcc tgttccgacc ctgccgctta ccggatacct gtccgccttt  26820
ctcccttcgg gaagcgtggc gctttctcat agctcacgct gtaggtatct cagttcggtg  26880
taggtcgttc gctccaagct gggctgtgtg cacgaacccc ccgttcagcc cgaccgctgc  26940
gccttatccg gtaactatcg tcttgagtcc aacccggtaa gacacgactt atcgccactg  27000
gcagcagcca ctggtaacag gattagcaga gcgaggtatg taggcggtgc tacagagttc  27060
ttgaagtggt ggcctaacta cggctacact agaaggacag tatttggtat ctgcgctctg  27120
ctgaagccag ttaccttcgg aaaaagagtt ggtagctctt gatccggcaa acaaaccacc  27180
gctggtagcg gtggtttttt tgtttgcaag cagcagatta cgcgcagaaa aaaaggatct  27240
caagaagatc ctttgatctt ttctacgggg tctgacgctc agtggaacga aaactcacgt  27300
taagggattt tggtcatgag attatcaaaa aggatcttca cctagatcct tttaaattaa  27360
aaatgaagtt ttaaatcaat ctaaagtata tatgagtaaa cttggtctga cagttaccaa  27420
tgcttaatca gtgaggcacc tatctcagcg atctgtctat ttcgttcatc catagttgcc  27480
tgactccccg tcgtgtagat aactacgata cgggagggct taccatctgg ccccagtgct  27540
gcaatgatac cgcgagaccc acgctcaccg gctccagatt tatcagcaat aaaccagcca  27600
gccggaaggg ccgagcgcag aagtggtcct gcaactttat ccgcctccat ccagtctatt  27660
aattgttgcc gggaagctag agtaagtagt tcgccagtta atagtttgcg caacgttgtt  27720
gccattgctg caggggggggg gggggggggg gacttccatt gttcattcca cggacaaaaa  27780
cagagaaagg aaacgacaga ggccaaaaag cctcgctttc agcacctgtc gtttcctttc  27840
ttttcagagg gtattttaaa taaaaacatt aagttatgac gaagaagaac ggaaacgcct  27900
taaaccggaa aattttcata aatagcgaaa acccgcgagg tcgccgcccc gtaacctgtc  27960
ggatcaccgg aaaggacccg taaagtgata atgattatca tctacatatc acaacgtgcg  28020
tggaggccat caaaccacgt caaataatca attatgacgc aggtatcgta ttaattgatc  28080
tgcatcaact taacgtaaaa acaacttcag acaatacaaa tcagcgacac tgaatacggg  28140
gcaacctcat gtcccccccc cccccccccc tgcaggcatc gtggtgtcac gctcgtcgtt  28200
```

```
tggtatggct tcattcagct ccggttccca acgatcaagg cgagttacat gatcccccat  28260
gttgtgcaaa aaagcggtta gctccttcgg tcctccgatc gttgtcagaa gtaagttggc  28320
cgcagtgtta tcactcatgg ttatggcagc actgcataat tctcttactg tcatgccatc  28380
cgtaagatgc ttttctgtga ctggtgagta ctcaaccaag tcattctgag aatagtgtat  28440
gcggcgaccg agttgctctt gcccggcgtc aacacgggat aataccgcgc cacatagcag  28500
aactttaaaa gtgctcatca ttggaaaacg ttcttcgggg cgaaaactct caaggatctt  28560
accgctgttg agatccagtt cgatgtaacc cactcgtgca cccaactgat cttcagcatc  28620
ttttactttc accagcgttt ctgggtgagc aaaaacagga aggcaaaatg ccgcaaaaaa  28680
gggaataagg gcgacacgga aatgttgaat actcatactc ttcctttttc aatattattg  28740
aagcatttat cagggttatt gtctcatgag cggatacata tttgaatgta tttagaaaaa  28800
taaacaaata ggggttccgc gcacatttcc ccgaaaagtg ccacctgacg tctaagaaac  28860
cattattatc atgacattaa cctataaaaa taggcgtatc acgaggccct ttcgtcttca  28920
agaattcgga gcttttgcca ttctcaccgg attcagtcgt cactcatggt gatttctcac  28980
ttgataacct tatttttgac gaggggaaat taataggttg tattgatgtt ggacgagtcg  29040
gaatcgcaga ccgataccag gatcttgcca tcctatggaa ctgcctcggt gagttttctc  29100
cttcattaca gaaacggctt tttcaaaaat atggtattga taatcctgat atgaataaat  29160
tgcagtttca tttgatgctc gatgagtttt tctaatcaga attggttaat tggttgtaac  29220
actggcagag cattacgctg acttgacggg acggcggctt tgttgaataa atcgaacttt  29280
tgctgagttg aaggatcaga tcacgcatct tcccgacaac gcagaccgtt ccgtggcaaa  29340
gcaaaagttc aaaatcacca actggtccac ctacaacaaa gctctcatca accgtggctc  29400
cctcactttc tggctggatg atggggcgat tcaggcctgg tatgagtcag caacaccttc  29460
ttcacgaggc agacctcagc gccagaaggc cgccagagag gccgagcgcg gccgtgaggc  29520
ttggacgcta gggcagggca tgaaaaagcc cgtagcgggc tgctacgggc gtctgacgcg  29580
gtggaaaggg ggaggggatg ttgtctacat ggctctgctg tagtgagtgg gttgcgctcc  29640
ggcagcggtc ctgatcaatc gtcacccttt ctcggtcctt caacgttcct gacaacgagc  29700
ctccttttcg ccaatccatc gacaatcacc gcgagtccct gctcgaacgc tgcgtccgga  29760
ccggcttcgt cgaaggcgtc tatcgcggcc cgcaacagcg gcgagagcgg agcctgttca  29820
acggtgccgc cgcgctcgcc ggcatcgctg tcgccggcct gctcctcaag cacggcccca  29880
acagtgaagt agctgattgt catcagcgca ttgacggcgt ccccggccga aaaacccgcc  29940
tcgcagagga agcgaagctg cgcgtcggcc gtttccatct gcggtgcgcc cggtcgcgtg  30000
ccggcatgga tgcgcgcgcc atcgcggtag gcgagcagcg cctgcctgaa gctgcgggca  30060
ttcccgatca gaaatgagcg ccagtcgtcg tcggctctcg gcaccgaatg cgtatgattc  30120
tccgccagca tggcttcggc cagtgcgtcg agcagcgccc gcttgttcct gaagtgccag  30180
taaagcgccg gctgctgaac cccaaccgt tccgccagtt tgcgtgtcgt cagaccgtct  30240
acgccgacct cgttcaacag gtccagggcg gcacggatca ctgtattcgg ctgcaacttt  30300
gtcatgcttg acactttatc actgataaac ataatatgtc caccaactta tcagtgataa  30360
agaatccgcg cgttcaatcg gaccagcgga ggctggtccg gaggccagac gtgaaaccca  30420
acatacccct gatcgtaatt ctgagcactg tcgcgctcga cgctgtcggc atcggcctga  30480
ttatgccggt gctgccgggc ctcctgcgcg atctggttca ctcgaacgac gtcaccgccc  30540
```

```
actatggcat tctgctggcg ctgtatgcgt tggtgcaatt tgcctgcgca cctgtgctgg  30600
gcgcgctgtc ggatcgtttc gggcggcggc caatcttgct cgtctcgctg gccggcgcca  30660
ctgtcgacta cgccatcatg gcgacagcgc ctttcctttg ggttctctat atcgggcgga  30720
tcgtggccgg catcaccggg gcgactgggg cggtagccgg cgcttatatt gccgatatca  30780
ctgatggcga tgagcgcgcg cggcacttcg gcttcatgag cgcctgtttc gggttcggga  30840
tggtcgcggg acctgtgctc ggtgggctga tgggcggttt ctccccccac gctccgttct  30900
tcgccgcggc agccttgaac ggcctcaatt tcctgacggg ctgtttcctt ttgccggagt  30960
cgcacaaagg cgaacgccgg ccgttacgcc gggaggctct caacccgctc gcttcgttcc  31020
ggtgggcccg gggcatgacc gtcgtcgccg ccctgatggc ggtcttcttc atcatgcaac  31080
ttgtcggaca ggtgccggcc gcgctttggg tcattttcgg cgaggatcgc tttcactggg  31140
acgcgaccac gatcggcatt tcgcttgccg catttggcat tctgcattca ctcgcccagg  31200
caatgatcac cggccctgta gccgcccggc tcggcgaaag gcgggcactc atgctcggaa  31260
tgattgccga cggcacaggc tacatcctgc ttgccttcgc gacacgggga tggatggcgt  31320
tcccgatcat ggtcctgctt gcttcgggtg gcatcggaat gccggcgctg caagcaatgt  31380
tgtccaggca ggtggatgag gaacgtcagg ggcagctgca aggctcactg gcggcgctca  31440
ccagcctgac ctcgatcgtc ggacccctcc tcttcacggc gatctatgcg gcttctataa  31500
caacgtggaa cgggtgggca tggattgcag gcgctgccct ctacttgctc tgcctgccgg  31560
cgctgcgtcg cgggctttgg agcggcgcag ggcaacgagc cgatcgctga tcgtggaaac  31620
gataggccta tgccatgcgg gtcaaggcga cttccggcaa gctatacgcg ccctaggagt  31680
gcggttggaa cgttggccca gccagatact cccgatcacg agcaggacgc cgatgatttg  31740
aagcgcactc agcgtctgat ccaagaacaa ccatcctagc aacacggcgg tccccgggct  31800
gagaaagccc agtaaggaaa caactgtagg ttcgagtcgc gagatccccc ggaaccaaag  31860
gaagtaggtt aaacccgctc cgatcaggcc gagccacgcc aggccgagaa cattggttcc  31920
tgtaggcatc gggattggcg gatcaaacac taaagctact ggaacgagca gaagtcctcc  31980
ggccgccagt tgccaggcgg taaaggtgag cagaggcacg ggaggttgcc acttgcgggt  32040
cagcacggtt ccgaacgcca tggaaaccgc ccccgccagg cccgctgcga cgccgacagg  32100
atctagcgct gcgtttggtg tcaacaccaa cagcgccacg cccgcagttc cgcaaatagc  32160
ccccaggacc gccatcaatc gtatcgggct acctagcaga gcggcagaga tgaacacgac  32220
catcagcggc tgcacagcgc ctaccgtcgc cgcgaccccg cccggcaggc ggtagaccga  32280
aataaacaac aagctccaga atagcgaaat attaagtgcg ccgaggatga agatgcgcat  32340
ccaccagatt cccgttggaa tctgtcggac gatcatcacg agcaataaac ccgccggcaa  32400
cgcccgcagc agcataccgg cgacccctcg gcctcgctgt tcgggctcca cgaaaacgcc  32460
ggacagatgc gccttgtgag cgtccttggg gccgtcctcc tgtttgaaga ccgacagccc  32520
aatgatctcg ccgtcgatgt aggcgccgaa tgccacggca tctcgcaacc gttcagcgaa  32580
cgcctccatg ggctttttct cctcgtgctc gtaaacggac ccgaacatct ctggagcttt  32640
cttcagggcc gacaatcgga tctcgcggaa atcctgcacg tcggccgctc caagccgtcg  32700
aatctgagcc ttaatcacaa ttgtcaattt taatcctctg tttatcggca gttcgtagag  32760
cgcgccgtgc gtcccgagcg atactgagcg aagcaagtgc gtcgagcagt gcccgcttgt  32820
tcctgaaatg ccagtaaagc gctggctgct gaacccccag ccggaactga ccccacaagg  32880
ccctagcgtt tgcaatgcac caggtcatca ttgacccagg cgtgttccac caggccgctg  32940
```

```
cctcgcaact cttcgcaggc ttcgccgacc tgctcgcgcc acttcttcac gcgggtggaa  33000
tccgatccgc acatgaggcg gaaggtttcc agcttgagcg ggtacggctc ccggtgcgag  33060
ctgaaatagt cgaacatccg tcgggccgtc ggcgacagct tgcggtactt ctcccatatg  33120
aatttcgtgt agtggtcgcc agcaaacagc acgacgattt cctcgtcgat caggacctgg  33180
caacgggacg ttttcttgcc acggtccagg acgcggaagc ggtgcagcag cgacaccgat  33240
tccaggtgcc caacgcggtc ggacgtgaag cccatcgccg tcgcctgtag gcgcgacagg  33300
cattcctcgg ccttcgtgta ataccggcca ttgatcgacc agcccaggtc ctggcaaagc  33360
tcgtagaacg tgaaggtgat cggctcgccg ataggggtgc gcttcgcgta ctccaacacc  33420
tgctgccaca ccagttcgtc atcgtcggcc cgcagctcga cgccggtgta ggtgatcttc  33480
acgtccttgt tgacgtggaa aatgaccttg ttttgcagcg cctcgcgcgg gattttcttg  33540
ttgcgcgtgg tgaacagggc agagcgggcc gtgtcgtttg gcatcgctcg catcgtgtcc  33600
ggccacggcg caatatcgaa caaggaaagc tgcatttcct tgatctgctg cttcgtgtgt  33660
ttcagcaacg cggcctgctt ggcctcgctg acctgttttg ccaggtcctc gccggcggtt  33720
tttcgcttct tggtcgtcat agttcctcgc gtgtcgatgg tcatcgactt cgccaaacct  33780
gccgcctcct gttcgagacg acgcgaacgc tccacggcgg ccgatggcgc gggcagggca  33840
gggggagcca gttgcacgct gtcgcgctcg atcttggccg tagcttgctg gaccatcgag  33900
ccgacggact ggaaggtttc gcggggcgca cgcatgacgg tgcggcttgc gatggtttcg  33960
gcatcctcgg cggaaaaccc cgcgtcgatc agttcttgcc tgtatgcctt ccggtcaaac  34020
gtccgattca ttcaccctcc ttgcgggatt gccccgactc acgccggggc aatgtgccct  34080
tattcctgat ttgacccgcc tggtgccttg gtgtccagat aatccacctt atcggcaatg  34140
aagtcggtcc cgtagaccgt ctggccgtcc ttctcgtact tggtattccg aatcttgccc  34200
tgcacgaata ccagcgaccc cttgcccaaa tacttgccgt gggcctcggc ctgagagcca  34260
aaacacttga tgcggaagaa gtcggtgcgc tcctgcttgt cgccggcatc gttgcgccac  34320
tcttcattaa ccgctatatc gaaaattgct tgcggcttgt tagaattgcc atgacgtacc  34380
tcggtgtcac gggtaagatt accgataaac tggaactgat tatggctcat atcgaaagtc  34440
tccttgagaa aggagactct agtttagcta aacattggtt ccgctgtcaa gaactttagc  34500
ggctaaaatt ttgcgggccg cgaccaaagg tgcgaggggc ggcttccgct gtgtacaacc  34560
agatattttt caccaacatc cttcgtctgc tcgatgagcg gggcatgacg aaacatgagc  34620
tgtcggagag ggcaggggtt tcaatttcgt ttttatcaga cttaaccaac ggtaaggcca  34680
acccctcgtt gaaggtgatg gaggccattg ccgacgccct ggaaactccc ctacctcttc  34740
tcctggagtc caccgacctt gaccgcgagg cactcgcgga gattgcgggt catcctttca  34800
agagcagcgt gccgcccgga tacgaacgca tcagtgtggt tttgccgtca cataaggcgt  34860
ttatcgtaaa gaaatggggc gacgacaccc gaaaaaagct gcgtggaagg ctctgacgcc  34920
aagggttagg gcttgcactt ccttctttag ccgctaaaac ggccccttct ctgcgggccg  34980
tcggctcgcg catcatatcg acatcctcaa cggaagccgt gccgcgaatg gcatcgggcg  35040
ggtgcgcttt gacagttgtt ttctatcaga accccctacgt cgtgcggttc gattagctgt  35100
ttgtcttgca ggctaaacac tttcggtata tcgtttgcct gtgcgataat gttgctaatg  35160
atttgttgcg taggggttac tgaaaagtga gcgggaaaga agagtttcag accatcaagg  35220
agcgggccaa gcgcaagctg gaacgcgaca tgggtgcgga cctgttggcc gcgctcaacg  35280
```

```
acccgaaaac cgttgaagtc atgctcaacg cggacggcaa ggtgtggcac gaacgccttg  35340
gcgagccgat gcggtacatc tgcgacatgc ggcccagcca gtcgcaggcg attatagaaa  35400
cggtggccgg attccacggc aaagaggtca cgcggcattc gcccatcctg gaaggcgagt  35460
tccccttgga tggcagccgc tttgccggcc aattgccgcc ggtcgtggcc gcgccaacct  35520
ttgcgatccg caagcgcgcg gtcgccatct tcacgctgga acagtacgtc gaggcgggca  35580
tcatgacccg cgagcaatac gaggtcatta aaagcgccgt cgcggcgcat cgaaacatcc  35640
tcgtcattgg cggtactggc tcgggcaaga ccacgctcgt caacgcgatc atcaatgaaa  35700
tggtcgcctt caacccgtct gagcgcgtcg tcatcatcga ggacaccggc gaaatccagt  35760
gcgccgcaga gaacgccgtc caataccaca ccagcatcga cgtctcgatg acgctgctgc  35820
tcaagacaac gctgcgtatg cgccccgacc gcatcctggt cggtgaggta cgtggccccg  35880
aagcccttga tctgttgatg gcctggaaca ccgggcatga aggaggtgcc gccaccctgc  35940
acgcaaacaa ccccaaagcg ggcctgagcc ggctcgccat gcttatcagc atgcacccgg  36000
attcaccgaa acccattgag ccgctgattg gcgaggcggt tcatgtggtc gtccatatcg  36060
ccaggacccc tagcggccgt cgagtgcaag aaattctcga agttcttggt tacgagaacg  36120
gccagtacat caccaaaacc ctgtaaggag tatttccaat gacaacggct gttccgttcc  36180
gtctgaccat gaatcgcggc attttgttct accttgccgt gttcttcgtt ctcgctctcg  36240
cgttatccgc gcatccggcg atggcctcgg aaggcaccgg cggcagcttg ccatatgaga  36300
gctggctgac gaacctgcgc aactccgtaa ccggcccggt ggccttcgcg ctgtccatca  36360
tcggcatcgt cgtcgccggc ggcgtgctga tcttcggcgg cgaactcaac gccttcttcc  36420
gaaccctgat cttcctggtt ctggtgatgg cgctgctggt cggcgcgcag aacgtgatga  36480
gcaccttctt cggtcgtggt gccgaaatcg cggccctcgg caacggggcg ctgcaccagg  36540
tgcaagtcgc ggcggcggat gccgtgcgtg cggtagcggc tggacggctc gcctaatcat  36600
ggctctgcgc acgatcccca tccgtcgcgc aggcaaccga gaaaacctgt tcatgggtgg  36660
tgatcgtgaa ctggtgatgt tctcgggcct gatggcgttt gcgctgattt tcagcgccca  36720
agagctgcgg gccaccgtgg tcggtctgat cctgtggttc ggggcgctct atgcgttccg  36780
aatcatggcg aaggccgatc cgaagatgcg gttcgtgtac ctgcgtcacc gccggtacaa  36840
gccgtattac ccggcccgct cgaccccgtt ccgcgagaac accaatagcc aagggaagca  36900
ataccgatga tccaagcaat tgcgattgca atcgcgggcc tcggcgcgct tctgttgttc  36960
atcctctttg cccgcatccg cgcggtcgat gccgaactga aactgaaaaa gcatcgttcc  37020
aaggacgccg gcctggccga tctgctcaac tacgccgctg tcgtcgatga cggcgtaatc  37080
gtgggcaaga acggcagctt tatggctgcc tggctgtaca agggcgatga caacgcaagc  37140
agcaccgacc agcagcgcga agtagtgtcc gcccgcatca accaggccct cgcgggcctg  37200
ggaagtgggt ggatgatcca tgtggacgcc gtgcggcgtc ctgctccgaa ctacgcggag  37260
cggggcctgt cggcgttccc tgaccgtctg acggcagcga ttgaagaaga gcgctcggtc  37320
ttgccttgct cgtcggtgat gtacttcacc agctccgcga agtcgctctt cttgatggag  37380
cgcatgggga cgtgcttggc aatcacgcgc accccccggc cgttttagcg gctaaaaaag  37440
tcatggctct gccctcgggc ggaccacgcc catcatgacc ttgccaagct cgtcctgctt  37500
ctcttcgatc ttcgccagca gggcgaggat cgtggcatca ccgaaccgcg ccgtgcgcgg  37560
gtcgtcggtg agccagagtt tcagcaggcc gcccaggcgg cccaggtcgc cattgatgcg  37620
ggccagctcg cggacgtgct catagtccac gacgcccgtg attttgtagc cctggccgac  37680
```

```
ggccagcagg taggccgaca ggctcatgcc ggccgccgcc gccttttcct caatcgctct  37740
tcgttcgtct ggaaggcagt acaccttgat aggtgggctg cccttcctgg ttggcttggt  37800
ttcatcagcc atccgcttgc cctcatctgt tacgccggcg gtagccggcc agcctcgcag  37860
agcaggattc ccgttgagca ccgccaggtg cgaataaggg acagtgaaga aggaacaccc  37920
gctcgcgggt gggcctactt cacctatcct gcccggctga cgccgttgga tacaccaagg  37980
aaagtctaca cgaacccttt ggcaaaatcc tgtatatcgt gcgaaaaagg atggatatac  38040
cgaaaaaatc gctataatga ccccgaagca gggttatgca gcggaaaagc gctgcttccc  38100
tgctgttttg tggaatatct accgactgga aacaggcaaa tgcaggaaat tactgaactg  38160
aggggacagg cgagagacga tgccaaagag ctacaccgac gagctggccg agtgggttga  38220
atcccgcgcg gccaagaagc gccggcgtga tgaggctgcg gttgcgttcc tggcggtgag  38280
ggcggatgtc gaggcggcgt tagcgtccgg ctatgcgctc gtcaccattt gggagcacat  38340
gcgggaaacg gggaaggtca agttctccta cgagacgttc cgctcgcacg ccaggcggca  38400
catcaaggcc aagcccgccg atgtgcccgc accgcaggcc aaggctgcgg aacccgcgcc  38460
ggcacccaag acgccggagc cacggcggcc gaagcagggg ggcaaggctg aaaagccggc  38520
ccccgctgcg gccccgaccg gcttcacctt caacccaaca ccggacaaaa aggatctact  38580
gtaatggcga aaattcacat ggttttgcag ggcaagggcg gggtcggcaa gtcggccatc  38640
gccgcgatca ttgcgcagta caagatggac aaggggcaga caccccttgtg catcgacacc  38700
gacccggtga acgcgacgtt cgagggctac aaggccctga acgtccgccg gctgaacatc  38760
atggccggcg acgaaattaa ctcgcgcaac ttcgacaccc tggtcgagct gattgcgccg  38820
accaaggatg acgtggtgat cgacaacggt gccagctcgt tcgtgcctct gtcgcattac  38880
ctcatcagca accaggtgcc ggctctgctg caagaaatgg ggcatgagct ggtcatccat  38940
accgtcgtca ccggcggcca ggctctcctg gacacggtga gcggcttcgc ccagctcgcc  39000
agccagttcc cggccgaagc gcttttcgtg gtctggctga acccgtattg gggcctatc  39060
gagcatgagg gcaagagctt tgagcagatg aaggcgtaca cggccaacaa ggcccgcgtg  39120
tcgtccatca tccagattcc ggccctcaag gaagaaacct acggccgcga tttcagcgac  39180
atgctgcaag agcggctgac gttcgaccag gcgctggccg atgaatcgct cacgatcatg  39240
acgcggcaac gcctcaagat cgtgcggcgc ggcctgtttg aacagctcga cgcggcggcc  39300
gtgctatgag cgaccagatt gaagagctga tccgggagat tgcggccaag cacggcatcg  39360
ccgtcggccg cgacgacccg gtgctgatcc tgcataccat caacgcccgg ctcatggccg  39420
acagtgcggc caagcaagag gaaatccttg ccgcgttcaa ggaagagctg gaagggatcg  39480
cccatcgttg ggcgaggac gccaaggcca aagcggagcg gatgctgaac gcggccctgg  39540
cggccagcaa ggacgcaatg gcgaaggtaa tgaaggacag cgccgcgcag gcggccgaag  39600
cgatccgcag ggaaatcgac gacggccttg gccgccagct cgcggccaag gtcgcggacg  39660
cgcggcgcgt ggcgatgatg aacatgatcg ccggcggcat ggtgttgttc gcggccgccc  39720
tggtggtgtg ggcctcgtta tgaatcgcag aggcgcagat gaaaaagccc ggcgttgccg  39780
ggctttgttt ttgcgttagc tgggcttgtt tgacaggccc aagctctgac tgcgcccgcg  39840
ctcgcgctcc tgggcctgtt tcttctcctg ctcctgcttg cgcatcaggg cctggtgccg  39900
tcgggctgct tcacgcatcg aatcccagtc gccggccagc tcgggatgct ccgcgcgcat  39960
cttgcgcgtc gccagttcct cgatcttggg cgcgtgaatg cccatgcctt ccttgatttc  40020
```

```
gcgcaccatg tccagccgcg tgtgcagggt ctgcaagcgg gcttgctgtt gggcctgctg  40080
ctgctgccag gcggcctttg tacgcggcag ggacagcaag ccgggggcat tggactgtag  40140
ctgctgcaaa cgcgcctgct gacggtctac gagctgttct aggcggtcct cgatgcgctc  40200
cacctggtca tgctttgcct gcacgtagag cgcaagggtc tgctggtagg tctgctcgat  40260
gggcgcggat tctaagaggg cctgctgttc cgtctcggcc tcctgggccg cctgtagcaa  40320
atcctcgccg ctgttgccgc tggactgctt tactgccggg gactgctgtt gccctgctcg  40380
cgccgtcgtc gcagttcggc ttgcccccac tcgattgact gcttcatttc gagccgcagc  40440
gatgcgatct cggattgcgt caacggacgg ggcagcgcgg aggtgtccgg cttctccttg  40500
ggtgagtcgg tcgatgccat agccaaaggt ttccttccaa aatgcgtcca ttgctggacc  40560
gtgtttctca ttgatgcccg caagcatctt cggcttgacc gccaggtcaa gcgcgccttc  40620
atgggcggtc atgacggacg ccgccatgac cttgccgccg ttgttctcga tgtagccgcg  40680
taatgaggca atggtgccgc ccatcgtcag cgtgtcatcg acaacgatgt acttctggcc  40740
ggggatcacc tcccccctcga aagtcgggtt gaacgccagg cgatgatctg aaccggctcc  40800
ggttcgggcg accttctccc gctgcacaat gtccgtttcg acctcaaggc caaggcggtc  40860
ggccagaacg accgccatca tggccggaat cttgttgttc cccgccgcct cgacggcgag  40920
gactggaacg atgcggggct tgtcgtcgcc gatcagcgtc ttgagctggg caacagtgtc  40980
gtccgaaatc aggcgctcga ccaaattaag cgccgcttcc gcgtcgccct gcttcgcagc  41040
ctggtattca ggctcgttgg tcaaagaacc aaggtcgccg ttgcgaacca ccttcgggaa  41100
gtctccccac ggtgcgcgct cggctctgct gtagctgctc aagacgcctc cctttttagc  41160
cgctaaaact ctaacgagtg cgcccgcgac tcaacttgac gctttcggca cttacctgtg  41220
ccttgccact tgcgtcatag gtgatgcttt tcgcactccc gatttcaggt actttatcga  41280
aatctgaccg ggcgtgcatt acaaagttct tccccacctg ttggtaaatg ctgccgctat  41340
ctgcgtggac gatgctgccg tcgtggcgct gcgacttatc ggccttttgg gccatataga  41400
tgttgtaaat gccaggtttc agggccccgg ctttatctac cttctggttc gtccatgcgc  41460
cttggttctc ggtctggaca attctttgcc cattcatgac caggaggcgg tgtttcattg  41520
ggtgactcct gacggttgcc tctggtgtta aacgtgtcct ggtcgcttgc cggctaaaaa  41580
aaagccgacc tcggcagttc gaggccggct ttccctagag ccgggcgcgt caaggttgtt  41640
ccatctattt tagtgaactg cgttcgattt atcagttact ttcctcccgc tttgtgtttc  41700
ctcccactcg tttccgcgtc tagccgaccc ctcaacatag cggcctcttc ttgggctgcc  41760
tttgcctctt gccgcgcttc gtcacgctcg gcttgcaccg tcgtaaagcg ctcggcctgc  41820
ctggccgcct cttgcgccgc caacttcctt tgctcctggt gggcctcggc gtcggcctgc  41880
gccttcgctt tcaccgctgc caactccgtg cgcaaactct ccgcttcgcg cctggtggcg  41940
tcgcgctcgc cgcgaagcgc ctgcatttcc tggttggccg cgtccagggt cttgcggctc  42000
tcttctttga atgcgcgggc gtcctggtga gcgtagtcca gctcggcgcg cagctcctgc  42060
gctcgacgct ccacctcgtc ggcccgctgc gtcgccagcg cggcccgctg ctcggctcct  42120
gccagggcgg tgcgtgcttc ggccagggct tgccgctggc gtgcggccag ctcggccgcc  42180
tcggcggcct gctgctctag caatgtaacg cgcgcctggg cttcttccag ctcgcgggcc  42240
tgcgcctcga aggcgtcggc cagctccccg cgcacggctt ccaactcgtt gcgctcacga  42300
tcccagccgg cttgcgctgc ctgcaacgat tcattggcaa gggcctgggc ggcttgccag  42360
agggcggcca cggcctggtt gccggcctgc tgcaccgcgt ccggcacctg gactgccagc  42420
```

```
ggggcggcct gcgccgtgcg ctggcgtcgc cattcgcgca tgccggcgct ggcgtcgttc  42480
atgttgacgc gggcggcctt acgcactgca tccacggtcg ggaagttctc ccggtcgcct  42540
tgctcgaaca gctcgtccgc agccgcaaaa atgcggtcgc gcgtctcttt gttcagttcc  42600
atgttggctc cggtaattgg taagaataat aatactctta cctaccttat cagcgcaaga  42660
gtttagctga acagttctcg acttaacggc aggtttttta gcggctgaag ggcaggcaaa  42720
aaaagccccg cacggtcggc gggggcaaag ggtcagcggg aaggggatta gcgggcgtcg  42780
ggcttcttca tgcgtcgggg ccgcgcttct tgggatggag cacgacgaag cgcgcacgcg  42840
catcgtcctc ggccctatcg gcccgcgtcg cggtcaggaa cttgtcgcgc gctaggtcct  42900
ccctggtggg caccaggggc atgaactcgg cctgctcgat gtaggtccac tccatgaccg  42960
catcgcagtc gaggccgcgt tccttcaccg tctcttgcag gtcgcggtac gcccgctcgt  43020
tgagcggctg gtaacgggcc aattggtcgt aaatggctgt cggccatgag cggcctttcc  43080
tgttgagcca gcagccgacg acgaagccgg caatgcaggc ccctggcaca accaggccga  43140
cgccgggggc aggggatggc agcagctcgc caaccaggaa ccccgccgcg atgatgccga  43200
tgccggtcaa ccagcccttg aaactatccg gccccgaaac acccctgcgc attgcctgga  43260
tgctgcgccg gatagcttgc aacatcagga gccgtttctt ttgttcgtca gtcatggtcc  43320
gccctcacca gttgttcgta tcggtgtcgg acgaactgaa atcgcaagag ctgccggtat  43380
cggtccagcc gctgtccgtg tcgctgctgc cgaagcacgg cgaggggtcc gcgaacgccg  43440
cagacggcgt atccggccgc agcgcatcgc ccagcatggc cccggtcagc gagccgccgg  43500
ccaggtagcc cagcatggtg ctgttggtcg ccccggccac cagggccgac gtgacgaaat  43560
cgccgtcatt ccctctggat tgttcgctgc tcggcggggc agtgcgccgc gccggcggcg  43620
tcgtggatgg ctcgggttgg ctggcctgcg acggccggcg aaaggtgcgc agcagctcgt  43680
tatcgaccgg ctgcggcgtc ggggccgccg ccttgcgctg cggtcggtgt tccttcttcg  43740
gctcgcgcag cttgaacagc atgatcgcgg aaaccagcag caacgccgcg cctacgcctc  43800
ccgcgatgta gaacagcatc ggattcattc ttcggtcctc cttgtagcgg aaccgttgtc  43860
tgtgcggcgc gggtggcccg cgccgctgtc tttggggatc agccctcgat gagcgcgacc  43920
agtttcacgt cggcaaggtt cgcctcgaac tcctggccgt cgtcctcgta cttcaaccag  43980
gcatagcctt ccgccggcgg ccgacggttg aggataaggc gggcagggcg ctcgtcgtgc  44040
tcgacctgga cgatggcctt tttcagcttg tccgggtccg gctccttcgc gccctttttcc  44100
ttggcgtcct taccgtcctg gtcgccgtcc tcgccgtcct ggccgtcgcc ggcctccgcg  44160
tcacgctcgg catcagtctg gccgttgaag gcatcgacgg tgttgggatc gcggcccttc  44220
tcgtccagga actcgcgcag cagcttgacc gtgccgcgcg tgatttcctg ggtgtcgtcg  44280
tcaagccacg cctcgacttc ctccgggcgc ttcttgaagg ccgtcaccag ctcgttcacc  44340
acggtcacgt cgcgcacgcg gccggtgttg aacgcatcgg cgatcttctc cggcaggtcc  44400
agcagcgtga cgtgctgggt gatgaacgcc ggcgacttgc cgatttcctt ggcgatatcg  44460
cctttcttct tgcccttcgc cagctcgcgg ccaatgaagt cggcaatttc gcgcggggtc  44520
agctcgttgc gttgcaggtt ctcgataacc tggtcggctt cgttgtagtc gttgtcgatg  44580
aacgccggga tggacttctt gccggcccac ttcgagccac ggtagcggcg ggcgccgtga  44640
ttgatgatat agcggcccgg ctgctcctgg ttctcgcgca ccgaaatggg tgacttcacc  44700
ccgcgctctt tgatcgtggc accgatttcc gcgatgctct ccggggaaaa gccggggttg  44760
```

```
tcggccgtcc gcggctgatg cggatcttcg tcgatcaggt ccaggtccag ctcgataggg  44820
ccggaaccgc cctgagacgc cgcaggagcg tccaggaggc tcgacaggtc gccgatgcta  44880
tccaacccca ggccggacgg ctgcgccgcg cctgcggctt cctgagcggc cgcagcggtg  44940
tttttcttgg tggtcttggc ttgagccgca gtcattggga aatctccatc ttcgtgaaca  45000
cgtaatcagc cagggcgcga acctctttcg atgccttgcg cgcggccgtt ttcttgatct  45060
tccagaccgg cacaccggat gcgagggcat cggcgatgct gctgcgcagg ccaacggtgg  45120
ccggaatcat catcttgggg tacgcggcca gcagctcggc ttggtggcgc gcgtggcgcg  45180
gattccgcgc atcgaccttg ctgggcacca tgccaaggaa ttgcagcttg gcgttcttct  45240
ggcgcacgtt cgcaatggtc gtgaccatct tcttgatgcc ctggatgctg tacgcctcaa  45300
gctcgatggg ggacagcaca tagtcggccg cgaagagggc ggccgccagg ccgacgccaa  45360
gggtcggggc cgtgtcgatc aggcacacgt cgaagccttg gttcgccagg gccttgatgt  45420
tcgccccgaa cagctcgcgg gcgtcgtcca gcgacagccg ttcggcgttc gccagtaccg  45480
ggttggactc gatgagggcg aggcgcgcgg cctggccgtc gccggctgcg ggtgcggttt  45540
cggtccagcc gccggcaggg acagcgccga acagcttgct tgcatgcagg ccggtagcaa  45600
agtccttgag cgtgtaggac gcattgccct gggggtccag gtcgatcacg gcaacccgca  45660
agccgcgctc gaaaaagtcg aaggcaagat gcacaagggt cgaagtcttg ccgacgccgc  45720
ctttctggtt ggccgtgacc aaagttttca tcgtttggtt tcctgttttt tcttggcgtc  45780
cgcttcccac ttccggacga tgtacgcctg atgttccggc agaaccgccg ttacccgcgc  45840
gtacccctcg ggcaagttct tgtcctcgaa cgcggcccac acgcgatgca ccgcttgcga  45900
cactgcgccc ctggtcagtc ccagcgacgt tgcgaacgtc gcctgtggct tcccatcgac  45960
taagacgccc cgcgctatct cgatggtctg ctgccccact tccagcccct ggatcgcctc  46020
ctggaactgg ctttcggtaa gccgtttctt catggataac acccataatt tgctccgcgc  46080
cttggttgaa catagcggtg acagccgcca gcacatgaga gaagtttagc taaacatttc  46140
tcgcacgtca acacctttag ccgctaaaac tcgtccttgg cgtaacaaaa caaaagcccg  46200
gaaaccgggc tttcgtctct tgccgcttat ggctctgcac ccggctccat caccaacagg  46260
tcgcgcacgc gcttcactcg gttgcggatc gacactgcca gcccaacaaa gccggttgcc  46320
gccgccgcca ggatcgcgcc gatgatgccg gccacaccgg ccatcgccca ccaggtcgcc  46380
gccttccggt tccattcctg ctggtactgc ttcgcaatgc tggacctcgg ctcaccatag  46440
gctgaccgct cgatggcgta tgccgcttct cccccttggcg taaaacccag cgccgcaggc  46500
ggcattgcca tgctgcccgc cgctttcccg accacgacgc gcgcaccagg cttgcggtcc  46560
agaccttcgg ccacggcgag ctgcgcaagg acataatcag ccgccgactt ggctccacgc  46620
gcctcgatca gctcttgcac tcgcgcgaaa tccttggcct ccacggccgc catgaatcgc  46680
gcacgcggcg aaggctccgc agggccggcg tcgtgatcgc cgccgagaat gcccttcacc  46740
aagttcgacg acacgaaaat catgctgacg gctatcacca tcatgcagac ggatcgcacg  46800
aacccgctga attgaacacg agcacggcac ccgcgaccac tatgccaaga atgcccaagg  46860
taaaaattgc cggccccgcc atgaagtccg tgaatgcccc gacggccgaa gtgaagggca  46920
ggccgccacc caggccgccg ccctcactgc ccggcacctg gtcgctgaat gtcgatgcca  46980
gcacctgcgg cacgtcaatg cttccgggcg tcgcgctcgg gctgatcgcc catcccgtta  47040
ctgccccgat cccggcaatg gcaaggactg ccagcgctgc catttttggg gtgaggccgt  47100
tcgcggccga ggggcgcagc ccctgggggg atgggaggcc cgcgttagcg ggccgggagg  47160
```

```
gttcgagaag ggggggcacc ccccttcggc gtgcgcggtc acgcgcacag ggcgcagccc  47220

tggttaaaaa caaggtttat aaatattggt ttaaaagcag gttaaaagac aggttagcgg  47280

tggccgaaaa acgggcggaa acccttgcaa atgctggatt ttctgcctgt ggacagcccc  47340

tcaaatgtca ataggtgcgc ccctcatctg tcagcactct gcccctcaag tgtcaaggat  47400

cgcgcccctc atctgtcagt agtcgcgccc ctcaagtgtc aataccgcag ggcacttatc  47460

cccaggcttg tccacatcat ctgtgggaaa ctcgcgtaaa atcaggcgtt ttcgccgatt  47520

tgcgaggctg gccagctcca cgtcgccggc cgaaatcgag cctgcccctc atctgtcaac  47580

gccgcgccgg gtgagtcggc ccctcaagtg tcaacgtccg cccctcatct gtcagtgagg  47640

gccaagtttt ccgcgaggta tccacaacgc cggcggccgc ggtgtctcgc acacggcttc  47700

gacggcgttt ctggcgcgtt tgcagggcca tagacggccg ccagcccagc ggcgagggca  47760

accagcccgg tgagcgtcgg aaaggcgctg gaagccccgt agcgacgcgg agaggggcga  47820

gacaagccaa gggcgcaggc tcgatgcgca gcacgacata gccggttctc gcaaggacga  47880

gaatttccct gcggtgcccc tcaagtgtca atgaaagttt ccaacgcgag ccattcgcga  47940

gagccttgag tccacgctag atgagagctt tgttgtaggt ggaccagttg gtgattttga  48000

acttttgctt tgccacggaa cggtctgcgt tgtcgggaag atgcgtgatc tgatccttca  48060

actcagcaaa agttcgattt attcaacaaa gccacgttgt gtctcaaaat ctctgatgtt  48120

acattgcaca agataaaaat atatcatcat gaacaataaa actgtctgct tacataaaca  48180

gtaatacaag ggtgttatg agccatattc aacgggaaac gtcttgctcg ac          48232
```

<210> SEQ ID NO 15
<211> LENGTH: 1055
<212> TYPE: DNA
<213> ORGANISM: artificial sequence
<220> FEATURE:
<223> OTHER INFORMATION: ZMCAS1HINDIIIPRO fragment comprising 1.0 KB
ZmCAS1 promoter

<400> SEQUENCE: 15

```
aagctttttg gaaggctaag gagaggaagc cggcgagaag gagggggcgt tttacgtgtc     60

actgtcctgt cgtgttggct gttgacacga atcatttctt ccgcgcgtgg gaagaagaag    120

atgcacatta gcggcctgaa gtagagatgt caatggggaa ttccccagcg ggattaact    180

ccccagaccc gtacccatga acatagaccg gccccccatcc ccgaacccga acccgacctc    240

gggtacgaaa atcctcccat acccattccc gaccgggtac taaataccca tgggtatcca    300

tacccgaccc gattattcaa aaattaatgg gctttttatt tgttaaccgg cggacgcaat    360

gcttgggact ctaggttttt ttactttgtt gaccggctgg cggctgggct ttttcctaca    420

ggcccaaagt tggtcggcag ccactaggcc acacgtcaca ggcagcccac aagtaaatgt    480

cgttggattg ctggatggtg gaataaaaat cctagatgct agattgttct ggttccgggt    540

atttttctcc atggctaatc gggtttgggt ttagccctcc caaacccgaa cccgccatac    600

ccgatgggta agggatttat tccaaatcta tacccatggg gatttgtttt aacccatacc    660

ttaaccctaa tagaggaatt ccccacgggt aatcgggttt cggggcccat tgacatctct    720

agactgaagg cgtccaactc aaatcattaa aaagtgttga cgcacgcgct gatgcgccgg    780

ccgcacagca caggctgcac agcccgttta atcagcgatg gagccccggc cgtcagccag    840

ccaggtccgg cgtccgggtc tgcgccctgc ggcgtcactg ctgtcgccac cgtctccgat    900

ggtcccacat ccatccagcg ggccgcgcgt ggtacaaaag gctcttcctc gccgtcaggt    960
```

```
gcagctgccc aaacaccaga cacagactcc accaccccgc ttcgatcttc tgttgcagct   1020

gaaatctgtc agattctgca gttcattcct catga                              1055


<210> SEQ ID NO 16
<211> LENGTH: 1752
<212> TYPE: DNA
<213> ORGANISM: artificial sequence
<220> FEATURE:
<223> OTHER INFORMATION: ZMCAS1BAMPRO fragment comprising 1.7 KB ZmCAS1
      promoter

<400> SEQUENCE: 16

ggatccgggg cggaagatgg cagggacgcg gattcagggc ggacgcgctt gccgagggcg     60

cgggggacca cagcgtgcgt tacggggaca gggcgggcat cgcgaggacg ggtgcgggag    120

cggagccaca tctggtggtg gacgcctact ttgctctctt atagagtagt aaagattcgt    180

ggaccaaaca acaccctagc ttgtacaaat attcttaggc agttgctact gatgagagaa    240

aaataacatc actccactgc atttgcgtga tttattgaac agatcacaat tacatctatt    300

caaatttatt tacctgtacg tgtccgattt ttaggggagg atttttttac ggtatttttt    360

ttttaaaaaa ataaatttag gcaacaattt tatagaatcg agtgctttat ctattatctt    420

ttacaaggca cacgcgtaca ataaggtttg gtcgttcgtg acttggatag tggttttggt    480

tgcaattccg taattcttgg cataggatac agcccaaccc agaaaaaaat aatgttgcgg    540

tcagttctgg ctttgagatt cggagtacca cgtggcgtaa aggcaggccg tgtcttacag    600

atgaataaag gacctgggtc tcacgtgatt ggtttccagt ttcgtgcatc aagatgtgga    660

attttcaaac tgccgtcgtg tttgtttcgt cacataaaag ctttttggaa ggctaaggag    720

aggaagccgg cgagaaggag gggcgtttt acgtgtcact gtcctgtcgt gttggctgtt     780

gacacgaatc atttcttccg cgcgtgggaa gaagaagatg cacattagcg gcctgaagta    840

gagatgtcaa tggggaattc cccagcgggg attaactccc cagacccgta cccatgaaca    900

tagaccggcc cccatccccg aacccgaacc cgacctcggg tacgaaaatc ctcccatacc    960

cattcccgac cgggtactaa atacccatgg gtatccatac ccgacccgat tattcaaaaa   1020

ttaatgggct ttttatttgt taaccggcgg acgcaatgct tgggactcta ggttttttta   1080

ctttgttgac cggctggcgg ctgggctttt tcctacaggc ccaaagttgg tcggcagcca   1140

ctaggccaca cgtcacaggc agcccacaag taaatgtcgt tggattgctg gatggtggaa   1200

taaaaatcct agatgctaga ttgttctggt tccgggtatt tttctccatg gctaatcggg   1260

tttgggttta gccctcccaa acccgaaccc gccatacccg atgggtaagg gatttattcc   1320

aaatctatac ccatggggat ttgttttaac ccatacctta accctaatag aggaattccc   1380

cacgggtaat cgggtttcgg ggcccattga catctctaga ctgaaggcgt ccaactcaaa   1440

tcattaaaaa gtgttgacgc acgcgctgat gcgccggccg cacagcacag gctgcacagc   1500

ccgtttaatc agcgatggag ccccggccgt cagccagcca ggtccggcgt ccgggtctgc   1560

gccctgcggc gtcactgctg tcgccaccgt ctccgatggt cccacatcca tccagcgggc   1620

cgcgcgtggt acaaaaggct cttcctcgcc gtcaggtgca gctgcccaaa caccagacac   1680

agactccacc accccgcttc gatcttctgt tgcagctgaa atctgtcaga ttctgcagtt   1740

cattcctcat ga                                                       1752


<210> SEQ ID NO 17
<211> LENGTH: 354
```

<212> TYPE: PRT
<213> ORGANISM: Oryza sativa

<400> SEQUENCE: 17

```
Met Ala Ala Glu Cys Gly Ser Gly Asn Cys Asp Ala Trp Ala Ala Arg
1               5                   10                  15

Asp Pro Ser Gly Ile Leu Ser Pro Tyr Lys Phe Asn Arg Arg Ala Val
            20                  25                  30

Gln Ser Asp Asp Val Ser Leu Arg Ile Thr His Cys Gly Val Cys Tyr
        35                  40                  45

Ala Asp Val Ala Trp Thr Arg Asn Ile Leu Asn Asn Ser Met Tyr Pro
    50                  55                  60

Leu Val Pro Gly His Glu Ile Ala Gly Val Val Thr Glu Val Gly Ala
65                  70                  75                  80

Asp Val Lys Ser Phe Lys Val Gly Asp His Val Gly Val Gly Thr Tyr
                85                  90                  95

Val Asn Ser Cys Arg Asp Cys Glu Asn Cys Asn Ser Ser Leu Glu Asn
            100                 105                 110

Tyr Cys Ser Gln His Val Phe Thr Phe Asn Gly Val Asp Thr Asp Gly
        115                 120                 125

Thr Val Thr Lys Gly Gly Tyr Ser Thr His Ile Val Val His Glu Arg
    130                 135                 140

Tyr Cys Phe Lys Ile Pro Asp Gly Tyr Pro Leu Glu Lys Ala Ala Pro
145                 150                 155                 160

Leu Leu Cys Ala Gly Ile Thr Val Tyr Ser Pro Met Met Arg His Asn
                165                 170                 175

Met Asn Gln Pro Gly Lys Ser Leu Gly Val Ile Gly Leu Gly Gly Leu
            180                 185                 190

Gly His Met Ala Val Lys Phe Gly Lys Ala Phe Gly Leu Lys Val Thr
        195                 200                 205

Val Ile Ser Thr Ser Glu Ser Lys Arg Lys Glu Ala Ile Asp Leu Leu
    210                 215                 220

Gly Ala Asp Asn Phe Val Val Ser Ser Asp Glu Asn Gln Met Glu Thr
225                 230                 235                 240

Leu Lys Ser Ser Leu Asn Phe Ile Ile Asp Thr Ala Ser Gly Asp His
                245                 250                 255

Pro Phe Asp Pro Tyr Leu Thr Leu Leu Lys Val Gly Gly Val Met Ala
            260                 265                 270

Leu Leu Ser Phe Pro Ser Glu Ile Lys Val His Pro Ala Asn Leu Asn
        275                 280                 285

Leu Gly Gly Arg Ser Leu Ser Gly Ser Val Thr Gly Gly Thr Lys Asp
    290                 295                 300

Ile Gln Glu Met Ile Asn Phe Cys Ala Ala Asn Lys Ile Tyr Pro Asp
305                 310                 315                 320

Ile Glu Met Ile Lys Ile Asp Tyr Ile Asn Glu Ala Leu Gln Arg Leu
                325                 330                 335

Val Asp Arg Asp Val Arg Phe Arg Phe Val Ile Asp Ile Glu Asn Ser
            340                 345                 350

Phe Lys
```

<210> SEQ ID NO 18
<211> LENGTH: 6254
<212> TYPE: DNA
<213> ORGANISM: Oryza sativa

<400> SEQUENCE: 18

```
cagtcacaaa tttttggta attccgagaa aatttccgga aactccgaga acatttccag      60
aaagtttccg accatttccg agttccgacg gaaactgccc ttatcatttc cgattccgtt    120
tccgagaaaa tattttcgaa ttcgtttccg tttccgaaaa atccgaaaaa attctgaccg    180
acagattccg tttccgaaaa taggtccgga atccggaaag tttccgtacc gttttcaccc    240
ctaactggga caaaatgatt attttagtct aacatacatt gttaagtata ttaaagtcta    300
cggtctatct cacagcttac aaatggtgag atatgatatc ttttaacatt atttcataaa    360
acagtaaata agatgcccgg catcaagggg tgaaaacgat attgaaattt cccgaccata    420
ccgataccgt tttcggaaat ctaatataat aataatattt ttaccaatgg ctaccatttt    480
caaaatttag tttttttcta atttctatca gcgtggcatt gaagttaaca ctaaatatat    540
gaattcgtaa acattaaaat tttccgaccg tttcggttcg ttttcgaaaa aataataaaa    600
taatgatatc gtttccgacc atttctgata gttttcatcc ctaacggcat ccacgtgggc    660
tttcttccta gttgagtaaa aagtggagta ttgagagttt acacgagaga attattagtg    720
agattaagat ggaaatttga tttttagtcc taatatcttg tttagtaaat atggcggaaa    780
ttgacaggga gtttcgttgg agattatgtc attaataaaa acggatggct gagatttgtt    840
tatgcaaatt aaaggaggaa ttccccctat ccacgtattg aaagaggtgt tccttactca    900
attctccatt cccatctcat taaaattatc gtgttttcca actaaacaaa acaaacaaaa    960
cagataactt atccatctaa agttctaaac acctaatcac tcctcaaaaa ctacctccaa   1020
ccaaaacagg gccgtaaagg aaaatcttcc gtgtcgtcgt ctcctccgct ccttgcgcca   1080
agacgagtcg cggctcaaca gcggagaggc ggcgatctcc catctggcga gcagagcagg   1140
ggaggggaag ggatcttggt gagcatccac atcctcttcc tgactcatct ctctcccacc   1200
gggagtactt ctgtctggaa tttgcttgcg ttaaccctag cttctgttct aggtttggaa   1260
gaagctcttc tcttaatttc agagccttaa tcttaataca agtgacagtt tgtttgttcc   1320
ccaaaaagct gaatccgccc ctgtccagtg gtacgaattc agtttctgta gctgccagaa   1380
gaagtaaatt aaatttcatg ttataccatg ttctgaaact ctcaagaatg ttgatggaag   1440
ttgatggggt tctagtgtat aaaactggat cagtatttct ggttattgat tgggtttcac   1500
aaactgtgga agtataaatt ggatattata gagtacaagg agcagagatg gggcctaaca   1560
catgacacgt gcgttacaaa ggagaactgg agaagaggtg gattccttct caaattcccc   1620
gcccacagat tcccatctcc aacctccatc tccgtctcct cagagatcca catagcgact   1680
cccgatccag actaagcttg caaaactccc ttgccccagc agcgtcgaca gtgtggtgct   1740
gaccggcggc ttctgatcaa aatagtcagt tggattggtc ctgtcctgtc ctgtcctggt   1800
cctgaacctc taatctcttc atttcaaaac gaatagatga ctggattcat tttcctgcat   1860
tttaaactac tggtttttct ttttgttgtt tttgacattg ttcattgctg atataagtat   1920
caggggtata agattatgat ggatttatgg cattatgggt tcatctgagt tgattttttt   1980
ctatctgcag ttagagtggc atggctgctg aatgtggaag tggcaactgt gatgcttggg   2040
cagcgagaga tccttcaggg atcctctccc cgtacaagtt caaccgcagg ttaaatcaca   2100
ctacactccc ttgtgtattg attttccttt ttattttctt gatatgaatg tctttccagc   2160
actgttaaga aatcttcctt gtttccaagt gttttctcta actgcagaat gcactattct   2220
ggcaactaga atcatcacga ttgcagtttc agttagctgt gtgcttatct ggaacaagaa   2280
tgtgaacttg tcaagttacc tgttttgaat tttctaactt ttgcgcaaca tgataaactg   2340
```

```
gattacaaaa tctctatagt actttgctga atgttgtgat taactactca cagacaagat   2400
tttaaaatga tcttttccat ttttagtacc tattcttatg aattgttaat aacctggttt   2460
attattacca gggctgtaca aagtgacgat gtttccttga ggatcacaca ctgtggtgtt   2520
tgttatgctg atgttgcatg gacaaggaat atactcaaca attcgatgta ccctttagtc   2580
cctgggtaaa attattaact ttgttacttg aattttaaca aaagtatgga aaagaataaa   2640
cttctgttac agactataaa ttcatccatt tagctactgt atttgttgta aagataaaag   2700
ttcatgaaat tgtgtctaaa tttcaatatg agtaggcatg agatagcagg agttgtaact   2760
gaggttggtg cagacgtcaa gagcttcaaa gtgggtgacc atgtaggtgt tggcacatac   2820
gtgaattcat gccgggactg tgagaactgc aatagctctc tagagaacta ctgctcacaa   2880
catgtcttca ctttcaatgg tgttgacact gatgggactg tcacaaaggg aggatattct   2940
actcacatag tagtacatga gaggtatgga ttttgaccat gttttcttct gaaagttttc   3000
tgacaagaca acgaaaaatt tcatatactt atttctaatg gttgctcaac aatgttgtca   3060
caaaatcatc ctacattctg ctatgtaaat tttatatagg aaacaaatcc catgatgttc   3120
tgctaatgtc tctcttatga atatagcagc tattagttat tcctgtttac ttaattcaaa   3180
aaagaaccta tgagaaaatt gcatcttcct ttggaatggc aggtattgct ttaaaatacc   3240
tgatggctac cctttggaaa aggcagcacc tttactttgt gctggcatca ctgtatatag   3300
tccgatgatg cggcataata tgaaccagcc agggaagtca ctcggcgtca ttggacttgg   3360
tggcttgggt cacatggcag taaaatttgg gaaagccttt ggactgaaag tcacagttat   3420
tagtactagt gaatcaaaga gaaaagaagc tattgacctt cttggtgcag ataatttcgt   3480
ggtgtcatcg gatgaaaatc agatggaggt aatacacatt ctacattatg ttttacccca   3540
ttgttcacag ttatctacta tgaccatacc atgagtctta tcagtcaaat gccatttggt   3600
aaagatagct aacctgtact tctcatttat cttacgtact gaaagtggta atgacagatt   3660
cttcattgtt gcagaccttg aaaagctctc tgaacttcat tattgacaca gcctccggcg   3720
atcacccatt cgatccttat ctcacgcttc tgaaagttgg tggtgtaatg gcactactta   3780
gcttcccaag tgaaatcaaa gtgcatcctg caaaccttaa tctcggtaat gcacgtttct   3840
cataccaaaa tatatatggc tttttccaga gaggaaatat atctgtctgc taggatgggg   3900
agaaaattaa ttaattacaa ctaatctgga ctcatgtagg tgggcggagt ttatctggta   3960
gtgtaactgg aggtacgaag gacatccagg agatgataaa cttctgtgcg gcaaacaaaa   4020
tctacccaga tatcgagatg atcaagatag attacatcaa cgaggctctt cagaggcttg   4080
ttgaccggga tgtcagattt cgctttgtaa tcgacattga gaactcgttc aagtagtatc   4140
ttgatatctt cagtacacca ttaatgatag aagtgtatgc aataataata agtttaaatg   4200
tcctacaaga tgatgagacc atgagacagt tccagaacaa aatgttccat tttaagaagc   4260
aatttggttc tgttttcagt tattttcagg agtaaattgt attggtggta cacaaactta   4320
tttggtgggt gtaatttaat acataaactt gtttgttggg tgtaatttag tatataaatt   4380
tgtttgttgg gtgtagttta gtacataaac taaacttgtg aagtacttat tttggtacat   4440
gaacttatct aattcgtatg aatcacaatc aaaatggctt ggcaaagttg atccttcaaa   4500
gttgattttg attaggatat agcatgcaca agtggtgagt acgcataaga tatgctatat   4560
ttataaactt tgtttctact tttcatcatc attaaaatga tgaatttcct atgtttctat   4620
ctcttgttaa atggttttca tatatttttc tataatcatt atgtctcgat ctatcttttt   4680
```

```
attgaacata ctagagaaaa tgcctgtgcg ttgcaacggg tgaaaatgtt tgtggatcgc   4740

tatatattat acttctttta ggttttgggt cgaaagctca tcccatcggc cccaacccag   4800

gctttgagcc gaaagctcat ctcattgagc ccaacccaat ccaatatttc cctttgggcc   4860

tcatcgggcc gaaagctcat ctcatcggtc cctacccagg ctttgggccg aaagctcatc   4920

tcatcggtcc ctacctaggc tttgggccga aagctcatct catcgggccc aacccagtcc   4980

gatatttccc tttgctcgac ttctctcttc ggctgatatt tccctttgtt cgacttcggt   5040

tcaaacctgg agctactggc ccgactattt ccatttgttc gacttcggtt caaacctgga   5100

gctgcaggcc cgactacgtc catcaatacc catctcttcc ttctttttca acccaacccg   5160

cgatattttc gctgactatt gtccatcaat acccatctct tccttctttt ttaagcacaa   5220

cccagtccgt ctcattcctt cctttttcaa cccaatctag tccgatattt ccttttgctc   5280

gaccttttc agccgaaccc agttcgatat tttcctctac tcaacctttc tcttcctccc   5340

ctccaggccc gactacgtcc atcaataccc atctcttcct tctttttcaa cccaacccgc   5400

gatattttcc ccgactattg tccatcaata cccatctctt ccttcttttt taagcacaac   5460

ccagtccgtc tcatcccttc ctttttcaac ccaatctagt ccgatattaa tacccatctc   5520

ttccttcttt ttcaacccaa cccgcgatat tttccccgac tattgtccat caatacccat   5580

ctcttccttc tttttaagc acaacccagt ccgtctcatc ccttcctttt tcaacccaat   5640

atagtccgat atttcctttt gctcgacctt tttcagccga acccagttcc atattttcct   5700

ctactcaacc tttctcttcc tcccatcgtt aacccagtcc gatactttcc tctgctcgac   5760

ctttctcttc ctcccatcat tcgatcgagc ccatctctcc ctttattttc agtccaatcc   5820

agtccgatat ttctgcttgc tcaacctttt tcagcccaat ccagtccaat atttccgtct   5880

gcttgacctg tttcttgctc ccatcatttg atcaagccca tctattactt tattttcagc   5940

ccaacccagt ccgatatttc cctctactcg actattttca acccagttcg atatgtccct   6000

ttgctcagac ctttttcagc ccaacccagt tcactatctc tcttcggctc aaaccacaag   6060

tggagctaca ggtctagcga ctgtcatctt caacctacga aagacattcc cgtgcacata   6120

cgatgtcgaa gtcgttcctc acctcaataa ttccatgtct taccgtgcac atgcgatgtt   6180

ggagccgatc ctcccatcaa ttacgataaa atatttcttg atctcccaaa attggtctct   6240

cttcggctca aacc                                                      6254
```

```
<210> SEQ ID NO 19
<211> LENGTH: 2000
<212> TYPE: DNA
<213> ORGANISM: Oryza sativa

<400> SEQUENCE: 19

cagtcacaaa ttttttggta attccgagaa aatttccgga aactccgaga acatttccag     60

aaagtttccg accatttccg agttccgacg gaaactgccc ttatcatttc cgattccgtt    120

tccgagaaaa tattttcgaa ttcgtttccg tttccgaaaa atccgaaaaa attctgaccg    180

acagattccg tttccgaaaa taggtccgga atccggaaag tttccgtacc gttttcaccc    240

ctaactggga caaaatgatt attttagtct aacatacatt gttaagtata ttaaagtcta    300

cggtctatct cacagcttac aaatggtgag atatgatatc ttttaacatt atttcataaa    360

acagtaaata agatgcccgg catcaagggg tgaaaacgat attgaaattt cccgaccata    420

ccgataccgt tttcggaaat ctaatataat aataatattt ttaccaatgg ctaccatttt    480

caaaatttag ttttttteta atttctatca gcgtggcatt gaagttaaca ctaaatatat    540
```

```
gaattcgtaa acattaaaat tttccgaccg tttcggttcg ttttcgaaaa aataataaaa    600

taatgatatc gtttccgacc atttctgata gttttcatcc ctaacggcat ccacgtgggc    660

tttcttccta gttgagtaaa aagtggagta ttgagagttt acacgagaga attattagtg    720

agattaagat ggaaatttga tttttagtcc taatatcttg tttagtaaat atggcggaaa    780

ttgacaggga gtttcgttgg agattatgtc attaataaaa acggatggct gagatttgtt    840

tatgcaaatt aaaggaggaa ttccccctat ccacgtattg aaagaggtgt tccttactca    900

attctccatt cccatctcat taaaattatc gtgttttcca actaaacaaa acaaacaaaa    960

cagataactt atccatctaa agttctaaac acctaatcac tcctcaaaaa ctacctccaa   1020

ccaaaacagg gccgtaaagg aaaatcttcc gtgtcgtcgt ctcctccgct ccttgcgcca   1080

agacgagtcg cggctcaaca gcggagaggc ggcgatctcc catctggcga gcagagcagg   1140

ggaggggaag ggatcttggt gagcatccac atcctcttcc tgactcatct ctctcccacc   1200

gggagtactt ctgtctggaa tttgcttgcg ttaaccctag cttctgttct aggtttggaa   1260

gaagctcttc tcttaatttc agagccttaa tcttaataca agtgacagtt tgtttgttcc   1320

ccaaaaagct gaatccgccc ctgtccagtg gtacgaattc agtttctgta gctgccagaa   1380

gaagtaaatt aaatttcatg ttataccatg ttctgaaact ctcaagaatg ttgatggaag   1440

ttgatggggt tctagtgtat aaaactggat cagtatttct ggttattgat tgggtttcac   1500

aaactgtgga agtataaatt ggatattata gagtacaagg agcagagatg gggcctaaca   1560

catgacacgt gcgttacaaa ggagaactgg agaagaggtg gattccttct caaattcccc   1620

gcccacagat tcccatctcc aacctccatc tccgtctcct cagagatcca catagcgact   1680

cccgatccag actaagcttg caaaactccc ttgccccagc agcgtcgaca gtgtggtgct   1740

gaccggcggc ttctgatcaa aatagtcagt tggattggtc ctgtcctgtc ctgtcctggt   1800

cctgaacctc taatctcttc atttcaaaac gaatagatga ctggattcat tttcctgcat   1860

tttaaactac tggtttttct tttgttgtt tttgacattg ttcattgctg atataagtat   1920

caggggtata agattatgat ggatttatgg cattatgggt tcatctgagt tgattttttt   1980

ctatctgcag ttagagtggc                                               2000
```

<210> SEQ ID NO 20
<211> LENGTH: 354
<212> TYPE: PRT
<213> ORGANISM: Sorghum bicolor

<400> SEQUENCE: 20

```
Met Ala Ala Glu Ser Glu His Gly Asn Cys Asn Ala Trp Ala Ala Arg
1               5                   10                  15

Asp Pro Ser Gly Val Leu Ser Pro Tyr Ser Phe Asn Arg Arg Pro Val
            20                  25                  30

Gln Ser Ser Asp Val Ala Leu Lys Ile Leu Tyr Cys Gly Val Cys Tyr
        35                  40                  45

Ala Asp Val Val Trp Thr Arg Asn Met His His Asp Ser Lys Tyr Pro
    50                  55                  60

Val Val Pro Gly His Glu Ile Ala Gly Val Val Thr Gln Val Gly Ala
65                  70                  75                  80

Asp Val Lys Gly Phe Lys Val Gly Asp His Val Gly Val Gly Thr Tyr
                85                  90                  95

Val Asn Ser Cys Arg Asp Cys Glu Asn Cys Asn Ser Ser Leu Glu Asn
            100                 105                 110
```

```
His Cys Pro Lys Gly Val Tyr Thr Phe Asn Gly Ile Asp Thr Asp Gly
        115                 120                 125

Thr Val Thr Lys Gly Gly Tyr Ser Thr His Ile Val Val His Glu Arg
    130                 135                 140

Tyr Cys Phe Gln Ile Pro Asp Gly Tyr Pro Leu Ala Lys Ala Ala Pro
145                 150                 155                 160

Leu Leu Cys Ala Gly Ile Thr Val Tyr Thr Pro Met Met Arg His Asn
                165                 170                 175

Met Asn Gln Pro Gly Lys Ser Leu Gly Val Ile Gly Leu Gly Gly Leu
            180                 185                 190

Gly His Met Ala Val Lys Phe Gly Lys Ala Phe Gly Leu Lys Val Thr
        195                 200                 205

Val Leu Ser Thr Ser Glu Ser Lys Arg His Glu Ala Ile Ser Leu Leu
    210                 215                 220

Gly Ala Asp Asn Phe Val Ile Ser Ser Asp Thr Gln Gln Met Glu Ser
225                 230                 235                 240

Leu Arg Asn Ser Leu His Phe Ile Val Asp Thr Ala Ser Gly Asp His
                245                 250                 255

Pro Phe Asp Pro Tyr Leu Ser Leu Leu Met Val Gly Gly Val Met Ala
            260                 265                 270

Ile Val Gly Phe Pro Ser Glu Ile Lys Met His Pro Ala Ser Leu Asn
        275                 280                 285

Leu Gly Ala Arg Thr Leu Ser Gly Ser Val Thr Gly Gly Thr Lys Asp
    290                 295                 300

Ile Gln Glu Met Val Asn Phe Cys Ala Ala Asn Lys Ile Ser Pro Glu
305                 310                 315                 320

Ile Glu Ile Ile Lys Ile Asp Tyr Ile Asn Glu Ala Leu Thr Arg Leu
                325                 330                 335

Val Asn Arg Asp Val Lys Tyr Arg Phe Val Ile Asp Ile Glu Asn Ser
            340                 345                 350

Phe Lys
```

<210> SEQ ID NO 21
<211> LENGTH: 5242
<212> TYPE: DNA
<213> ORGANISM: Sorghum bicolor

<400> SEQUENCE: 21

```
aaaagtcaaa cgtcttataa tttgggatgg agtattaaac atgcataaac ctaggtaaat      60

taatatttca atcatacatg gtccaatgag tcttaatttt ttagcatagc taaagcatac     120

aattagtagc ctaccataaa agttttacca caatcaaagc acaaagagct acaattatga     180

attaaacaca aaaacacata tatctacagc tacaacaaaa atgttaaact aaagcatgtc     240

atattatata tctattatat agagcttgtc atgtggagtc taacaaaact gaattttcgt     300

ttttacaaat tttctatgat tttatagaat ttttttaaag ttttagtcag tttatgaaat     360

aaaaaagagc atgtgggcca catcagcaac cacattggca ggagagtcct tcgtgattgg     420

atggtggcta ggttctagac aaagtttatg gatctagatg agcgaaaaaa gtttatggac     480

atatgtgaga agtggagaaa agtttaagaa ccctcaacac atttgactca agaaagaata     540

acataaaacc aaccacacac taaatttaag gttgaaatcc aaatgatatg atatatgatg     600

aaatacaaac attcatgaga tttttataaa agaataaaga catagtaaat aaagcaaaga     660

atatataaaa aataagtata tagttatctg ttgacaaatt ttatatagta tattttataa     720
```

```
atacgaacta gtagatagtt ctagccaatc ctaaaacata atcaaacaca tagaaatcta    780
acatatttaa ggggtgtttg gttggaggtg ttaaagttta atatgtatta taacattttc    840
gttttatttg acaattagtg tctaatcatt gactaactag gcttaaaaga tttgtctggc    900
aaattacttt ctagttatgt ttttagtttc ataaataatc tatatttagt actttatgca    960
tatgtccaaa cattcgatgt gacgagagtt aaagtttaac tatggaaacc aaggccctta   1020
ctaaagaaat ctgttaacag atcaataaca gaagtcatat aaaaatcaaa tatcagaaaa   1080
taatgatcta tctatattat gaaaaaaaca agcgttcatg agtttgagtt tttttaccg    1140
tgtttgttat ttactaaaag aaaactacaa gtacttttat ctgttctatt tacaaggcac   1200
gggtctaatt ataagtttct tttacctttg aaattcttaa tattccgacg gtagtattag   1260
tcgtatgata caatactccc attcggccat tccattagct gaggccttgt ttagttccta   1320
aaaagttttg ccaaattttc agatttttcg tcacatcaaa ttttacggca tatgcatgaa   1380
acattaaata tagataaaaa gaataactaa ttacatagtt taactgtaat ttgtgagacg   1440
aatttttaaa atctaattaa tctataatta aataatattt gtcaaataca aacgtggtat   1500
aatgcctatt ttactaattt ttttgaaact acttcctccg tcccataaat aattgcattt   1560
ctttaacttc tatagtttat gtttgaccgt tcgtcttatt aaaaaatttt taataaatat   1620
tatttatttt ttcatgactt attttattgt tagatatatt ttttatgata atttatttat   1680
tttattattt gtacaaaaat ttaaataaaa taaatggtca aacattacta ttagcagtcg   1740
aagaaatgca tttatttatg ggacgaagag agtaaacaag gcctgaagct gaagcctgaa   1800
ggaagaaagg gaaaggggat tgacgcatgc actgatggtt cggccaggca caatcagcga   1860
tgaactcatg gctgacgaga agccccgtaa ctccggaagc caggtccgcg acgtcactgc   1920
tgtcggcacc ctctccaatc caatccatcc acccgtcaac ggagcatgat ccggtctgcg   1980
cccttccaac ttcttcccca ttataatttg ctcactcgcc ggcggccgct acctgctgca   2040
acccggcgac acccgaccga cagcctgctt gccacgcttg catcgaggag agttcgggga   2100
ccgcccggtg cagaaggaat cgacgcaggg gtgagtcttt tcccctcccc tcccatgtac   2160
ttcccgcctc gattcgactc caagggtcag cgatttcact gcgcttttcc ttagcatagg   2220
ctatctgaaa tttccttctg ttagagccga gtctttcgat ctgctgactt gtcacgaatt   2280
cattctgcag ttcagttcga atggctgctg aatcagagca cggcaactgc aatgcttggg   2340
cagcgagaga tccttctgga gttctctcac catacagctt taaccgcagg tggcttccca   2400
cccccccca cccccccccc cccccccccc cgcgtctcct gatctggaga aaagttgcgt   2460
catgtttagc actctgaata ctgtattctt gctatgctag actgtttctt tgggatagct   2520
atggaccgta ttgtttccat gtctttctgt gtacacgcta tatgtttggt tttcagtgtg   2580
tttcatacct gttatcaaat gagcaatatc ttggtgtgga gcaagtagtg cagctatttc   2640
tgctcgtggt ctgtcaaaca aaatcatgaa attgatgctt actatgggca ttgggtgaac   2700
attttaggtc tgatgggatt gcagaatttt gttcaacgtt ggcaggatct gccttttatt   2760
attaaaaaaa taagggaagc gacctaagtc aacaactata cagattgatt gcagaaattt   2820
gagtacaaat agcaacgtac ttgtcttttt gttcagctag cttgtctgtt tcattttta    2880
taacgtcttc ttatgagagc tactatgtgt aataattttc agaccagtgc aaagcagcga   2940
tgttgcgttg aagatcttat actgtggagt ctgttatgct gacgttgtct ggacacggaa   3000
tatgcaccat gattcaaaat atcctgtggt tcctgggtaa gcgtctgaca acaatttaga   3060
```

```
cttgtatcag ggaagggcat gtttcttatc aatcgcgaat tgcatttcaa gatccaactc   3120
tgaattgacc aggactagta gttttactag gtgttctaat ctaaggggca gaatatgact   3180
aatagttaca gactaacagc ccagatcaat acattgaacc cctctagagc aaacaaaaca   3240
tcatagtcag gagtatcgat taagtgtttg cccattgtcc aaaaatgatg tctgtgtact   3300
atatatttgt caatgatatt attcattggt gcaggcatga gatagctgga gtcgtaactc   3360
aggttggtgc agatgtcaaa ggctttaaag tgggtgacca tgtaggtgtt ggaacttatg   3420
tgaactcatg ccgagattgt gagaactgca atagctctct agagaaccac tgtccaaaag   3480
gagtttatac tttcaatggc attgatacag atggaactgt cacaaagggg ggttactcca   3540
ctcacattgt agtccatgaa aggtatggca gtactgtttt acttggctgt tcaaacaaga   3600
ctctttttat attgacaaaa gctattttag ggatgaaaac aggttccact gtgatttcat   3660
ttgcctattt aatcacactg tgtcgtgttc aagatgttat atacttctgt atgaaagtaa   3720
actctgggtc attgctgtcc ataaattttc atcacaatca atacatgatc aaagaattat   3780
atatgggtct atataagtca ttattgacac cttgatgctg attcgataca acctgtcaga   3840
taagggatgg catcttctgt tgattaattt gaactttagg tattgcttcc aaatacctga   3900
tggctatcct ttggcgaagg cagcacctct tctgtgtgct ggaataactg tgtatactcc   3960
aatgatgcga cacaacatga accaacctgg aaagtcactt ggggtcattg gactcggtgg   4020
tctaggtcac atggcagtga aatttggtaa agcatttggt ctgaaggtca cagttttgag   4080
tacaagtgaa tcaaagagac atgaagccat cagcctcctt ggagcggata attttgttat   4140
atcatcagat acacagcaga tggaggtact gctctggaca ttgcgtaatc tgaacgtacc   4200
taggcacctc gtacttcatc tgttccgaat atgagaaatt ttatttttgt cctaagtcaa   4260
aaaactctat aattgaccta gtttatagaa aaaagcacta gtatctacaa gaccaaattt   4320
attccattga atctcctgta gaatgtgttt ggtattgtag atgtcaatat atttttctat   4380
aaacttagtc aaagctagac aaaattgact taggataaaa ctaaaacatc ttacatttga   4440
aagggagaga atataccacg tttcccttct tgattatatg acaccatatt ttggtggggt   4500
tctttttgtt tctttatttt attgccaaag atgcaagcac atcacattgt tttcacatgg   4560
aacgaacaga tagcagatca ctttcgttct cattaatttg ctacttgact ttaaagttcc   4620
aggcagccag ttcagtatat gacattggat agtttcctta tgctgagaat aaagataaca   4680
gctaagtact ggctgttctg ctttacctga aaactgaccg tgaatatatg atctcttgct   4740
tttgcagtcc ctgagaaact ccctgcactt catagttgac accgcttctg gcgaccatcc   4800
atttgatcca tatctctctc tccttatggt tggtggtgtg atggcaattg tgggctttcc   4860
aagtgagatc aaaatgcatc ctgcaagcct taatcttggt aattctctgt tctgacactc   4920
tgtactaaaa agaaacgtgg tattagaagc caaattattc agatttaacc tgaactgttt   4980
tttaggtgca cggaccttgt ctggtagtgt tactggaggt acaaaagaca tccaagaaat   5040
ggttaacttc tgtgcggcga acaaaatctc tccagagatt gagatcatta agatagatta   5100
tatcaatgag gctctcacga ggcttgttaa ccgagatgtg aaataccgct ttgttatcga   5160
catcgagaac tctttcaagt aacatgctgg tctacatgct ctcagtcttt ctattaatat   5220
actagagcaa acacaaatgt ga                                           5242
```

<210> SEQ ID NO 22
<211> LENGTH: 2300
<212> TYPE: DNA
<213> ORGANISM: Sorghum bicolor

<400> SEQUENCE: 22

```
aaaagtcaaa cgtcttataa tttgggatgg agtattaaac atgcataaac ctaggtaaat     60
taatatttca atcatacatg gtccaatgag tcttaatttt ttagcatagc taaagcatac    120
aattagtagc ctaccataaa agttttacca caatcaaagc acaaagagct acaattatga    180
attaaacaca aaaacacata tatctacagc tacaacaaaa atgttaaact aaagcatgtc    240
atattatata tctattatat agagcttgtc atgtggagtc taacaaaact gaattttcgt    300
ttttacaaat tttctatgat tttatagaat ttttttaaag ttttagtcag tttatgaaat    360
aaaaaagagc atgtgggcca catcagcaac cacattggca ggagagtcct tcgtgattgg    420
atggtggcta ggttctagac aaagtttatg gatctagatg agcgaaaaaa gtttatggac    480
atatgtgaga agtggagaaa agtttaagaa ccctcaacac atttgactca agaaagaata    540
acataaaacc aaccacacac taaatttaag gttgaaatcc aaatgatatg atatatgatg    600
aaatacaaac attcatgaga tttttataaa agaataaaga catagtaaat aaagcaaaga    660
atatataaaa aataagtata tagttatctg ttgacaaatt ttatatagta tattttataa    720
atacgaacta gtagatagtt ctagccaatc ctaaaacata atcaaacaca tagaaatcta    780
acatatttaa ggggtgtttg gttggaggtg ttaaagttta atatgtatta taacattttc    840
gttttatttg acaattagtg tctaatcatt gactaactag gcttaaaaga tttgtctggc    900
aaattacttt ctagttatgt ttttagtttc ataaataatc tatatttagt actttatgca    960
tatgtccaaa cattcgatgt gacgagagtt aaagtttaac tatggaaacc aaggccctta   1020
ctaaagaaat ctgttaacag atcaataaca gaagtcatat aaaaatcaaa tatcagaaaa   1080
taatgatcta tctatattat gaaaaaaaca agcgttcatg agtttgagtt ttttttaccg   1140
tgtttgttat ttactaaaag aaaactacaa gtacttttat ctgttctatt tacaaggcac   1200
gggtctaatt ataagtttct tttacctttg aaattcttaa tattccgacg gtagtattag   1260
tcgtatgata caatactccc attcggccat tccattagct gaggccttgt ttagttccta   1320
aaaagttttg ccaaattttc agatttttcg tcacatcaaa ttttacggca tatgcatgaa   1380
acattaaata tagataaaaa gaataactaa ttacatagtt taactgtaat ttgtgagacg   1440
aatttttaaa atctaattaa tctataatta aataatattt gtcaaataca aacgtggtat   1500
aatgcctatt ttactaattt ttttgaaact acttcctccg tcccataaat aattgcattt   1560
ctttaacttc tatagtttat gtttgaccgt tcgtcttatt aaaaaatttt taataaatat   1620
tatttatttt ttcatgactt attttattgt tagatatatt ttttatgata atttatttat   1680
tttattattt gtacaaaaat ttaaataaaa taaatggtca aacattacta ttagcagtcg   1740
aagaaatgca tttatttatg ggacgaagag agtaaacaag gcctgaagct gaagcctgaa   1800
ggaagaaagg gaaaggggat tgacgcatgc actgatggtt cggccaggca caatcagcga   1860
tgaactcatg gctgacgaga agccccgtaa ctccggaagc caggtccgcg acgtcactgc   1920
tgtcggcacc ctctccaatc caatccatcc acccgtcaac ggagcatgat ccggtctgcg   1980
cccttccaac ttcttcccca ttataatttg ctcactcgcc ggcggccgct acctgctgca   2040
acccggcgac acccgaccga cagcctgctt gccacgcttg catcgaggag agttcgggga   2100
ccgcccggtg cagaaggaat cgacgcaggg gtgagtcttt tcccctcccc tcccatgtac   2160
```

-continued

```
ttcccgcctc gattcgactc caagggtcag cgatttcact gcgcttttcc ttagcatagg   2220

ctatctgaaa tttccttctg ttagagccga gtctttcgat ctgctgactt gtcacgaatt   2280

cattctgcag ttcagttcga                                               2300
```